(12) United States Patent
Breij et al.

(10) Patent No.: US 10,500,276 B2
(45) Date of Patent: *Dec. 10, 2019

(54) ANTIBODIES BINDING AXL

(71) Applicant: GENMAB A/S, Copenhagen V (DK)

(72) Inventors: Esther Breij, Utrecht (NL); David Satijn, Utrecht (NL); Edward Norbert Van Den Brink, Halfweg (NL); Dennis Verzijl, Amstelveen (NL); Rob N. De Jong, Utrecht (NL); Paul Parren, Utrecht (NL); Riemke Van Dijkhuizen Radersma, Zeist (NL)

(73) Assignee: GENMAB A/S, Copenhagen V (DK)

(*) Notice: Subject to any disclaimer, the term of this patent is extended or adjusted under 35 U.S.C. 154(b) by 0 days.

This patent is subject to a terminal disclaimer.

(21) Appl. No.: 16/270,317

(22) Filed: Feb. 7, 2019

(65) Prior Publication Data

US 2019/0160170 A1    May 30, 2019

Related U.S. Application Data

(62) Division of application No. 15/325,364, filed as application No. PCT/EP2015/065900 on Jul. 10, 2015.

(30) Foreign Application Priority Data

| Jul. 11, 2014 | (DK) | 2014 00380 |
| Sep. 1, 2014 | (DK) | 2014 00489 |
| Dec. 22, 2014 | (DK) | 2014 00746 |
| May 12, 2015 | (DK) | 2015 00283 |

(51) Int. Cl.
| *A61K 39/395* | (2006.01) |
| *C07K 16/28* | (2006.01) |
| *A61K 47/68* | (2017.01) |
| *A61K 39/00* | (2006.01) |
| *C07K 16/30* | (2006.01) |

(52) U.S. Cl.
CPC .... *A61K 39/39558* (2013.01); *A61K 47/6801* (2017.08); *A61K 47/6855* (2017.08); *A61K 47/6857* (2017.08); *A61K 47/6869* (2017.08); *C07K 16/2863* (2013.01); *C07K 16/3061* (2013.01); *A61K 2039/505* (2013.01); *A61K 2121/00* (2013.01); *C07K 2317/33* (2013.01); *C07K 2317/34* (2013.01); *C07K 2317/56* (2013.01); *C07K 2317/732* (2013.01); *C07K 2317/77* (2013.01); *C07K 2317/92* (2013.01)

(58) Field of Classification Search
CPC .......... A61K 39/39558; A61K 47/6869; A61K 47/6801; A61K 2039/505; C07K 16/2863; C07K 2317/56

See application file for complete search history.

(56) References Cited

U.S. PATENT DOCUMENTS

| 10,201,607 | B2* | 2/2019 | Breij | C07K 16/2863 |
| 2012/0121587 | A1 | 5/2012 | Maeda et al. | |
| 2013/0108644 | A1 | 5/2013 | Giaccia et al. | |
| 2017/0157250 | A1 | 6/2017 | Breij et al. | |
| 2018/0214549 | A1 | 8/2018 | Breij et al. | |
| 2018/0326084 | A1 | 11/2018 | Boshuizen et al. | |
| 2019/0022243 | A1 | 1/2019 | Boshuizen et al. | |

FOREIGN PATENT DOCUMENTS

| WO | 2009/063965 A1 | 5/2009 |
| WO | 2010/131733 A1 | 11/2010 |
| WO | 2011/014457 A1 | 2/2011 |
| WO | 2011159980 A1 | 12/2011 |
| WO | 2012/175691 A1 | 12/2012 |
| WO | 2012/175692 A1 | 12/2012 |
| WO | 2013/064685 A1 | 5/2013 |
| WO | 2013/090776 A1 | 6/2013 |
| WO | 2014/068139 A1 | 5/2014 |
| WO | 2014/174111 A1 | 10/2014 |
| WO | 2015/193430 A1 | 12/2015 |
| WO | 2016/091891 A1 | 6/2016 |

OTHER PUBLICATIONS

Alley, SC. et al, "Antibody-drug conjugates: targeted drug delivery for cancer," Current Opinion in Chem. Bio., vol. 14: 529-537 (2010).
Bansal, N. et al., "Axl receptor tyrosine kinase is up-regulated in metformin resistant prostate cancer cells," Oncotarget, vol. 6(17):15321-15331 (2015).
Blakely, C. et al., "Resiliency of Lung Cancers to EGFR Inhibitor Treatment Unveiled, Offering Opportunities to Divide and Conquer EGFR Inhibitor Resistance," Cancer Discov., vol. 2(10):872-875 (2012).
Brand, TM et al., "AXL Is a Logical Molecular Target in Head and Neck Squamous Cell Carcinoma," Clin Cancer Res., vol. 21(11):2601-2612 (2015).
Breij, E. et al., "Abstract 634: Novel antibody-drug conjugates targeting Axl show anti-tumor activity in solid cancer xenograft models," American Association of Cancer Research, In: Proceedings of the 106th Annual Meeting of the American Association for Cancer Research; Apr. 18-22, 2015; Philadelphia (PA): AACR; Cancer Res 2015;75(15 Suppl):Abstract nr 634, 2 pages.
Breij, E., "Preclinical efficacy studies using HuMax-Axl-ADC, a novel antibody-drug conjugate targeting Axl-expressing solid cancers," Journal of Clinical Oncolocgy, vol. 33 (15 Supp): 1-2 (Abstract 3066) (2015) 4 pages.

(Continued)

*Primary Examiner* — Ruixiang Li
(74) *Attorney, Agent, or Firm* — Nelson Mullins Riley & Scarborough LLP; Jane E. Remillard, Esq.; Christopher L. Frank

(57) ABSTRACT

The present invention relates to anti-AXL antibodies, immunoconjugates, compositions and method of treatment of cancer with such anti-AXL antibodies, immunoconjugates, or compositions.

35 Claims, 25 Drawing Sheets
Specification includes a Sequence Listing.

(56) References Cited

OTHER PUBLICATIONS

Dufies, M. et al., "Mechanisms of AXL overexpression and function in Imatinib-resistant chronic myeloid leukemia cells," Oncotarget, vol. 2(11):874-885 (2011).
Elkabets, M. et al., "AXL mediates resistance to PI3K? inhibition by activating the EGFR/PKC/mTOR axis in head and neck and esophageal squamous cell carcinomas.," Cancer Cell., vol. 27(4):533-546 (2015).
Hafizi, S. et al., "Gas6 and Protein S. Vitamin K-dependent ligands for the Axl receptor tyrosine kinase subfamily," FEBS Journal, vol. 273: 5231-5244 (2006).
Hector, A. et al., "The Axl receptor tyrosine kinase is an adverse prognostic factor and a therapeutic target in esophageal adenocarcinoma," Cancer Biology & Therapy, vol. 10(10): 1009-1018 (2010).
Hong, F. et al., "Receptor tyrosine kinase AXL is induced by chemotherapy drugs and overexpression of AXL confers drug resistance in acute myeloid leukemia," Cancer Lett., vol. 268(2):314-324 (2008).
Hong, J. et al., "ABL Regulation by AXL Rromotes Cisplatin Resistance in Esophageal Cancer," Cancer Res., vol. 73 (1):331-340 (2013).
Huang, F. et al., "Differential Mechanisms of Acquired Resistance to Insulin-like Growth Factor-I Receptor Antibody Therapy or to a Small-Molecule Inhibitor, BMS-754807, in a Human Rhabdomyosarcoma Model," Cancer Res., vol. 70 (18):7221-7231 (2010).
Iida, S. et al., "Activation of AXL and Antitumor Effects of a Monoclonal Antibody to AXL in Lung Adenocarcinoma," Anticancer Research, vol. 34:1821-1828 (2014).
Kim, H-R., "Epithelial-mesenchymal transition leads to crizotinib resistance in H2228 lung cancer cells with EML4-ALK translocation," Mol Oncol., vol. 7(6):1093-1102 (2013).
Konieczkowski, D.J. et al., "A melanoma cell state distinction influences sensitivity to MAPK pathway inhibitors," Cancer Discov., vol. 4(7): 816-827 (2014).
Koorstra, J-B. et al., "The Axl receptor tyrosine kinase confers an adverse prognostic influence in pancreatic cancer and represents a new therapeutic target," Cancer Biol Ther., vol. 8(7): 1-9 (2009).
Leconet, W. et al., "Preclinical validation of AXL receptor as a target for antibody-based pancreatic cancer immunotherapy," Oncogene, 1-10 (2013).
Li, Y. et al., "Axl as a potential therapeutic target in cancer: role of Axl in tumor growth, metastasis and angiogenesis," Oncogene, vol. 28(39) 3442-3455 (2009).
Linger, RM et al, "Mer and Axl receptor tyrosine kinases are novel therapeutic targets in NSCLC," Abstract A29 Only, 1 page, Journal of Thoracic Oncology, vol. 5(6)(Supp 3):S235 (2010).
Linger, RM. et al, "Taking aim at Mer and Axl receptor tyrosine kinases as novel therapeutic targets in solid tumors," Expert Opin. Ther. Targets, vol. 14(10):1073-1090 (2010).
Liu, L. et al. "Novel mechanism of lapatinib resistance in HER2-positive breast tumor cells: activation of AXL.," Cancer Res., vol. 69(17):6871-6878 (2009).
Liu, R. et al., "Induction, regulation, and biologic function of Axl receptor tyrosine kinase in Kaposi sarcoma," Blood, vol. 116(2): 297-305 (2010).
Mahadevan, D. et al., "Novel receptor tyrosine kinase targeted combination therapies for imatinib-resistant gastrointestinal stromal tumors (GIST).," Oncotarget, vol. 6(4):1954-1966 (2015).
Müller, J. et al., "Low MITF/AXL ratio predicts early resistance to multiple targeted drugs in melanoma," Nat Commun., vol. 5(5712): 10 pages (2014).
Paccez, JD. et al, "The receptor tyrosine kinase Axl in cancer: biological functions and therapeutic implications," Int. J. Cancer, vol. 134 (5):1024-1033 (2013).
Shieh, Y-S. et al., "Expression of Axl in Lung Adenocarcinoma and Correlation with Tumor Progression," Neoplasia, vol. 7(12): 1058-1064 (2005).
Sun, W.S. et al., "Coexpression of growth arrest-specific gene 6 and receptor tyrosine kinases Axl and Sky in human uterine endometrial cancers," Annals of Oncology, vol. 14(6):898-906 (2003).
Wilson, C. et al., "AXL inhibition sensitizes mesenchymal cancer cells to antimitotic drugs," Cancer Res., vol. 74 (20):5878-90 (2014).
Ye, X. et al., "An anti-Axl monoclonal antibody attenuates xenograft tumor growth and enhances the effect of multiple anticancer therapies," Oncogene, vol. 29: 5254-5264 (2010).
Zhang, Z. et al., "Activation of the AXL kinase causes resistance to EGFR-targeted therapy in lung cancer," Nat Genet., vol. 44(8):852-860 (2012).
U.S. Appl. No. 16/248,402, filed Jan. 15, 2019, Esther Breij.
U.S. Appl. No. 15/938,961, filed Mar. 28, 2018, Esther Breij.
U.S. Appl. No. 15/325,364, filed Jan. 10, 2017, Esther Breij.
U.S. Appl. No. 16/069,395, filed Jul. 11, 2018, Julia Boshuizen.
U.S. Appl. No. 15/742,818, filed Jan. 8, 2018, Julia Boshuizen.
U.S. Appl. No. 15/938,961, filed Sep. 13, 2018.
U.S. Appl. No. 15/938,961, filed May 2, 2018.
U.S. Appl. No. 15/325,364, filed Aug. 30, 2018.
U.S. Appl. No. 15/325,364, filed Apr. 19, 2018.

* cited by examiner

FIG. 6A, FIG. 6B, FIG. 6C, FIG. 6D, FIG. 6E

ANTIBODIES BINDING AXL

RELATED APPLICATIONS

This application is a divisional of U.S. patent application Ser. No. 15/325,364, filed Jan. 10, 2017, which is a 35 U.S.C. 371 national stage filing of International Application No. PCT/EP2015/065900, filed Jul. 10, 2015, which claims priority to Danish Patent Application Nos. PA 2015 00283, PA 2014 00746, PA 2014 00489 and PA 2014 00380, filed on May 12, 2015, Dec. 22, 2014, Sep. 1, 2014, and Jul. 11, 2014, respectively. The contents of the aforementioned applications are hereby incorporated by reference.

SEQUENCE LISTING

The instant application contains a Sequence Listing which has been submitted via EFS-Web and is hereby incorporated by reference in its entirety. Said ASCII copy, created on Feb. 7, 2019, is named GMI_161CUSDV_Sequence_Listing.txt and is 114,062 bytes in size.

FIELD OF INVENTION

The present invention relates to antibodies binding AXL, immunoconjugates, compositions comprising such antibodies or immunoconjugates, and uses of said antibodies and immunoconjugates.

BACKGROUND

The TAM subfamily of mammalian Receptor Tyrosine Kinases (RTKs) consists of AXL, Tyro3 and Mer. AXL is a 104-140 kDa transmembrane protein which has transforming abilities [1]. AXL can be activated upon binding of its ligand, the vitamin K-dependent growth arrest-specific factor 6 (Gas6). Gas6 binding to AXL leads to AXL dimerization, autophosphorylation and subsequent activation of intracellular signaling pathways, such as the PI3K/AKT, mitogen-activated protein kinase (MAPK), STAT and NF-κB cascades [2]. In cancer cells, AXL enhances tumor cell motility, invasion, migration, and is involved in epithelial-to-mesenchymal transition (EMT) [3]. Furthermore, AXL expression has been implicated in resistance to chemotherapy and targeted therapy, such as Epidermal Growth Factor Recptor (EGFR) targeted therapy (Wilson 2014, Brand 2013, Zhang 2012) or inhibitors of the B-raf (BRAF) pathway (Muller, 2014).

The extracellular domain of TAM receptor family members is composed of a combination of two N-terminal immunoglobulin (Ig)-like domains and two fibronectin Type III (FNIII) repeats [1]. The ligand Gas6 binds to the Ig-like domains I and II of AXL [14].

Upregulation of AXL has been reported in a variety of cancers, including gastric, prostate, ovarian, and lung cancer [1]. Furthermore, AXL is overexpressed in breast and pancreatic cancers and is significantly associated with higher metastasis frequency and with poor overall survival [2].

Targeted inhibition of RTKs may be effective as antitumor and/or metastatic therapy. Such targeted inhibition of AXL and/or the ligand Gas6 comprises both small molecules and anti-AXL antibodies [3]. Anti-AXL antibodies have been described that attenuate non-small cell lung carcinoma xenograft growth in vivo by downregulation of receptor expression, reducing tumor cell proliferation and inducing apoptosis [4]. Furthermore, various monoclonal antibodies have been described that block binding of the ligand Gas6 to AXL [2], [5], and [7].

Anti-AXL antibodies have been described previously [8]-[13]. However, a need for anti-AXL antibodies having improved anti-tumor activity remains.

SUMMARY OF INVENTION

It is an object of the present invention to provide anti-AXL antibodies. Thus, in one aspect, the present invention relates to an antibody which binds to AXL, wherein the antibody, does not compete for AXL binding with the ligand Growth Arrest-Specific 6 (Gash).

In another aspect, the present invention relates to a bispecific antibody comprising a first binding region of an antibody according to the invention, and a second binding region which binds a different target or epitope than said first antigen-binding region.

In another aspect, the present invention relates to an immunoconjugate comprising the antibody or bispecific antibody according to the invention, and a therapeutic moiety, such as a cytotoxic agent, a chemotherapeutic drug, a cytokine, an immunosuppressant, antibiotic, or a radioisotope.

In another aspect, the present invention relates to a composition comprising the antibody, bispecific antibody, or immunoconjugate according to the invention.

In another aspect, the present invention relates to a pharmaceutical composition comprising the antibody, bispecific antibody, or immunoconjugate according to the invention, and a pharmaceutically acceptable carrier.

In another aspect, the present invention relates to a nucleic acid construct encoding an antibody according to the invention.

In another aspect, the present invention relates to an expression vector comprising one or more nucleic acid constructs according to the invention.

In another aspect, the present invention relates to a host cell comprising a vector according to the invention.

In another aspect, the present invention relates to a hybridoma which produces the antibody according to the invention.

In another aspect, the present invention relates to the antibody, bispecific antibody, or immunoconjugate according to the invention for use as a medicament.

In another aspect, the present invention relates to the antibody, bispecific antibody, or immunoconjugate according to the invention for use in the treatment of cancer.

In another aspect, the present invention relates to a method of treatment of cancer comprising administering the antibody, bispecific antibody, immunoconjugate, composition, or pharmaceutical composition according to the invention, to a subject in need thereof.

In another aspect, the present invention relates to a method of diagnosing a disease characterized by involvement or accumulation of AXL-expressing cells, comprising administering an antibody, bispecific antibody, immunoconjugate, composition, or a pharmaceutical composition according to the invention, to a subject, optionally wherein the antibody is labeled with a detectable agent, and wherein the amount of AXL-expressing cells correlates with or is indicative of disease.

In another aspect, the present invention relates to a method for inhibiting growth and/or proliferation of a tumor cell expressing AXL, comprising administration, to an individual in need thereof, of an antibody, bispecific antibody, immunoconjugate, composition, or pharmaceutical composition according to the invention.

In another aspect, the present invention relates to a method for producing an antibody according to the invention, the method comprising the steps a) culturing a host cell or hybridoma according to the invention, and b) purifying the antibody from the culture media.

In another aspect, the present invention relates to a diagnostic composition comprising an antibody or bispecific antibody according to the invention.

In another aspect, the present invention relates to a method for detecting the presence of AXL antibody, or a cell expressing AXL, in a sample comprising the steps of a) contacting the sample with an antibody, bispecific antibody, immunoconjugate according to the invention, under conditions that allow for formation of a complex between the antibody, bispecific antibody, or immunoconjugate and AXL; and b) analyzing whether a complex has been formed.

In another aspect, the present invention relates to a kit for detecting the presence of AXL antigen, or a cell expressing AXL, in a sample comprising i) an antibody, bispecific antibody, or immunoconjugate according to the invention; and ii) instructions for use of the kit.

In another aspect, the present invention relates to an anti-idiotypic antibody which binds to an anti-AXL antibody according to the invention. s

BRIEF DESCRIPTION OF FIGURES

(FIG. 2A) hsAXL and mock, (FIG. 2B) hsAXL-mmECD, (FIG. 2C) hsAXL-mmIg1, (FIG. 2D) hsAXL-mmIg2, (FIG. 2E) hsAXL-mmFN1, (FIG. 2F) hsAXL-mmFN2.

FIGS. 6A-6E: Antibody VH and VL variants that allow binding to AXL. Antibodies with identical VL or VH regions were aligned and differences in VH (FIGS. 6A-6D) or VL (FIG. 6E) sequences, respectively, were identified and indicated by boxes in the figures. CDR regions are underlined.

(FIG. 10A) Average tumor size after therapeutic treatment with AXL-ADCs the PAXF1657 model. An unconjugated AXL Humab (FIG. 10B) and an untargeted ADC (FIG. 10C) do not show anti-tumor activity, indicating that the therapeutic capacity of AXL-ADCs was dependent on the cytotoxic activity of MMAE and on target binding, error bars represent S.E.M.

(FIG. 11A) hsAXL and mock, (FIG. 11B) hsAXL-mmECD, (FIG. 11C) hsAXL-mmIg1, (FIG. 11D) hsAXL-mmIg2, (FIG. 11E) hsAXL-mmFN1, (FIG. 11F) hsAXL-mmFN2.

FIGS. 13A and 13I3 show results from 2 independent experiments.

FIGS. 14A and 14B show results from 2 independent experiments.

(FIG. 21A) Average tumor size after therapeutic treatment with IgG1-AXL-107-vcMMAE in the esophageal cancer PDX model ES0195. IgG1-b12 and IgG1-b12-MMAE were included as isotype control antibody and isotype control ADC, respectively. (FIG. 21B) Tumor size in individual mice on day 32 after injection of MDA-MB-231-luc D3H2LN tumor cells in the mammary fat pads of female SCID mice. * $p<0.05$; ** $p<0.0001$ FIGS. 22A and 22B. Therapeutic effect of AXL-ADCs in a patient-derived cervical cancer xenograft model.

(FIG. 23A) Average tumor size after therapeutic treatment with IgG1-AXL-183-vcMMAE or IgG1-AXL-726-vcMMAE in an orthotopic MDA-MB-231-luc D3H2LN xenograft model. IgG1-b12 and IgG1-b12-MMAE were included as isotype control antibody and isotype control ADC, respectively. (FIG. 23B) Tumor size in individual mice on day 32 after injection of MDA-MB-231-luc D3H2LN tumor cells in the mammary fat pads of female SCID mice. * $p<0.001$.

DETAILED DESCRIPTION

Antibodies

Figure 1A:
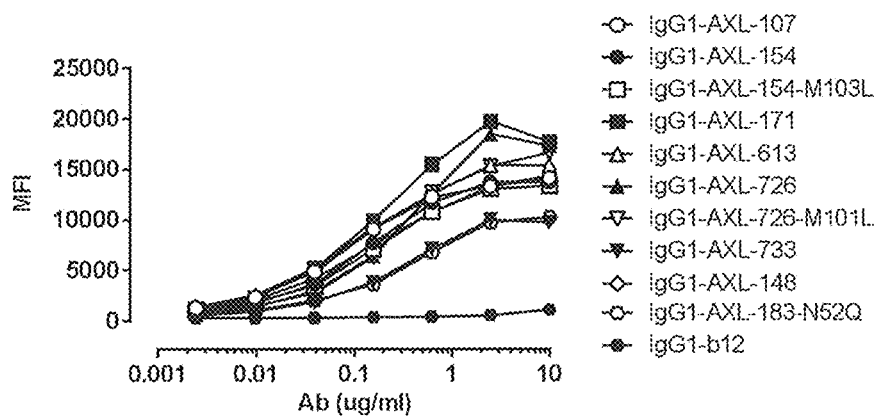
FIGS. 1A-1C: Binding curves of anti-AXL antibodies to HEK293 cells transfected with (FIG. 1A) human AXL-ECD, (FIG. 1B) cynomolgus AXL-ECD, or (FIG. 1C) mouse AXL-ECD. Data shown are mean fluorescence intensities (MFI) of one representative experiment, as described in Example 2.

In one aspect, the present invention relates to an antibody which binds to AXL, wherein the antibody, does not compete for AXL binding with the ligand Growth Arrest-Specific 6 (Gash).

The term "antibody" as used herein is intended to refer to an immunoglobulin molecule, a fragment of an immunoglobulin molecule, or a derivative of either thereof, which has the ability to specifically bind to an antigen under typical physiological and/or tumor-specific conditions with a half-life of significant periods of time, such as at least about 30 minutes, at least about 45 minutes, at least about one hour, at least about two hours, at least about four hours, at least about 8 hours, at least about 12 hours, about 24 hours or more, about 48 hours or more, about 3, 4, 5, 6, 7 or more days, etc., or any other relevant functionally-defined period (such as a time sufficient to induce, promote, enhance, and/or modulate a physiological response associated with antibody binding to the antigen and/or time sufficient for the antibody to be internalized). The binding region (or binding domain which may be used herein, both having the same meaning) which interacts with an antigen, comprises variable regions of both the heavy and light chains of the immunoglobulin molecule. The constant regions of the antibodies (Abs) may mediate the binding of the immunoglobulin to host tissues or factors, including various cells of the immune system (such as effector cells) and components of the complement system such as C1q, the first component in the classical pathway of complement activation. As indicated above, the term antibody as used herein, unless otherwise stated or clearly contradicted by context, includes fragments of an antibody that retain the ability to specifically interact, such as bind, to the antigen. It has been shown that the antigen-binding function of an antibody may be performed by fragments of a full-length antibody. Examples of binding fragments encompassed within the term "antibody" include (i) a Fab' or Fab fragment, a monovalent fragment consisting of the VL, VH, CL and CH1 domains, or a monovalent antibody as described in [15]; (ii) F(ab')$_2$ fragments, bivalent fragments comprising two Fab fragments linked by a disulfide bridge at the hinge region; (iii) an Fd fragment consisting essentially of the VH and CH1 domains; (iv) an Fv fragment consisting essentially of the VL and VH domains of a single arm of an antibody, (v) a dAb fragment [16], which consists essentially of a VH domain and is also called domain antibody [17]; (vi) camelid or nanobodies [18] and (vii) an isolated complementarity determining region (CDR). Furthermore, although the two domains of the Fv fragment, VL and VH, are coded for by separate genes, they may be joined, using recombinant methods, by a synthetic linker that enables them to be made as a single protein chain in which the VL and VH regions pair to form monovalent molecules (known as single chain antibodies or single chain Fv (scFv), see for instance [19] and [20]). Such single chain antibodies are encompassed within the term antibody unless otherwise noted or clearly indicated by context. Although such fragments are generally included within the meaning of antibody, they collectively and each independently are unique features of the present invention, exhibiting different biological properties and utility. These and other useful antibody fragments in the context of the present invention are discussed further herein. It also should be understood that the term antibody, unless specified otherwise, also includes polyclonal antibodies, monoclonal antibodies (mAbs), antibody-like polypeptides, such as chimeric antibodies and humanized antibodies, as well as 'antibody fragments' or 'fragments thereof' retaining the ability to specifically bind to the antigen (antigen-binding fragments) provided by any known technique, such as enzymatic cleavage, peptide synthesis, and recombinant techniques, and retaining the ability to be conjugated to a toxin. An antibody as generated can possess any isotype.

The term "immunoglobulin heavy chain" or "heavy chain of an immunoglobulin" as used herein is intended to refer to one of the heavy chains of an immunoglobulin. A heavy chain is typically comprised of a heavy chain variable region (abbreviated herein as VH) and a heavy chain constant region (abbreviated herein as CH) which defines the isotype of the immunoglobulin. The heavy chain constant region typically is comprised of three domains, CH1, CH2, and CH3. The term "immunoglobulin" as used herein is intended to refer to a class of structurally related glycoproteins consisting of two pairs of polypeptide chains, one pair of light (L) low molecular weight chains and one pair of heavy (H) chains, all four potentially inter-connected by disulfide bonds. The structure of immunoglobulins has been well characterized (see for instance [21]). Within the structure of the immunoglobulin, the two heavy chains are inter-connected via disulfide bonds in the so-called "hinge region". Equally to the heavy chains each light chain is typically comprised of several regions; a light chain variable region (abbreviated herein as VL) and a light chain constant region. The light chain constant region typically is comprised of one domain, CL. Furthermore, the VH and VL regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each VH and VL is typically composed of three CDRs and four FRs, arranged from amino-terminus to carboxy-terminus in the following order: FR1, CDR1, FR2, CDR2, FR3, CDR3, FR4. CDR sequences are defined according to IMGT (see [22] and [23]).

The term "antigen-binding region" or "binding region" as used herein, refers to a region of an antibody which is capable of binding to the antigen. The antigen can be any molecule, such as a polypeptide, e.g. present on a cell, bacterium, or virion. The terms "antigen" and "target" may, unless contradicted by the context, be used interchangeably in the context of the present invention.

The term "binding" as used herein refers to the binding of an antibody to a predetermined antigen or target, typically with a binding affinity corresponding to a $K_D$ of about $10^{-6}$ M or less, e.g. $10^{-7}$ M or less, such as about $10^{-8}$ M or less, such as about $10^{-9}$ M or less, about $10^{-10}$ M or less, or about $10^{-11}$ M or even less when determined by for instance surface plasmon resonance (SPR) technology in a BIAcore 3000 instrument using the antigen as the ligand and the protein as the analyte, and binds to the predetermined antigen with an affinity corresponding to a $K_D$ that is at least ten-fold lower, such as at least 100 fold lower, for instance at least 1,000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the $K_D$ of the protein, so that when the $K_D$ of the protein is very low (that is, the protein is highly specific), then the amount with which the affinity for the antigen is lower than the affinity for a non-specific antigen may be at least 10,000 fold. The term "$K_D$" (M), as used herein, refers to the dissociation equilibrium constant of a particular antibody-antigen interaction, and is obtained by dividing $k_d$ by $k_a$.

The term "$k_d$" (sec$^{-1}$), as used herein, refers to the dissociation rate constant of a particular antibody-antigen interaction. Said value is also referred to as the $k_{off}$ value or off-rate.

The term "$k_a$" (M$^{-1}$×sec$^{-1}$), as used herein, refers to the association rate constant of a particular antibody-antigen interaction. Said value is also referred to as the $k_{on}$ value or on-rate.

The term "$K_A$" (M$^{-1}$), as used herein, refers to the association equilibrium constant of a particular antibody-antigen interaction and is obtained by dividing $k_a$ by $k_d$.

The term "AXL" as used herein, refers to the protein entitled AXL, which is also referred to as UFO or JTK11, a 894 amino acid protein with a molecular weight of 104-140 kDa that is part of the subfamily of mammalian TAM Receptor Tyrosine Kinases (RTKs). The molecular weight is variable due to potential differences in glycosylation of the protein. The AXL protein consists of two extracellular immunoglobulin-like (Ig-like) domains on the N-terminal end of the protein, two membrane-proximal extracellular fibronectin type III (FNIII) domains, a transmembrane domain and an intracellular kinase domain. AXL is activated upon binding of its ligand Gas6, by ligand-independent homophilic interactions between AXL extracellular domains, by autophosphorylation in presence of reactive oxygen species [24] or by transactivation through EGFR (Meyer, 2013), and is aberrantly expressed in several tumor types. In humans, the AXL protein is encoded by a nucleic acid sequence encoding the amino acid sequence shown in SEQ ID NO:130 (human AXL protein: Swissprot P30530; cynomolgus AXL protein: Genbank accession HB387229.1)).

The term "ligand-independent homophilic interactions" as used herein, refers to association between two AXL molecules (expressed on neighboring cells) that occurs in absence of the ligand.

The term "antibody binding AXL" as used herein, refers to any antibody binding an epitope on the extracellular part of AXL.

The term "epitope" means a protein determinant capable of specific binding to an antibody. Epitopes usually consist of surface groupings of molecules such as amino acids, sugar side chains or a combination thereof and usually have specific three dimensional structural characteristics, as well as specific charge characteristics. Conformational and non-conformational epitopes are distinguished in that the binding to the former but not the latter is lost in the presence of denaturing solvents. The epitope may comprise amino acid residues which are directly involved in the binding, and other amino acid residues, which are not directly involved in the binding, such as amino acid residues which are effectively blocked or covered by the specific antigen binding peptide (in other words, the amino acid residue is within the footprint of the specific antigen binding peptide).

The term "ligand" as used herein, refers to a substance, such as a hormone, peptide, ion, drug or protein, that binds specifically and reversibly to another protein, such as a receptor, to form a larger complex. Ligand binding to a receptor may alter its chemical conformation, and determines its functional state. For instance, a ligand may function as agonist or antagonist.

The term "Growth Arrest-Specific 6" or "Gas6" as used herein, refers to a 721 amino acid protein, with a molecular weight of 75-80 kDa, that functions as a ligand for the TAM family of receptors, including AXL. Gas6 is composed of an N-terminal region containing multiple gamma-carboxyglutamic acid residues (Gla), which are responsible for the specific interaction with the negatively charged phospholipid membrane. Although the Gla domain is not necessary for binding of Gas6 to AXL, it is required for activation of AXL. Gas6 may also be termed as the "ligand to AXL".

The terms "monoclonal antibody", "monoclonal Ab", "monoclonal antibody composition", "mAb", or the like, as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. The human monoclonal antibodies may be produced by a hybridoma which includes a B cell obtained from a transgenic or transchromosomal non-human animal, such as a transgenic mouse, having a genome comprising a human heavy chain transgene and a light chain transgene, fused to an immortalized cell.

In one embodiment, maximal antibody binding in the presence of Gas6 is at least 90%, such as at least 95%, such as at least 97%, such as at least 99%, such as 100%, of binding in absence of Gas6, as determined by the method disclosed in Example 2.

Competition between anti-AXL and the ligand Gas6 to AXL may be determined as described in Example 2 under the heading "Interference of anti-AXL binding with Gas6 binding". Thus, in one embodiment, the antibody does not compete for AXL binding with the ligand Gas6, wherein the competing for binding is determined in an assay comprising the steps of i) incubating AXL-expressing cells with Gas6,
ii) adding anti-AXL antibodies to be tested,
iii) adding a fluorescently labelled secondary reagent detecting anti-AXL antibodies and
iv) analyzing the cells by FACS.

In another embodiment, the antibody does not compete for binding with the ligand Gas6, wherein the competing for binding is determined in an assay comprising the steps of i) incubating AXL-expressing cells with anti-AXL antibodies,
ii) adding Gas6,
iii) adding a fluorescently labelled secondary reagent detecting Gas6, and
iv) analyzing the cells by FACS.

In one embodiment, the antibody has a binding affinity ($K_D$) in the range of $0.3 \times 10^{-9}$ to $63 \times 10^{-9}$ M to AXL, and wherein said binding affinity is measured using a Bio-layer Interferometry using soluble AXL extracellular domain.

The binding affinity may be determined as described in Example 2. Thus, in one embodiment, the antibody has a binding affinity of $0.3 \times 10^{-9}$ to $63 \times 10^{-9}$ M to the antigen, wherein the binding affinity is determined by a method comprising the steps of;

i) loading anti-human Fc Capture biosensors with anti-AXL antibodies, and
ii) determining association and dissociation of soluble recombinant AXL extracellular domain by Bio-Layer Interferometry at different concentrations.

The term "soluble recombinant AXL extracellular domain" as used herein, refers to an AXL extracellular domain that has been expressed recombinantly. Due to absence of the transmembrane and intracellular domain, recombinant AXL extracellular domain is not attached to a, e.g. cell surface and stays in solution. It is well-known how to express a protein recombinantly, see e.g. [25], and thus, it is within the knowledge of the skilled person to provide such recombinant AXL extracellular domain.

In one embodiment, the antibody has a dissociation rate of $6.9 \times 10^{-5}$ s$^{-1}$ to $9.7 \times 10^{-3}$ s$^{-1}$ to AXL, and wherein the dissociation rate is measured by Bio-layer Interferometry using soluble recombinant AXL extracellular domain.

The binding affinity may be determined as described above (and in Example 2). Thus, in one embodiment, the antibody has a dissociation rate of $6.9 \times 10^{-5}$ s$^{-1}$ to $9.7 \times 10^{-3}$ s$^{-1}$ to AXL, and wherein the dissociation rate is measured by a method comprising the steps of i) loading anti-human Fc Capture biosensors with anti-AXL antibodies, and
ii) determining association and dissociation of recombinant AXL extracellular domain by Bio-Layer Interferometry at different concentrations.

The term "dissociation rate" as used herein, refers to the rate at which an antigen-specific antibody bound to its antigen, dissociates from that antigen, and is expressed as s$^{-1}$. Thus, in the context of an antibody binding AXL, the term "dissociation rate", refers to the antibody binding AXL dissociates from the recombinant extracellular domain of AXL, and is expressed as s$^{-1}$.

In one embodiment, AXL is human AXL. The amino acid sequence of AXL is according to Swissprot P30530.

In one embodiment, AXL is cynomolgus monkey AXL (Genbank accession HB387229.1).

In one embodiment, the antibody comprises at least one binding region comprising variable heavy chain (VH) CDR1, CDR2, and CDR3 sequences having at least 95%, such as at least 96%, such as at least 97%, such as at least 98%, such as at least 99%, sequence identity to sequences are selected from the group consisting of:

a) SEQ ID Nos.: 36, 37, and 38, respectively [107];
b) SEQ ID Nos.: 93, 94, and 95, respectively [613];
c) SEQ ID Nos.: 93, 126, and 127, respectively [613/608-01/610-01/620-06];
d) SEQ ID Nos.: 46, 47, and 48, respectively [148];
e) SEQ ID Nos.: 57, 58, and 59, respectively [171];
f) SEQ ID Nos.: 78, 79, and 80, respectively [187];
g) SEQ ID Nos.: 46, 119, and 120, respectively [148/140];
h) SEQ ID Nos.: 51, 52, and 53, respectively [154];
i) SEQ ID Nos.: 72, 73, and 75, respectively [183];
j) SEQ ID Nos.: 72, 74, and 75, respectively [183-N52Q];
k) SEQ ID Nos.: 114, 115, and 116, respectively [733];
l) SEQ ID Nos.: 123, 124, and 125, respectively [171/172/181];
m) SEQ ID Nos.: 108, 109, and 110, respectively [726];
n) SEQ ID Nos.: 108, 121, and 122, respectively [726/187];
o) SEQ ID Nos.: 41, 42, and 43, respectively [140];
p) SEQ ID Nos.: 62, 63, and 64, respectively [172];
q) SEQ ID Nos.: 67, 68, and 69, respectively [181];
r) SEQ ID Nos.: 51, 52, and 54, respectively [154-M103L];
s) SEQ ID Nos.: 78, 79, and 80, respectively [187];
t) SEQ ID Nos.: 83, 84, and 85, respectively [608-01];
u) SEQ ID Nos.: 88, 89, and 90, respectively [610-01];
v) SEQ ID Nos.: 98, 99, and 100, respectively, [613-08];
w) SEQ ID Nos.: 103, 104, and 105, respectively [620-06]; and
x) SEQ ID Nos.: 108, 109, and 111, respectively [726-M101L].

In one embodiment, the antibody comprises at least one binding region comprising variable heavy chain (VH) CDR1, CDR2, and CDR3 sequences having at most 5 mutations or substitutions, such as at most 4 mutations or substitutions, such as at most 3 mutations or substitutions, such as at most 2 mutations or substitutions, such as at most 1 mutation or substitution, in total across the CDR sequences in said variable heavy chain selected from the group consisting of:

a) SEQ ID Nos.: 36, 37, and 38, respectively [107];
b) SEQ ID Nos.: 93, 94, and 95, respectively [613];
c) SEQ ID Nos.: 93, 126, and 127, respectively [613/608-01/610-01/620-06];
d) SEQ ID Nos.: 46, 47, and 48, respectively [148];
e) SEQ ID Nos.: 57, 58, and 59, respectively [171];
f) SEQ ID Nos.: 78, 79, and 80, respectively [187];
g) SEQ ID Nos.: 46, 119, and 120, respectively [148/140];
h) SEQ ID Nos.: 51, 52, and 53, respectively [154];
i) SEQ ID Nos.: 72, 73, and 75, respectively [183];
j) SEQ ID Nos.: 72, 74, and 75, respectively [183-N52Q];
k) SEQ ID Nos.: 114, 115, and 116, respectively [733];
l) SEQ ID Nos.: 123, 124, and 125, respectively [171/172/181];
m) SEQ ID Nos.: 108, 109, and 110, respectively [726];
n) SEQ ID Nos.: 108, 121, and 122, respectively [726/187];
o) SEQ ID Nos.: 41, 42, and 43, respectively [140];
p) SEQ ID Nos.: 62, 63, and 64, respectively [172];
q) SEQ ID Nos.: 67, 68, and 69, respectively [181];
r) SEQ ID Nos.: 51, 52, and 54, respectively [154-M103L];

s) SEQ ID Nos.:78, 79, and 80, respectively [187];

t) SEQ ID Nos.: 83, 84, and 85, respectively [608-01];

u) SEQ ID Nos.: 88, 89, and 90, respectively [610-01];

v) SEQ ID Nos.: 98, 99, and 100, respectively, [613-08];

w) SEQ ID Nos.: 103, 104, and 105, respectively [620-06]; and x) SEQ ID Nos.: 108, 109, and 111, respectively [726-M101L].

Hereby embodiments are provided wherein mutations or substitutions of up to five mutations or substitutions are allowed across the three CDR sequences in the variable heavy chain. The mutations or substitutions may be of conservative, physical or functional amino acids such that mutations or substitutions do not change the epitope or preferably do not modify binding affinity to the epitope more than 30%, such as more than 20% or such as more than 10%. The conservative, physical or functional amino acids are selected from the 20 natural amino acids i.e. Arg, His, Lys, Asp, Glu, Ser, Thr, Asn, Gln, Cys, Gly, Pro, Ala, Ile, Leu, Met, Phe, Trp, Tyr and Val.

In one embodiment, the antibody comprises at least one binding region comprising variable heavy chain (VH) CDR1, CDR2, and CDR3 sequences are selected from the group consisting of;

a) SEQ ID Nos.: 36, 37, and 38, respectively [107];

b) SEQ ID Nos.: 93, 94, and 95, respectively [613];

c) SEQ ID Nos.: 93, 126, and 127, respectively [613/608-01/610-01/620-06];

d) SEQ ID Nos.: 46, 47, and 48, respectively [148];

e) SEQ ID Nos.: 57, 58, and 59, respectively [171];

f) SEQ ID Nos.: 78, 79, and 80, respectively [187];

g) SEQ ID Nos.: 46, 119, and 120, respectively [148/140];

h) SEQ ID Nos.: 51, 52, and 53, respectively [154];

i) SEQ ID Nos.: 72, 73, and 75, respectively [183];

j) SEQ ID Nos.: 72, 74, and 75, respectively [183-N52Q];

k) SEQ ID Nos.: 114, 115, and 116, respectively [733];

l) SEQ ID Nos.: 123, 124, and 125, respectively [171/172/181];

m) SEQ ID Nos.: 108, 109, and 110, respectively [726];

n) SEQ ID Nos.: 108, 121, and 122, respectively [726/187];

o) SEQ ID Nos.: 41, 42, and 43, respectively [140];

p) SEQ ID Nos.: 62, 63, and 64, respectively [172];

q) SEQ ID Nos.: 67, 68, and 69, respectively [181];

r) SEQ ID Nos.: 51, 52, and 54, respectively [154-M103L];

s) SEQ ID Nos.:78, 79, and 80, respectively [187];

t) SEQ ID Nos.: 83, 84, and 85, respectively [608-01];

u) SEQ ID Nos.: 88, 89, and 90, respectively [610-01];

v) SEQ ID Nos.: 98, 99, and 100, respectively, [613-08];

w) SEQ ID Nos.: 103, 104, and 105, respectively [620-06]; and x) SEQ ID Nos.: 108, 109, and 111, respectively [726-M101L].

In one particular embodiment, the VH CDR1, CDR2, and CDR3 are selected from either a), d), g), or k).

In one embodiment, the at least one binding region comprises a VH region and a variable light chain (VL) region having at least 95%, such as at least 97%, such as at least 99%, such as 100%, sequence identity with the sequences independently selected from the group consisting of;

a) a VH region comprising the CDR1, CDR2, and CDR3 sequences of SEQ ID Nos.: 36, 37, and 38, respectively; and a VL region comprising the CDR1, CDR2, and CDR3 sequences of SEQ ID Nos.: 39, GAS, and 40, respectively, [107];

b) a VH region comprising the CDR1, CDR2, and CDR3 sequences of SEQ ID Nos.: 46, 47, and 48, respectively; and a VL region comprising the CDR1, CDR2, and CDR3 sequences of SEQ ID Nos.: 49, AAS, and 50, respectively, [148];

c) a VH region comprising the CDR1, CDR2, and CDR3 sequences of SEQ ID Nos.: 114, 115, and 116, respectively, and a VL region comprising the CDR1, CDR2, and CDR3 sequences of SEQ ID Nos.: 117, DAS, and 118, respectively [733];

d) a VH region comprising the CDR1, CDR2, and CDR3 sequences of SEQ ID Nos.: 51, 52, and 53, respectively; and a VL region comprising the CDR1, CDR2, and CDR3 sequences of SEQ ID Nos.: 55, GAS, and 56, respectively [154];

e) a VH region comprising the CDR1, CDR2, and CDR3 sequences of SEQ ID Nos.: 51, 52, and 54, respectively; and a VL region comprising the CDR1, CDR2, and CDR3 sequences of SEQ ID Nos.: 55, GAS, and 56, respectively [154-M103L];

f) a VH region comprising the CDR1, CDR2, and CDR3 sequences of SEQ ID Nos.: 57, 58, and 59, respectively; and a VL region comprising the CDR1, CDR2, and CDR3 sequences of SEQ ID Nos.: 60, GAS, and 61, respectively, [171];

g) a VH region comprising the CDR1, CDR2, and CDR3 sequences of SEQ ID Nos.: 62, 63, and 64, respectively; and a VL region comprising the CDR1, CDR2, and CDR3 sequences of SEQ ID Nos.: 65, GAS, and 66, respectively, [172];

h) a VH region comprising the CDR1, CDR2, and CDR3 sequences of SEQ ID Nos.: 67, 68, and 69, respectively; and a VL region comprising the CDR1, CDR2, and CDR3 sequences of SEQ ID Nos.: 70, GAS, and 71, respectively, [181];

i) a VH region comprising the CDR1, CDR2, and CDR3 sequences of SEQ ID Nos.: 72, 73, and 75, respectively; and a VL region comprising the CDR1, CDR2, and CDR3 sequences of SEQ ID Nos.: 76, ATS, and 77, respectively, [183];

j) a VH region comprising the CDR1, CDR2, and CDR3 sequences of SEQ ID Nos.: 72, 74, and 75, respectively; and a VL region comprising the CDR1, CDR2, and CDR3 sequences of SEQ ID Nos.: 76, ATS, and 77, respectively, [183-N52Q];

k) a VH region comprising the CDR1, CDR2, and CDR3 sequences of SEQ ID Nos.: 78, 79, and 80, respectively; and a VL region comprising the CDR1, CDR2, and CDR3 sequences of SEQ ID Nos.: 81, AAS, and 82, respectively, [187];

l) a VH region comprising the CDR1, CDR2, and CDR3 sequences of SEQ ID Nos.: 83, 84, and 85, respectively; and a VL region comprising the CDR1, CDR2, and CDR3 sequences of SEQ ID Nos.: 86, GAS, and 87, respectively, [608-01];

m) a VH region comprising the CDR1, CDR2, and CDR3 sequences of SEQ ID Nos.: 88, 89, and 90, respectively; and a VL region comprising the CDR1, CDR2, and CDR3 sequences of SEQ ID Nos.: 91, GAS, and 92, respectively, [610-01];

n) a VH region comprising the CDR1, CDR2, and CDR3 sequences of SEQ ID Nos.: 93, 94, and 95, respectively; and a VL region comprising the CDR1, CDR2, and CDR3 sequences of SEQ ID Nos.: 96, GAS, and 97, respectively, [613];

o) a VH region comprising the CDR1, CDR2, and CDR3 sequences of SEQ ID Nos.: 98, 99, and 100, respectively;

and a VL region comprising the CDR1, CDR2, and CDR3 sequences of SEQ ID Nos.: 10, DAS, and 102, respectively, [613-08];

p) a VH region comprising the CDR1, CDR2, and CDR3 sequences of SEQ ID Nos.: 103, 104, and 105, respectively; and a VL region comprising the CDR1, CDR2, and CDR3 sequences of SEQ ID Nos.: 106, GAS, and 107, respectively, [620-06];

q) a VH region comprising the CDR1, CDR2, and CDR3 sequences of SEQ ID Nos.: 108, 109, and 110, respectively; and a VL region comprising the CDR1, CDR2, and CDR3 sequences of SEQ ID Nos.: 112, AAS, and 113, respectively, [726];

r) a VH region comprising the CDR1, CDR2, and CDR3 sequences of SEQ ID Nos.: 108, 109, and 111, respectively; and a VL region comprising the CDR1, CDR2, and CDR3 sequences of SEQ ID Nos.: 112, AAS, and 113, respectively, [726-M101L];

s) a VH region comprising the CDR1, CDR2, and CDR3 sequences of SEQ ID Nos.: 41, 42, and 43, respectively; and a VL region comprising the CDR1, CDR2, and CDR3 sequences of SEQ ID Nos.: 44, AAS, and 45, respectively, [140];

t) a VH region comprising the CDR1, CDR2, and CDR3 sequences of SEQ ID Nos.: 93, 94, and 95, respectively, and a VL region comprising the CDR1, CDR2, and CDR3 sequences of SEQ ID Nos.: 128, XAS, wherein X is D or G, and 129, respectively, [613/613-08];

u) a VH region comprising the CDR1, CDR2, and CDR3 sequences of SEQ ID Nos.: 46, 119, and 120, respectively; and a VL region comprising CDR1, CDR2, and CDR3 sequences of SEQ ID Nos.: 49, AAS, and 50, respectively, [148/140];

v) a VH region comprising the CDR1, CDR2, and CDR3 sequences of SEQ ID Nos.: 123, 124, and 125, respectively; and a VL region comprising CDR1, CDR2, and CDR3 sequences of SEQ ID Nos.: 60, GAS, and 61, respectively [171/172/181]; and w) a VH region comprising the CDR1, CDR2, and CDR3 sequences of SEQ ID Nos.: 121, 109, and 122, respectively; and a VL region comprising the CDR1, CDR2, and CDR3 sequences of SEQ ID Nos.: 112, AAS, and 113, respectively [726/187]; and x) a VH region comprising the CDR1, CDR2, and CDR3 sequences of SEQ ID Nos.:93, 126, and 127, respectively; and a VL region comprising the CDR1, CDR2, and CDR3 sequences of SEQ ID Nos.: 96, GAS, and 97, respectively [613/608-01/610-01/620-06].

In one embodiment, the at least one binding region comprises a VH region and a variable light chain (VL) region having, at most 5 mutations or substitutions selected from conservative, physical or functional amino acids, such as at most 4 mutations or substitutions selected from conservative, physical or functional amino acids, such as at most 3 mutations or substitutions selected from conservative, physical or functional amino acids, such as at most 2 mutations selected from conservative, physical or functional amino acids or substitutions, such as at most 1 mutation or substitution selected from a conservative, physical or functional amino acid, in total across the CDR sequences in said variable heavy chain and variable light chain selected from the group consisting of:

a) a VH region comprising the CDR1, CDR2, and CDR3 sequences of SEQ ID Nos.: 36, 37, and 38, respectively; and a VL region comprising the CDR1, CDR2, and CDR3 sequences of SEQ ID Nos.: 39, GAS, and 40, respectively, [107];

b) a VH region comprising the CDR1, CDR2, and CDR3 sequences of SEQ ID Nos.: 46, 47, and 48, respectively; and a VL region comprising the CDR1, CDR2, and CDR3 sequences of SEQ ID Nos.: 49, AAS, and 50, respectively, [148];

c) a VH region comprising the CDR1, CDR2, and CDR3 sequences of SEQ ID Nos.: 114, 115, and 116, respectively, and a VL region comprising the CDR1, CDR2, and CDR3 sequences of SEQ ID Nos.: 117, DAS, and 118, respectively [733];

d) a VH region comprising the CDR1, CDR2, and CDR3 sequences of SEQ ID Nos.: 51, 52, and 53, respectively; and a VL region comprising the CDR1, CDR2, and CDR3 sequences of SEQ ID Nos.: 55, GAS, and 56, respectively [154];

e) a VH region comprising the CDR1, CDR2, and CDR3 sequences of SEQ ID Nos.: 51, 52, and 54, respectively; and a VL region comprising the CDR1, CDR2, and CDR3 sequences of SEQ ID Nos.: 55, GAS, and 56, respectively [154-M1031];

f) a VH region comprising the CDR1, CDR2, and CDR3 sequences of SEQ ID Nos.: 57, 58, and 59, respectively; and a VL region comprising the CDR1, CDR2, and CDR3 sequences of SEQ ID Nos.: 60, GAS, and 61, respectively, [171];

g) a VH region comprising the CDR1, CDR2, and CDR3 sequences of SEQ ID Nos.: 62, 63, and 64, respectively; and a VL region comprising the CDR1, CDR2, and CDR3 sequences of SEQ ID Nos.: 65, GAS, and 66, respectively, [172];

h) a VH region comprising the CDR1, CDR2, and CDR3 sequences of SEQ ID Nos.: 67, 68, and 69, respectively; and a VL region comprising the CDR1, CDR2, and CDR3 sequences of SEQ ID Nos.: 70, GAS, and 71, respectively, [181];

i) a VH region comprising the CDR1, CDR2, and CDR3 sequences of SEQ ID Nos.: 72, 73, and 75, respectively; and a VL region comprising the CDR1, CDR2, and CDR3 sequences of SEQ ID Nos.: 76, ATS, and 77, respectively, [183];

j) a VH region comprising the CDR1, CDR2, and CDR3 sequences of SEQ ID Nos.: 72, 74, and 75, respectively; and a VL region comprising the CDR1, CDR2, and CDR3 sequences of SEQ ID Nos.: 76, ATS, and 77, respectively, [183-N52Q];

k) a VH region comprising the CDR1, CDR2, and CDR3 sequences of SEQ ID Nos.: 78, 79, and 80, respectively; and a VL region comprising the CDR1, CDR2, and CDR3 sequences of SEQ ID Nos.: 81, AAS, and 82, respectively, [187];

l) a VH region comprising the CDR1, CDR2, and CDR3 sequences of SEQ ID Nos.: 83, 84, and 85, respectively; and a VL region comprising the CDR1, CDR2, and CDR3 sequences of SEQ ID Nos.: 86, GAS, and 87, respectively, [608-01];

m) a VH region comprising the CDR1, CDR2, and CDR3 sequences of SEQ ID Nos.: 88, 89, and 90, respectively; and a VL region comprising the CDR1, CDR2, and CDR3 sequences of SEQ ID Nos.: 91, GAS, and 92, respectively, [610-01];

n) a VH region comprising the CDR1, CDR2, and CDR3 sequences of SEQ ID Nos.: 93, 94, and 95, respectively; and a VL region comprising the CDR1, CDR2, and CDR3 sequences of SEQ ID Nos.: 96, GAS, and 97, respectively, [613];

o) a VH region comprising the CDR1, CDR2, and CDR3 sequences of SEQ ID Nos.: 98, 99, and 100, respectively;

and a VL region comprising the CDR1, CDR2, and CDR3 sequences of SEQ ID Nos.: 10, DAS, and 102, respectively, [613-08];

p) a VH region comprising the CDR1, CDR2, and CDR3 sequences of SEQ ID Nos.: 103, 104, and 105, respectively; and a VL region comprising the CDR1, CDR2, and CDR3 sequences of SEQ ID Nos.: 106, GAS, and 107, respectively, [620-06];

q) a VH region comprising the CDR1, CDR2, and CDR3 sequences of SEQ ID Nos.: 108, 109, and 110, respectively; and a VL region comprising the CDR1, CDR2, and CDR3 sequences of SEQ ID Nos.: 112, AAS, and 113, respectively, [726];

r) a VH region comprising the CDR1, CDR2, and CDR3 sequences of SEQ ID Nos.: 108, 109, and 111, respectively; and a VL region comprising the CDR1, CDR2, and CDR3 sequences of SEQ ID Nos.: 112, AAS, and 113, respectively, [726-M101L];

s) a VH region comprising the CDR1, CDR2, and CDR3 sequences of SEQ ID Nos.: 41, 42, and 43, respectively; and a VL region comprising the CDR1, CDR2, and CDR3 sequences of SEQ ID Nos.: 44, AAS, and 45, respectively, [140];

t) a VH region comprising the CDR1, CDR2, and CDR3 sequences of SEQ ID Nos.: 93, 94, and 95, respectively, and a VL region comprising the CDR1, CDR2, and CDR3 sequences of SEQ ID Nos.: 128, XAS, wherein X is D or G, and 129, respectively, [613/613-08];

u) a VH region comprising the CDR1, CDR2, and CDR3 sequences of SEQ ID Nos.: 46, 119, and 120, respectively; and a VL region comprising CDR1, CDR2, and CDR3 sequences of SEQ ID Nos.: 49, AAS, and 50, respectively, [148/140];

v) a VH region comprising the CDR1, CDR2, and CDR3 sequences of SEQ ID Nos.: 123, 124, and 125, respectively; and a VL region comprising CDR1, CDR2, and CDR3 sequences of SEQ ID Nos.: 60, GAS, and 61, respectively [171/172/181]; and w) a VH region comprising the CDR1, CDR2, and CDR3 sequences of SEQ ID Nos.: 121, 109, and 122, respectively; and a VL region comprising the CDR1, CDR2, and CDR3 sequences of SEQ ID Nos.: 112, AAS, and 113, respectively [726/187]; and x) a VH region comprising the CDR1, CDR2, and CDR3 sequences of SEQ ID Nos.:93, 126, and 127, respectively; and a VL region comprising the CDR1, CDR2, and CDR3 sequences of SEQ ID Nos.: 96, GAS, and 97, respectively [613/608-01/610-01/620-06].

Hereby embodiments are provided wherein mutations or substitutions of up to five mutations or substitutions are allowed across the three CDR sequences in the variable heavy chain and variable light chain. The up to five mutations or substitutions may be distributed across the three CDR sequences of the variable heavy chain and the three CDR sequences of the variable light chain. The up to five mutations or substitutions may be distributed across the six CDR sequences of the binding region. The mutations or substitutions may be of conservative, physical or functional amino acids such that mutations or substitutions do not change the epitope or preferably do not modify binding affinity to the epitope more than 30%, such as more than 20% or such as more than 10%. The conservative, physical or functional amino acids are selected from the 20 natural amino acids found i.e, Arg, His, Lys, Asp, Glu, Ser, Thr, Asn, Gln, Cys, Gly, Pro, Ala, Ile, Leu, Met, Phe, Trp, Tyr and Val.

In a particular embodiment, the at least one binding region comprises a VH region and a variable light chain (VL) region selected from the group consisting of;

a) a VH region comprising the CDR1, CDR2, and CDR3 sequences of SEQ ID Nos.: 36, 37, and 38, respectively; and a VL region comprising the CDR1, CDR2, and CDR3 sequences of SEQ ID Nos.: 39, GAS, and 40, respectively, [107];

b) a VH region comprising the CDR1, CDR2, and CDR3 sequences of SEQ ID Nos.: 46, 47, and 48, respectively; and a VL region comprising the CDR1, CDR2, and CDR3 sequences of SEQ ID Nos.: 49, AAS, and 50, respectively, [148];

c) a VH region comprising the CDR1, CDR2, and CDR3 sequences of SEQ ID Nos.: 114, 115, and 116, respectively, and a VL region comprising the CDR1, CDR2, and CDR3 sequences of SEQ ID Nos.: 117, DAS, and 118, respectively [733];

d) a VH region comprising the CDR1, CDR2, and CDR3 sequences of SEQ ID Nos.: 51, 52, and 53, respectively; and a VL region comprising the CDR1, CDR2, and CDR3 sequences of SEQ ID Nos.: 55, GAS, and 56, respectively [154];

e) a VH region comprising the CDR1, CDR2, and CDR3 sequences of SEQ ID Nos.: 51, 52, and 54, respectively; and a VL region comprising the CDR1, CDR2, and CDR3 sequences of SEQ ID Nos.: 55, GAS, and 56, respectively [154-M103L];

f) a VH region comprising the CDR1, CDR2, and CDR3 sequences of SEQ ID Nos.: 57, 58, and 59, respectively; and a VL region comprising the CDR1, CDR2, and CDR3 sequences of SEQ ID Nos.: 60, GAS, and 61, respectively, [171];

g) a VH region comprising the CDR1, CDR2, and CDR3 sequences of SEQ ID Nos.: 62, 63, and 64, respectively; and a VL region comprising the CDR1, CDR2, and CDR3 sequences of SEQ ID Nos.: 65, GAS, and 66, respectively, [172];

h) a VH region comprising the CDR1, CDR2, and CDR3 sequences of SEQ ID Nos.: 67, 68, and 69, respectively; and a VL region comprising the CDR1, CDR2, and CDR3 sequences of SEQ ID Nos.: 70, GAS, and 71, respectively, [181];

i) a VH region comprising the CDR1, CDR2, and CDR3 sequences of SEQ ID Nos.: 72, 73, and 75, respectively; and a VL region comprising the CDR1, CDR2, and CDR3 sequences of SEQ ID Nos.: 76, ATS, and 77, respectively, [183];

j) a VH region comprising the CDR1, CDR2, and CDR3 sequences of SEQ ID Nos.: 72, 74, and 75, respectively; and a VL region comprising the CDR1, CDR2, and CDR3 sequences of SEQ ID Nos.: 76, ATS, and 77, respectively, [183-N52Q];

k) a VH region comprising the CDR1, CDR2, and CDR3 sequences of SEQ ID Nos.: 78, 79, and 80, respectively; and a VL region comprising the CDR1, CDR2, and CDR3 sequences of SEQ ID Nos.: 81, AAS, and 82, respectively, [187];

l) a VH region comprising the CDR1, CDR2, and CDR3 sequences of SEQ ID Nos.: 83, 84, and 85, respectively; and a VL region comprising the CDR1, CDR2, and CDR3 sequences of SEQ ID Nos.: 86, GAS, and 87, respectively, [608-01];

m) a VH region comprising the CDR1, CDR2, and CDR3 sequences of SEQ ID Nos.: 88, 89, and 90, respectively; and a VL region comprising the CDR1, CDR2, and CDR3 sequences of SEQ ID Nos.: 91, GAS, and 92, respectively, [610-01];

n) a VH region comprising the CDR1, CDR2, and CDR3 sequences of SEQ ID Nos.: 93, 94, and 95, respectively; and a VL region comprising the CDR1, CDR2, and CDR3 sequences of SEQ ID Nos.: 96, GAS, and 97, respectively, [613];

o) a VH region comprising the CDR1, CDR2, and CDR3 sequences of SEQ ID Nos.: 98, 99, and 100, respectively; and a VL region comprising the CDR1, CDR2, and CDR3 sequences of SEQ ID Nos.: 10, DAS, and 102, respectively, [613-08];

p) a VH region comprising the CDR1, CDR2, and CDR3 sequences of SEQ ID Nos.: 103, 104, and 105, respectively; and a VL region comprising the CDR1, CDR2, and CDR3 sequences of SEQ ID Nos.: 106, GAS, and 107, respectively, [620-06];

q) a VH region comprising the CDR1, CDR2, and CDR3 sequences of SEQ ID Nos.: 108, 109, and 110, respectively; and a VL region comprising the CDR1, CDR2, and CDR3 sequences of SEQ ID Nos.: 112, AAS, and 113, respectively, [726];

r) a VH region comprising the CDR1, CDR2, and CDR3 sequences of SEQ ID Nos.: 108, 109, and 111, respectively; and a VL region comprising the CDR1, CDR2, and CDR3 sequences of SEQ ID Nos.: 112, AAS, and 113, respectively, [726-M101L];

s) a VH region comprising the CDR1, CDR2, and CDR3 sequences of SEQ ID Nos.: 41, 42, and 43, respectively; and a VL region comprising the CDR1, CDR2, and CDR3 sequences of SEQ ID Nos.: 44, AAS, and 45, respectively, [140];

t) a VH region comprising the CDR1, CDR2, and CDR3 sequences of SEQ ID Nos.: 93, 94, and 95, respectively, and a VL region comprising the CDR1, CDR2, and CDR3 sequences of SEQ ID Nos.: 128, XAS, wherein X is D or G, and 129, respectively, [613/613-08];

u) a VH region comprising the CDR1, CDR2, and CDR3 sequences of SEQ ID Nos.: 46, 119, and 120, respectively; and a VL region comprising CDR1, CDR2, and CDR3 sequences of SEQ ID Nos.: 49, AAS, and 50, respectively, [148/140];

v) a VH region comprising the CDR1, CDR2, and CDR3 sequences of SEQ ID Nos.: 123, 124, and 125, respectively; and a VL region comprising CDR1, CDR2, and CDR3 sequences of SEQ ID Nos.: 60, GAS, and 61, respectively [171/172/181]; and w) a VH region comprising the CDR1, CDR2, and CDR3 sequences of SEQ ID Nos.: 121, 109, and 122, respectively; and a VL region comprising the CDR1, CDR2, and CDR3 sequences of SEQ ID Nos.: 112, AAS, and 113, respectively [726/187]; and x) a VH region comprising the CDR1, CDR2, and CDR3 sequences of SEQ ID Nos.:93, 126, and 127, respectively; and a VL region comprising the CDR1, CDR2, and CDR3 sequences of SEQ ID Nos.: 96, GAS, and 97, respectively [613/608-01/610-01/620-06].

In one embodiment, the at least one binding region comprises a VH region and a VL region selected from the group consisting of;

a) a VH region comprising SEQ ID No: 1 and a VL region comprising SEQ ID No: 2 [107];

b) a VH region comprising SEQ ID No: 5 and a VL region comprising SEQ ID No: 6 [148];

c) a VH region comprising SEQ ID No: 34 and a VL region comprising SEQ ID No: 35 [733]

d) a VH region comprising SEQ ID No: 7 and a VL region comprising SEQ ID No: 9 [154];

e) a VH region comprising SEQ ID No: 10 and a VL region comprising SEQ ID No: 11 [171];

f) a VH region comprising SEQ ID No: 16 and a VL region comprising SEQ ID No: 18 [183];

g) a VH region comprising SEQ ID No: 25 and a VL region comprising SEQ ID No: 26 [613];

h) a VH region comprising SEQ ID No: 31 and a VL region comprising SEQ ID No: 33 [726];

i) a VH region comprising SEQ ID No: 3 and a VL region comprising SEQ ID No: 4 [140];

j) a VH region comprising SEQ ID No:8 and a VL region comprising SEQ ID No:9 [154-M103L];

k) a VH region comprising SEQ ID No:12 and a VL region comprising SEQ ID No:13 [172];

l) a VH region comprising SEQ ID No:14 and a VL region comprising SEQ ID No:15 [181];

m) a VH region comprising SEQ ID No:17 and a VL region comprising SEQ ID No:18 [183-N52Q];

n) a VH region comprising SEQ ID No:19 and a VL region comprising SEQ ID No:20 [187];

o) a VH region comprising SEQ ID No:21 and a VL region comprising SEQ ID No:22 [608-01];

p) a VH region comprising SEQ ID No:23 and a VL region comprising SEQ ID No:24 [610-01];

q) a VH region comprising SEQ ID No:27 and a VL region comprising SEQ ID No:28 [613-08];

r) a VH region comprising SEQ ID No:29 and a VL region comprising SEQ ID No:30 [620-06]; and s) a VH region comprising SEQ ID No:32 and a VL region comprising SEQ ID No:33 [726-M101L].

In one embodiment, the at least one binding region comprises a variable heavy chain (VH) region and a variable light chain (VL) region having at most 10 mutations or substitutions, at most 5 mutations or substitutions, such as at most 4 mutations or substitutions, such as at most 3 mutations or substitutions, such as at most 2 mutations or substitutions, such as at most 1 mutation or substitution, across said variable heavy chain and variable light chain sequences selected from the group consisting of;

In one embodiment, the at least one binding region comprises a VH region and a VL region selected from the group consisting of;

a) a VH region comprising SEQ ID No: 1 and a VL region comprising SEQ ID No: 2 [107];

b) a VH region comprising SEQ ID No: 5 and a VL region comprising SEQ ID No: 6 [148];

c) a VH region comprising SEQ ID No: 34 and a VL region comprising SEQ ID No: 35 [733]

d) a VH region comprising SEQ ID No: 7 and a VL region comprising SEQ ID No: 9 [154];

e) a VH region comprising SEQ ID No: 10 and a VL region comprising SEQ ID No: 11 [171];

f) a VH region comprising SEQ ID No: 16 and a VL region comprising SEQ ID No: 18 [183];

g) a VH region comprising SEQ ID No: 25 and a VL region comprising SEQ ID No: 26 [613];

h) a VH region comprising SEQ ID No: 31 and a VL region comprising SEQ ID No: 33 [726];

i) a VH region comprising SEQ ID No: 3 and a VL region comprising SEQ ID No: 4 [140];

j) a VH region comprising SEQ ID No:8 and a VL region comprising SEQ ID No:9 [154-M1031];

k) a VH region comprising SEQ ID No:12 and a VL region comprising SEQ ID No:13 [172];

l) a VH region comprising SEQ ID No:14 and a VL region comprising SEQ ID No:15 [181];

m) a VH region comprising SEQ ID No:17 and a VL region comprising SEQ ID No:18 [183-N52Q];

n) a VH region comprising SEQ ID No:19 and a VL region comprising SEQ ID No:20 [187];

o) a VH region comprising SEQ ID No:21 and a VL region comprising SEQ ID No:22 [608-01];

p) a VH region comprising SEQ ID No:23 and a VL region comprising SEQ ID No:24 [610-01];

q) a VH region comprising SEQ ID No:27 and a VL region comprising SEQ ID No:28 [613-08];

r) a VH region comprising SEQ ID No:29 and a VL region comprising SEQ ID No:30 [620-06]; and s) a VH region comprising SEQ ID No:32 and a VL region comprising SEQ ID No:33 [726-M101L].

Hereby embodiments are provided wherein mutations or substitutions of up to 10 mutations or substitutions are allowed across the variable heavy chain and variable light chain. The up to 10 mutations or substitutions may be distributed across the full length of the variable heavy chain and the variable light chain of each binding region. The mutations or substitutions may be of conservative, physical or functional amino acids such that the mutations or substitutions do not change the epitope and preferably do not modify binding affinity to the epitope more than 30%, such as more than 20% or such as more than 10%. The conservative, physical or functional amino acids are selected from the 20 natural amino acids found i.e. Arg, His, Lys, Asp, Glu, Ser, Thr, Asn, Gln, Cys, Gly, Pro, Ala, Ile, Leu, Met, Phe, Trp, Tyr and Val.

In one embodiment, the at least one binding region comprises a variable heavy chain (VH) region and a variable light chain (VL) region having at most 10 mutations or substitutions selected from conservative, physical or functional amino acids, at most 5 mutations or substitutions selected from conservative, physical or functional amino acids, such as at most 4 mutations or substitutions selected from conservative, physical or functional amino acids, such as at most 3 mutations or substitutions selected from conservative, physical or functional amino acids, such as at most 2 mutations selected from conservative, physical or functional amino acids or substitutions, such as at most 1 mutation or substitution selected from a conservative, physical or functional amino acid, across said variable heavy chain and variable light chain sequences selected from the group consisting of;

In one embodiment, the at least one binding region comprises a VH region and a VL region selected from the group consisting of;

a) a VH region comprising SEQ ID No: 1 and a VL region comprising SEQ ID No: 2 [107];

b) a VH region comprising SEQ ID No: 5 and a VL region comprising SEQ ID No: 6 [148];

c) a VH region comprising SEQ ID No: 34 and a VL region comprising SEQ ID No: 35 [733]

d) a VH region comprising SEQ ID No: 7 and a VL region comprising SEQ ID No: 9 [154];

e) a VH region comprising SEQ ID No: 10 and a VL region comprising SEQ ID No: 11 [171];

f) a VH region comprising SEQ ID No: 16 and a VL region comprising SEQ ID No: 18 [183];

g) a VH region comprising SEQ ID No: 25 and a VL region comprising SEQ ID No: 26 [613];

h) a VH region comprising SEQ ID No: 31 and a VL region comprising SEQ ID No: 33 [726];

i) a VH region comprising SEQ ID No: 3 and a VL region comprising SEQ ID No: 4 [140];

j) a VH region comprising SEQ ID No:8 and a VL region comprising SEQ ID No:9 [154-M103L];

k) a VH region comprising SEQ ID No:12 and a VL region comprising SEQ ID No:13 [172];

l) a VH region comprising SEQ ID No:14 and a VL region comprising SEQ ID No:15 [181];

m) a VH region comprising SEQ ID No:17 and a VL region comprising SEQ ID No:18 [183-N52Q];

n) a VH region comprising SEQ ID No:19 and a VL region comprising SEQ ID No:20 [187];

o) a VH region comprising SEQ ID No:21 and a VL region comprising SEQ ID No:22 [608-01];

p) a VH region comprising SEQ ID No:23 and a VL region comprising SEQ ID No:24 [610-01];

q) a VH region comprising SEQ ID No:27 and a VL region comprising SEQ ID No:28 [613-08];

r) a VH region comprising SEQ ID No:29 and a VL region comprising SEQ ID No:30 [620-06]; and s) a VH region comprising SEQ ID No:32 and a VL region comprising SEQ ID No:33 [726-M101L].

Hereby embodiments are provided wherein mutations or substitutions of up to 10 mutations or substitutions are allowed across the variable heavy chain and variable light chain. The up to 10 mutations or substitutions may be distributed across the variable heavy chain and the variable light chain. The up to 10 mutations or substitutions may be distributed across the binding region. The mutations or substitutions may be of conservative, physical or functional amino acids such that mutations or substitutions do not change the epitope or modify binding to the epitope.

In one aspect, the present invention relates to antibodies witch binds to an extracellular domain of AXL without competing or interfering with Gas6 binding to AXL. In a particular embodiment, the antibody binds to the extracellular domain Ig1-like domain without competing or interfering with Gas6 binding to AXL. In one embodiment, the antibody binds to the extracellular domain Ig1-like and show no more than a 20% reduction in maximal Gas6 binding to AXL. In one embodiment, the antibody show no more than a 15% reduction in maximal Gas6 binding to AXL. In one embodiment, the antibody show no more than a 10% reduction in maximal Gas6 binding to AXL. In one embodiment, the antibody show no more than a 5% reduction in maximal Gas6 binding to AXL. In one embodiment, the antibody show no more than a 4% reduction in maximal Gas6 binding to AXL In one embodiment, the antibody show no more than a 2% reduction in maximal Gas6 binding to AXL. In one embodiment, the antibody show no more than a 1% reduction in maximal Gas6 binding. In one embodiment the antibody binds to the extracellular domain Ig2-like domain without competing or interfering with Gas6 binding to AXL. In one embodiment, the antibody binds to the extracellular domain Ig2-like and show no more than a 20%, such as no more than 15%, such as no more than 10%, such as no more than 5%, such as no more than 4%, such as no more than 2%, such as no more than 1%, reduction in maximal Gas6 binding to AXL. The embodiment's ability to compete with or reduce Gas6 binding may be determined as disclosed in Example 2 or Example 12. In one embodiment the antibody binds to the extracellular domain Ig2-like domain without competing or interfering with maximal Gas6 binding to AXL.

In one embodiment, the antibody binds to an epitope on AXL which epitope is recognized by an antibody herein described.

Methods of determining an epitope to which an antibody binds is well-known in the art, and thus, the skilled person would know how to determine such an epitope. However, an example of determining whether an antibody binds within any epitope herein defined would be by point mutations of the AXL extracellular domain. It is within the knowledge of the skilled person to introduce point mutation(s) in the AXL extracellular domain and test for antibody binding to point mutated AXL extracellular domains. When referring to amino acid positions within the AXL protein in the context of epitopes, the numbering has been determined as described in Example 7. Thus, numbering of amino acid positions defining the epitope was done based on the sequences put forth in FIG. 6, i.e. the first amino acid in the shown sequence was numbered as position '1', the second as position '2', etc.

In one embodiment, the antibody binds to an epitope within the Ig1-like domain of AXL, the epitope comprises or requires the amino acids corresponding to positions L121 to Q129 or T112 to Q124 of human AXL. In one embodiment, the antibody binds to an epitope within the Ig1-like domain of AXL, the epitope comprises or requires one or more amino acids corresponding to positions L121 to Q129 or T112 to Q124 of human AXL. In one embodiment the epitope comprises one or more amino acid in position L121, G122, H123, Q124, T125, F126, V127, 5128, Q129 or more amino acid in position T112, G113, Q114, Y115, Q116, C117, L118, V119, F120, L121, G122, H123, Q124.

In another embodiment, the antibody binds to an epitope within the Ig2-like domain of AXL which epitope comprises or requires the amino acids corresponding to position D170 or the combination of D179 and T182 to R190 of human AXL.

In one embodiment, the antibody binds to an epitope within the Ig2-like domain of AXL which epitope comprises or requires the amino acids corresponding to position D170 or the combination of D179 and one or more amino acids corresponding to positions T182 to R190 of human AXL. In one embodiment the epitope comprises one or more amino acid in position T182, A183, P183, G184, H185, G186, P187, Q189, R190.

In another embodiment, the antibody binds to an epitope within the FN1-like domain of human AXL which epitope comprises or requires the amino acids corresponding to positions Q272 to A287 and G297 to P301 of human AXL.

In another embodiment, the antibody binds to an epitope within the FN2-like domain of human AXL which epitope comprises or requires the amino acids corresponding to positions A359, R386, and Q436 to K439 of human AXL.

In one embodiment, the antibody binds to an epitope within the FN1-like domain of human AXL.

In one embodiment, the antibody binds to an epitope on AXL which epitope is recognized by any one of the antibodies defined by a)) a VH region comprising the CDR1, CDR2, and CDR3 sequences of SEQ ID Nos.: 36, 37, and 38, respectively; and a VL region comprising the CDR1, CDR2, and CDR3 sequences of SEQ ID Nos.: 39, GAS, and 40, respectively, [107];

b) a VH region comprising the CDR1, CDR2, and CDR3 sequences of SEQ ID Nos.: 46, 47, and 48, respectively; and a VL region comprising the CDR1, CDR2, and CDR3 sequences of SEQ ID Nos.: 49, AAS, and 50, respectively, [148];

c) a VH region comprising the CDR1, CDR2, and CDR3 sequences of SEQ ID Nos.: 114, 115, and 116, respectively, and a VL region comprising the CDR1, CDR2, and CDR3 sequences of SEQ ID Nos.: 117, DAS, and 118, respectively [733];

d) a VH region comprising the CDR1, CDR2, and CDR3 sequences of SEQ ID Nos.: 51, 52, and 53, respectively; and a VL region comprising the CDR1, CDR2, and CDR3 sequences of SEQ ID Nos.: 55, GAS, and 56, respectively [154];

e) a VH region comprising the CDR1, CDR2, and CDR3 sequences of SEQ ID Nos.: 51, 52, and 54, respectively; and a VL region comprising the CDR1, CDR2, and CDR3 sequences of SEQ ID Nos.: 55, GAS, and 56, respectively [154-M103L];

f) a VH region comprising the CDR1, CDR2, and CDR3 sequences of SEQ ID Nos.: 57, 58, and 59, respectively; and a VL region comprising the CDR1, CDR2, and CDR3 sequences of SEQ ID Nos.: 60, GAS, and 61, respectively, [171];

g) a VH region comprising the CDR1, CDR2, and CDR3 sequences of SEQ ID Nos.: 62, 63, and 64, respectively; and a VL region comprising the CDR1, CDR2, and CDR3 sequences of SEQ ID Nos.: 65, GAS, and 66, respectively, [172];

h) a VH region comprising the CDR1, CDR2, and CDR3 sequences of SEQ ID Nos.: 67, 68, and 69, respectively; and a VL region comprising the CDR1, CDR2, and CDR3 sequences of SEQ ID Nos.: 70, GAS, and 71, respectively, [181];

i) a VH region comprising the CDR1, CDR2, and CDR3 sequences of SEQ ID Nos.: 72, 73, and 75, respectively; and a VL region comprising the CDR1, CDR2, and CDR3 sequences of SEQ ID Nos.: 76, ATS, and 77, respectively, [183];

j) a VH region comprising the CDR1, CDR2, and CDR3 sequences of SEQ ID Nos.: 72, 74, and 75, respectively; and a VL region comprising the CDR1, CDR2, and CDR3 sequences of SEQ ID Nos.: 76, ATS, and 77, respectively, [183-N52Q];

k) a VH region comprising the CDR1, CDR2, and CDR3 sequences of SEQ ID Nos.: 78, 79, and 80, respectively; and a VL region comprising the CDR1, CDR2, and CDR3 sequences of SEQ ID Nos.: 81, AAS, and 82, respectively, [187];

l) a VH region comprising the CDR1, CDR2, and CDR3 sequences of SEQ ID Nos.: 83, 84, and 85, respectively; and a VL region comprising the CDR1, CDR2, and CDR3 sequences of SEQ ID Nos.: 86, GAS, and 87, respectively, [608-01];

m) a VH region comprising the CDR1, CDR2, and CDR3 sequences of SEQ ID Nos.: 88, 89, and 90, respectively; and a VL region comprising the CDR1, CDR2, and CDR3 sequences of SEQ ID Nos.: 91, GAS, and 92, respectively, [610-01];

n) a VH region comprising the CDR1, CDR2, and CDR3 sequences of SEQ ID Nos.: 93, 94, and 95, respectively; and a VL region comprising the CDR1, CDR2, and CDR3 sequences of SEQ ID Nos.: 96, GAS, and 97, respectively, [613];

o) a VH region comprising the CDR1, CDR2, and CDR3 sequences of SEQ ID Nos.: 98, 99, and 100, respectively; and a VL region comprising the CDR1, CDR2, and CDR3 sequences of SEQ ID Nos.: 10, DAS, and 102, respectively, [613-08];

p) a VH region comprising the CDR1, CDR2, and CDR3 sequences of SEQ ID Nos.: 103, 104, and 105, respectively;

and a VL region comprising the CDR1, CDR2, and CDR3 sequences of SEQ ID Nos.: 106, GAS, and 107, respectively, [620-06];

q) a VH region comprising the CDR1, CDR2, and CDR3 sequences of SEQ ID Nos.: 108, 109, and 110, respectively; and a VL region comprising the CDR1, CDR2, and CDR3 sequences of SEQ ID Nos.: 112, AAS, and 113, respectively, [726];

r) a VH region comprising the CDR1, CDR2, and CDR3 sequences of SEQ ID Nos.: 108, 109, and 111, respectively; and a VL region comprising the CDR1, CDR2, and CDR3 sequences of SEQ ID Nos.: 112, AAS, and 113, respectively, [726-M101L];

s) a VH region comprising the CDR1, CDR2, and CDR3 sequences of SEQ ID Nos.: 41, 42, and 43, respectively; and a VL region comprising the CDR1, CDR2, and CDR3 sequences of SEQ ID Nos.: 44, AAS, and 45, respectively, [140];

t) a VH region comprising the CDR1, CDR2, and CDR3 sequences of SEQ ID Nos.: 93, 94, and 95, respectively, and a VL region comprising the CDR1, CDR2, and CDR3 sequences of SEQ ID Nos.: 128, XAS, wherein X is D or G, and 129, respectively, [613/613-08];

u) a VH region comprising the CDR1, CDR2, and CDR3 sequences of SEQ ID Nos.: 46, 119, and 120, respectively; and a VL region comprising CDR1, CDR2, and CDR3 sequences of SEQ ID Nos.: 49, AAS, and 50, respectively, [148/140];

v) a VH region comprising the CDR1, CDR2, and CDR3 sequences of SEQ ID Nos.: 123, 124, and 125, respectively; and a VL region comprising CDR1, CDR2, and CDR3 sequences of SEQ ID Nos.: 60, GAS, and 61, respectively [171/172/181]; and w) a VH region comprising the CDR1, CDR2, and CDR3 sequences of SEQ ID Nos.: 121, 109, and 122, respectively; and a VL region comprising the CDR1, CDR2, and CDR3 sequences of SEQ ID Nos.: 112, AAS, and 113, respectively [726/187]; and x) a VH region comprising the CDR1, CDR2, and CDR3 sequences of SEQ ID Nos.:93, 126, and 127, respectively; and a VL region comprising the CDR1, CDR2, and CDR3 sequences of SEQ ID Nos.: 96, GAS, and 97, respectively [613/608-01/610-01/620-06].

In one embodiment, the antibody comprises a heavy chain of an isotype selected from the group consisting of IgG1, IgG2, IgG3, and IgG4.

The term "isotype" as used herein refers to the immunoglobulin class (for instance IgG1, IgG2, IgG3, IgG4, IgD, IgA, IgE, or IgM) or any allotypes thereof, such as IgG1m (za) and IgG1m(0) that is encoded by heavy chain constant region genes. Further, each heavy chain isotype can be combined with either a kappa (κ) or lambda (λ) light chain.

In one embodiment, the isotype is IgG1, optionally allotype IgG1m(f).

In one embodiment, the antibody is a full-length monoclonal antibody, optionally a full-length monoclonal IgG1,κ antibody.

The term "full-length antibody" when used herein, refers to an antibody (e.g., a parent or variant antibody) which contains all heavy and light chain constant and variable domains corresponding to those that are normally found in a wild-type antibody of that isotype. A full-length antibody according to the present invention may be produced by a method comprising the steps of (i) cloning the CDR sequences into a suitable vector comprising complete heavy chain sequences and complete light chain sequence, and (ii) expressing the complete heavy and light chain sequences in suitable expression systems. It is within the knowledge of the skilled person to produce a full-length antibody when starting out from either CDR sequences or full variable region sequences. Thus, the skilled person would know how to generate a full-length antibody according to the present invention.

In one embodiment, the antibody is a human antibody.

The term "human antibody", as used herein, is intended to include antibodies having variable and framework regions derived from human germline immunoglobulin sequences and a human immunoglobulin constant domain. The human antibodies of the invention may include amino acid residues not encoded by human germline immunoglobulin sequences (e.g., mutations, insertions or deletions introduced by random or site-specific mutagenesis in vitro or by somatic mutation in vivo). However, the term "human antibody", as used herein, is not intended to include antibodies in which CDR sequences derived from the germline of another non-human species, such as a mouse, have been grafted onto human framework sequences.

As used herein, a human antibody is "derived from" a particular germline sequence if the antibody is obtained from a system using human immunoglobulin sequences, for instance by immunizing a transgenic mouse carrying human immunoglobulin genes or by screening a human immunoglobulin gene library, and wherein the selected human antibody is at least 90%, such as at least 95%, for instance at least 96%, such as at least 97%, for instance at least 98%, or such as at least 99% identical in amino acid sequence to the amino acid sequence encoded by the germline immunoglobulin gene. Typically, outside the heavy chain CDR3, a human antibody derived from a particular human germline sequence will display no more than 20 amino acid differences, e.g. no more than 10 amino acid differences, such as no more than 9, 8, 7, 6 or 5, for instance no more than 4, 3, 2, or 1 amino acid difference from the amino acid sequence encoded by the germline immunoglobulin gene.

The antibody according to the present invention may comprise amino acid modifications in the immunoglobulin heavy and/or light chains. In a particular embodiment, amino acids in the Fc region of the antibody may be modified.

The term "Fc region" as used herein, refers to a region comprising, in the direction from the N- to C-terminal end of the antibody, at least a hinge region, a CH2 region and a CH3 region. An Fc region of the antibody may mediate the binding of the immunoglobulin to host tissues or factors, including various cells of the immune system (such as effector cells) and components of the complement system.

The term "hinge region" as used herein refers to the hinge region of an immunoglobulin heavy chain. Thus, for example the hinge region of a human IgG1 antibody corresponds to amino acids 216-230 according to the Eu numbering as set forth in Kabat [26]. However, the hinge region may also be any of the other subtypes as described herein.

The term "CH1 region" or "CH1 domain" as used herein refers to the CH1 region of an immunoglobulin heavy chain. Thus, for example the CH1 region of a human IgG1 antibody corresponds to amino acids 118-215 according to the Eu numbering as set forth in Kabat [26]. However, the CH1 region may also be any of the other subtypes as described herein.

The term "CH2 region" or "CH2 domain" as used herein refers to the CH2 region of an immunoglobulin heavy chain. Thus, for example the CH2 region of a human IgG1 antibody corresponds to amino acids 231-340 according to the Eu numbering as set forth in Kabat [26]. However, the CH2 region may also be any of the other subtypes as described herein.

The term "CH3 region" or "CH3 domain" as used herein refers to the CH3 region of an immunoglobulin heavy chain. Thus for example the CH3 region of a human IgG1 antibody corresponds to amino acids 341-447 according to the Eu numbering as set forth in Kabat [26]. However, the CH3 region may also be any of the other subtypes as described herein.

In another embodiment, the antibody is an effector-function-deficient antibody, a stabilized IgG4 antibody or a monovalent antibody.

In one particular embodiment, the heavy chain has been modified such that the entire hinge region has been deleted.

In one embodiment, the sequence of the antibody has been modified so that it does not comprise any acceptor sites for N-linked glycosylation.

In one embodiment, the antibody is a single-chain antibody.

In further aspect, the present invention relates to a multispecific antibody comprising at least a first binding region of an antibody according to any aspect or embodiment herein described, and a second binding region which binds a different target or epitope than the first binding region. The term "multispecific antibody" as used herein, refers to antibodies wherein the binding regions two to at least two, such as at least three, different antigens or at least two, such as at least three, different epitopes on the same antigen.

In one embodiment, the present invention relates to a bispecific antibody comprising a first binding region of an antibody according to any aspect or embodiments herein described, and a second binding region which binds a different target or epitope than the first binding region.

The term "bispecific" as used herein, refers to binding molecules, such as antibodies wherein the binding regions of the binding molecule bind to two different antigens or two different epitopes on the same antigen.

The term "bispecific antibody" refers to an antibody having specificities for at least two different, typically non-overlapping, epitopes. Such epitopes may be on the same or different targets. If the epitopes are on different targets, such targets may be on the same cell or different cells, cell types or structures, such as extracellular tissue.

The term "different target" as used herein, refers to another protein, molecule or the like than AXL or an AXL fragment.

Examples of bispecific antibody molecules which may be used in the present invention comprise (i) a single antibody that has two arms comprising different antigen-binding regions, (ii) a single chain antibody that has specificity to two different epitopes, e.g., via two scFvs linked in tandem by an extra peptide linker; (iii) a dual-variable-domain antibody (DVD-Ig™), where each light chain and heavy chain contains two variable domains in tandem through a short peptide linkage [29]; (iv) a chemically-linked bispecific (Fab')2 fragment; (v) a Tandab®, which is a fusion of two single chain diabodies resulting in a tetravalent bispecific antibody that has two binding sites for each of the target antigens; (vi) a flexibody, which is a combination of scFvs with a diabody resulting in a multivalent molecule; (vii) a so called "dock and lock" molecule (Dock-and-Lock®), based on the "dimerization and docking domain" in Protein Kinase A, which, when applied to Fabs, can yield a trivalent bispecific binding protein consisting of two identical Fab fragments linked to a different Fab fragment; (viii) a so-called Scorpion molecule, comprising, e.g., two scFvs fused to both termini of a human Fab-arm; and (ix) a diabody.

In one embodiment, the bispecific antibody of the present invention is a diabody, a cross-body, such as CrossMabs, or a bispecific antibody obtained via a controlled Fab arm exchange (such as described in [30]).

Examples of different classes of bispecific antibodies include but are not limited to (i) IgG-like molecules with complementary CH3 domains to force heterodimerization; (ii) recombinant IgG-like dual targeting molecules, wherein the two sides of the molecule each contain the Fab fragment or part of the Fab fragment of at least two different antibodies; (iii) IgG fusion molecules, wherein full length IgG antibodies are fused to extra Fab fragment or parts of Fab fragment; (iv) Fc fusion molecules, wherein single chain Fv molecules or stabilized diabodies are fused to heavy-chain constant-domains, Fc-regions or parts thereof; (v) Fab fusion molecules, wherein different Fab-fragments are fused together, fused to heavy-chain constant-domains, Fc-regions or parts thereof; and (vi) ScFv- and diabody-based and heavy chain antibodies (e.g., domain antibodies, Nanobodies®) wherein different single chain Fv molecules or different diabodies or different heavy-chain antibodies (e.g. domain antibodies, Nanobodies®) are fused to each other or to another protein or carrier molecule fused to heavy-chain constant-domains, Fc-regions or parts thereof.

Examples of IgG-like molecules with complementary CH3 domains molecules include but are not limited to the Triomab® (Trion Pharma/Fresenius Biotech, [31]), the Knobs-into-Holes (Genentech, [32]), CrossMAbs (Roche, [33]) and the electrostatically-matched (Amgen, [34] and [35]; Chugai, [36]; Oncomed, [37]), the LUZ-Y (Genentech), DIG-body and PIG-body (Pharmabcine), the Strand Exchange Engineered Domain body (SEEDbody)(EMD Serono, [38]), the Biclonics (Merus), FcΔAdp (Regeneron, [39]), bispecific IgG1 and IgG2 (Pfizer/Rinat, [40]), Azymetric scaffold (Zymeworks/Merck, [41]), mAb-Fv (Xencor, [42]), bivalent bispecific antibodies (Roche [43]) and DuoBody® molecules (Genmab A/S, [30]).

Examples of recombinant IgG-like dual targeting molecules include but are not limited to Dual Targeting (DT)-Ig (GSK/Domantis), Two-in-one Antibody (Genentech), Cross-linked Mabs (Karmanos Cancer Center), mAb2 (F-Star, [44]), Zybodies™ (Zyngenia), approaches with common light chain (Crucell/Merus, [45]), κλBodies (Novlmmune) and CovX-body (CovX/Pfizer).

Examples of IgG fusion molecules include but are not limited to Dual Variable Domain (DVD)-Ig™ (Abbott, [46]), Dual domain double head antibodies (Unilever; Sanofi Aventis, [47]), IgG-like Bispecific (ImClone/Eli Lilly), Ts2Ab (MedImmune/AZ) and BsAb (Zymogenetics), HERCULES (Biogen Idec, [48]), scFv fusion (Novartis), scFv fusion (Changzhou Adam Biotech Inc, [49]) and TvAb (Roche, [50], [51]).

Examples of Fc fusion molecules include but are not limited to ScFv/Fc Fusions (Academic Institution), SCORPION (Emergent BioSolutions/Trubion, Zymogenetics/BMS), Dual Affinity Retargeting Technology (Fc-DART™) (MacroGenics, [52], [53]) and Dual(ScFv)2-Fab (National Research Center for Antibody Medicine—China).

Examples of Fab fusion bispecific antibodies include but are not limited to F(ab)2 (Medarex/AMGEN), Dual-Action or Bis-Fab (Genentech), Dock-and-Lock® (DNL) (ImmunoMedics), Bivalent Bispecific (Biotecnol) and Fab-Fv (UCB-Celltech).

Examples of ScFv-, diabody-based and domain antibodies include but are not limited to Bispecific T Cell Engager (BiTE®) (Micromet, Tandem Diabody (Tandab™) (Affimed), Dual Affinity Retargeting Technology (DART) (MacroGenics), Single-chain Diabody (Academic), TCR-like Antibodies (AIT, ReceptorLogics), Human Serum Albumin ScFv Fusion (Merrimack) and COMBODY (Epigen Biotech), dual targeting Nanobodies® (Ablynx), dual targeting heavy chain only domain antibodies.

A bispecific antibody according the present invention may be generated by introducing modifications in the constant region of the antibody.

Unless otherwise stated or contradicted by context, the amino acids of the constant region sequences are herein numbered according to the Eu-index of numbering (described in [26]). The terms "Eu-index of numbering" and "Eu numbering as set forth in Kabat" may be used interchangeably and have the same meaning and purpose. Thus, an amino acid or segment in one sequence that "corresponds to" an amino acid or segment in another sequence is one that aligns with the other amino acid or segment using a standard sequence alignment program such as ALIGN, ClustalW or similar, typically at default settings and has at least 50%, at least 80%, at least 90%, or at least 95% identity to a human IgG1 heavy chain. It is well-known in the art how to align a sequence or segment in a sequence and thereby determine the corresponding position in a sequence to an amino acid position according to the present invention.

The term "amino acid corresponding to positions" as used herein refers to an amino acid position number in a human IgG1 heavy chain.

The present invention also provides antibodies comprising functional variants of the VL region, VH region, or one or more CDRs of the antibodies of the examples. A functional variant of a VL, VH, or CDR used in the context of an AXL antibody still allows the antibody to retain at least a substantial proportion (at least about 50%, 60%, 70%, 80%, 90%, 95%, 99% or more) of the affinity/avidity and/or the specificity/selectivity of the parent antibody and in some cases such an AXL antibody may be associated with greater affinity, selectivity and/or specificity than the parent antibody.

Such functional variants typically retain significant sequence identity to the parent antibody. The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences may be accomplished using a mathematical algorithm, which is well-known in the art.

The VH, VL and/or CDR sequences of variants may differ from those of the parent antibody sequences through mostly conservative substitutions; for instance at least about 35%, about 50% or more, about 60% or more, about 70% or more, about 75% or more, about 80% or more, about 85% or more, about 90% or more, (e.g., about 65-95%, such as about 92%, 93% or 94%) of the substitutions in the variant are conservative amino acid residue replacements.

The VH, VL and/or CDR sequences of variants may differ from those of the parent antibody sequences through mostly conservative substitutions; for instance 10 or less, such as 9 or less, 8 or less, 7 or less, 6 or less, 5 or less, 4 or less, 3 or less, 2 or less or 1 of the substitutions in the variant are conservative amino acid residue replacements.

The term "amino acid" and "amino acid residue" may herein be used interchangeably, and are not to be understood limiting.

In the context of the present invention, the amino acid may be defined by conservative or non-conservative amino acids, and may therefore be classified accordingly. Amino acid residues may also be divided into classes defined by alternative physical and functional properties. Thus, classes of amino acids may be reflected in one or both of the following tables:

| Amino acid residue of conservative class | |
|---|---|
| Acidic Residues | D and E |
| Basic Residues | K, R, and H |
| Hydrophilic Uncharged Residues | S, T, N, and Q |
| Aliphatic Uncharged Residues | G, A, V, L, and I |
| Non-polar Uncharged Residues | C, M, and P |
| Aromatic Residues | F, Y, and W |

| Alternative Physical and Functional Classifications of Amino Acid Residues | |
|---|---|
| Alcohol group-containing residues | S and T |
| Aliphatic residues | I, L, V, and M |
| Cycloalkenyl-associated residues | F, H, W, and Y |
| Hydrophobic residues | A, C, F, G, H, I, L, M, R, T, V, W, and Y |
| Negatively charged residues | D and E |
| Polar residues | C, D, E, H, K, N, Q, R, S, and T |
| Positively charged residues | H, K, and R |
| Small residues | A, C, D, G, N, P, S, T, and V |
| Very small residues | A, G, and S |
| Residues involved in turn formation | A, C, D, E, G, H, K, N, Q, R, S, P, and T |
| Flexible residues | Q, T, K, S, G, P, D, E, and R |

In the context of the present invention, a substitution in an antibody is indicated as:

Original amino acid—position—substituted amino acid;

Referring to the well-recognized nomenclature for amino acids, the three letter code, or one letter code, is used, including the codes "Xaa" or "X" to indicate any amino acid residue. Thus, Xaa or X may typically represent any of the 20 naturally occurring amino acids. The term "naturally occurring" as used herein refers to any one of the following amino acid residues; glycine, alanine, valine, leucine, isoleucine, serine, threonine, lysine, arginine, histidine, aspartic acid, asparagine, glutamic acid, glutamine, proline, tryptophan, phenylalanine, tyrosine, methionine, and cysteine. Accordingly, the notation "K409R" or "Lys409Arg" means, that the antibody comprises a substitution of Lysine with Arginine in amino acid position 409.

Substitution of an amino acid at a given position to any other amino acid is referred to as:

Original amino acid—position; or e.g. "K409"

For a modification where the original amino acid(s) and/or substituted amino acid(s) may comprise more than one, but not all amino acid(s), the more than one amino acid may be separated by "," or "/". E.g. the substitution of Lysine with Arginine, Alanine, or Phenylalanine in position 409 is:

"Lys409Arg,Ala,Phe" or "Lys409Arg/Ala/Phe" or "K409R,A,F" or "K409R/A/F" or "K409 to R, A, or F".

Such designation may be used interchangeably in the context of the invention but have the same meaning and purpose.

Furthermore, the term "a substitution" embraces a substitution into any one or the other nineteen natural amino acids, or into other amino acids, such as non-natural amino acids. For example, a substitution of amino acid K in position 409 includes each of the following substitutions: 409A, 409C, 409D, 409E, 409F, 409G, 409H, 409I, 409L, 409M, 409N, 409Q, 409R, 409S, 409T, 409V, 409W, 409P, and 409Y. This is, by the way, equivalent to the designation 409X, wherein the X designates any amino acid other than the original amino acid. These substitutions may also be designated K409A, K409C, etc. or K409A,C, etc. or K409A/C/etc. The same applies by analogy to each and every position mentioned herein, to specifically include herein any one of such substitutions.

The antibody according to the invention may also comprise a deletion of an amino acid residue. Such deletion may be denoted "del", and includes, e.g., writing as K409del. Thus, in such embodiments, the Lysine in position 409 has been deleted from the amino acid sequence.

In one particular embodiment, the bispecific antibody comprises a first and a second heavy chain, each of the first and second heavy chain comprises at least a hinge region, a CH2 and CH3 region, wherein in the first heavy chain at least one of the amino acids in the positions corresponding to positions selected from the group consisting of K409, T366, L368, K370, D399, F405, and Y407 in a human IgG1 heavy chain has been substituted, and in the second heavy chain at least one of the amino acids in the positions corresponding to a position selected from the group consisting of F405, T366, L368, K370, D399, Y407, and K409 in a human IgG1 heavy chain has been substituted, and wherein the first and the second heavy chains are not substituted in the same positions.

In one embodiment, in the first heavy chain the amino acid in the position corresponding to K409 in a human IgG1 heavy chain is not K, L or M and optionally the amino acid in the position corresponding to F405 in a human IgG1 heavy chain is F, and in the second heavy chain the amino acid in the position corresponding to F405 in a human IgG1 heavy chain is not F and the amino acid in the position corresponding to K409 in a human IgG1 heavy chain is K.

In one embodiment, in the first heavy chain, the amino acid in the position corresponding to F405 in a human IgG1 heavy chain is not F, R, and G, and in the second heavy chain the amino acids in the positions corresponding to a position selected from the group consisting of: T366, L368, K370, D399, Y407, and K409 in a human IgG1 heavy chain has been substituted.

In one embodiment, the amino acid in position corresponding to K409 in a human IgG1 heavy chain is another than K, L or M in the first heavy chain, and in the second heavy chain the amino acid in position corresponding to F405 in a human IgG1 heavy chain is not F and optionally the amino acid in the position corresponding to K409 in a human IgG1 heavy chain is K.

In one embodiment, the amino acid in the position corresponding to F405 in a human IgG1 heavy chain is L in said first heavy chain, and the amino acid in the position corresponding to K409 in a human IgG1 heavy chain is R in said second heavy chain, or vice versa.

Thus, in one embodiment, the amino acid in the position corresponding to K409 in a human IgG1 heavy chain is R in the first heavy chain, and the amino acid in the position corresponding to F405 in a human IgG1 heavy chain is L in the second heavy chain.

In another embodiment, both the first and the second binding region of the bispecific antibody bind AXL. However, the first binding region comprises a different set of CDR sequences than the second binding region. Thus, in a particular embodiment, the bispecific antibody comprising a first and a second binding region, and a first and a second heavy chain, wherein the first and the second binding regions each comprise a VH and VL region selected from the group consisting of;

a) a first VH region comprising the CDR1, CDR2, and CDR3 sequences of SEQ ID Nos.: 36, 37, and 38, respectively; and a first VL region comprising the CDR1, CDR2, and CDR3 sequences of SEQ ID Nos.: 39, GAS, and 40, respectively, [107]; and a second VH region comprising the CDR1, CDR2, and CDR3 sequences of SEQ ID Nos.: 46, 47, and 48, respectively; and a second VL region comprising the CDR1, CDR2, and CDR3 sequences of SEQ ID Nos.: 49, AAS, and 50, respectively, [148];

b) a first VH region comprising the CDR1, CDR2, and CDR3 sequences of SEQ ID Nos.: 36, 37, and 38, respectively; and a first VL region comprising the CDR1, CDR2, and CDR3 sequences of SEQ ID Nos.: 39, GAS, and 40, respectively, [107]; and a second VH region comprising the CDR1, CDR2, and CDR3 sequences of SEQ ID Nos.: 114, 115, and 116, respectively, and a second VL region comprising the CDR1, CDR2, and CDR3 sequences of SEQ ID Nos.: 117, DAS, and 118, respectively [733];

c) a first VH region comprising the CDR1, CDR2, and CDR3 sequences of SEQ ID Nos.: 36, 37, and 38, respectively; and a first VL region comprising the CDR1, CDR2, and CDR3 sequences of SEQ ID Nos.: 39, GAS, and 40, respectively, [107]; and a second VH region comprising the CDR1, CDR2, and CDR3 sequences of SEQ ID Nos.: 41, 42, and 43, respectively; and a second VL region comprising the CDR1, CDR2, and CDR3 sequences of SEQ ID Nos.: 44, AAS, and 45, respectively, [140];

d) a first VH region comprising the CDR1, CDR2, and CDR3 sequences of SEQ ID Nos.: 36, 37, and 38, respectively; and a first VL region comprising the CDR1, CDR2, and CDR3 sequences of SEQ ID Nos.: 39, GAS, and 40, respectively, [107]; and a second VH region comprising the CDR1, CDR2, and CDR3 sequences of SEQ ID Nos.: 51, 52, and 55, respectively; and a second VL region comprising the CDR1, CDR2, and CDR3 sequences of SEQ ID Nos.: 55, GAS, and 56, respectively. [154];

e) a first VH region comprising the CDR1, CDR2, and CDR3 sequences of SEQ ID Nos.: 36, 37, and 38, respectively; and a first VL region comprising the CDR1, CDR2, and CDR3 sequences of SEQ ID Nos.: 39, GAS, and 40, respectively, [107]; and a second VH region comprising the CDR1, CDR2, and CDR3 sequences of SEQ ID Nos.: 51, 52, and 54, respectively; and a second VL region comprising the CDR1, CDR2, and CDR3 sequences of SEQ ID Nos.: 55, GAS, and 56, respectively. [154-M103L];

f) a first VH region comprising the CDR1, CDR2, and CDR3 sequences of SEQ ID Nos.: 36, 37, and 38, respectively; and a first VL region comprising the CDR1, CDR2, and CDR3 sequences of SEQ ID Nos.: 39, GAS, and 40, respectively, [107]; and a second VH region comprising the CDR1, CDR2, and CDR3 sequences of SEQ ID Nos.: 57, 58, and 59, respectively; and a second VL region comprising the CDR1, CDR2, and CDR3 sequences of SEQ ID Nos.: 60, GAS, and 61, respectively, [171];

g) a first VH region comprising the CDR1, CDR2, and CDR3 sequences of SEQ ID Nos.: 36, 37, and 38, respectively; and a first VL region comprising the CDR1, CDR2, and CDR3 sequences of SEQ ID Nos.: 39, GAS, and 40, respectively, [107]; and a second VH region comprising the CDR1, CDR2, and CDR3 sequences of SEQ ID Nos.: 62, 63, and 64, respectively; and a second VL region comprising the CDR1, CDR2, and CDR3 sequences of SEQ ID Nos.: 65, GAS, and 66, respectively, [172];

h) a first VH region comprising the CDR1, CDR2, and CDR3 sequences of SEQ ID Nos.: 36, 37, and 38, respectively; and a first VL region comprising the CDR1, CDR2, and CDR3 sequences of SEQ ID Nos.: 39, GAS, and 40, respectively, [107]; and a second VH region comprising the CDR1, CDR2, and CDR3 sequences of SEQ ID Nos.: 67, 68, and 69, respectively; and a second VL region comprising the CDR1, CDR2, and CDR3 sequences of SEQ ID Nos.: 70, GAS, and 71, respectively, [181];

i) a first VH region comprising the CDR1, CDR2, and CDR3 sequences of SEQ ID Nos.: 36, 37, and 38, respectively; and a first VL region comprising the CDR1, CDR2, and CDR3 sequences of SEQ ID Nos.: 39, GAS, and 40, respectively, [107]; and a second VH region comprising the CDR1, CDR2, and CDR3 sequences of SEQ ID Nos.: 72, 73, and 75, respectively; and a second VL region comprising the CDR1, CDR2, and CDR3 sequences of SEQ ID Nos.: 76, ATS, and 77, respectively, [183];

j) a first VH region comprising the CDR1, CDR2, and CDR3 sequences of SEQ ID Nos.: 36, 37, and 38, respectively; and a first VL region comprising the CDR1, CDR2, and CDR3 sequences of SEQ ID Nos.: 39, GAS, and 40, respectively, [107]; and a second VH region comprising the CDR1, CDR2, and CDR3 sequences of SEQ ID Nos.: 72, 74, and 75, respectively; and a second VL region comprising the CDR1, CDR2, and CDR3 sequences of SEQ ID Nos.: 76, ATS, and 77, respectively, [183-N52Q];

k) a first VH region comprising the CDR1, CDR2, and CDR3 sequences of SEQ ID Nos.: 36, 37, and 38, respectively; and a first VL region comprising the CDR1, CDR2, and CDR3 sequences of SEQ ID Nos.: 39, GAS, and 40, respectively, [107]; and a second VH region comprising the CDR1, CDR2, and CDR3 sequences of SEQ ID Nos.: 78, 79, and 80, respectively; and a second VL region comprising the CDR1, CDR2, and CDR3 sequences of SEQ ID Nos.: 81, AAS, and 82, respectively, [187];

l) a first VH region comprising the CDR1, CDR2, and CDR3 sequences of SEQ ID Nos.: 36, 37, and 38, respectively; and a first VL region comprising the CDR1, CDR2, and CDR3 sequences of SEQ ID Nos.: 39, GAS, and 40, respectively, [107]; and a second VH region comprising the CDR1, CDR2, and CDR3 sequences of SEQ ID Nos.: 83, 84, and 85, respectively; and a second VL region comprising the CDR1, CDR2, and CDR3 sequences of SEQ ID Nos.: 86, GAS, and 87, respectively, [608-01];

m) a first VH region comprising the CDR1, CDR2, and CDR3 sequences of SEQ ID Nos.: 36, 37, and 38, respectively; and a first VL region comprising the CDR1, CDR2, and CDR3 sequences of SEQ ID Nos.: 39, GAS, and 40, respectively, [107]; and a second VH region comprising the CDR1, CDR2, and CDR3 sequences of SEQ ID Nos.: 88, 89, and 90, respectively; and a second VL region comprising the CDR1, CDR2, and CDR3 sequences of SEQ ID Nos.: 91, GAS, and 92, respectively, [610-01];

n) a first VH region comprising the CDR1, CDR2, and CDR3 sequences of SEQ ID Nos.: 36, 37, and 38, respectively; and a first VL region comprising the CDR1, CDR2, and CDR3 sequences of SEQ ID Nos.: 39, GAS, and 40, respectively, [107]; and a second VH region comprising the CDR1, CDR2, and CDR3 sequences of SEQ ID Nos.: 94, 95, and 95, respectively; and a second VL region comprising the CDR1, CDR2, and CDR3 sequences of SEQ ID Nos.: 96, GAS, and 97, respectively, [613];

o) a first VH region comprising the CDR1, CDR2, and CDR3 sequences of SEQ ID Nos.: 36, 37, and 38, respectively; and a first VL region comprising the CDR1, CDR2, and CDR3 sequences of SEQ ID Nos.: 39, GAS, and 40, respectively, [107]; and a second VH region comprising the CDR1, CDR2, and CDR3 sequences of SEQ ID Nos.: 98, 99, and 100, respectively; and a second VL region comprising the CDR1, CDR2, and CDR3 sequences of SEQ ID Nos.: 101, DAS, and 102, respectively, [613-08];

p) a first VH region comprising the CDR1, CDR2, and CDR3 sequences of SEQ ID Nos.: 36, 37, and 38, respectively; and a first VL region comprising the CDR1, CDR2, and CDR3 sequences of SEQ ID Nos.: 39, GAS, and 40, respectively, [107]; and a second VH region comprising the CDR1, CDR2, and CDR3 sequences of SEQ ID Nos.: 103, 104, and 105, respectively; and a second VL region comprising the CDR1, CDR2, and CDR3 sequences of SEQ ID Nos.: 106, GAS, and 107, respectively, [620-06];

q) a first VH region comprising the CDR1, CDR2, and CDR3 sequences of SEQ ID Nos.: 36, 37, and 38, respectively; and a first VL region comprising the CDR1, CDR2, and CDR3 sequences of SEQ ID Nos.: 39, GAS, and 40, respectively, [107]; and a second VH region comprising the CDR1, CDR2, and CDR3 sequences of SEQ ID Nos.: 108, 109, and 110, respectively; and a second VL region comprising the CDR1, CDR2, and CDR3 sequences of SEQ ID Nos.: 112, AAS, and 113, respectively, [726];

r) a first VH region comprising the CDR1, CDR2, and CDR3 sequences of SEQ ID Nos.: 36, 37, and 38, respectively; and a first VL region comprising the CDR1, CDR2, and CDR3 sequences of SEQ ID Nos.: 39, GAS, and 40, respectively, [107]; and a second VH region comprising the CDR1, CDR2, and CDR3 sequences of SEQ ID Nos.: 108, 109, and 111, respectively; and a second VL region comprising the CDR1, CDR2, and CDR3 sequences of SEQ ID Nos.: 112, AAS, and 113, respectively, [726-M101L];

s) a first VH region comprising the CDR1, CDR2, and CDR3 sequences of SEQ ID Nos.: 46, 47, and 48, respectively; and a first VL region comprising the CDR1, CDR2, and CDR3 sequences of SEQ ID Nos.: 49, AAS, and 50, respectively, [148]; and a second VH region comprising the CDR1, CDR2, and CDR3 sequences of SEQ ID Nos.: 114, 115, and 116, respectively, and a second VL region comprising the CDR1, CDR2, and CDR3 sequences of SEQ ID Nos.: 117, DAS, and 118, respectively [733];

t) a first VH region comprising the CDR1, CDR2, and CDR3 sequences of SEQ ID Nos.: 46, 47, and 48, respectively; and a first VL region comprising the CDR1, CDR2, and CDR3 sequences of SEQ ID Nos.:

49, AAS, and 50, respectively, [148]; and a second VH region comprising the CDR1, CDR2, and CDR3 sequences of SEQ ID Nos.: 41, 42, and 43, respectively; and a second VL region comprising the CDR1, CDR2, and CDR3 sequences of SEQ ID Nos.: 44, AAS, and 45, respectively, [107];

u) a first VH region comprising the CDR1, CDR2, and CDR3 sequences of SEQ ID Nos.: 46, 47, and 48, respectively; and a first VL region comprising the CDR1, CDR2, and CDR3 sequences of SEQ ID Nos.: 49, AAS, and 50, respectively, [148]; and a second VH region comprising the CDR1, CDR2, and CDR3 sequences of SEQ ID Nos.: 51, 52, and 55, respectively; and a second VL region comprising the CDR1, CDR2, and CDR3 sequences of SEQ ID Nos.: 55, GAS, and 56, respectively. [154];

v) a first VH region comprising the CDR1, CDR2, and CDR3 sequences of SEQ ID Nos.: 46, 47, and 48, respectively; and a first VL region comprising the CDR1, CDR2, and CDR3 sequences of SEQ ID Nos.: 49, AAS, and 50, respectively, [148]; and a second VH region comprising the CDR1, CDR2, and CDR3 sequences of SEQ ID Nos.: 51, 52, and 54, respectively; and a second VL region comprising the CDR1, CDR2, and CDR3 sequences of SEQ ID Nos.: 55, GAS, and 56, respectively. [154-M103L];

w) a first VH region comprising the CDR1, CDR2, and CDR3 sequences of SEQ ID Nos.: 46, 47, and 48, respectively; and a first VL region comprising the CDR1, CDR2, and CDR3 sequences of SEQ ID Nos.: 49, AAS, and 50, respectively, [148]; and a second VH region comprising the CDR1, CDR2, and CDR3 sequences of SEQ ID Nos.: 57, 58, and 59, respectively; and a second VL region comprising the CDR1, CDR2, and CDR3 sequences of SEQ ID Nos.: 60, GAS, and 61, respectively, [171];

x) a first VH region comprising the CDR1, CDR2, and CDR3 sequences of SEQ ID Nos.: 46, 47, and 48, respectively; and a first VL region comprising the CDR1, CDR2, and CDR3 sequences of SEQ ID Nos.: 49, AAS, and 50, respectively, [148]; and a second VH region comprising the CDR1, CDR2, and CDR3 sequences of SEQ ID Nos.: 62, 63, and 64, respectively; and a second VL region comprising the CDR1, CDR2, and CDR3 sequences of SEQ ID Nos.: 65, GAS, and 66, respectively, [172];

y) a first VH region comprising the CDR1, CDR2, and CDR3 sequences of SEQ ID Nos.: 46, 47, and 48, respectively; and a first VL region comprising the CDR1, CDR2, and CDR3 sequences of SEQ ID Nos.: 49, AAS, and 50, respectively, [148]; and a second VH region comprising the CDR1, CDR2, and CDR3 sequences of SEQ ID Nos.: 67, 68, and 69, respectively; and a second VL region comprising the CDR1, CDR2, and CDR3 sequences of SEQ ID Nos.: 70, GAS, and 71, respectively, [181];

z) a first VH region comprising the CDR1, CDR2, and CDR3 sequences of SEQ ID Nos.: 46, 47, and 48, respectively; and a first VL region comprising the CDR1, CDR2, and CDR3 sequences of SEQ ID Nos.: 49, AAS, and 50, respectively, [148]; and a second VH region comprising the CDR1, CDR2, and CDR3 sequences of SEQ ID Nos.: 72, 73, and 75, respectively; and a second VL region comprising the CDR1, CDR2, and CDR3 sequences of SEQ ID Nos.: 76, ATS, and 77, respectively, [183];

aa) a first VH region comprising the CDR1, CDR2, and CDR3 sequences of SEQ ID Nos.: 46, 47, and 48, respectively; and a first VL region comprising the CDR1, CDR2, and CDR3 sequences of SEQ ID Nos.: 49, AAS, and 50, respectively, [148]; and a second VH region comprising the CDR1, CDR2, and CDR3 sequences of SEQ ID Nos.: 72, 74, and 75, respectively; and a second VL region comprising the CDR1, CDR2, and CDR3 sequences of SEQ ID Nos.: 76, ATS, and 77, respectively, [183-N52Q];

bb) a first VH region comprising the CDR1, CDR2, and CDR3 sequences of SEQ ID Nos.: 46, 47, and 48, respectively; and a first VL region comprising the CDR1, CDR2, and CDR3 sequences of SEQ ID Nos.: 49, AAS, and 50, respectively, [148]; and a second VH region comprising the CDR1, CDR2, and CDR3 sequences of SEQ ID Nos.: 78, 79, and 80, respectively; and a second VL region comprising the CDR1, CDR2, and CDR3 sequences of SEQ ID Nos.: 81, AAS, and 82, respectively, [187];

cc) a first VH region comprising the CDR1, CDR2, and CDR3 sequences of SEQ ID Nos.: 46, 47, and 48, respectively; and a first VL region comprising the CDR1, CDR2, and CDR3 sequences of SEQ ID Nos.: 49, AAS, and 50, respectively, [148]; and a second VH region comprising the CDR1, CDR2, and CDR3 sequences of SEQ ID Nos.: 83, 84, and 85, respectively; and a second VL region comprising the CDR1, CDR2, and CDR3 sequences of SEQ ID Nos.: 86, GAS, and 87, respectively, [608-01];

dd) a first VH region comprising the CDR1, CDR2, and CDR3 sequences of SEQ ID Nos.: 46, 47, and 48, respectively; and a first VL region comprising the CDR1, CDR2, and CDR3 sequences of SEQ ID Nos.: 49, AAS, and 50, respectively, [148]; and a second VH region comprising the CDR1, CDR2, and CDR3 sequences of SEQ ID Nos.: 88, 89, and 90, respectively; and a second VL region comprising the CDR1, CDR2, and CDR3 sequences of SEQ ID Nos.: 91, GAS, and 92, respectively, [610-01];

ee) a first VH region comprising the CDR1, CDR2, and CDR3 sequences of SEQ ID Nos.: 46, 47, and 48, respectively; and a first VL region comprising the CDR1, CDR2, and CDR3 sequences of SEQ ID Nos.: 49, AAS, and 50, respectively, [148]; and a second VH region comprising the CDR1, CDR2, and CDR3 sequences of SEQ ID Nos.: 94, 95, and 95, respectively; and a second VL region comprising the CDR1, CDR2, and CDR3 sequences of SEQ ID Nos.: 96, GAS, and 97, respectively, [613];

ff) a first VH region comprising the CDR1, CDR2, and CDR3 sequences of SEQ ID Nos.: 46, 47, and 48, respectively; and a first VL region comprising the CDR1, CDR2, and CDR3 sequences of SEQ ID Nos.: 49, AAS, and 50, respectively, [148]; and a second VH region comprising the CDR1, CDR2, and CDR3 sequences of SEQ ID Nos.: 98, 99, and 100, respectively; and a second VL region comprising the CDR1, CDR2, and CDR3 sequences of SEQ ID Nos.: 101, DAS, and 102, respectively, [613-08];

gg) a first VH region comprising the CDR1, CDR2, and CDR3 sequences of SEQ ID Nos.: 46, 47, and 48, respectively; and a first VL region comprising the CDR1, CDR2, and CDR3 sequences of SEQ ID Nos.: 49, AAS, and 50, respectively, [148]; and a second VH region comprising the CDR1, CDR2, and CDR3 sequences of SEQ ID Nos.: 103, 104, and 105, respectively; and a second VL region comprising the CDR1, CDR2, and CDR3 sequences of SEQ ID Nos.: 106, GAS, and 107, respectively, [620-06];

hh) a first VH region comprising the CDR1, CDR2, and CDR3 sequences of SEQ ID Nos.: 46, 47, and 48, respectively; and a first VL region comprising the CDR1, CDR2, and CDR3 sequences of SEQ ID Nos.: 49, AAS, and 50, respectively, [148]; and a second VH region comprising the CDR1, CDR2, and CDR3 sequences of SEQ ID Nos.: 108, 109, and 110, respectively; and a second VL region comprising the CDR1, CDR2, and CDR3 sequences of SEQ ID Nos.: 112, AAS, and 113, respectively, [726];

ii) a first VH region comprising the CDR1, CDR2, and CDR3 sequences of SEQ ID Nos.: 46, 47, and 48, respectively; and a first VL region comprising the CDR1, CDR2, and CDR3 sequences of SEQ ID Nos.: 49, AAS, and 50, respectively, [148]; and a second VH region comprising the CDR1, CDR2, and CDR3 sequences of SEQ ID Nos.: 108, 109, and 111, respectively; and a second VL region comprising the CDR1, CDR2, and CDR3 sequences of SEQ ID Nos.: 112, AAS, and 113, respectively, [726-M101L];

jj) a first VH region comprising the CDR1, CDR2, and CDR3 sequences of SEQ ID Nos.: 114, 115, and 116, respectively; and a first VL region comprising the CDR1, CDR2, and CDR3 sequences of SEQ ID Nos.: 117, DAS, and 118, respectively, [733]; and a second VH region comprising the CDR1, CDR2, and CDR3 sequences of SEQ ID Nos.: 41, 42, and 43, respectively; and a second VL region comprising the CDR1, CDR2, and CDR3 sequences of SEQ ID Nos.: 44, AAS, and 45, respectively, [140];

kk) a first VH region comprising the CDR1, CDR2, and CDR3 sequences of SEQ ID Nos.: 114, 115, and 116, respectively; and a first VL region comprising the CDR1, CDR2, and CDR3 sequences of SEQ ID Nos.: 117, DAS, and 118, respectively, [733]; and a second VH region comprising the CDR1, CDR2, and CDR3 sequences of SEQ ID Nos.: 51, 52, and 55, respectively; and a second VL region comprising the CDR1, CDR2, and CDR3 sequences of SEQ ID Nos.: 55, GAS, and 56, respectively. [154];

ll) a first VH region comprising the CDR1, CDR2, and CDR3 sequences of SEQ ID Nos.: 114, 115, and 116, respectively; and a first VL region comprising the CDR1, CDR2, and CDR3 sequences of SEQ ID Nos.: 117, DAS, and 118, respectively, [733]; and a second VH region comprising the CDR1, CDR2, and CDR3 sequences of SEQ ID Nos.: 51, 52, and 54, respectively; and a second VL region comprising the CDR1, CDR2, and CDR3 sequences of SEQ ID Nos.: 55, GAS, and 56, respectively. [154-M103L];

mm) a first VH region comprising the CDR1, CDR2, and CDR3 sequences of SEQ ID Nos.: 114, 115, and 116, respectively; and a first VL region comprising the CDR1, CDR2, and CDR3 sequences of SEQ ID Nos.: 117, DAS, and 118, respectively, [733]; and a second VH region comprising the CDR1, CDR2, and CDR3 sequences of SEQ ID Nos.: 57, 58, and 59, respectively; and a second VL region comprising the CDR1, CDR2, and CDR3 sequences of SEQ ID Nos.: 60, GAS, and 61, respectively, [171];

nn) a first VH region comprising the CDR1, CDR2, and CDR3 sequences of SEQ ID Nos.: 114, 115, and 116, respectively; and a first VL region comprising the CDR1, CDR2, and CDR3 sequences of SEQ ID Nos.: 117, DAS, and 118, respectively, [733]; and a second VH region comprising the CDR1, CDR2, and CDR3 sequences of SEQ ID Nos.: 62, 63, and 64, respectively; and a second VL region comprising the CDR1, CDR2, and CDR3 sequences of SEQ ID Nos.: 65, GAS, and 66, respectively, [172];

oo) a first VH region comprising the CDR1, CDR2, and CDR3 sequences of SEQ ID Nos.: 114, 115, and 116, respectively; and a first VL region comprising the CDR1, CDR2, and CDR3 sequences of SEQ ID Nos.: 117, DAS, and 118, respectively, [733]; and a second VH region comprising the CDR1, CDR2, and CDR3 sequences of SEQ ID Nos.: 67, 68, and 69, respectively; and a second VL region comprising the CDR1, CDR2, and CDR3 sequences of SEQ ID Nos.: 70, GAS, and 71, respectively, [181];

pp) a first VH region comprising the CDR1, CDR2, and CDR3 sequences of SEQ ID Nos.: 114, 115, and 116, respectively; and a first VL region comprising the CDR1, CDR2, and CDR3 sequences of SEQ ID Nos.: 117, DAS, and 118, respectively, [733]; and a second VH region comprising the CDR1, CDR2, and CDR3 sequences of SEQ ID Nos.: 72, 73, and 75, respectively; and a second VL region comprising the CDR1, CDR2, and CDR3 sequences of SEQ ID Nos.: 76, ATS, and 77, respectively, [183];

qq) a first VH region comprising the CDR1, CDR2, and CDR3 sequences of SEQ ID Nos.: 114, 115, and 116, respectively; and a first VL region comprising the CDR1, CDR2, and CDR3 sequences of SEQ ID Nos.: 117, DAS, and 118, respectively, [733]; and a second VH region comprising the CDR1, CDR2, and CDR3 sequences of SEQ ID Nos.: 72, 74, and 75, respectively; and a second VL region comprising the CDR1, CDR2, and CDR3 sequences of SEQ ID Nos.: 76, ATS, and 77, respectively, [183-N52Q];

rr) a first VH region comprising the CDR1, CDR2, and CDR3 sequences of SEQ ID Nos.: 114, 115, and 116, respectively; and a first VL region comprising the CDR1, CDR2, and CDR3 sequences of SEQ ID Nos.: 117, DAS, and 118, respectively, [733]; and a second VH region comprising the CDR1, CDR2, and CDR3 sequences of SEQ ID Nos.: 78, 79, and 80, respectively; and a second VL region comprising the CDR1, CDR2, and CDR3 sequences of SEQ ID Nos.: 81, AAS, and 82, respectively, [187];

ss) a first VH region comprising the CDR1, CDR2, and CDR3 sequences of SEQ ID Nos.: 114, 115, and 116, respectively; and a first VL region comprising the CDR1, CDR2, and CDR3 sequences of SEQ ID Nos.: 117, DAS, and 118, respectively, [733]; and a second VH region comprising the CDR1, CDR2, and CDR3 sequences of SEQ ID Nos.: 83, 84, and 85, respectively; and a second VL region comprising the CDR1, CDR2, and CDR3 sequences of SEQ ID Nos.: 86, GAS, and 87, respectively, [608-01];

tt) a first VH region comprising the CDR1, CDR2, and CDR3 sequences of SEQ ID Nos.: 114, 115, and 116, respectively; and a first VL region comprising the CDR1, CDR2, and CDR3 sequences of SEQ ID Nos.: 117, DAS, and 118, respectively, [733]; and a second VH region comprising the CDR1, CDR2, and CDR3 sequences of SEQ ID Nos.: 88, 89, and 90, respectively; and a second VL region comprising the CDR1, CDR2, and CDR3 sequences of SEQ ID Nos.: 91, GAS, and 92, respectively, [610-01];

uu) a first VH region comprising the CDR1, CDR2, and CDR3 sequences of SEQ ID Nos.: 114, 115, and 116, respectively; and a first VL region comprising the CDR1, CDR2, and CDR3 sequences of SEQ ID Nos.: 117, DAS, and 118, respectively, [733]; and a second VH region comprising the CDR1, CDR2, and CDR3 sequences of SEQ ID Nos.: 94, 95, and 95, respectively; and a second VL region comprising the CDR1, CDR2, and CDR3 sequences of SEQ ID Nos.: 96, GAS, and 97, respectively, [613];

vv) a first VH region comprising the CDR1, CDR2, and CDR3 sequences of SEQ ID Nos.: 114, 115, and 116, respectively; and a first VL region comprising the CDR1, CDR2, and CDR3 sequences of SEQ ID Nos.: 117, DAS, and 118, respectively, [733]; and a second VH region comprising the CDR1, CDR2, and CDR3 sequences of SEQ ID Nos.: 98, 99, and 100, respectively; and a second VL region comprising the CDR1, CDR2, and CDR3 sequences of SEQ ID Nos.: 101, DAS, and 102, respectively, [613-08];

ww) a first VH region comprising the CDR1, CDR2, and CDR3 sequences of SEQ ID Nos.: 114, 115, and 116, respectively; and a first VL region comprising the CDR1, CDR2, and CDR3 sequences of SEQ ID Nos.: 117, DAS, and 118, respectively, [733]; and a second VH region comprising the CDR1, CDR2, and CDR3 sequences of SEQ ID Nos.: 103, 104, and 105, respectively; and a second VL region comprising the CDR1, CDR2, and CDR3 sequences of SEQ ID Nos.: 106, GAS, and 107, respectively, [620-06];

xx) a first VH region comprising the CDR1, CDR2, and CDR3 sequences of SEQ ID Nos.: 114, 115, and 116, respectively; and a first VL region comprising the CDR1, CDR2, and CDR3 sequences of SEQ ID Nos.: 117, DAS, and 118, respectively, [733]; and a second VH region comprising the CDR1, CDR2, and CDR3 sequences of SEQ ID Nos.: 108, 109, and 110, respectively; and a second VL region comprising the CDR1, CDR2, and CDR3 sequences of SEQ ID Nos.: 112, AAS, and 113, respectively, [726]; and yy) a first VH region comprising the CDR1, CDR2, and CDR3 sequences of SEQ ID Nos.: 114, 115, and 116, respectively; and a first VL region comprising the CDR1, CDR2, and CDR3 sequences of SEQ ID Nos.: 117, DAS, and 118, respectively, [733]; and a second VH region comprising the CDR1, CDR2, and CDR3 sequences of SEQ ID Nos.: 108, 109, and 111, respectively; and a second VL region comprising the CDR1, CDR2, and CDR3 sequences of SEQ ID Nos.: 112, AAS, and 113, respectively, [726-M101L];

Anti-AXL Antibody Drug Conjugate—Immunoconjugates

The antibodies according to any aspect or embodiment of the present invention may be conjugated to a therapeutic or diagnostic moiety, such as a cytotoxic agent, a chemotherapeutic drug, a cytokine, an immunosuppressant, antibiotic, or a radioisotope. Such conjugates are referred to herein as "immunoconjugates". Immunoconjugates which include one or more cytotoxins are referred to as "immunotoxins". Antibodies conjugated to a cytotoxic agent, drug or the like are also known as antibody-drug conjugates (ADC). An immunoconjugate may have a half-life of sufficient periods of time for the antibody-drug conjugate to be internalized, degraded and induce cell killing by the released toxin.

Thus, in another aspect, the present invention relates to an immunoconjugate comprising the antibody according to any aspect or embodiment herein described, or a bispecific antibody according to any aspect or embodiment herein described, and a therapeutic moiety, such as a cytotoxic agent, a chemotherapeutic drug, a cytokine, an immunosuppressant, antibiotic, or a radioisotope. The cytotoxic agent, chemotherapeutic drug, cytokine, immunosuppressant, antibiotic, or radioisotope may be conjugated to the antibody or the bispecific antibody via a linker.

ADCs are often designed such that the cytotoxic payload is inactive when conjugated to the antibody. The cytotoxic payload may be released intracellularly upon internalization of the ADC after binding to the plasma-membrane of cells, or alternatively in response to proteolytic activity in the tumor microenvironment. The term "internalized" or "internalization" as used herein, refers to a biological process in which molecules such as the antibody according to the present invention, are engulfed by the cell membrane and drawn into the interior of the cell. It may also be referred to as "endocytosis".

Thus, the antibodies according to any aspect or embodiment of the present invention may be internalized into the cell upon binding to the target, AXL.

In some instances it may be desired to use antibodies which undergo internalization. Such antibodies that have good internalization properties may be suited for conjugation to a cytotoxic agent, drug, or the like, optionally via a linker, which is designed to be cleaved intracellularly.

Once internalized, the ADC may be delivered to lysosomes in most cases, where effective drug release takes advantage of the catabolic environment found with these organelles. It is typically a linker that connects the antibody with a cytotoxic agent. Thus, specialized linkers have been designed to be cleaved only in a specific microenvironment found in or on the target tumor cell or in the tumor microenvironment. Examples include linkers that are cleaved by acidic conditions, reducing conditions, or specific proteases.

Stability of the antibody-linker-drug in circulation is important because this allows antibody-mediated delivery of the drug to specific target cells. In addition, the long circulating half-life of the ADC provides exposure for several days to weeks post injection. Drugs that are conjugated through non-cleavable linkers and protease-cleavable linkers are generally more stable in circulation than disulfide and hydrazone linkers, although the stability of the latter two linkers can be tuned by altering the neighboring chemical structure [6].

In one embodiment, the therapeutic moiety is a cytotoxic agent.

A cytotoxin or cytotoxic agent includes any agent that is detrimental to (e.g., kills) cells. Suitable cytotoxic agents for forming immunoconjugates of the present invention include taxol, tubulysins, duostatins, cytochalasin B, gramicidin D, ethidium bromide, emetine, mitomycin, etoposide, tenoposide, vincristine, vinblastine, colchicin, doxorubicin, daunorubicin, dihydroxy anthracin dione, maytansine or an analog or derivative thereof, mitoxantrone, mithramycin, actinomycin D, 1-dehydrotestosterone, glucocorticoids, procaine, tetracaine, lidocaine, propranolol, and puromycin; calicheamicin or analogs or derivatives thereof; antimetabolites (such as methotrexate, 6-mercaptopurine, 6-thioguanine, cytarabine, fludarabin, 5-fluorouracil, decarbazine, hydroxyurea, asparaginase, gemcitabine, cladribine), alkylating agents (such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin; as well as duocarmycin A, duocarmycin SA, CC-1065 (a.k.a.

rachelmycin), or analogs or derivatives of CC-1065), dolastatin, auristatin, pyrrolo[2,1-c][1,4] benzodiazepins (PDBs), indolinobenzodiazepine (IGNs) or analogues thereof, antibiotics (such as dactinomycin (formerly actinomycin), bleomycin, daunorubicin (formerly daunomycin), doxorubicin, idarubicin, mithramycin, mitomycin, mitoxantrone, plicamycin, anthramycin (AMC)), anti-mitotic agents (e.g., tubulin-targeting agents), such as diphtheria toxin and related molecules (such as diphtheria A chain and active fragments thereof and hybrid molecules); ricin toxin (such as ricin A or a deglycosylated ricin A chain toxin), cholera toxin, a Shiga-like toxin (SLT-I, SLT-II, SLT-IIV), LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alpha-sarcin, *Aleurites fordii* proteins, dianthin proteins, *Phytolacca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, and enomycin toxins. Other suitable conjugated molecules include antimicrobial/lytic peptides such as CLIP, Magainin 2, mellitin, Cecropin, and P18; ribonuclease (RNase), DNase I, Staphylococcal enterotoxin-A, pokeweed antiviral protein, diphtherin toxin, and *Pseudomonas* endotoxin. See, for example, Pastan et al., Cell 47, 641 (1986) and Goldenberg, Calif. A Cancer Journal for Clinicians 44, 43 (1994). Therapeutic agents that may be administered in combination with anti-AXL antibodies or antibody-drug conjugates of the present invention as described elsewhere herein, such as, e.g., anti-cancer cytokines or chemokines, are also candidates for therapeutic moieties useful for conjugation to an antibody disclosed in the present invention.

The term "cytotoxic agent" as used herein, refers to any agent that is detrimental to (e.g., kills) cells. For a description of these classes of drugs which are well known in the art, and their mechanisms of action, see [54]. Additional techniques relevant to the preparation of antibody immunotoxins are provided in for instance [55] and [56].

In one embodiment, the cytotoxic agent is linked to said antibody, or fragment thereof, with a cleavable linker, such as N-succinimydyl 4-(2-pyridyldithio)-pentanoate (SSP), maleimidocaproyl-valine-citrulline-p-aminobenzyloxycarbonyl (mc-vc-PAB) or AV-1 K-lock valine-citrulline.

The term "cleavable linker" as used herein, refers to a subset of linkers that are catalyzed by specific proteases in the targeted cell or in the tumor microenvironment, resulting in release of the cytotoxic agent. Examples of cleavable linkers are linkers based on chemical motifs including disulfides, hydrazones or peptides. Another subset of cleavable linker, adds an extra linker motif between the cytotoxic agent and the primary linker, i.e. the site that attaches the linker-drug combination to the antibody. In some embodiments, the extra linker motif is cleavable by a cleavable agent that is present in the intracellular environment (e. g. within a lysosome or endosome or caveola). The linker can be, e. g. a peptidyl linker that is cleaved by an intracellular peptidase or protease enzyme, including but not limited to, a lysosomal or endosomal protease. In some embodiments, the peptidyl linker is at least two amino acids long or at least three amino acids long. Cleaving agents can include cathepsins B and D and plasmin, all of which are known to hydrolyze dipeptide drug derivatives resulting in the release of active drug inside the target cells (see e. g. Dubowchik and Walker, 1999, Pharm. Therapeutics 83:67-123). In a specific embodiment, the peptidyl linker cleavable by an intracellular protease is a Val-Cit (valine-citrulline) linker or a Phe-Lys (phenylalanine-lysine) linker (see e.g. U.S. Pat. No. 6,214,345, which describes the synthesis of doxorubicin with the Val-Cit linker). An advantage of using intracellular proteolytic release of the therapeutic agent is that the agent is typically attenuated when conjugated and the serum stabilities of the conjugates are typically high.

In another embodiment, the cytotoxic agent is linked to said antibody, or fragment thereof, with a non-cleavable linker, such as succinimidyl-4(N-maleimidomethyl)cyclohexane-1-carboxylate (MCC) or maleimidocaproyl (MC).

The term "noncleavable linker" as used herein, refers to a subset of linkers which, in contrast to cleavable linkers, do not comprise motifs that are specifically and predictably recognized by intracellular or extracellular proteases. Thus, ADCs based on non-cleavable linkers are not released or cleaved form the antibody until the complete antibody-linker-drug complex is degraded in the lysosomal compartment. Examples of a non-cleavable linker are thioethers. In yet another embodiment, the linker unit is not cleavable and the drug is released by antibody degradation (see [57]). Typically, such a linker is not substantially sensitive to the extracellular environment. As used herein, "not substantially sensitive to the extracellular environment" in the context of a linker means that no more than 20%, typically no more than about 15%, more typically no more than about 10%, and even more typically no more than about 5%, no more than about 3%, or no more than about 1% of the linkers, in a sample of antibody drug conjugate compound, are cleaved when the antibody drug conjugate compound is present in an extracellular environment (e.g. plasma). Whether a linker is not substantially sensitive to the extracellular environment can be determined for example by incubating with plasma the antibody drug conjugate compound for a predetermined time period (e.g. 2, 4, 8, 16 or 24 hours) and then quantitating the amount of free drug present in the plasma.

In one embodiment, cytotoxic agent is selected from the group: DNA-targeting agents, e.g. DNA alkylators and cross-linkers, such as calicheamicin, duocarmycin, rachelmycin (CC-1065), pyrrolo[2,1-c][1,4] benzodiazepines (PBDs), and indolinobenzodiazepine (IGN); microtubule-targeting agents, such as duostatin, such as duostatin-3, auristatin, such as monomethylauristatin E (MMAE) and monomethylauristatin F (MMAF), dolastatin, maytansine, N(2')-deacetyl-N(2')-(3-marcapto-1-oxopropyl)-maytansine (DM1), and tubulysin; and nucleoside analogs; or an analogs, derivatives, or prodrugs thereof.

In one embodiment, the immunoconjugate comprise a combination of;
i) the cytotoxic agent and said cleavable linker having bystander kill capacity;
ii) the cytotoxic agent and said cleavable linker not having bystander kill capacity;
iii) the cytotoxic agent and said non-cleavable linker having bystander kill capacity; or
iv) the cytotoxic agent and said non-cleavable linker not having bystander kill capacity.

The term "bystander killing effect", "bystander kill", "bystander kill capacity" or "bystander cytotoxicity" as used herein, refers to the effect where the cytotoxic agent that is conjugated to the antibody by either a cleavable or non-cleavable linker has the capacity to diffuse across cell membranes after the release from the antibody and thereby cause killing of neighboring cells. When the cytotoxic agent is conjugated by a cleavable or non-cleavable linker, it may be either the cytotoxic agent only or the cytotoxic agent with a part of the linker that has the bystander kill capacity. The capacity to diffuse across cell membranes is related to the hydrophobicity of the the cytotoxic agent or the combination of the cytotoxic agent and the linker. Such cytotoxic agents may advantageously be membrane-permeable toxins, such as MMAE that has been released from the antibody by proteases. Especially in tumors with heterogeneous target expression and in solid tumors where antibody penetration may be limited, a bystander killing effect may be desirable.

The term "no bystander kill capacity", "no bystander killing effect", "no-bystander kill" or "no bystander cytotoxicity" as used herein, refers to the effect where the cytotoxic agent that is conjugated to the antibody by either a cleavable or non-cleavable linker does not have the capacity to diffuse across cell membranes after release from the antibody. Thus, such cytotoxic agents or combinations of the cytotoxic agent with the linker, will not be able to kill neighboring cells upon release from the antibody. It is believed without being bound by theory, that such combinations of a cytotoxic agent and either a cleavable or non-cleavable linker will only kill cells expressing the target that the antibody binds.

A stable link between the antibody and cytotoxic agent is an important factor of an ADC. Both cleavable and non-cleavable types of linkers have been proven to be safe in preclinical and clinical trials.

of the mitotic spindle, resulting in mitotic arrest and apoptosis. The microtubule-targeting agents can be derived from e.g. natural substances such as plant alkaloids, and prevent cells from undergoing mitosis by disrupting or stabilizing microtubule polymerization, thus preventing formation of the mitotic spindle and subsequent cell division, resulting in inhibition of cancerous growth. Examples of microtubule-targeting agents are paclitaxel, docetaxel, vinblastine, vincristine, vinorelbine, duostatins, auristatins, maytansanoids, tubulysins, and dolastatin.

In one embodiment, the cytotoxic agent is auristatins or auristatin peptide analogs and derivates ([131]; [132]). Auristatins have been shown to interfere with microtubule dynamics, GTP hydrolysis and nuclear and cellular division [133] and have anti-cancer [134] and anti-fungal activity [135]. The auristatin drug moiety may be attached to the antibody via a linker, through the N (amino) terminus or the C (terminus) of the peptidic drug moiety.

Exemplary auristatin embodiments include the N-terminus-linked monomethyl auristatin drug moieties DE and DF, disclosed in [136] and described in [137].

In a particular embodiment, the cytotoxic agent is monomethyl auristatin E (MMAE);

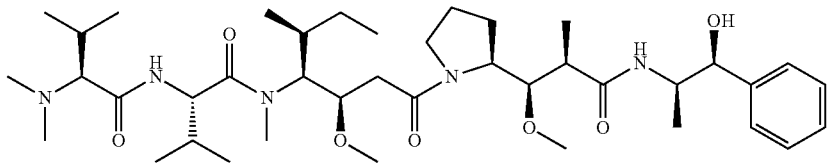 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C)C(C)C]

In one embodiment, the cytotoxic agent is chosen from the group of microtubule targeting agents, such as auristatins and maytansinoids.

The term "microtubule-targeting agent" as used herein, refers to an agent or drug which inhibits mitosis (cell division). Microtubules are structures that are essential for proper separation of DNA during cell division, and microtubule function critically depends on 'dynamic instability', i.e. the process in which microtubule structures are continuously elongated and shortened. Microtubule-targeting agents disrupt or stabilize microtubules, which prevents formation wherein the antibody is linked to MMAE at the nitrogen (N) on the left-hand side of the chemical structure above by the appropriate linker.

In one embodiment, the cytotoxic agent monomethyl auristatin E (MMAE) is linked to the antibody via a valine-citrulline (VC) linker.

In another embodiment, the cytotoxic agent monomethyl auristatin E (MMAE) is linked to the antibody via a valine-citrulline (VC) linker and the maleimidocaproyl (MC)linker, wherein the combination of the cytotoxic agent and the linkers has the chemical structure;

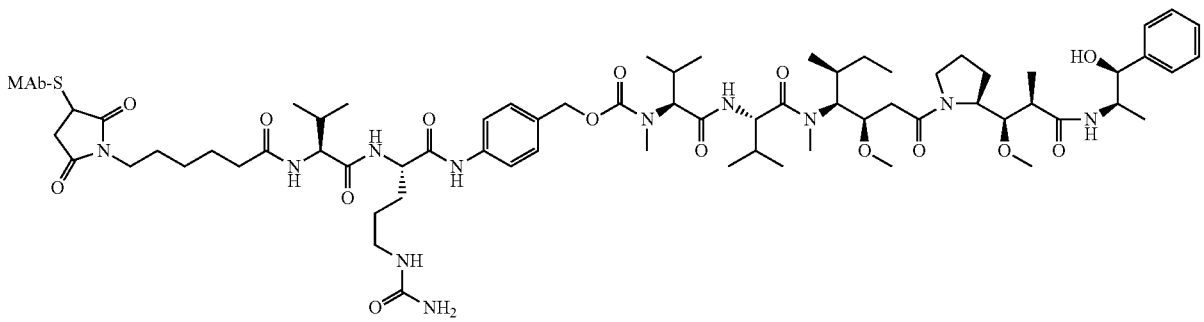

wherein MAb is the antibody.

In one embodiment, the cytotoxic agent is monomethyl auristatin F (MMAF);

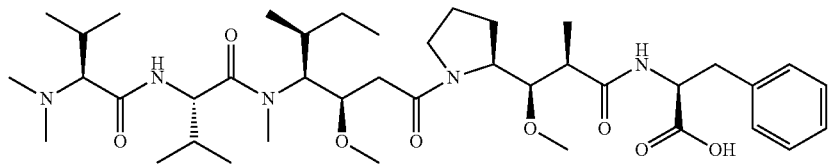 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)C)C(C)C]

wherein the antibody is linked to MMAF at the nitrogen (N) on the left-hand side of the chemical structure above by the appropriate linker.

In one embodiment, the cytotoxic agent monomethyl auristatin F (MMAF) is linked to the antibody via a maleimidocaproyl (mc)-linker, wherein the combination of the cytotoxic agent and linker has the chemical structure;

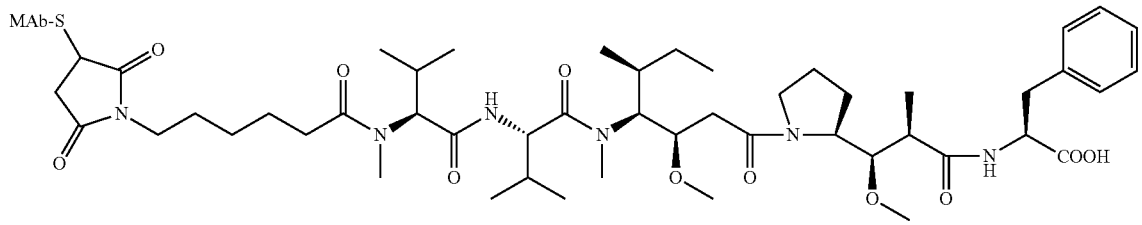

wherein MAb is the antibody.

In one embodiment, the cytotoxic agent is duostatin3.

In another particular embodiment, the cytotoxic agent is a DNA-targeting agent.

The term "DNA-acting agent" as used herein, refers to a specific class of cytotoxic agents which are able to alkylate and/or cross-link DNA. An example of such a DNA-acting agent is IGN agents comprising indolino-benzodiazepinedimers and pyrrolo[2,1-c][1,4]benzodiazepines (PBDs) which are highly potent by virtue of their ability to alkylate and cross-link DNA. Another example is IGN agents comprising indolino-benzodiazepinemonomers which are highly potent by virtue of the ability to alkylate only DNA. Duocarmycins are another class of DNA-acting agents. Duocarmycins are small-molecule, synthetic DNA minor groove binding alkylating agents. These compounds are suitable to target solid tumors as well as hematological tumors.

In one embodiment, the immunoconjugate comprises two to four cytotoxic molecules per antibody. Depending on the chemical properties of the toxin and the linker-toxin combination, two to four cytotoxic molecules per antibody may be superior to more heavily loaded conjugates that are cleared more rapidly from the circulation than less loaded conjugates. The cytotoxic agent loading is represented by p and is the average number of cytotoxic agent moieties per antibody in a molecule (also designated as the drug to antibody ratio, DAR). The cytotoxic agent loading may range from 1 to 20 drug moieties per antibody and may occur on amino acids with useful functional groups such as, but not limited to, amino or sulfhydryl groups, as in lysine or cysteine.

In one embodiment, the number of cytotoxic agents per antibody is from 1 to 8, such as 2 to 7, such as 2 to 6, such as 2 to 5, such as 2 to 4, and such as 2 to 3.

In another embodiment, the immunoconjugate comprises four to eight cytotoxic molecules per antibody. In another embodiment, the immunoconjugate comprises six to ten cytotoxic molecules per antibody. In yet another embodiment, the immunoconjugate comprises 10 to 30, such as 15 to 25, such as 20, cytotoxic molecules per antibody.

Depending on the way of conjugation, p may be limited by the number of attachment sites on the antibody, for example where the attachment is a cysteine thiol or a lysine. Generally, antibodies do not contain many free and reactive cysteine thiol groups which may be linked to a drug moiety as most cysteine thiol residues in antibodies exist as disulfide bridges. Therefore, in those embodiments, where the cytotoxic agent is conjugated via a cysteine thiol, the antibody may be reduced with reducing agent such as dithiothreitol (DTT) or tricarbonylethylphosphine (TCEP), under partial or fully reducing conditions, to generate reactive cysteine thiol groups. In certain embodiments, the drug loading for an ADC of the invention ranges from 1 to about 8, as a maximum of 8 free cysteine thiol groups becomes available after (partial) reduction of the antibody (there are 8 cysteines involved in inter-chain disulfide bonding).

In one embodiment, the drug linker moiety is vcMMAE. The vcMMAE drug linker moiety and conjugation methods are disclosed in [27]; [28]; [145], [146]; and [147], (which are incorporated herein by reference) vcMMAE is form by conjugation of the linker mc-vc-PAB and the cytotoxic moiety MMAE, and the vcMMAE drug linker moiety is bound to the anti-AXL antibodies at the cysteine residues using a method similar to those disclosed therein.

In one embodiment, the drug linker moiety is mcMMAF. The mcMMAF drug linker moiety and conjugation methods are disclosed in [138]; [139], and [140] (which are incorporated herein by reference), and the mcMMAF drug linker moiety is bound to the anti-AXL antibodies at the cysteine residues using a method similar to those disclosed therein.

In one embodiment, the cytotoxic agent is linked to 1 or 2 lysines within the antibody amino acid sequence by K-Lock™ conjugation as described in [58], [148], and [149], and the duostatin3 (also known as Duo3) is bound to the anti-AXL antibodies at the lysine residues using a method similar to those described therein.

Other linker technologies may be used in the anti-AXL antibody drug conjugates of the invention, such as linkers comprising a hydroxyl group.

In one embodiment, the linker is attached to free cysteine residues of the anti-AXL antibody obtained by (partial) reduction of the anti-AXL antibody.

In a particular embodiment, the linker is mc-vc-PAB and the cytotoxic agent is MMAE; or the linker SSP and the cytotoxic agent is DM1.

In a particular embodiment, the linker is MMC and the cytotoxic agent is DM1; or the linker is MC and the cytotoxic agent is MMAF.

In a particular embodiment, the linker is the cleavable linker AV1-K lock and the cytotoxic agent is duostatin3.

In one embodiment the immunoconjugate comprises the linker mc-vc-PAB, the cytotoxic agent MMAE and an antibody wherein the at least one binding region comprises a VH region and a VL region selected from the group consisting of;
- a) a VH region comprising SEQ ID No: 1 and a VL region comprising SEQ ID No: 2 [107];
- b) a VH region comprising SEQ ID No: 5 and a VL region comprising SEQ ID No: 6 [148];
- c) a VH region comprising SEQ ID No: 34 and a VL region comprising SEQ ID No: 35 [733]
- d) a VH region comprising SEQ ID No: 7 and a VL region comprising SEQ ID No: 9 [154];
- e) a VH region comprising SEQ ID No: 10 and a VL region comprising SEQ ID No: 11 [171];
- f) a VH region comprising SEQ ID No: 16 and a VL region comprising SEQ ID No: 18 [183];
- g) a VH region comprising SEQ ID No: 25 and a VL region comprising SEQ ID No: 26 [613];
- h) a VH region comprising SEQ ID No: 31 and a VL region comprising SEQ ID No: 33 [726];
- i) a VH region comprising SEQ ID No: 3 and a VL region comprising SEQ ID No: 4 [140];
- j) a VH region comprising SEQ ID No:8 and a VL region comprising SEQ ID No:9 [154-M103L];
- k) a VH region comprising SEQ ID No:12 and a VL region comprising SEQ ID No:13 [172];
- l) a VH region comprising SEQ ID No:14 and a VL region comprising SEQ ID No:15 [181];
- m) a VH region comprising SEQ ID No:17 and a VL region comprising SEQ ID No:18 [183-N52Q];
- n) a VH region comprising SEQ ID No:19 and a VL region comprising SEQ ID No:20 [187];
- o) a VH region comprising SEQ ID No:21 and a VL region comprising SEQ ID No:22 [608-01];
- p) a VH region comprising SEQ ID No:23 and a VL region comprising SEQ ID No:24 [610-01];
- q) a VH region comprising SEQ ID No:27 and a VL region comprising SEQ ID No:28 [613-08];
- r) a VH region comprising SEQ ID No:29 and a VL region comprising SEQ ID No:30 [620-06]; and
- s) a VH region comprising SEQ ID No:32 and a VL region comprising SEQ ID No:33 [726-M101L].

In another alternative embodiment, an anti-AXL antibody drug conjugate disclosed in the present invention comprises a conjugated nucleic acid or nucleic acid-associated molecule. In one such embodiment, the conjugated nucleic acid is a cytotoxic ribonuclease, an antisense nucleic acid, an inhibitory RNA molecule (e.g., a siRNA molecule) or an immunostimulatory nucleic acid (e.g., an immunostimulatory CpG motif-containing DNA molecule).

In another alternative embodiment, an anti-AXL antibody of the invention is conjugated to an aptamer or a ribozyme or a functional peptide analog or derivate thereof.

In another alternative embodiment, anti-AXL antibody drug conjugates comprising one or more radiolabeled amino acids are provided. A radiolabeled anti-AXL antibody may be used for both diagnostic and therapeutic purposes (conjugation to radiolabeled molecules is another possible feature). Non-limiting examples of labels for polypeptides include $^3$H, $^{14}$C, $^{15}$N, $^{35}$S, $^{90}$Y, $^{99}$Tc, and $^{125}$I, $^{131}$I, and $^{186}$Re. Methods for preparing radiolabeled amino acids and related peptide derivatives are known in the art (see for instance [59] and [60], [61], [62], [63], [64] and [65]U.S. Pat. No. 5,697,902. For example, a radioisotope may be conjugated by a chloramine T method.

In one embodiment, the antibody is conjugated to a radioisotope or to a radioisotope-containing chelate. For example, the antibody can be conjugated to a chelator linker, e.g. DOTA, DTPA or tiuxetan, which allows for the antibody to be complexed with a radioisotope. The antibody may also or alternatively comprise or be conjugated to one or more radiolabeled amino acids or other radiolabeled molecules. A radiolabeled anti-AXL antibody may be used for both diagnostic and therapeutic purposes. Non-limiting examples of radioisotopes include $^3$H, $^{14}$C, $^{15}$N, $^{35}$S, $^{90}$Y, $^{99}$Tc, $^{125}$I, $^{111}$In, $^{131}$I, $^{186}$Re, $^{213}$Bs, $^{225}$Ac and $^{227}$Th.

Anti-AXL antibodies may also be chemically modified by covalent conjugation to a polymer to for instance increase their circulating half-life. Exemplary polymers, and methods to attach them to peptides, are illustrated in for instance [66]; [67]; [68]; and [69]. Additional polymers include polyoxyethylated polyols and polyethylene glycol (PEG) (e.g., a PEG with a molecular weight of between about 1,000 and about 40,000, such as between about 2,000 and about 20,000). This may for example be used if the anti-AXL antibody is a fragment.

Any method known in the art for conjugating the anti-AXL antibody according to the present invention to the conjugated molecule(s), such as those described above, may be employed, including the methods described by [70], [71] and [72]. Such antibodies may be produced by chemically conjugating the other moiety to the N-terminal side or C-terminal side of the anti-AXL antibody (e.g., an anti-AXL antibody H or L chain) (see, e.g., [73]). Such conjugated antibody derivatives may also be generated by conjugation at internal residues or sugars, or non-naturally occurring amino acids or additional amino acids that have been introduced into the antibody constant domain, where appropriate.

The agents may be coupled either directly or indirectly to an anti-AXL antibody disclosed in the present invention. One example of indirect coupling of a second agent is coupling via a spacer moiety to cysteine or lysine residues in the antibody. In one embodiment, an anti-AXL antibody is conjugated, via a spacer or linker, to a prodrug molecule that can be activated in vivo to a therapeutic drug. After administration, the spacers or linkers are cleaved by tumor cell-associated enzymes or other tumor-specific conditions, by which the active drug is formed. Examples of such pro-drug technologies and linkers are described in [74], [75], [76], [77], [78] and [79] (all incorporated herein by reference) Suitable antibody-pro-drug technology and duocarmycin analogs can also be found in [80] (incorporated herein by reference).

In one embodiment, the anti-AXL antibody of the present invention is attached to a chelator linker, e.g. tiuxetan, which allows for the antibody to be conjugated to a radioisotope.

Compositions

In a further aspect, the invention relates to a composition comprising the antibody, the bispecific antibody, or the immunoconjugate of the invention.

In another aspect, the invention relates to a pharmaceutical composition comprising the antibody, bispecific or immunoconjugate according to the invention and a pharmaceutical carrier.

The pharmaceutical compositions may be formulated with pharmaceutically acceptable carriers or diluents as well as any other known adjuvants and excipients in accordance with conventional techniques such as those disclosed in [81].

The pharmaceutically acceptable carriers or diluents as well as any other known adjuvants and excipients should be suitable for the antibody or antibody conjugate of the present invention and the chosen mode of administration. Suitability for carriers and other components of pharmaceutical compositions is determined based on the lack of significant negative impact on the desired biological properties of the chosen compound or pharmaceutical composition of the present invention (e.g., less than a substantial impact (10% or less relative inhibition, 5% or less relative inhibition, etc.) upon antigen binding).

A pharmaceutical composition of the present invention may also include diluents, fillers, salts, buffers, detergents (e.g., a nonionic detergent, such as Tween-20 or Tween-80), stabilizers (e.g., sugars or protein-free amino acids), preservatives, tissue fixatives, solubilizers, and/or other materials suitable for inclusion in a pharmaceutical composition.

The actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical composition may be administered by any suitable route and mode. Suitable routes of administering a compound of the present invention in vivo and in vitro are well known in the art and may be selected by those of ordinary skill in the art.

In one embodiment, the pharmaceutical composition of the present invention is administered parenterally.

The terms "parenteral administration" and "administered parenterally" as used herein refers to modes of administration other than enteral and topical administration, usually by injection, and include epidermal, intravenous, intramuscular, intra-arterial, intrathecal, intracapsular, intra-orbital, intracardiac, intradermal, intraperitoneal, intratendinous, transtracheal, subcutaneous, subcuticular, intra-articular, subcapsular, subarachnoid, intraspinal, intracranial, intrathoracic, epidural and intrasternal injection and infusion.

In one embodiment, the pharmaceutical composition of the present invention is administered by intravenous or subcutaneous injection or infusion.

Pharmaceutically acceptable carriers include any and all suitable solvents, dispersion media, coatings, antibacterial and antifungal agents, isotonicity agents, antioxidants and absorption-delaying agents, and the like that are physiologically compatible with a compound of the present invention.

Examples of suitable aqueous and non-aqueous carriers which may be employed in the pharmaceutical compositions of the present invention include water, saline, phosphate-buffered saline, ethanol, dextrose, polyols (such as glycerol, propylene glycol, polyethylene glycol, and the like), and suitable mixtures thereof, vegetable oils, such as olive oil, corn oil, peanut oil, cottonseed oil, and sesame oil, carboxymethyl cellulose colloidal solutions, tragacanth gum and injectable organic esters, such as ethyl oleate, and/or various buffers. Other carriers are well known in the pharmaceutical arts.

Pharmaceutically acceptable carriers include sterile aqueous solutions or dispersions and sterile powders for the extemporaneous preparation of sterile injectable solutions or dispersion.

The use of such media and agents for pharmaceutically active substances is known in the art. Except insofar as any conventional media or agent is incompatible with the active compound, use thereof in the pharmaceutical compositions of the present invention is contemplated.

Proper fluidity may be maintained, for example, by the use of coating materials, such as lecithin, by the maintenance of the required particle size in the case of dispersions, and by the use of surfactants.

Pharmaceutical compositions of the present invention may also comprise pharmaceutically acceptable antioxidants for instance (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Pharmaceutical compositions of the present invention may also comprise isotonicity agents, such as sugars, polyalcohols, such as mannitol, sorbitol, glycerol or sodium chloride in the compositions.

The pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The compounds of the present invention may be prepared with carriers that will protect the compound against rapid release, such as a controlled release formulation, including implants, transdermal patches, and micro-encapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, poly-ortho-esters, and polylactic acid alone or with a wax, or other materials well known in the art. Methods for the preparation of such formulations are generally known to those skilled in the art. See e.g., [82].

In one embodiment, the compounds of the present invention may be formulated to ensure proper distribution in vivo. Pharmaceutically acceptable carriers for parenteral administration include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated. Other active or therapeutic compounds may also be incorporated into the compositions.

Pharmaceutical compositions for injection must typically be sterile and stable under the conditions of manufacture and storage. The composition may be formulated as a solution, micro-emulsion, liposome, or other ordered structure suitable to high drug concentration. The carrier may be an aqueous or a non-aqueous solvent or dispersion medium containing for instance water, ethanol, polyols (such as glycerol, propylene glycol, polyethylene glycol, and the like), and suitable mixtures thereof, vegetable oils, such as olive oil, and injectable organic esters, such as ethyl oleate. The proper fluidity may be maintained, for example, by the use of a coating such as lecithin, by the maintenance of the required particle size in the case of dispersion and by the use of surfactants. In many cases, it will be preferable to include isotonic agents, for example, sugars, polyalcohols such as glycerol, mannitol, sorbitol, or sodium chloride in the composition. Prolonged absorption of the injectable compositions may be brought about by including in the composition an agent that delays absorption, for example, monostearate salts and gelatin. Sterile injectable solutions may be prepared by incorporating the active compound in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, examples of methods of preparation are vacuum-drying and freeze-drying (lyophilization) that yield a powder of the active ingredient plus any additional desired ingredient from a previously sterile-filtered solution thereof.

Sterile injectable solutions may be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, examples of methods of preparation are vacuum-drying and freeze-drying (lyophilization) that yield a powder of the active ingredient plus any additional desired ingredient from a previously sterile-filtered solution thereof.

The pharmaceutical composition of the present invention may contain one antibody, bispecific antibody or ADC of the present invention, a combination of an antibody, a bispecific antibody or ADC according to the invention with another therapeutic compound, or a combination of compounds of the present invention.

Nucleic Acid Constructs, Expression Vectors, and Host Cells

In one aspect, the present invention relates to a nucleic acid construct encoding one or more sequences set out in Table 1. Thus, the present invention relates to nucleic acid constructs encoding any one of the sequences set out in SEQ ID Nos.: 1 to 135. In one embodiment, the nucleic acid construct encodes at least one of the amino acid sequence selected from the group consisting of SEQ ID Nos.: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, and 135. Thus, in one embodiment, the nucleic acid construct encodes an antibody according to any aspect or embodiment herein described.

In a particular embodiment, the nucleic acid construct encodes at least one of the amino acid sequences selected from the group consisting of SEQ ID Nos.: 46, 47, 48, 49, 50, 36, 37, 38, 39, 40, 114, 115, 116, 117, and 118.

In a further aspect, the invention relates to an expression vector encoding an antibody of the invention. Thus, the expression vector comprises one or more nucleic acid constructs according to any aspect or embodiment herein described. Such expression vectors may in one embodiment be used to express the anti-AXL antibody of the present invention. The expressed anti-AXL antibody may subsequently be conjugated to a moiety as described herein. In another embodiment the anti-AXL antibody may subsequently be used to generate a bispecific antibody as described herein.

In one embodiment, the expression vector of the invention comprises a nucleic acid sequence encoding one or more of the heavy chain (VH) CDR3 amino acid sequences selected from the group consisting of: SEQ ID Nos.: 38, 43, 48, 53, 54, 59, 64, 69, 75, 80, 85, 90, 95, 100, 105, 110, 111, 116, 120, 122, 125, and 127.

In a particular embodiment, the expression vector of the invention comprises a nucleic acid sequence encoding one or more of the VH CDR1, CDR2, and CDR3 amino acid sequences selected from the group consisting of: SEQ ID Nos.: 36-38, 41-43, 46-48, 51-54, 57-59, 62-64, 67-69, 72-75, 78-80, 83-85, 88-90, 93-95, 98-100, 103-105, 108-110, and 114-116.

In one embodiment, the expression vector of the invention comprises a nucleic acid sequence encoding one or more of the light chain (VL) CDR3 amino acid sequences selected from the group consisting of: SEQ ID Nos.: 40, 45, 50, 56, 61, 66, 71, 77, 82, 87, 92, 97, 102, 107, 113, and 118.

In another particular embodiment, the expression vector of the invention comprises a nucleic acid sequence encoding one or more of the VH amino acid sequences selected from the group consisting of: SEQ ID Nos.: 1, 3, 5, 7, 8, 10, 12, 14, 16, 17, 19, 21, 23, 25, 27, 29, 31, 32, and 34.

In another particular embodiment, the expression vector of the invention comprises a nucleic acid sequence encoding one or more of the VL amino acid sequences selected from the group consisting of: SEQ ID Nos.: 2, 4, 6, 9, 11, 13, 15, 18, 20, 22, 24, 26, 28, 30, 33, and 35.

In one embodiment, the expression vector of the invention comprises a nucleic acid sequence encoding one or more of the amino acid sequences selected from the group consisting of: SEQ ID Nos.: 1 to 35.

In a particular embodiment, the expression vector of the invention comprises a nucleic acid sequence encoding variants of one or more of the above amino acid sequences, said variants having at most 25 amino acid modifications, such as 20, such as at most 15, 14, 13, 12, or 11 amino acid modifications, such as 10, 9, 8, 7, 6, 5, 4, 3, 2, or 1 amino acid modifications, such as deletions or insertions, preferably substitutions, such as conservative or non-conservative substitutions, or at least 80% identity to any of said sequences, such as at least 85% identity or 90% identity or 95% identity, such as 96% identity or 97% identity or 98% identity or 99% identity to any of the aforementioned amino acid sequences. The present invention also relates to nucleic acid sequences different from the above mentioned nucleic acid sequences but which due to the variance of the genetic code encode the same amino acid sequence as an antibody of the present invention. E.g. the nucleic acid sequence may vary but result in an identical amino acid sequence as any amino acid sequence herein described. It is well-known for the skilled person how to identify such further nucleic acid sequences based on the genetic code.

In a further embodiment, the expression vector further comprises a nucleic acid sequence encoding the constant region of a light chain, a heavy chain or both light and heavy chains of an antibody, e.g. a human IgG1, κ monoclonal antibody.

Such expression vectors as described above may be used for recombinant production of antibodies of the invention.

An expression vector in the context of the present invention may be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, an anti-AXL antibody-encoding nucleic acid is comprised in a naked DNA or RNA vector, including, for example, a linear expression element (as described in for instance [83]), a compacted nucleic acid vector (as described in for instance [84] and/or [85]), a plasmid vector such as pBR322, pUC 19/18, or pUC 118/119, a "midge" minimally-sized nucleic acid vector (as described in for instance [86]), or as a precipitated nucleic acid vector construct, such as a CaP04-precipitated construct (as described in for instance [87], [88], [89], and [90]). Such nucleic acid vectors and the usage thereof are well known in the art (see for instance [91] and [92]).

In one embodiment, the vector is suitable for expression of the anti-AXL antibody in a bacterial cell. Examples of such vectors include expression vectors such as BlueScript (Stratagene), pIN vectors ([93], pET vectors (Novagen, Madison Wis.) and the like).

An expression vector may also or alternatively be a vector suitable for expression in a yeast system. Any vector suitable for expression in a yeast system may be employed. Suitable vectors include, for example, vectors comprising constitutive or inducible promoters such as alpha factor, alcohol oxidase and PGH (reviewed in: [94], and [95]).

A nucleic acid construct and/or vector may also comprises a nucleic acid sequence encoding a secretion/localization sequence, which can target a polypeptide, such as a nascent polypeptide chain, to the periplasmic space or into cell culture media. Such sequences are known in the art, and include secretion leader or signal peptides, organelle targeting sequences (e. g., nuclear localization sequences, ER retention signals, mitochondrial transit sequences, chloroplast transit sequences), membrane localization/anchor sequences (e. g., stop transfer sequences, GPI anchor sequences), and the like.

In an expression vector of the invention, anti-AXL antibody-encoding nucleic acids may comprise or be associated with any suitable promoter, enhancer, and other expression-facilitating elements. Examples of such elements include strong expression promoters (e. g., human CMV IE promoter/enhancer as well as RSV, SV40, SL3-3, MMTV, and HIV LTR promoters), effective poly (A) termination sequences, an origin of replication for plasmid product in *E. coli*, an antibiotic resistance gene as selectable marker, and/or a convenient cloning site (e.g., a polylinker). Nucleic acids may also comprise an inducible promoter as opposed to a constitutive promoter such as CMV IE (the skilled artisan will recognize that such terms are actually descriptors of a degree of gene expression under certain conditions).

In one embodiment, the anti-AXL-antibody-encoding expression vector may be positioned in and/or delivered to the host cell or host animal via a viral vector.

In an even further aspect, the invention relates to a recombinant eukaryotic or prokaryotic host cell, such as a transfectoma, which produces an anti-AXL antibody of the invention as defined herein or a bispecific molecule of the invention as defined herein. Examples of host cells include yeast, bacterial and mammalian cells, such as CHO or HEK cells or derivatives thereof. For example, in one embodiment, the present invention provides a cell comprising a nucleic acid stably integrated into the cellular genome that comprises a sequence coding for expression of an anti-AXL antibody of the present invention. In another embodiment, the present invention provides a cell comprising a non-integrated nucleic acid, such as a plasmid, cosmid, phagemid, or linear expression element, which comprises a sequence coding for expression of an anti-AXL antibody of the invention.

In a further aspect, the present invention relates to a host cell comprising a vector according to any aspect and embodiments herein described. In one embodiment, the anti-AXL antibodies described herein are provided by use of recombinant eukaryotic, prokaryotic or microbial host cell which produces the antibody. Accordingly, the invention provides a recombinant host cell, such as a recombinant prokaryotic, recombinant eukaryotic, or recombinant microbial host cell. Examples of host cells include yeast, bacterial and mammalian cells, such as CHO or HEK-293 cells. For example, in one embodiment, the host cell comprises a nucleic acid stably integrated into the cellular genome that comprises a sequence coding for expression of an anti-AXL antibody described herein. In one embodiment, the host cell comprises a nucleic acid stably integrated into the cellular genome that comprise a sequence coding for expression of a first or a second polypeptide described herein. In another embodiment, the host cell comprises a non-integrated nucleic acid, such as a plasmid, cosmid, phagemid, or linear expression element, which comprises a sequence coding for expression of an anti-AXL antibody, a first or a second polypeptide described herein.

The term "recombinant host cell" (or simply "host cell"), as used herein, is intended to refer to a cell into which an expression vector has been introduced. It should be understood that such terms are intended to refer not only to the particular subject cell, but also to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, transfectomas, such as CHO cells, HEK-293 cells, PER.C6, NS0 cells, and lymphocytic cells, and prokaryotic cells such as *E. coli* and other eukaryotic hosts such as plant cells and fungi.

The term "transfectoma", as used herein, includes recombinant eukaryotic host cells expressing the antibody or a target antigen, such as CHO cells, PER.C6, NS0 cells, HEK-293 cells, plant cells, or fungi, including yeast cells.

In another aspect, the present invention relates to a hybridoma which produces an antibody according to any aspect or embodiment herein described. Thus, an antibody may be obtained from hybridomas prepared from murine splenic B cells obtained from mice immunized with an antigen of interest, for instance in form of cells expressing the antigen on the surface, or a nucleic acid encoding an antigen of interest. Monoclonal antibodies may also be obtained from hybridomas derived from antibody-expressing cells of immunized humans or non-human mammals such as rabbits, rats, dogs, primates, etc.

Human antibodies may be generated using transgenic or transchromosomal mice, e.g. HuMAb mice, carrying parts of the human immune system rather than the mouse system. The HuMAb mouse contains a human immunoglobulin gene minilocus that encodes unrearranged human heavy (μ and γ) and κ light chain immunoglobulin sequences, together with targeted mutations that inactivate the endogenous μ and κ chain loci [96]. Accordingly, the mice exhibit reduced expression of mouse IgM or κ and in response to immunization, the introduced human heavy and light chain transgenes, undergo class switching and somatic mutation to generate high affinity human IgG,κ monoclonal antibodies [96], [97], [98] and [99]. The preparation of HuMAb mice is described in detail in [100], [101], [102], [103], and [104]. See also [105] to [121]. Splenocytes from these transgenic mice may be used to generate hybridomas that secrete human monoclonal antibodies according to well-known techniques.

Further, human antibodies of the present invention or antibodies of the present invention from other species may be identified through display-type technologies, including, without limitation, phage display, retroviral display, ribosomal display, mammalian display, yeast display and other techniques known in the art, and the resulting molecules may be subjected to additional maturation, such as affinity maturation, as such techniques are well known in the art.

Thus, in one aspect, the present invention relates to a method for producing an antibody according to any aspect or embodiment herein described, comprising the steps
  a) culturing a host cell or hybridoma according to any aspect or embodiment herein described; and
  b) purifying the antibody from the culture media.

Therapeutic Applications

In another aspect, the invention relates to the antibody, bispecific antibody, or immunoconjugate or ADC of the present invention, as defined in any aspect or embodiment herein, for use as a medicament.

The anti-AXL antibodies of the present invention can be used in the treatment or prevention of disorders involving cells expressing AXL. For example, the antibodies may be administered to cells in culture, e.g., in vitro or ex vivo, or to human subjects, e.g., in vivo, to treat or prevent disorders involving AXL-expressing cells. As used herein, the term "subject" is typically a human to whom the anti-AXL antibody or ADC is administered. Subjects may for instance include human patients having disorders that may be corrected or ameliorated by modulating AXL function or by killing of the AXL-expressing cell, directly or indirectly.

In one aspect, the present invention relates to the antibody, bispecific antibody, or immunoconjugate of the present invention, as defined in any aspect or embodiment herein, for use in the treatment of cancer.

In one aspect, the invention provides a method for modulating AXL-associated signaling in an AXL-expressing cell by contacting the cell with an anti-AXL antibody or ADC according to any aspect or embodiment herein described.

In one embodiment, the invention provides a method for killing an AXL-expressing cell by contacting the cell with an anti-AXL antibody or ADC of the invention. Without being limited to theory, antibody-mediated or ADC-mediated crosslinking or clustering (e.g., due to the Fc-region of AXL-bound antibodies binding to FcR-expressing cells) of AXL molecules on the surface of a cell can lead to apoptosis of the cell.

In one embodiment, the invention provides a method for killing an AXL-expressing cell by contacting the cell with an AXL-specific antibody or ADC of the invention in the presence of effector cells capable of inducing an Fc-dependent cellular response such as ADCC or ADCP. In this embodiment, the antibody is typically full-length and of an isotype leading to an ADCC or ADCP response, such as, e.g., an IgG1,κ isotype.

In one embodiment, the invention provides a method for killing an AXL-expressing cell by contacting the cell with an AXL-specific antibody or ADC of the invention in the presence of complement proteins, such as complement proteins present in normal human serum, that may be activated and thereby inducing CDC after binding of AXL-specific antibody or ADC to the plasma membrane of AXL-expressing cells. In this embodiment, the antibody is typically full-length and of an isotype capable of inducing activation of the complement system, such as, e.g., an IgG1,κ isotype.

The anti-AXL antibodies of the invention may be characterized by internalization upon binding to AXL, making them suitable for an ADC approach using an ADC as described in any aspect or embodiment described herein.

Accordingly, in one embodiment, the invention provides a method for killing an AXL-expressing cell by contacting the cell with an ADC of the invention which requires internalization and trafficking to lysosomes for specific (i.e. cleavable linker) or non-specific (non-cleavable linker) proteolytic cleavage of the anti-AXL antibody-linker-drug complex.

In one embodiment, the present invention relates to a method for interfering with AXL-mediated regulation of the innate or adaptive immune response, such as by binding of an AXL-specific antibody or ADC according to the invention to AXL-expressing macrophages, dendritic cells or NK cells.

In another embodiment, the invention provides for a method of killing an AXL-expressing cell by contacting the cell with an ADC of the invention wherein the anti-AXL antibody is linked to a therapeutic moiety via a linker allowing for release of the drug once the ADC is internalized, e.g., by a change in pH or reducing conditions. Suitable linker technology is known in the art, as described above.

In another aspect, the present invention provides methods for treating or preventing a disorder involving cells expressing AXL in a subject, which method comprises administration of a therapeutically effective amount of an anti-AXL antibody, bispecific antibody or ADC of the present invention to a subject in need thereof. The method typically involves administering to a subject an anti-AXL antibody, a bispecific antibody or ADC according to the present invention in an amount effective to treat or prevent the disorder.

In a particular aspect, an anti-AXL antibody or ADC is administered prophylactically in order to reduce the risk of developing cancer, delay the onset of an event in cancer progression or reduce the risk of recurrence when a cancer is in remission and/or a primary tumor has been surgically removed. In the latter case, the anti-AXL antibody could, for example, be administered in association with (i.e., before, during, or after) the surgery. Prophylactic administration may also be useful in patients wherein it is difficult to locate a tumor that is believed to be present due to other biological factors.

Cells with high AXL expression, such as over-expression or aberrant expression of AXL, as found in some cancer cells, are particularly good targets for the anti-AXL antibodies, bispecific antibodies or ADCs of the invention, since more antibodies or ADCs may be bound per tumor cell.

Tissues that heterogeneously express AXL such as tumor tissue may also be a suitable target for the anti-AXL antibodies, bispecific antibodies, ADCs or anti-AXL-ADCs of the invention. Thus, in one aspect, the disorder involving cells expressing AXL is cancer, i.e., a tumorigenic disorder, such as a disorder characterized by the presence of tumor cells expressing AXL including, for example, disorders where the cells are from a solid tumor or hematological tumor. AXL expression has been described in, e.g., non-small-cell lung cancer (NSCLC; [122]), pancreatic cancer [123], esophageal cancer [124], endometrial cancer [125].

Exemplary cells expressing AXL thus include cancer cells such as, e.g., cells from non-small cell lung cancer, pancreatic cancer and esophageal cancer.

In one aspect, the present invention provides methods for treating or preventing cancer comprising administering the antibody, the bispecific antibody, the immunoconjugate, the composition, or the pharmaceutical composition according to the present invention to a subject in need thereof.

In one embodiment, the cancer is a solid tumor expressing AXL or an AXL-expressing hematological cancer. In one embodiment, the hematological cancer is Acute Myeloid Leukemia (AML). In one embodiment, the solid tumor expressing AXL is lung cancer or epidermoid carcinoma.

Thus, the present invention relates to methods comprising administration of a therapeutically effective amount of an anti-AXL antibody or ADC of the present invention to a subject in need thereof.

In one aspect, the present invention relates to a method for inhibiting growth and/or proliferation of a tumor cell expressing AXL, comprising administration, to an individual in need thereof, of an antibody, bispecific antibody, immunoconjugate, composition, or pharmaceutical composition according to any aspect or embodiment herein described.

In one aspect, the present invention relates to a method for inhibiting migration and/or invasion of a tumor cell expressing AXL, comprising administration, to an individual in need thereof, of an antibody, bispecific antibody, immunoconjugate, composition, or pharmaceutical composition according to any aspect or embodiment herein described.

In one aspect, the present invention relates to a method for inhibiting resistance to targeted therapy, such as EGFR- or BRAF-targeted therapy, or to chemotherapeutic agents, comprising administration, to an individual in need thereof, of an antibody, bispecific antibody, immunoconjugate, composition, or pharmaceutical composition according to any aspect or embodiment herein described.

In one aspect, the present invention relates to a method for targeting or inhibiting tumor-associated macrophages, comprising administration, to an individual in need thereof, of an antibody, bispecific antibody, immunoconjugate, composition, or pharmaceutical composition according to any aspect or embodiment herein described.

In one aspect, the present invention provides methods for treating or preventing a solid tumor, which method comprises administration of a therapeutically effective amount of an anti-AXL antibody or ADC of the present invention to a subject in need thereof, and wherein the solid tumor is a melanoma, carcinoma, sarcoma, adenoma and/or a glioma. In one embodiment, the cancer is selected from the group consisting of endometrial/cervical cancer, lung cancer (such as, e.g., small cell lung cancer or non-small cell lung cancer), thyroid cancer, colon cancer, kidney cancer, ovary cancer, breast cancer, esophagus cancer, skin cancer, malignant melanoma and pancreatic cancer.

In one embodiment, the cancer is pancreatic cancer, such as unresectable advanced or metastatic pancreatic cancer. In other separate and specific embodiments, the cancer is endometrial/cervical cancer, or lung cancer. In one embodiment the cancer is a thyroid cancer. In one embodiment the cancer is a colon cancer. In one embodiment the cancer is a kidney cancer. In one embodiment the cancer is ovarian cancer. In one embodiment the cancer is breast cancer such as estrogen receptor alpha negative cancer or estrogen receptor alpha positive. In one embodiment the cancer is triple negative breast cancer (i.e. breast cancer tested negative for estrogen receptors (ER–), progesterone receptors (PR–), and human epidermal growth factor receptor 2 (HER2–). In one embodiment the cancer is esophagus cancer. In one embodiment the cancer is skin cancer. In one embodiment the cancer is melanoma such as malignant melanoma. In one embodiment the cancer is Acute Myeloid Leukemia (AML). In one embodiment the cancer is resistant to chemotherapy, thyrosine kinase inhibitors and or BRAF inhibitors. In one embodiment the cancer is resistant to EGFR targeted therapy.

In one aspect, the present invention relates to an antibody binding to the extracellular domain of AXL such as the Ig1-like domain of AXL, such as the Ig2-like domain of AXL, such as the FN1 domain of AXL, or such as the FN2 domain of AXL, wherein said antibody is for use as a medicament.

In a particular embodiment the antibody comprises at least one binding region comprising a VH region and a VL region, wherein the VH region comprises the CDR1, CDR2 and CDR3 sequences of SEQ ID Nos.: 36, 37 and 38, and the VL region comprises the sequences of SEQ ID Nos.: 39, GAS, and 40, wherein said antibody is for use as a medicament.

In a particular embodiment the antibody comprises at least one binding region comprising a VH region and a VL region, wherein the VH region comprises the CDR1, CDR2 and CDR3 sequences of SEQ ID Nos.: 36, 37 and 38, and the VL region comprises the sequences of SEQ ID Nos.: 39, GAS, and 40, wherein said antibody is for use in treatment or prevention of cancer.

In on embodiment the antibody comprises at least one binding region comprising a VH region and a VL region, wherein the VH region comprises the CDR1, CDR2 and CDR3 sequences of SEQ ID Nos.: 36, 37 and 38, and the VL region comprises the sequences of SEQ ID Nos.: 39, GAS, and 40, wherein said antibody is for use in treatment or prevention of thyroid cancer.

In on embodiment the antibody comprises at least one binding region comprising a VH region and a VL region, wherein the VH region comprises the CDR1, CDR2 and CDR3 sequences of SEQ ID Nos.: 36, 37 and 38, and the VL region comprises the sequences of SEQ ID Nos.: 39, GAS, and 40, wherein said antibody is for use in treatment or prevention of colon cancer.

In on embodiment the antibody comprises at least one binding region comprising a VH region and a VL region, wherein the VH region comprises the CDR1, CDR2 and CDR3 sequences of SEQ ID Nos.: 36, 37 and 38, and the VL region comprises the sequences of SEQ ID Nos.: 39, GAS, and 40, wherein said antibody is for use in treatment or prevention of kidney cancer.

In on embodiment the antibody comprises at least one binding region comprising a VH region and a VL region, wherein the VH region comprises the CDR1, CDR2 and CDR3 sequences of SEQ ID Nos.: 36, 37 and 38, and the VL region comprises the sequences of SEQ ID Nos.: 39, GAS, and 40, wherein said antibody is for use in treatment or prevention of ovarian cancer.

In on embodiment the antibody comprises at least one binding region comprising a VH region and a VL region, wherein the VH region comprises the CDR1, CDR2 and CDR3 sequences of SEQ ID Nos.: 36, 37 and 38, and the VL region comprises the sequences of SEQ ID Nos.: 39, GAS, and 40, wherein said antibody is for use in treatment or prevention of breast cancer.

In on embodiment the antibody comprises at least one binding region comprising a VH region and a VL region, wherein the VH region comprises the CDR1, CDR2 and CDR3 sequences of SEQ ID Nos.: 36, 37 and 38, and the VL region comprises the sequences of SEQ ID Nos.: 39, GAS, and 40, wherein said antibody is for use in treatment or prevention of triple negative breast cancer.

In on embodiment the antibody comprises at least one binding region comprising a VH region and a VL region, wherein the VH region comprises the CDR1, CDR2 and CDR3 sequences of SEQ ID Nos.: 36, 37 and 38, and the VL region comprises the sequences of SEQ ID Nos.: 39, GAS, and 40, wherein said antibody is for use in treatment or prevention of esophagus cancer.

In on embodiment the antibody comprises at least one binding region comprising a VH region and a VL region, wherein the VH region comprises the CDR1, CDR2 and CDR3 sequences of SEQ ID Nos.: 36, 37 and 38, and the VL region comprises the sequences of SEQ ID Nos.: 39, GAS, and 40, wherein said antibody is for use in treatment or prevention of skin cancer.

In on embodiment the antibody comprises at least one binding region comprising a VH region and a VL region, wherein the VH region comprises the CDR1, CDR2 and CDR3 sequences of SEQ ID Nos.: 36, 37 and 38, and the VL region comprises the sequences of SEQ ID Nos.: 39, GAS, and 40, wherein said antibody is for use in treatment or prevention of melanoma such as malignant melanoma.

In on embodiment the antibody comprises at least one binding region comprising a VH region and a VL region, wherein the VH region comprises the CDR1, CDR2 and CDR3 sequences of SEQ ID Nos.: 36, 37 and 38, and the VL region comprises the sequences of SEQ ID Nos.: 39, GAS, and 40, wherein said antibody is for use in treatment or prevention of lung cancer (such as, e.g., small cell lung cancer or non-small cell lung cancer (NSCLC)).

In on embodiment the antibody comprises at least one binding region comprising a VH region and a VL region, wherein the VH region comprises the CDR1, CDR2 and CDR3 sequences of SEQ ID Nos.: 36, 37 and 38, and the VL region comprises the sequences of SEQ ID Nos.: 39, GAS, and 40, wherein said antibody is for use in treatment or prevention of Acute Myeloid Leukemia (AML).

Hereby embodiments are provided for the treatment or prevention of cancer. Said embodiments may be coupled or linked to a cytotoxic agent to increase the efficacy or effect of the treatment.

In a particular aspect of the present invention the antibodies disclosed herein may be linked to a cytotoxic agent such as an auristatin (such as, e.g monomethyl auristatin E (MMAE)) to form an immunoconjugate for use as a medicament, such as e.g. for the treatment or prevention of cancer.

In one aspect the present invention relates to an immunoconjugate comprising an antibody which binds to AXL, wherein the antibody does not compete for AXL binding with the ligand Gas6.

In one embodiment the invention relates to an immunoconjugate comprising an antibody comprising at least one binding region comprising a VH region and a VL region, wherein the VH region comprises the CDR1, CDR2 and CDR3 sequences of SEQ ID Nos.: 36, 37 and 38, and the VL region comprises the sequences of SEQ ID Nos.: 39, GAS, and 40, wherein said antibody is linked to monomethyl auristatin E to form an immunoconjugate, and said immunoconjugate is for use as a medicament.

In one embodiment the invention relates to an immunoconjugate comprising an antibody comprising at least one binding region comprising a VH region and a VL region, wherein the VH region comprises the CDR1, CDR2 and CDR3 sequences of SEQ ID Nos.: 36, 37 and 38, and the VL region comprises the sequences of SEQ ID Nos.: 39, GAS, and 40, wherein said antibody is linked to monomethyl auristatin E to form an immunoconjugate, and said immunoconjugate is for use in treatment or prevention of cancer. In one embodiment thereof said antibody is linked to monomethyl auristatin E by the linker mc-vc-PAB.

In one embodiment the invention relates to an immunoconjugate comprising an antibody comprising at least one binding region comprising a VH region and a VL region, wherein the VH region comprises the CDR1, CDR2 and CDR3 sequences of SEQ ID Nos.: 36, 37 and 38, and the VL region comprises the sequences of SEQ ID Nos.: 39, GAS, and 40, wherein said antibody is linked to monomethyl auristatin E to form an immunoconjugate, and said immunoconjugate is for use in treatment or prevention of thyroid cancer. In one embodiment thereof said antibody is linked to monomethyl auristatin E by the linker mc-vc-PAB.

In one embodiment the invention relates to an immunoconjugate comprising an antibody comprising at least one binding region comprising a VH region and a VL region, wherein the VH region comprises the CDR1, CDR2 and CDR3 sequences of SEQ ID Nos.: 36, 37 and 38, and the VL region comprises the sequences of SEQ ID Nos.: 39, GAS, and 40, wherein said antibody is linked to monomethyl auristatin E to form an immunoconjugate, and said immunoconjugate is for use in treatment or prevention of colon cancer. In one embodiment thereof said antibody is linked to monomethyl auristatin E by the linker mc-vc-PAB.

In one embodiment the invention relates to an immunoconjugate comprising an antibody comprising at least one binding region comprising a VH region and a VL region, wherein the VH region comprises the CDR1, CDR2 and CDR3 sequences of SEQ ID Nos.: 36, 37 and 38, and the VL region comprises the sequences of SEQ ID Nos.: 39, GAS, and 40, wherein said antibody is linked to monomethyl auristatin E to form an immunoconjugate, and said immunoconjugate is for use in treatment or prevention of kidney cancer. In one embodiment thereof said antibody is linked to monomethyl auristatin E by the linker mc-vc-PAB.

In one embodiment the invention relates to an immunoconjugate comprising an antibody comprising at least one binding region comprising a VH region and a VL region, wherein the VH region comprises the CDR1, CDR2 and CDR3 sequences of SEQ ID Nos.: 36, 37 and 38, and the VL region comprises the sequences of SEQ ID Nos.: 39, GAS, and 40, wherein said antibody is linked to monomethyl auristatin E to form an immunoconjugate, and said immunoconjugate is for use in treatment or prevention of ovarian cancer. In one embodiment thereof said antibody is linked to monomethyl auristatin E by the linker mc-vc-PAB.

In one embodiment the invention relates to an immunoconjugate comprising an antibody comprising at least one binding region comprising a VH region and a VL region, wherein the VH region comprises the CDR1, CDR2 and CDR3 sequences of SEQ ID Nos.: 36, 37 and 38, and the VL region comprises the sequences of SEQ ID Nos.: 39, GAS, and 40, wherein said antibody is linked to monomethyl auristatin E to form an immunoconjugate, and said immunoconjugate is for use in treatment or prevention of breast cancer. In one embodiment thereof said antibody is linked to monomethyl auristatin E by the linker mc-vc-PAB.

In one embodiment the invention relates to an immunoconjugate comprising an antibody comprising at least one binding region comprising a VH region and a VL region, wherein the VH region comprises the CDR1, CDR2 and CDR3 sequences of SEQ ID Nos.: 36, 37 and 38, and the VL region comprises the sequences of SEQ ID Nos.: 39, GAS, and 40, wherein said antibody is linked to monomethyl auristatin E to form an immunoconjugate, and said immunoconjugate is for use in treatment or prevention of triple negative breast cancer. In one embodiment thereof said antibody is linked to monomethyl auristatin E by the linker mc-vc-PAB.

In one embodiment the invention relates to an immunoconjugate comprising an antibody comprising at least one binding region comprising a VH region and a VL region, wherein the VH region comprises the CDR1, CDR2 and CDR3 sequences of SEQ ID Nos.: 36, 37 and 38, and the VL region comprises the sequences of SEQ ID Nos.: 39, GAS, and 40, wherein said antibody is linked to monomethyl auristatin E to form an immunoconjugate, and said immunoconjugate is for use in treatment or prevention of lung cancer. In one embodiment thereof said antibody is linked to monomethyl auristatin E by the linker mc-vc-PAB.

In one embodiment the invention relates to an immunoconjugate comprising an antibody comprising at least one binding region comprising a VH region and a VL region, wherein the VH region comprises the CDR1, CDR2 and CDR3 sequences of SEQ ID Nos.: 36, 37 and 38, and the VL region comprises the sequences of SEQ ID Nos.: 39, GAS, and 40, wherein said antibody is linked to monomethyl auristatin E to form an immunoconjugate, and said immunoconjugate is for use in treatment or prevention of esophagus cancer. In one embodiment thereof said antibody is linked to monomethyl auristatin E by the linker mc-vc-PAB.

In one embodiment the invention relates to an immunoconjugate comprising an antibody comprising at least one binding region comprising a VH region and a VL region, wherein the VH region comprises the CDR1, CDR2 and CDR3 sequences of SEQ ID Nos.: 36, 37 and 38, and the VL region comprises the sequences of SEQ ID Nos.: 39, GAS, and 40, wherein said antibody is linked to monomethyl auristatin E to form an immunoconjugate, and said immunoconjugate is for use in treatment or prevention of melanoma such as malignant melanoma. In one embodiment thereof said antibody is linked to monomethyl auristatin E by the linker mc-vc-PAB.

In one embodiment the invention relates to an immunoconjugate comprising an antibody comprising at least one binding region comprising a VH region and a VL region, wherein the VH region comprises the CDR1, CDR2 and CDR3 sequences of SEQ ID Nos.: 36, 37 and 38, and the VL region comprises the sequences of SEQ ID Nos.: 39, GAS, and 40, wherein said antibody is linked to monomethyl auristatin E to form an immunoconjugate, and said immunoconjugate is for use in treatment or prevention of lung cancer. In one embodiment thereof said antibody is linked to monomethyl auristatin E by the linker mc-vc-PAB.

In one embodiment the invention relates to an immunoconjugate comprising an antibody comprising at least one binding region comprising a VH region and a VL region, wherein the VH region comprises the CDR1, CDR2 and CDR3 sequences of SEQ ID Nos.: 36, 37 and 38, and the VL region comprises the sequences of SEQ ID Nos.: 39, GAS, and 40, wherein said antibody is linked to monomethyl auristatin E to form an immunoconjugate, and said immunoconjugate is for use in treatment or prevention of Acute Myeloid Leukemia. In one embodiment thereof said antibody is linked to monomethyl auristatin E by the linker mc-vc-PAB.

Hereby embodiments are provided wherein the antibody is linked to a cytotoxic agent such as an auristatin to form an immunoconjugate. The antibody and the cytotoxic agent may be linked by a maleimidocaproyl-valine-citrulline-p-aminobenzyloxycarbonyl (mc-vc-PAB) linker.

In an additional aspect of the invention, the invention relates to antibodies that bind to the extracellular domain of AXL such as the Ig2-like domain of AXL, wherein said antibody is for use as a medicament.

In a particular embodiment the antibody comprises at least one binding region comprising a VH region and a VL region, wherein the VH region comprises the CDR1, CDR2 and CDR3 sequences of SEQ ID Nos.: 46, 47 and 48, and the VL region comprises the sequences of SEQ ID Nos.: 49, AAS, and 50, wherein said antibody is for use as a medicament.

In a particular embodiment the antibody comprises at least one binding region comprising a VH region and a VL region, wherein the VH region comprises the CDR1, CDR2 and CDR3 sequences of SEQ ID Nos.: 46, 47 and 48, and the VL region comprises the sequences of SEQ ID Nos.: 49, AAS, and 50, wherein said antibody is for use in treatment or prevention of cancer.

In on embodiment the antibody comprises at least one binding region comprising a VH region and a VL region, wherein the VH region comprises the CDR1, CDR2 and CDR3 sequences of SEQ ID Nos.: 46, 47 and 48, and the VL region comprises the sequences of SEQ ID Nos.: 49, AAS, and 50, wherein said antibody is for use in treatment or prevention of thyroid cancer.

In on embodiment the antibody comprises at least one binding region comprising a VH region and a VL region, wherein the VH region comprises the CDR1, CDR2 and CDR3 sequences of SEQ ID Nos.: 46, 47 and 48, and the VL region comprises the sequences of SEQ ID Nos.: 49, AAS, and 50, wherein said antibody is for use in treatment or prevention of colon cancer.

In on embodiment the antibody comprises at least one binding region comprising a VH region and a VL region, wherein the VH region comprises the CDR1, CDR2 and CDR3 sequences of SEQ ID Nos.: 46, 47 and 48, and the VL region comprises the sequences of SEQ ID Nos.: 49, AAS, and 50, wherein said antibody is for use in treatment or prevention of kidney cancer.

In on embodiment the antibody comprises at least one binding region comprising a VH region and a VL region, wherein the VH region comprises the CDR1, CDR2 and CDR3 sequences of SEQ ID Nos.: 46, 47 and 48, and the VL region comprises the sequences of SEQ ID Nos.: 49, AAS, and 50, wherein said antibody is for use in treatment or prevention of ovarian cancer.

In on embodiment the antibody comprises at least one binding region comprising a VH region and a VL region, wherein the VH region comprises the CDR1, CDR2 and CDR3 sequences of SEQ ID Nos.: 46, 47 and 48, and the VL region comprises the sequences of SEQ ID Nos.: 49, AAS, and 50, wherein said antibody is for use in treatment or prevention of breast cancer.

In on embodiment the antibody comprises at least one binding region comprising a VH region and a VL region, wherein the VH region comprises the CDR1, CDR2 and CDR3 sequences of SEQ ID Nos.: 46, 47 and 48, and the VL region comprises the sequences of SEQ ID Nos.: 49, AAS, and 50, wherein said antibody is for use in treatment or prevention of triple negative breast cancer.

In on embodiment the antibody comprises at least one binding region comprising a VH region and a VL region, wherein the VH region comprises the CDR1, CDR2 and CDR3 sequences of SEQ ID Nos.: 46, 47 and 48, and the VL region comprises the sequences of SEQ ID Nos.: 49, AAS, and 50, wherein said antibody is for use in treatment or prevention of esophagus cancer.

In on embodiment the antibody comprises at least one binding region comprising a VH region and a VL region, wherein the VH region comprises the CDR1, CDR2 and CDR3 sequences of SEQ ID Nos.: 46, 47 and 48, and the VL region comprises the sequences of SEQ ID Nos.: 49, AAS, and 50, wherein said antibody is for use in treatment or prevention of skin cancer.

In on embodiment the antibody comprises at least one binding region comprising a VH region and a VL region, wherein the VH region comprises the CDR1, CDR2 and CDR3 sequences of SEQ ID Nos.: 46, 47 and 48, and the VL region comprises the sequences of SEQ ID Nos.: 49, AAS, and 50, wherein said antibody is for use in treatment or prevention of melanoma such as malignant melanoma.

In on embodiment the antibody comprises at least one binding region comprising a VH region and a VL region, wherein the VH region comprises the CDR1, CDR2 and CDR3 sequences of SEQ ID Nos.: 46, 47 and 48, and the VL region comprises the sequences of SEQ ID Nos.: 49, AAS, and 50 wherein said antibody is for use in treatment or prevention of lung cancer (such as, e.g., small cell lung cancer or non-small cell lung cancer).

In on embodiment the antibody comprises at least one binding region comprising a VH region and a VL region, wherein the VH region comprises the CDR1, CDR2 and CDR3 sequences of SEQ ID Nos.: 46, 47 and 48, and the VL region comprises the sequences of SEQ ID Nos.: 49, AAS, and 50, wherein said antibody is for use in treatment or prevention of Acute Myeloid Leukemia (AML).

Hereby embodiments are provided for the treatment or prevention of cancer. Said embodiments may be coupled or linked with a cytotoxic agent to increase the efficacy or effect of the treatment.

In a particular aspect of the present invention the antibodies disclosed herein may be linked with a cytotoxic agent such as an auristatin (such as, e.g monomethyl auristatin E (MMAE)) to form an immunoconjugate for use as a medicament, such as e.g. for the treatment or prevention of cancer.

In one embodiment the invention relates to an immunoconjugate comprising an antibody comprising at least one binding region comprising a VH region and a VL region, wherein the VH region comprises the CDR1, CDR2 and CDR3 sequences of SEQ ID Nos.: 46, 47 and 48, and the VL region comprises the sequences of SEQ ID Nos.: 49, AAS, and 50, wherein said antibody is linked to monomethyl auristatin E to form an immunoconjugate, and said immunoconjugate is for use as a medicament.

In one embodiment the invention relates to an immunoconjugate comprising an antibody comprising at least one binding region comprising a VH region and a VL region, wherein the VH region comprises the CDR1, CDR2 and CDR3 sequences of SEQ ID Nos.: 46, 47 and 48, and the VL region comprises the sequences of SEQ ID Nos.: 49, AAS, and 50, wherein said antibody is linked to monomethyl auristatin E to form an immunoconjugate, and said immunoconjugate is for in treatment or prevention of cancer.

In one embodiment the invention relates to an immunoconjugate comprising an antibody comprising at least one binding region comprising a VH region and a VL region, wherein the VH region comprises the CDR1, CDR2 and CDR3 sequences of SEQ ID Nos.: 46, 47 and 48, and the VL region comprises the sequences of SEQ ID Nos.: 49, AAS, and 50, wherein said antibody is linked to monomethyl auristatin E to form an immunoconjugate, and said immunoconjugate is for use in treatment or prevention of thyroid cancer. In one embodiment thereof said antibody is linked to monomethyl auristatin E by the linker mc-vc-PAB.

In one embodiment the invention relates to an immunoconjugate comprising an antibody comprising at least one binding region comprising a VH region and a VL region, wherein the VH region comprises the CDR1, CDR2 and CDR3 sequences of SEQ ID Nos.: 46, 47 and 48, and the VL region comprises the sequences of SEQ ID Nos.: 49, AAS, and 50, wherein said antibody is linked to monomethyl auristatin E to form an immunoconjugate, and said immunoconjugate is for use in treatment or prevention of colon cancer. In one embodiment thereof said antibody is linked to monomethyl auristatin E by the linker mc-vc-PAB.

In one embodiment the invention relates to an immunoconjugate comprising an antibody comprising at least one binding region comprising a VH region and a VL region, wherein the VH region comprises the CDR1, CDR2 and CDR3 sequences of SEQ ID Nos.: 46, 47 and 48, and the VL region comprises the sequences of SEQ ID Nos.: 49, AAS, and 50, wherein said antibody is linked to monomethyl auristatin E to form an immunoconjugate, and said immunoconjugate is for use in treatment or prevention of kidney cancer. In one embodiment thereof said antibody is linked to monomethyl auristatin E by the linker mc-vc-PAB.

In one embodiment the invention relates to an immunoconjugate comprising an antibody comprising at least one binding region comprising a VH region and a VL region, wherein the VH region comprises the CDR1, CDR2 and CDR3 sequences of SEQ ID Nos.: 46, 47 and 48, and the VL region comprises the sequences of SEQ ID Nos.: 49, AAS, and 50, wherein said antibody is linked to monomethyl auristatin E to form an immunoconjugate, and said immunoconjugate is for use in treatment or prevention of ovarian cancer. In one embodiment thereof said antibody is linked to monomethyl auristatin E by the linker mc-vc-PAB.

In one embodiment the invention relates to an immunoconjugate comprising an antibody comprising at least one binding region comprising a VH region and a VL region, wherein the VH region comprises the CDR1, CDR2 and CDR3 sequences of SEQ ID Nos.: 46, 47 and 48, and the VL region comprises the sequences of SEQ ID Nos.: 49, AAS, and 50, wherein said antibody is linked to monomethyl auristatin E to form an immunoconjugate, and said immunoconjugate is for use in treatment or prevention of breast cancer. In one embodiment thereof said antibody is linked to monomethyl auristatin E by the linker mc-vc-PAB.

In one embodiment the invention relates to an immunoconjugate comprising an antibody comprising at least one binding region comprising a VH region and a VL region, wherein the VH region comprises the CDR1, CDR2 and CDR3 sequences of SEQ ID Nos.: 46, 47 and 48, and the VL region comprises the sequences of SEQ ID Nos.: 49, AAS, and 50, wherein said antibody is linked to monomethyl auristatin E to form an immunoconjugate, and said immunoconjugate is for use in treatment or prevention of triple negative breast cancer. In one embodiment thereof said antibody is linked to monomethyl auristatin E by the linker mc-vc-PAB.

In one embodiment the invention relates to an immunoconjugate comprising an antibody comprising at least one binding region comprising a VH region and a VL region, wherein the VH region comprises the CDR1, CDR2 and CDR3 sequences of SEQ ID Nos.: 46, 47 and 48, and the VL region comprises the sequences of SEQ ID Nos.: 49, AAS, and 50, wherein said antibody is linked to monomethyl auristatin E to form an immunoconjugate, and said immunoconjugate is for use in treatment or prevention of lung cancer. In one embodiment thereof said antibody is linked to monomethyl auristatin E by the linker mc-vc-PAB.

In one embodiment the invention relates to an immunoconjugate comprising an antibody comprising at least one binding region comprising a VH region and a VL region, wherein the VH region comprises the CDR1, CDR2 and CDR3 sequences of SEQ ID Nos.: 46, 47 and 48, and the VL region comprises the sequences of SEQ ID Nos.: 49, AAS, and 50, wherein said antibody is linked to monomethyl auristatin E to form an immunoconjugate, and said immunoconjugate is for use in treatment or prevention of esophagus cancer. In one embodiment thereof said antibody is linked to monomethyl auristatin E by the linker mc-vc-PAB.

In one embodiment the invention relates to an immunoconjugate comprising an antibody comprising at least one binding region comprising a VH region and a VL region, wherein the VH region comprises the CDR1, CDR2 and CDR3 sequences of SEQ ID Nos.: 46, 47 and 48, and the VL region comprises the sequences of SEQ ID Nos.: 49, AAS, and 50, wherein said antibody is linked to monomethyl auristatin E to form an immunoconjugate, and said immunoconjugate is for use in treatment or prevention of melanoma such as malignant melanoma. In one embodiment thereof said antibody is linked to monomethyl auristatin E by the linker mc-vc-PAB.

In one embodiment the invention relates to an immunoconjugate comprising an antibody comprising at least one binding region comprising a VH region and a VL region, wherein the VH region comprises the CDR1, CDR2 and CDR3 sequences of SEQ ID Nos.: 46, 47 and 48, and the VL region comprises the sequences of SEQ ID Nos.: 49, AAS, and 50, wherein said antibody is linked to monomethyl auristatin E to form an immunoconjugate, and said immunoconjugate is for use in treatment or prevention of lung cancer. In one embodiment thereof said antibody is linked to monomethyl auristatin E by the linker mc-vc-PAB.

In one embodiment the invention relates to an immunoconjugate comprising an antibody comprising at least one binding region comprising a VH region and a VL region, wherein the VH region comprises the CDR1, CDR2 and CDR3 sequences of SEQ ID Nos.: 46, 47 and 48, and the VL region comprises the sequences of SEQ ID Nos.: 49, AAS, and 50 wherein said antibody is linked to monomethyl auristatin E to form an immunoconjugate, and said immunoconjugate is for use in treatment or prevention of Acute Myeloid Leukemia. In one embodiment thereof said antibody is linked to monomethyl auristatin E by the linker mc-vc-PAB.

Hereby embodiments are provided wherein the antibody is linked to a cytotoxic agent such as an auristatin to form an immunoconjugate. The antibody and the cytotoxic agent may be linked by a maleimidocaproyl-valine-citrulline-p-aminobenzyloxycarbonyl (mc-vc-PAB) linker.

In an embodiment selection of patients to be treated with anti-AXL antibodies is based on the level of AXL expression in a sample, such as a sample containing tumor cells, or by detecting AXL-expressing tumors using labeled anti-AXL antibodies or antibody fragments, e.g., those of the invention. Exemplary diagnostic assays for determining AXL-expression using AXL antibodies of the invention are described herein. The efficient dosages and dosage regimens for the anti-AXL antibody or ADC depend on the disease or condition to be treated and may be determined by the persons skilled in the art.

A physician having ordinary skill in the art may readily determine and prescribe the effective amount of the pharmaceutical composition required. In relation hereto, when referring to a pharmaceutical composition it is to be understood also to comprise a composition as such, or vice versa. For example, the physician could start doses of the anti-AXL antibody employed in the pharmaceutical composition at levels lower than that required in order to achieve the desired therapeutic effect and gradually increase the dosage until the desired effect is achieved. In general, a suitable dose of a pharmaceutical composition of the present invention will be that amount of the compound which is the lowest dose effective to produce a therapeutic effect according to a particular dosage regimen. Such an effective dose will generally depend upon the factors described above.

For example, an "effective amount" for therapeutic use may be measured by its ability to stabilize the progression of disease. The ability of a compound to inhibit cancer may, for example, be evaluated in an animal model system predictive of efficacy in human tumors. Alternatively, this property of a composition may be evaluated by examining the ability of the compound to inhibit cell growth or to induce cytotoxicity by in vitro assays known to the skilled practitioner. A therapeutically effective amount of a therapeutic compound may decrease tumor size, or otherwise ameliorate symptoms in a subject. One of ordinary skill in the art would be able to determine such amounts based on such factors as the subject's size, the severity of the subject's symptoms, and the particular composition or route of administration selected.

An exemplary, non-limiting range for a therapeutically effective amount of an anti-AXL antibody of the present invention is about 0.1-100 mg/kg, such as about 0.1-50 mg/kg, for example about 0.1-20 mg/kg, such as about 0.1-10 mg/kg, for instance about 0.5, about such as 0.3, about 1, about 3 mg/kg, about 5 mg/kg or about 8 mg/kg.

An exemplary, non-limiting range for a therapeutically effective amount of an anti-AXL ADC of the invention is 0.02-100 mg/kg, such as about 0.02-30 mg/kg, such as about 0.05-10 mg/kg or 0.1-3 mg/kg, for example about 0.5-2 mg/kg.

Administration may e.g. be intravenous, intramuscular, intraperitoneal, or subcutaneous, and for instance administered proximal to the site of the target.

Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation.

In one embodiment, the efficacy-safety window is optimized by lowering specific toxicity such as for example by lowering the drug-antibody ratio (DAR) and/or mixing of anti-AXL ADC with unlabeled anti-AXL antibody.

In one embodiment, the efficacy of the treatment is monitored during the therapy, e.g. at predefined points in time. In one embodiment, the efficacy may be monitored by measuring the level of AXL in a sample containing tumor cells, by visualization of the disease area, or by other diagnostic methods described further herein, e.g. by performing one or more PET-CT scans, for example using a labeled anti-AXL antibody, fragment or mini-antibody derived from the AXL-specific antibody of the present invention.

If desired, an effective daily dose of a pharmaceutical composition may be administered as two, three, four, five, six or more sub-doses administered separately at appropriate intervals throughout the day, optionally, in unit dosage forms. In another embodiment, the anti-AXL antibodies are administered by slow continuous infusion over a long period, such as more than 24 hours, in order to minimize any unwanted side effects.

While it is possible for a compound of the present invention to be administered alone, it is preferable to administer the compound as a pharmaceutical composition as described above.

An effective dose of an anti-AXL antibody, bispecific antibody or ADC of the invention may also be administered using a weekly, biweekly or triweekly dosing period. The dosing period may be restricted to, e.g., 8 weeks, 12 weeks or until clinical progression has been established.

For example, in one embodiment, the anti-AXL antibody, bispecific antibody or ADC is administered by infusion in a weekly dosage of between 10 and 500 mg/m$^2$, such as between 200 and 400 mg/m$^2$. Such administration may be repeated, e.g., 1 to 8 times, such as 3 to 5 times. The administration may be performed by continuous infusion over a period of from 1 to 24 hours, such as of from 1 to 12 hours.

In another embodiment, the anti-AXL antibody, bispecific antibody or ADC is administered by infusion every three weeks in a dosage of between 10 and 500 mg/m$^2$, such as between 50-200 mg/m$^2$. Such administration may be repeated, e.g., 1 to 8 times, such as 3 to 5 times. The administration may be performed by continuous infusion over a period of from 1 to 24 hours, such as of from 1 to 12 hours.

In one embodiment, an anti-AXL ADC is administered as a single dose of about 0.1-10 mg/kg, such as about 1-3 mg/kg, every week or every third week for up to twelve times, up to eight times, or until clinical progression. The administration may be performed by continuous infusion over a period of from 1 to 24 hours, such as of from 1 to 12 hours. Such regimens may be repeated one or more times as necessary, for example, after 6 months or 12 months. The dosage may be determined or adjusted by measuring the amount of compound of the present invention in the blood upon administration by for instance taking out a biological sample and using anti-idiotypic antibodies which target the antigen binding region of the anti-AXL antibodies of the present invention.

In one embodiment, the anti-AXL antibodies are administered as maintenance therapy, such as, e.g., once a week for a period of six months or more.

As non-limiting examples, treatment according to the present invention may be provided as a daily dosage of a compound of the present invention in an amount of about 0.1-100 mg/kg, such as 0.2, 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of days 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of weeks 1, 2, 3, 4, 5, 6, 7, 8, 9, 10, 11, 12, 13, 14, 15, 16, 17, 18, 19 or 20 after initiation of treatment, or any combination thereof, using single or divided doses every 24, 12, 8, 6, 4, or 2 hours, or any combination thereof.

Parenteral compositions may be formulated in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the present invention are dictated by and directly dependent on (a) the unique characteristics of the active compound and the particular therapeutic effect to be achieved, and (b) the limitations inherent in the art of compounding such an active compound for the treatment of sensitivity in individuals.

Diagnostic Applications

The anti-AXL antibodies of the invention may also be used for diagnostic purposes, using a composition comprising an anti-AXL antibody as described herein. Accordingly, the invention provides diagnostic methods and compositions using the anti-AXL antibodies described herein. Such methods and compositions can be used for purely diagnostic purposes, such as detecting or identifying a disease involving AXL-expressing cells, as well as for monitoring of the progress of therapeutic treatments, monitoring disease progression, assessing status after treatment, monitoring for recurrence of disease, evaluating risk of developing a disease, and the like.

In one aspect, the anti-AXL antibodies of the present invention are used ex vivo, such as in diagnosing a disease in which cells expressing AXL are indicative of disease or involved in the pathogenesis, by detecting levels of AXL or levels of cells which express AXL on their cell surface in a sample taken from a patient. This may be achieved, for example, by contacting the sample to be tested, optionally along with a control sample, with the anti-AXL antibody under conditions that allow for binding of the antibody to AXL. Complex formation can then be detected (e.g., using an ELISA). When using a control sample along with the test sample, the level of anti-AXL antibody or anti-AXL antibody-AXL complex is analyzed in both samples and a statistically significant higher level of anti-AXL antibody or anti-AXL antibody-AXL complex in the test sample indicates a higher level of AXL in the test sample compared with the control sample.

Examples of conventional immunoassays in which anti-AXL antibodies of the present invention can be used include, without limitation, ELISA, RIA, FACS assays, plasmon resonance assays, chromatographic assays, tissue immunohistochemistry, Western blot, and/or immunoprecipitation.

Accordingly, in one embodiment, the present invention relates to a method of diagnosing a disease characterized by involvement or accumulation of AXL-expressing cells, comprising administering an antibody, bispecific antibody, immunoconjugate, composition or pharmaceutical composition according to any aspect or embodiment herein described, to a subject, optionally wherein the antibody is labeled with a detectable label, and wherein the amount of AXL-expressing cells correlates with or is indicative of disease.

In one embodiment, the invention relates to a method for detecting the presence of AXL antigen, or a cell expressing AXL, in a sample comprising:

contacting the sample with an anti-AXL antibody of the invention under conditions that allow for binding of the anti-AXL antibody to AXL in the sample; and analyzing whether a complex has been formed. Typically, the sample is a biological sample. The term "AXL antigen" as used in this context, refers both soluble and cell bound AXL antigen.

In one embodiment, the sample is a tissue sample known or suspected of containing AXL antigen and/or cells expressing AXL. For example, in situ detection of AXL expression may be accomplished by removing a histological specimen from a patient, and providing the antibody of the present invention to such a specimen. The antibody may be provided by applying or by overlaying the antibody to the specimen, which is then detected using suitable means. It is then possible to determine not only the presence of AXL or AXL-expressing cells, but also the distribution of AXL or AXL-expressing cells in the examined tissue (e.g., in the context of assessing the spread of cancer cells). Using the present invention, those of ordinary skill will readily perceive that any of a wide variety of histological methods (such as staining procedures) may be modified in order to achieve such in situ detection.

In the above assays, the anti-AXL antibody can be labeled with a detectable substance to allow AXL-bound antibody to be detected. Alternatively, bound (primary) anti-AXL antibody may be detected by a secondary antibody which is labeled with a detectable substance and which binds to the primary antibody. Furthermore, in the above assays, a diagnostic composition comprising an antibody or bispecific antibody according to any aspect or embodiments herein described may be used. Thus, in one aspect, the present invention relates to a diagnostic composition comprising an antibody or bispecific antibody according to any aspect or embodiment herein described.

The level of AXL in a sample can also be estimated by a competition immunoassay utilizing AXL standards labeled with a detectable substance and an unlabeled anti-AXL antibody. In this type of assay, the biological sample, the labeled AXL standard(s) and the anti-AXL antibody are combined, and the amount of labeled AXL standard bound to the unlabeled anti-AXL antibody is determined. The amount of AXL in the biological sample is inversely proportional to the amount of labeled AXL standard bound to the anti-AXL antibody.

Suitable labels for the anti-AXL antibody, secondary antibody and/or AXL standard used in in vitro diagnostic techniques include, without limitation, various enzymes, prosthetic groups, fluorescent materials, luminescent materials, and radioactive materials. Examples of suitable enzymes include horseradish peroxidase, alkaline phosphatase, β-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride and phycoerythrin; an example of a luminescent material includes luminol; and examples of suitable radioactive material include $^{125}$I, $^{131}$I, $^{35}$S, and $^3$H.

In one aspect, the anti-AXL antibodies of the invention are used in the in vivo imaging of AXL-expressing tissues such as tumors. For in vivo methods, antibody fragments such as, e.g., (Fab')$_2$, Fab and Fab' fragments, are particularly advantageous because of their rapid distribution kinetics.

In vivo imaging can be performed by any suitable technique. For example, an anti-AXL antibody (such as, e.g., a fragment) labeled with $^{99}$Tc, $^{131}$I, $^{111}$In or other gamma-ray emitting isotope may be used to image anti-AXL antibody accumulation or distribution in AXL-expressing tissues such as tumors with a gamma scintillation camera (e.g., an Elscint Apex 409ECT device), typically using low-energy, high resolution collimator or a low-energy all-purpose collimator. Alternatively, labeling with $^{89}$Zr, $^{76}$Br, $^{18}$F or other positron-emitting radionuclide may be used to image anti-AXL antibody or antibody fragment distribution in tumors using positron emission tomography (PET). The images obtained by the use of such techniques may be used to assess biodistribution of AXL in a patient, mammal, or tissue, for example in the context of using AXL as a biomarker for the presence of cancer cells. Variations on this technique may include the use of magnetic resonance imaging (MRI) to improve imaging over gamma camera techniques. Conventional immunoscintigraphy methods and principles are described in, e.g., [126], [127], and [128]. Moreover, such images may also, or alternatively, serve as the basis for surgical techniques to remove tumors. Furthermore, such in vivo imaging techniques may allow for the identification and localization of a tumor in a situation where a patient is identified as having a tumor (due to the presence of other biomarkers, metastases, etc.), but the tumor cannot be identified by traditional analytical techniques. All of these methods are features of the present invention.

The in vivo imaging and other diagnostic methods provided by the present invention are particularly useful in the detection of micrometastases in a human patient (e.g., a patient not previously diagnosed with cancer or a patient in a period of recovery/remission from a cancer).

In one embodiment, the present invention provides an in vivo imaging method wherein an anti-AXL antibody of the present invention is conjugated to a detection-promoting radio-opaque agent, the conjugated antibody is administered to a host, such as by injection into the bloodstream, and the presence and location of the labeled antibody in the host is assayed. Through this technique and any other diagnostic method provided herein, the present invention provides a method for screening for the presence of disease-related cells in a human patient or a biological sample taken from a human patient and/or for assessing the distribution of anti-AXL antibody prior to anti-AXL ADC therapy.

For diagnostic imaging, radioisotopes may be bound to an anti-AXL antibody either directly or indirectly by using an intermediary functional group. Useful intermediary functional groups include chelators, such as ethylenediaminetetraacetic acid and diethylenetriaminepentaacetic acid (see for instance [129]).

In addition to radioisotopes and radio-opaque agents, diagnostic methods may be performed using anti-AXL antibodies that are conjugated to dyes (such as with the biotin-streptavidin complex), contrast agents, fluorescent compounds or molecules and enhancing agents (e.g. paramagnetic ions) for magnetic resonance imaging (MRI) (see, e.g., [130], which describes MRI techniques and the preparation of antibodies conjugated to a MRI enhancing agent). Such diagnostic/detection agents may be selected from agents for use in MRI, and fluorescent compounds. In order to load an anti-AXL antibody with radioactive metals or paramagnetic ions, it may be necessary to react it with a reagent having a long tail to which a multiplicity of chelating groups are attached for binding the ions. Such a tail may be a polymer such as a polylysine, polysaccharide, or another derivatized or derivatizable chain having pendant groups to which may be bound chelating groups such as, e.g., porphyrins, polyamines, crown ethers, bisthiosemicarbazones, polyoximes, and like groups known to be useful for this purpose. Chelates may be coupled to anti-AXL antibodies using standard chemistries.

Thus, the present invention provides a diagnostic anti-AXL antibody, wherein the anti-AXL antibody is conjugated to a contrast agent (such as for magnetic resonance imaging, computed tomography, or ultrasound contrast-enhancing agent) or a radionuclide that may be, for example, a gamma-, beta-, alpha-, Auger electron-, or positron-emitting isotope.

In a further aspect, the invention relates to a kit for detecting the presence of AXL antigen or a cell expressing AXL, in a sample, comprising:

an anti-AXL antibody, bispecific antibody, or immunoconjugate or ADC of the invention; and instructions for use of the kit.

In one embodiment, the present invention provides a kit for diagnosis of cancer comprising a container comprising an anti-AXL antibody, and one or more reagents for detecting binding of the anti-AXL antibody to AXL. Reagents may include, for example, fluorescent tags, enzymatic tags, or other detectable tags. The reagents may also include secondary or tertiary antibodies or reagents for enzymatic reactions, wherein the enzymatic reactions produce a product that may be visualized. In one embodiment, the present invention provides a diagnostic kit comprising one or more anti-AXL antibodies, of the present invention in labeled or unlabeled form in suitable container(s), reagents for the incubations for an indirect assay, and substrates or derivatizing agents for detection in such an assay, depending on the nature of the label. Control reagent(s) and instructions for use also may be included.

Diagnostic kits may also be supplied for use with an anti-AXL antibody, such as a conjugated/labeled anti-AXL antibody, for the detection of the presence of AXL in a tissue sample or host. Thus, the anti-AXL antibody according to the present invention may also be used as, e.g. part of a, companion diagnostic, for example as the primary antibody in an immunohistochemistry assay designed to detect AXL expression in solid tumor, lymph node or other tissue biopsies. Alternatively, the anti-AXL antibodies according to the present invention may be used as the primary antibody in a flow cytometry-based or immunocytochemistry assay to identify AXL-expressing cells in blood, bone marrow, fine needles aspirates, e.g. lymph node aspirates, or peritoneal fluid to identify AXL-expressing tumor cells. Anti-AXL antibodies according to the present invention may be used to identify soluble AXL, e.g. in an ELISA-based assay. Anti-AXL antibodies according to the present invention may be used as a companion diagnostic, for instance as radioconjugates, that can be used for imaging studies in patients. In such diagnostic kits, as well as in kits for therapeutic uses described elsewhere herein, an anti-AXL antibody typically may be provided in a lyophilized form in a container, either alone or in conjunction with additional antibodies specific for a target cell or peptide. Typically, a pharmaceutically acceptable carrier (e.g., an inert diluent) and/or components thereof, such as a Tris, phosphate, or carbonate buffer, stabilizers, preservatives, biocides, inert proteins, e.g., serum albumin, or the like, also are included (typically in a separate container for mixing) and additional reagents (also typically in separate container(s)). In certain kits, a secondary antibody capable of binding to the AXL-specific Ab, which typically is present in a separate container, is also included. The second antibody is typically conjugated to a label and formulated in a manner similar to the anti-AXL antibody of the present invention. Using the methods described above and elsewhere herein, anti-AXL antibodies may be used to define subsets of cancer/tumor cells and characterize such cells and related tumor tissues.

Anti-Idiotypic Antibodies

In a further aspect, the invention relates to an anti-idiotypic antibody which binds to an anti-AXL antibody of the invention as described herein.

An anti-idiotypic (Id) antibody is an antibody which recognizes unique determinants generally associated with the antigen-binding site of an antibody. An anti-Id antibody may be prepared by immunizing an animal of the same species and genetic type as the source of an anti-AXL monoclonal antibody with the monoclonal antibody against which an anti-Id is being prepared. The immunized animal typically can recognize and respond to the idiotypic determinants of the immunizing antibody by producing an antibody to these idiotypic determinants (the anti-Id antibody). Such antibodies are described in for instance U.S. Pat. No. 4,699,880. Such antibodies are further features of the present invention.

An anti-Id antibody may also be used as an "immunogen" to induce an immune response in yet another animal, producing a so-called anti-anti-Id antibody. An anti-anti-Id antibody may be epitopically identical to the original monoclonal antibody, which induced the anti-Id antibody. Thus, by using antibodies to the idiotypic determinants of a monoclonal antibody, it is possible to identify other clones expressing antibodies of identical specificity. Anti-Id antibodies may be varied (thereby producing anti-Id antibody variants) and/or derivatized by any suitable technique, such as those described elsewhere herein with respect to AXL-specific antibodies of the present invention. For example, a monoclonal anti-Id antibody may be coupled to a carrier such as keyhole limpet hemocyanin (KLH) and used to immunize BALB/c mice. Sera from these mice typically will contain anti-anti-Id antibodies that have the binding properties similar, if not identical, to an original/parent anti-AXL antibody.

Sequences

TABLE 1

| SEQ ID NO: | Name | Amino acid sequence | Comments |
|---|---|---|---|
| SEQ ID NO: 1 | 107 VH | EVQLLESGGGLVQPGGSLRLSCAASGFTFSSYAMNWV RQAPGKGLEWVSTTSGSGASTYYADSVKGRFTISRDNS KNTLYLQMNSLRAEDTAVYYCAKIWIAFDIWGQGTMV TVSS | HCo12-BalbC Ig1 domain binding Ab |
| SEQ ID NO: 2 | 107 VL | EIVLTQSPGTLSLSPGERATLSCRASQSVSSSYLAWYQQ KPGQAPRLLIYGASSRATGIPDRFSGSGSGTDFTLTISRLE PEDFAVYYCQQYGSSPYTFGQGTKLEIK | |

TABLE 1-continued

| SEQ ID NO: | Name | Amino acid sequence | Comments |
|---|---|---|---|
| SEQ ID NO: 3 | 140 VH | EVQLLESGGGLVQPGGSLRLSCAASGFTFSSYAMTWVR QAPGKGLEWVSAISISGASTFYADSVKGRFTISRDNSKN TLSLQMNSLRAEDTAVYFCRGYSGYVYDAFDIWGQGT MVTVSS | |
| SEQ ID NO: 4 | 140 VL | DIQMTQSPSSLSASVGDRVTITCRASQGISNWLAWYQ QKPEKAPKSLIYAASSLQSGVPSRFSGSGSGTDFTLTISSL QPEDFATYYCQQYNSYPLTFGGGTKVEIK | |
| SEQ ID NO: 5 | 148 VH | EVQLLESGGGLVQPGGSLRLSCAASGFTFSSYAMTWVR QAPGKGLEWVSAISISGGSTFYADSVKGRFTISRDNSKN TLYLQMNSLRAEDTAVYYCRGYSGYVYDAFDFWGQGT MVTVSS | HCo12-BalbC Ig2 domain binding Ab |
| SEQ ID NO: 6 | 148 VL | DIQMTQSPSSLSASVGDRVTITCRASQGISNWLAWYQ QKPEKAPKSLIYAASSLQSGVPSRFSGSGSGTDFTLTISSL QPEDFATYYCQQYNSYPLTFGGGTKVEIK | |
| SEQ ID NO: 7 | 154 VH | EVQLLDSGGGLVQPGGSLRLSCAASGFTFSSYAMSWVR QAPGKGLEWVSAISIGGGNAYYADSVKGRFTISRDNSK NTLYLQMNSLRAADTAVYYCAKPGFIMVRGPLDYWG QGALVTVSS | HCo12-BalbC FN1 domain binding Ab |
| SEQ ID NO: 8 | 154-M103L VH | EVQLLDSGGGLVQPGGSLRLSCAASGFTFSSYAMSWVR QAPGKGLEWVSAISIGGGNAYYADSVKGRFTISRDNSK NTLYLQMNSLRAADTAVYYCAKPGFILVRGPLDYWGQ GALVTVSS | |
| SEQ ID NO: 9 | 154 VL | EIVLTQSPGTLSLSPGERATLSCRASQSVSNSYLAWYQQ KPGQAPRLLIYGASSRATGIPDRFSGSGSGTDFTLTISRLE PEDFAVYYCQQYGSSPYTFGQGTKLEIK | |
| SEQ ID NO: 10 | 171 VH | EVQLLESGGGLVQPGGSLRLSCAASGFTFSSYAMSWVR QAPGKGLEWVSDISVSGGSTYYADSVKGRFTISRDNSK NTLYLQMNSLRAEDTAVYYCAKEGYIWFGESLSYAFDI WGQGTMVTVSS | HCo17-BalbC Ig2 domain binding Ab |
| SEQ ID NO: 11 | 171 VL | EIVLTQSPGTLSLSPGERATLSCRASQSVSSSYLAWYQQ KPGQAPRLLIYGASSRATGIPDRFSGSGSGTDFTLTISRLE PEDFAVYYCQQYGRSFTFGPGTKVDIK | |
| SEQ ID NO: 12 | 172 VH | EVQLLESGGGLVQPGGSLRLSCAASGFTFSNYAMSWV RQAPGKGLEWVSDISVSGGSTYYADSVKGRFTISRDNS KNTLYLQMNSLRAEDTAVYYCAKEGYIWFGESLSYAFDI WGQGTMVTVSS | |
| SEQ ID NO: 13 | 172 VL | EIVLTQSPGTLSLSPGERATLSCRASQSVSSSYLAWYQQ KPGQAPRLLIYGASSRATGIPDRFSGSGSGTDFTLTISRLE PEDFAVYYCQQYGRSFTFGPGTKVDIK | |
| SEQ ID NO: 14 | 181 VH | EVQLLESGGGLVQPGGSLRLSCAASGFTFSSYAMSWVR QAPGKGLEWVSDISVSGGSTYYADSVKGRFTISRDNSK NTLYLHMNSLRAEDTAVYYCAKEGYIWFGESLSYAFDI WGQGTMVTVSS | |
| SEQ ID NO: 15 | 181 VH | EIVLTQSPGTLSLSPGERATLSCRASQSVSSSYLAWYQQ KPGQAPRLLIYGASSRATGIPDRFSGSGSGTDFTLTISRLE PEDFAVYYCQQYGRSFTFGPGTKVDIK | |
| SEQ ID NO: 16 | 183 VH | QVQLQQWGAGLLKPSETLSLTCAVYGGSFSGYYWSWI RQPPGKGLEWIGEINQSGSTNYNPSLKSRVTISVDTSKN QFSLKLSSVTAADTSVYYCASGNWDHFFDYWGQGTLV TVSS | HCo17-BalbC FN1 domain binding Ab |
| SEQ ID NO: 17 | 183-N52Q VH | QVQLQQWGAGLLKPSETLSLTCAVYGGSFSGYYWSWI RQPPGKGLEWIGEIQQSGSTNYNPSLKSRVTISVDTSKN QFSLKLSSVTAADTSVYYCASGNWDHFFDYWGQGTLV TVSS | |
| SEQ ID NO: 18 | 183 VL | DIQMTQSPSSVSASVGDRVTITCRASQGISSWLAWYQ HKPGKAPKLLIYATSSLQSGVTSRFSGSGSGTDFTLTISSL QPEDFATYYCQQAKSFPWTFGQGTKVEIK | |
| SEQ ID NO: 19 | 187 VH | QVPLQQWGAGLLKPSETLSLTCAVYGGSFSGYHWSWI RQPPGKGLEWIGEISHSGRTNYNPSLKSRVTISIDTSKNQ FSLKLSSVTAADTAVYYCASFITMIRGTIITHFDYWGQGT LVTVSS | |

TABLE 1-continued

| SEQ ID NO: | Name | Amino acid sequence | Comments |
| --- | --- | --- | --- |
| SEQ ID NO: 20 | 187 VL | DIQMTQSPSSLSASVGDRVTITCRASQGISSWLAWYQQ KPEKAPKSLIYAASSLQSGVPSRFSGSGSGTDFTLTISSLQ PEDFATYYCQQYHSYPYTFGQGTKLEIK | |
| SEQ ID NO: 21 | 608-01 VH | QVQLVQSGAEVKKPGSSVKVSCKASGGTFSSYAISWVR QAPGQGLEWMGRIIPIFGIANYVQKFQGRVTITADKST STAYMELSSLRAEDTAVYYCARRGDYYGSGSPDVFDIW GQGTMVTVSS | |
| SEQ ID NO: 22 | 608-01 VL | EIVLTQSPGTLSLSPGERATLSCRASQSVSSSYLAWYQQ KPGQAPRLLIYGASSRATGIPDRFSGSGSGTDFTLTISRLE PEDFAVYYCQQYGSSYTFGQGTKLEIK | |
| SEQ ID NO: 23 | 610-01 VH | QVQLVQSGAEVKKPGSSVKVSCKASGGTFSSYAISWVR QAPGQGLEWMGRIIPIFGIANYVQKFQGRVTITADKST STAYMELSSLRAEDTAVYYCARRGNYYGSGSPDVFDIW GQGTMVTVSS | |
| SEQ ID NO: 24 | 610-01 VL | EIVLTQSPGTLSLSPGERATLSCRASQSVSSSYLAWYQQ KPGQAPRLLIYGASSRATGIPDRFSGSGSGTDFTLTISRLE PEDFAVYYCQQYGSSYTFGQGTKLEIK | |
| SEQ ID NO: 25 | 613 VH | QVQLVQSGAEVKKPGSSVKVSCKASGGTFSSYAINWM RQAPGQGLEWMGRIIPIFGIVNYAQKFQGRVTLTADKS TSTAYMELSSLRSEDTAVYYCARRGNYYGSGSPDVFDI WGQGTMVTVSS | HCo20 Ig1 domain binding Ab |
| SEQ ID NO: 26 | 613 VL | EIVLTQSPGTLSLSPGERATLSCRASQSVSSSYLAWYQQ KPGQAPRLLIYGASSRATGIPDRFSGSGSGTDFTLTISRLE PEDFAVYYCQQYGSSYTFGQGTKLEIK | |
| SEQ ID NO: 27 | 613-08 VH | QVQLVQSGAEVKKPGSSVKVSCKASGGTFSSYAINWM RQAPGQGLEWMGRIIPIFGIVNYAQKFQGRVTLTADKS TSTAYMELSSLRSEDTAVYYCARRGNYYGSGSPDVFDI WGQGTMVTVSS | |
| SEQ ID NO: 28 | 613-08 VL | EIVLTQSPATLSLSPGERATLSCRASQSVSSYLAWYQQK PGQAPRLLIYDASNRATGIPARFSGSGSGTDFTLTISSLEP EDFAVYYCQQRSNWLTFGGGTKVEIK | |
| SEQ ID NO: 29 | 620-06 VH | QVQLVQSGAEVKKPGSSVKVSCKASGGTFSSYAISWVR QAPGQGLEWMGRIIPIFGIANYAQKFQGRVTITADKST STAYMELSSLRSEDTAVYYCARRGNYYGSGSPDVFDIW GQGTMVTVSS | |
| SEQ ID NO: 30 | 620-06 VL | EIVLTQSPGTLSLSPGERATLSCRASQSVSSSYLAWYQQ KPGQAPRLLIYGASSRATGIPDRFSGSGSGTDFTLTISRLE PEDFAVYYCQQYGSSYTFGQGTKLEIK | |
| SEQ ID NO: 31 | 726 VH | QVQLQQWGAGLLKPSETLSLTCAIDGGSFSGYYWSWIR QPPGKGLEWIGEISHSGRTNYNPSLKSRVTISIDTSKNQF SLKLSSVAAADTAVYYCARFITMIRGAIITHFDYWGQGA LVTVSS | HCo17-BalbC FN2 domain binding Ab |
| SEQ ID NO: 32 | 726-M101L VH | QVQLQQWGAGLLKPSETLSLTCAIDGGSFSGYYWSWIR QPPGKGLEWIGEISHSGRTNYNPSLKSRVTISIDTSKNQF SLKLSSVAAADTAVYYCARFITLIRGAIITHFDYWGQGAL VTVSS | |
| SEQ ID NO: 33 | 726 VL | DIQMTQSPSSLSASVGDRVTITCRASQGISSWLAWYQQ KPEKAPKSLIYAASSLQSGVPSRFSGSGSGTDFTLTISSLQ PEDFATYYCQQYHSYPYTFGQGTKLEIK | |
| SEQ ID NO: 34 | 733 VH | QVQLVESGGGVVQPGRSLRLSCAASGFSFSTYAMHWV RQAPGKGLEWVAVISYDGDNKYSADSVKGRFTISRDNS KNTLYLQMNSLRAEDTAVYYCARGRKLGIDAFDIWGQ GTMVTVSS | HCo17-BalbC FN1 domain binding Ab |
| SEQ ID NO: 35 | 733 VL | AIQLTQSPSSLSASVGDRVTITCRASQGISSALAWYQQK PGKAPKLLIYDASSLESGVPSRFSGSGSGTDFTLTISGLQP EDFATYYCQQFNSYPFTFGPGTKVDIK | |
| SEQ ID NO: 36 | 107 VH CDR1 | GFTFSSYA | |
| SEQ ID NO: 37 | 107 VH CDR2 | TSGSGAST | |
| SEQ ID NO: 38 | 107 VH CDR3 | AKIWIAFDI | |

TABLE 1-continued

| SEQ ID NO: | Name | Amino acid sequence | Comments |
|---|---|---|---|
| SEQ ID NO: 39 | 107 VL CDR1<br>107 VL CDR2 | QSVSSSY<br>GAS | |
| SEQ ID NO: 40 | 107 VL CDR3 | QQYGSSPYT | |
| SEQ ID NO: 41 | 140 VH CDR1 | GFTFSSYA | |
| SEQ ID NO: 42 | 140 VH CDR2 | ISISGAST | |
| SEQ ID NO: 43 | 140 VH CDR3 | RGYSGYVYDAFDI | |
| SEQ ID NO: 44 | 140 VL CDR1<br>140 VL CDR2 | QGISNW<br>AAS | |
| SEQ ID NO: 45 | 140 VL CDR3 | QQYNSYPLT | |
| SEQ ID NO: 46 | 148 VH CDR1 | GFTFSSYA | |
| SEQ ID NO: 47 | 148 VH CDR2 | ISISGGST | |
| SEQ ID NO: 48 | 148 VH CDR3 | RGYSGYVYDAFDF | |
| SEQ ID NO: 49 | 148 VL CDR1<br>148 VL CDR2 | QGISNW<br>AAS | |
| SEQ ID NO: 50 | 148 VL CDR3 | QQYNSYPLT | |
| SEQ ID NO: 51 | 154 VH CDR1 | GFTFSSYA | |
| SEQ ID NO: 52 | 154 VH CDR2 | ISIGGGNA | |
| SEQ ID NO: 53 | 154 VH CDR3 | AKPGFIMVRGPLDY | |
| SEQ ID NO: 54 | 154-M103L VH CDR3 | AKPGFILVRGPLDY | |
| SEQ ID NO: 55 | 154 VL CDR1<br>154 VL CDR2 | QSVSNSY<br>GAS | |
| SEQ ID NO: 56 | 154 VL CDR3 | QQYGSSPYT | |
| SEQ ID NO: 57 | 171 VH CDR1 | GFTFSSYA | |
| SEQ ID NO: 58 | 171 VH CDR2 | ISVSGGST | |
| SEQ ID NO: 59 | 171 VH CDR3 | AKEGYIWFGESLSYAFDI | |
| SEQ ID NO: 60 | 171 VL CDR1<br>171 VL CDR2 | QSVSSSY<br>GAS | |
| SEQ ID NO: 61 | 171 VL CDR3 | QQYGRSFT | |
| SEQ ID NO: 62 | 172 VH CDR1 | GFTFSNYA | |
| SEQ ID NO: 63 | 172 VH CDR2 | ISVSGGST | |
| SEQ ID NO: 64 | 172 VH CDR3 | AKEGYIWFGESLSYAFDI | |
| SEQ ID NO: 65 | 172 VL CDR1<br>172 VL CDR2 | QSVSSSY<br>GAS | |
| SEQ ID NO: 66 | 172 VL CDR3 | QQYGRSFT | |
| SEQ ID NO: 67 | 181 VH CDR1 | GFTFSSYA | |
| SEQ ID NO: 68 | 181 VH CDR2 | ISVSGGST | |
| SEQ ID NO: 69 | 181 VH CDR3 | AKEGYIWFGESLSYAFDI | |
| SEQ ID NO: 70 | 181 VL CDR1<br>181 VL CDR2 | QSVSSSY<br>GAS | |
| SEQ ID NO: 71 | 181 VL CDR3 | QQYGRSFT | |
| SEQ ID NO: 72 | 183 VH CDR1 | GGSFSGYY | |
| SEQ ID NO: 73 | 183 VH CDR2 | INQSGST | |

TABLE 1-continued

| SEQ ID NO: | Name | Amino acid sequence | Comments |
|---|---|---|---|
| SEQ ID NO: 74 | 183-N52Q VH CDR2 | IQQSGST | |
| SEQ ID NO: 75 | 183 VH CDR3 | ASGNWDHFFDY | |
| SEQ ID NO: 76 | 183 VL CDR1<br>183 VL CDR2 | QGISSW<br>ATS | |
| SEQ ID NO: 77 | 183 VL CDR3 | QQAKSFPWT | |
| SEQ ID NO: 78 | 187 VH CDR1 | GGSFSGYH | |
| SEQ ID NO: 79 | 187 VH CDR2 | ISHSGRT | |
| SEQ ID NO: 80 | 187 VH CDR3 | ASFITMIRGTIITHFDY | |
| SEQ ID NO: 81 | 187 VL CDR1<br>187 VL CDR2 | QGISSW<br>AAS | |
| SEQ ID NO: 82 | 187 VL CDR3 | QQYHSYPYT | |
| SEQ ID NO: 83 | 608-01 VH CDR1 | GGTFSSYA | |
| SEQ ID NO: 84 | 608-01 VH CDR2 | IIPIFGIA | |
| SEQ ID NO: 85 | 608-01 VH CDR3 | ARRGDYYGSGSPDVFDI | |
| SEQ ID NO: 86 | 608-01 VL CDR1<br>608-01 VL CDR2 | QSVSSSY<br>GAS | |
| SEQ ID NO: 87 | 608-01 VL CDR3 | QQYGSSYT | |
| SEQ ID NO: 88 | 610-01 VH CDR1 | GGTFSSYA | |
| SEQ ID NO: 89 | 610-01 VH CDR2 | IIPIFGIA | |
| SEQ ID NO: 90 | 610-01 VH CDR3 | ARRGNYYGSGSPDVFDI | |
| SEQ ID NO: 91 | 610-01 VL CDR1<br>610-01 VL CDR2 | QSVSSSY<br>GAS | |
| SEQ ID NO: 92 | 610-01 VL CDR3 | QQYGSSYT | |
| SEQ ID NO: 93 | 613 VH CDR1 | GGTFSSYA | |
| SEQ ID NO: 94 | 613 VH CDR2 | IIPIFGIV | |
| SEQ ID NO: 95 | 613 VH CDR3 | ARRGNYYGSGSPDVFDI | |
| SEQ ID NO: 96 | 613 VL CDR1<br>613 VL CDR2 | QSVSSSY<br>GAS | |
| SEQ ID NO: 97 | 613 VL CDR3 | QQYGSSYT | |
| SEQ ID NO: 98 | 613-08 VH CDR1 | GGTFSSYA | |
| SEQ ID NO: 99 | 613-08 VH CDR2 | IIPIFGIV | |
| SEQ ID NO: 100 | 613-08 VH CDR3 | ARRGNYYGSGSPDVFDI | |
| SEQ ID NO: 101 | 613-08 VL CDR1<br>613-08 VL CDR2 | QSVSSY<br>DAS | |
| SEQ ID NO: 102 | 613-08 VL CDR3 | QQRSNWLT | |
| SEQ ID NO: 103 | 620-06 VH CDR1 | GGTFSSYA | |
| SEQ ID NO: 104 | 620-06 VH CDR2 | IIPIFGIA | |
| SEQ ID NO: 105 | 620-06 VH CDR3 | ARRGNYYGSGSPDVFDI | |
| SEQ ID NO: 106 | 620-06 VL CDR1<br>620-06 VL CDR2 | QSVSSSY<br>GAS | |
| SEQ ID NO: 107 | 620-06 VL CDR3 | QQYGSSYT | |
| SEQ ID NO: 108 | 726 VH CDR1 | GGSFSGYY | |

TABLE 1-continued

| SEQ ID NO: | Name | Amino acid sequence | Comments |
|---|---|---|---|
| SEQ ID NO: 109 | 726 VH CDR2 | ISHSGRT | |
| SEQ ID NO: 110 | 726 VH CDR3 | ARFITMIRGAIITHFDY | |
| SEQ ID NO: 111 | 726-M101L VH CDR3 | ARFITLIRGAIITHFDY | |
| SEQ ID NO: 112 | 726 VL CDR1<br>726 VL CDR2 | QGISSW<br>AAS | |
| SEQ ID NO: 113 | 726 VL CDR3 | QQYHSYPYT | |
| SEQ ID NO: 114 | 733 VH CDR1 | GFSFSTYA | |
| SEQ ID NO: 115 | 733 VH CDR2 | ISYDGDNK | |
| SEQ ID NO: 116 | 733 VH CDR3 | ARGRKLGIDAFDI | |
| SEQ ID NO: 117 | 733 VL CDR1<br>733 VL CDR2 | QGISSA<br>DAS | |
| SEQ ID NO: 118 | 733 VL CDR3 | QQFNSYPFT | |
| SEQ ID NO: 119 | Ig2 domain VH CDR2 | ISISGXST - wherein X is A or G | |
| SEQ ID NO: 120 | Ig2 domain VH CDR3 | RGYSGYVYDAFDX - wherein X is I or F | |
| SEQ ID NO: 121 | FN2 domain VH CDR1 | GGSFSGYX - wherein X is H or Y | |
| SEQ ID NO: 122 | FN2 domain VH CDR3 | AX1FITMIRGX2IITHFDY - wherein X1 is S or R; and X2 is T or A | |
| SEQ ID NO: 123 | FN1 domain VH CDR1 | GFTFSXYA - wherein X is S or N | |
| SEQ ID NO: 124 | FN1 domain VH CDR2 | ISVSGGST | |
| SEQ ID NO: 125 | FN1 domain VH CDR3 | AKEGYIWFGESLSYAFDI | |
| SEQ ID NO: 126 | Ig1 domain VH CDR2 | IIPIFGIX - wherein X is A or V | |
| SEQ ID NO: 127 | Ig1 domain VH CDR3 | ARRGXYYGSGSPDVFDI - wherein X is D or N | |
| SEQ ID NO: 128 | Ig1 domain VL CDR1<br>Ig1 domain VL CDR2 | QSVXSSY - wherein X is S or del<br>XAS - wherein X is D or G | |
| SEQ ID NO: 129 | Ig1 domain VL CDR3 | QQX1X2X3X4X5T - wherein X1 is R or Y; X2 is S or G; X3 is N or S; X4 is W or S; and X5 is L or Y | |
| SEQ ID NO: 130 | Human AXL protein (Swissprot P30530) | MAWRCPRMGRVPLAWCLALCGWACMAPRGTQAEES<br>PFVGNPGNITGARGLTGTLRCQLQVGEPPEVHWLRD<br>GQILELADSTQTQVPLGEDEQDDWIVVSQLRITSLQLSD<br>TGQYQCLVFLGHQTFVSQPGYVGLEGLPYFLEEPEDRTV<br>AANTPFNLSCQAQGPPEPVDLLWLQDAVPLATAPGHG<br>PQRSLHVPGLNKTSSFSCEAHNAKGVTTSRTATITVLPQ<br>QPRNLHLVSRQPTELEVAWTPGLSGIYPLTHCTLQAVLS<br>DDGMGIQAGEPDPPEEPLTSQASVPPHQLRLGSLHPHT<br>PYHIRVACTSSQGPSSWTHWLPVETPEGVPLGPPENISA<br>TRNGSQAFVHWQEPRAPLQGTLLGYRLAYQGQDTPEV<br>LMDIGLRQEVTLELQGDGSVSNLTVCVAAYTAAGDGP<br>WSLPVPLEAWRPGQAQPVHQLVKEPSTPAFSWPWWY<br>VLLGAVVAAACVLILALFLVHRRKKETRYGEVFEPTVERG<br>ELVVRYRVRKSYSRRTTEATLNSLGISEELKEKLRDVMVD<br>RHKVALGKTLGEGEFGAVMEGQLNQDDSILKVAVKTM<br>KIAICTRSELEDFLSEAVCMKEFDHPNVMRLIGVCFQGS<br>ERESFPAPVVILPFMKHGDLHSFLLYSRLGDQPVYLPTQ<br>MLVKFMADIASGMEYLSTKRFIHRDLAARNCMLNENM<br>SVCVADFGLSKKIYNGDYYRQGRIAKMPVKWIAIESLAD<br>RVYTSKSDVWSFGVTMWEIATRGQTPYPGVENSEIYDY | |

TABLE 1-continued

| SEQ ID NO: | Name | Amino acid sequence | Comments |
|---|---|---|---|
| | | LRQGNRLKQPADCLDGLYALMSRCWELNPQDRPSFTE<br>LREDLENTLKALPPAQEPDEILYVNMDEGGGYPEPPGA<br>AGGADPPTQPDPKDSCSCLTAAEVHPAGRYVLCPSTTP<br>SPAQPADRGSPAAPGQEDGA | |
| SEQ ID NO: 131 | Mus musculus AXL | MAWRCPRMGRVPLAWCLALCGWACMYPYDVPDYAA<br>HKDTQTEAGSPFVGNPGNITGARGLTGTLRCELQVQGE<br>PPEVVWLRDGQILELADNTQTQVPLGEDWQDEWKVV<br>SQLRISALQLSDAGEYQCMVHLEGRTFVSQPGFVGLEG<br>LPYFLEEPEDKAVPANTPFNLSCQAQGPPEPVTLLWLQ<br>DAVPLAPVTGHSSQHSLQTPGLNKTSSFSCEAHNAKGV<br>TTSRTATITVLPQRPHHLHVVSRQPTELEVAWTPGLSGI<br>YPLTHCNLQAVLSDDGVGIWLGKSDPPEDPLTLQVSVP<br>PHQLRLEKLLPHTPYHIRISCSSSQGPSPWTHWLPVETTE<br>GVPLGPPENVSAMRNGSQVLVRWQEPRVPLQGTLLGY<br>RLAYRGQDTPEVLMDIGLTREVTLELRGDRPVANLTVSV<br>TAYTSAGDGPWSLPVPLEPWRPGQGQPLHHLVSEPPP<br>RAFSWPWWYVLLGAVVAAACVLILALFLVHRRKKETRY<br>GEVFEPTVERGELVVRYRVRKSYSRRTTEATLNSLGISEEL<br>KEKLRDVMVDRHKVALGKTLGEGEFGAVMEGQLNQD<br>DSILKVAVKTMKIAICTRSELEDFLSEAVCMKEFDHPNV<br>MRLIGVCFQGSERESFPAPVVILPFMKHGDLHSFLLYSRL<br>GDQPVYLPTQMLVKFMADIASGMEYLSTKRFIHRDLAA<br>RNCMLNENMSVCVADFGLSKKIYNGDYYRQGRIAKMP<br>VKWIAIESLADRVYTSKSDVWSFGVTMWEIATRGQTPY<br>PGVENSEIYDYLRQGNRLKQPADCLDGLYALMSRCWEL<br>NPQDRPSFTELREDLENTLKALPPAQEPDEILYVNMDEG<br>GGYPEPPGAAGGADPPTQPDPKDSCSCLTAAEVHPAG<br>RYVLCPSTTPSPAQPADRGSPAAPGQEDGA | |
| SEQ ID NO: 132 | Homo sapiens AXL -<br>Mus musculus Ig1<br>domain | MAWRCPRMGRVPLAWCLALCGWACMAPRGTQAEES<br>PFVGNPGNITGARGLTGTLRCQLQVQGEPPEVHWLRD<br>GQILELADSTQTQVPLGEDEQDDWIVVSQLRITSLQLSD<br>TGQYQCLVFLGHQTFVSQPGYVGLEGLPYFLEEPEDKAV<br>PANTPFNLSCQAQGPPEPVTLLWLQDAVPLAPVTGHSS<br>QHSLQTPGLNKTSSFSCEAHNAKGVTTSRTATITVLPQQ<br>PRNLHLVSRQPTELEVAWTPGLSGIYPLTHCTLQAVLSD<br>DGMGIQAGEPDPPEEPLTSQASVPPHQLRLGSLHPHTP<br>YHIRVACTSSQGPSSWTHWLPVETPEGVPLGPPENISAT<br>RNGSQAFVHWQEPRAPLQGTLLGYRLAYQGQDTPEVL<br>MDIGLRQEVTLELQGDGSVSNLTVCVAAYTAAGDGPW<br>SLPVPLEAWRPGQAQPVHQLVKEPSTPAFSWPWWYV<br>LLGAVVAAACVLILALFLVHRRKKETRYGEVFEPTVERGE<br>LVVRYRVRKSYSRRTTEATLNSLGISEELKEKLRDVMVDR<br>HKVALGKTLGEGEFGAVMEGQLNQDDS<br>ILKVAVKTMKIAICTRSELEDFLSEAVCMKEFDHPNVMR<br>LIGVCFQGSERESFPAPVVILPFMKHGDLHSFLLYSRLGD<br>QPVYLPTQMLVKFMADIASGMEYLSTKRFIHRDLAARN<br>CMLNENMSVCVADFGLSKKIYNGDYYRQGRIAKMPVK<br>WIAIESLADRVYTSKSDVWSFGVTMWEIATRGQTPYPG<br>VENSEIYDYLRQGNRLKQPADCLDGLYALMSRCWELNP<br>QDRPSFTELREDLENTLKALPPAQEPDEILYVNMDEGG<br>GYPEPPGAAGGADPPTQPDPKDSCSCLTAAEVHPAGRY<br>VLCPSTTPSPAQPADRGSPAAPGQEDGA | |
| SEQ ID NO: 133 | Homo sapiens AXL -<br>Mus musculus Ig2<br>domain | MAWRCPRMGRVPLAWCLALCGWACMAPRGTQAEES<br>PFVGNPGNITGARGLTGTLRCQLQVQGEPPEVHWLRD<br>GQILELADSTQTQVPLGEDEQDDWIVVSQLRITSLQLSD<br>TGQYQCLVFLGHQTFVSQPGYVGLEGLPYFLEEPEDKAV<br>PANTPFNLSCQAQGPPEPVTLLWLQDAVPLAPVTGHSS<br>QHSLQTPGLNKTSSFSCEAHNAKGVTTSRTATITVLPQQ<br>PRNLHLVSRQPTELEVAWTPGLSGIYPLTHCTLQAVLSD<br>DGMGIQAGEPDPPEEPLTSQASVPPHQLRLGSLHPHTP<br>YHIRVACTSSQGPSSWTHWLPVETPEGVPLGPPENISAT<br>RNGSQAFVHWQEPRAPLQGTLLGYRLAYQGQDTPEVL<br>MDIGLRQEVTLELQGDGSVSNLTVCVAAYTAAGDGPW<br>SLPVPLEAWRPGQAQPVHQLVKEPSTPAFSWPWWYV<br>LLGAVVAAACVLILALFLVHRRKKETRYGEVFEPTVERGE<br>LVVRYRVRKSYSRRTTEATLNSLGISEELKEKLRDVMVDR<br>HKVALGKTLGEGEFGAVMEGQLNQDDS<br>ILKVAVKTMKIAICTRSELEDFLSEAVCMKEFDHPNVMR<br>LIGVCFQGSERESFPAPVVILPFMKHGDLHSFLLYSRLGD<br>QPVYLPTQMLVKFMADIASGMEYLSTKRFIHRDLAARN<br>CMLNENMSVCVADFGLSKKIYNGDYYRQGRIAKMPVK<br>WIAIESLADRVYTSKSDVWSFGVTMWEIATRGQTPYPG<br>VENSEIYDYLRQGNRLKQPADCLDGLYALMSRCWELNP | |

TABLE 1-continued

| SEQ ID NO: | Name | Amino acid sequence | Comments |
|---|---|---|---|
| | | QDRPSFTELREDLENTLKALPPAQEPDEILYVNMDEGG GYPEPPGAAGGADPPTQPDPKDSCSCLTAAEVHPAGRY VLCPSTTPSPAQPADRGSPAAPGQEDGA | |
| SEQ ID NO: 134 | Homo sapiens AXL - Mus musculus FN1 domain | MAWRCPRMGRVPLAWCLALCGWACMAPRGTQAEES PFVGNPGNITGARGLTGTLRCQLQVQGEPPEVHWLRD GQILELADSTQTQVPLGEDEQDDWIVVSQLRITSLQLSD TGQYQCLVFLGHQTFVSQPGYVGLEGLPYFLEEPEDRTV AANTPFNLSCQAQGPPEPVDLLWLQDAVPLATAPGHG PQRSLHVPGLNKTSSFSCEAHNAKGVTTSRTATITVLPQ RPHHLHVVSRQPTELEVAWTPGLSGIYPLTHCNLQAVLS DDGVGIWLGKSDPPEDPLTLQVSVPPHQLRLEKLLPHTP YHIRISCSSSQGPSPWTHWLPVETTEGVPLGPPENISAT RNGSQAFVHWQEPRAPLQGTLLGYRLAYQGQDTPEVL MDIGLRQEVTLELQGDGSVSNLTVCVAAYTAAGDGPW SLPVPLEAWRPGQAQPVHQLVKEPSTPAFSWPWWYV LLGAVVAAACVLILALFLVHRRKKETRYGEVFEPTVERGE LVVRYRVRKSYSRRTTEATLNSLGISEELKEKLRDVMVDR HKVALGKTLGEGEFGAVMEGQLNQDDS ILKVAVKTMKIAICTRSELEDFLSEAVCMKEFDHPNVMR LIGVCFQGSERESFPAPVVILPFMKHGDLHSFLLYSRLGD QPVYLPTQMLVKFMADIASGMEYLSTKRFIHRDLAARN CMLNENMSVCVADFGLSKKIYNGDYYRQGRIAKMPVK WIAIESLADRVYTSKSDVWSFGVTMWEIATRGQTPYPG VENSEIYDYLRQGNRLKQPADCLDGLYALMSRCWELNP QDRPSFTELREDLENTLKALPPAQEPDEILYVNMDEGG GYPEPPGAAGGADPPTQPDPKDSCSCLTAAEVHPAGRY VLCPSTTPSPAQPADRGSPAAPGQEDGA | |
| SEQ ID NO: 135 | Homo sapiens AXL - Mus musculus FN2 domain | MAWRCPRMGRVPLAWCLALCGWACMAPRGTQAEES PFVGNPGNITGARGLTGTLRCQLQVQGEPPEVHWLRD GQILELADSTQTQVPLGEDEQDDWIVVSQLRITSLQLSD TGQYQCLVFLGHQTFVSQPGYVGLEGLPYFLEEPEDRTV AANTPFNLSCQAQGPPEPVDLLWLQDAVPLATAPGHG PQRSLHVPGLNKTSSFSCEAHNAKGVTTSRTATITVLPQ QPRNLHVSRQPTELEVAWTPGLSGIYPLTHCTLQAVLS DDGMGIQAGEPDPPEEPLTSQASVPPHQLRLGSLHPHT PYHIRVACTSSQGPSSWTHWLPVETPEGVPLGPPENVS AMRNGSQVLVRWQEPRVPLQGTLLGYRLAYRGQDTPE VLMDIGLTREVTLELRGDRPVANLTVSVTAYTSAGDGP WSLPVPLEPWRPGQGQPLHHLVSEPPPRAFSWPWWY VLLGAVVAAACVLILALFLVHRRKKETRYGEVFEPTVERG ELVVRYRVRKSYSRRTTEATLNSLGISEELKEKLRDVMVD RHKVALGKTLGEGEFGAVMEGQLNQDDSILKVAVKTM KIAICTRSELEDFLSEAVCMKEFDHPNVMRLIGVCFQGS ERESFPAPVVILPFMKHGDLHSFLLYSRLGDQPVYLPTQ MLVKFMADIASGMEYLSTKRFIHRDLAARNCMLNENM SVCVADFGLSKKIYNGDYYRQGRIAKMPVKWIAIESLAD RVYTSKSDVWSFGVTMWEIATRGQTPYPGVENSEIYDY LRQGNRLKQPADCLDGLYALMSRCWELNPQDRPSFTE LREDLENTLKALPPAQEPDEILYVNMDEGGGYPEPPGA AGGADPPTQPDPKDSCSCLTAAEVHPAGRYVLCPSTTP SPAQPADRGSPAAPGQEDGA | |
| SEQ ID NO: 136 | 511 VH | EVQLLESGGGLVQPGGSLRLSCAASGFTFSSYAMNWV RQAPGKGLEWVSGISGSGGHTYHADSVKGRFTISRDNS KNTLYLQMNSLRAEDTAVYYCAKDRYDILTGYYNLLDY WGQGTLVTVSS | Ig2 domain binding Ab |
| SEQ ID NO: 137 | 511 VH CDR1 | GFTFSSYA | |
| SEQ ID NO: 138 | 511 VH CDR2 | ISGSGGHT | |
| SEQ ID NO: 139 | 511 VH CDR3 | AKDRYDILTGYYNLLDY | |
| SEQ ID NO: 140 | 511 VL | DIQMTQSPSSLSASVGDRVTITCRASQGISSWLAWYQQ KPEEAPKSLIYAASSLQSGVPSRFSGSGSGTDFTLTISSLQ PEDFATYYCQQYNSYPLTFGGGAKVEIK | |
| SEQ ID NO: 141 | 511 VL CDR1 511 VL CDR2 | QGISSW AAS | |
| SEQ ID NO: 142 | 511 VL CDR3 | QQYNSYPLT | |
| SEQ ID NO: 143 | 061 VH | QVQLVQSGAEVKKPGASVKVSCKASGYAFTGYGISWVR QAPGQGLEWIGWISAYNGNTNYVQNLQDRVTMTTDT STSTAYMELRSLRSDDTAVYYCARDHISMLRGIIIRNYW GQGTLVTVSS | Ig1 domain binding Ab |

TABLE 1-continued

| SEQ ID NO: | Name | Amino acid sequence | Comments |
|---|---|---|---|
| SEQ ID NO: 144 | 061 VL | EIVLTQSPATLSLSPGERATLSCRASQSVSSYLAWYQQKP GQAPRLLIYDASNRATGIPARFSGSGSGTDFTLTISSLEPE DFAVYYCQQRSSWPRLTFGGGTKVEIK | |
| SEQ ID NO: 145 | 137 VH | QVQLVQSGAEVKKPGSSVKVSCKASGGTFSRYAISWVR QAPGQGLEWMGRIIPIVGIANYAQKFQGRVTLTADKST STAYMELSSLRSEDTAVYYCAREAGYSSSWYAEYFQHW GQGTLVTVSS | |
| SEQ ID NO: 146 | 137 VL | EIVLTQSPGTLSLSPGERATLSCRASQSVSSNYLAWYQQ KPGQAPRLLIYGASSRATGFPDRFSGSGSGTDFTLTISRL EPEDFAVYYCQQYGSSPYTFGQGTKLEIK | |
| SEQ ID NO: 147 | Cynomolgus monkey AXL (GenBank number HB387229.1) | AWRCPRMGRVPLAWCLALCGWVCMAPRGTQAEESP FVGNPGNITGARGLTGTLRCQLQVQGEPPEVHWLRDG QILELADSTQTQVPLGEDEQDDWIVVSQLRIASLQLSDA GQYQCLVFLGHQNFVSQPGYVGLEGLPYFLEEPEDRTV AANTPFNLSCQAQGPPEPVDLLWLQDAVPLATAPGHG PQRNLHVPGLNKTSSFSCEAHNAKGVTTSRTATITVLPQ QPRNLHLVSRQPTELEVAWTPGLSGIYPLTHCTLQAVLS DDGMGIQAGEPDPPEEPLTLQASVPPHQLRLGSLHPHT PYHIRVACTSSQGPSSWTHWLPVETPEGVPLGPPENISA TRNGSQAFVHWQEPRAPLQGTLLGYRLAYQGQDTPEV LMDIGLRQEVTLELQGDGSVSNLTVCVAAYTAAGDGP WSLPVPLEAWRPGQAQPVHQLVKETSAPAFSWPWW YILLGAVVAAACVLILALFLVHRRKKETRYGEVFEPTVER GELVVRYRVRKSYSRRTTEATLNSLGISEELKEKLRDVMV DRHKVALGKTLGEGEFGAVMEGQLNQDDSILKVAVKT MKIAICTRSELEDFLSEAVCMKEFDHPNVMRLIGVCFQG SERESFPAPVVILPFMKHGDLHSFLLYSRLGDQPVYLPTQ MLVKFMADIASGMEYLSTKRFIHRDLAARNCMLNENM SVCVADFGLSKKIYNGDYYRQGRIAKMPVKWIAIESLAD RVYTSKSDVWSFGVTMWEIATRGQTPYPGVENSEIYDY LRQGNRLKQPADCLDGLYALMSRCWELNPQDRPSFTE LREDLENTLKALPPAQEPDEILYVNMDEGGGYPEPPGA AGGADPPTQLDPKDSCSCLTSAEVHPAGRYVLCPSTAPS PAQPADRGSPAAPGQEDGA | |

The present invention is further illustrated by the following examples which should not be construed as further limiting.

EXAMPLES

Example 1—Immunization and Generation of AXL Antibodies

Expression Constructs for AXL

The following codon-optimized constructs for expression of various full-length AXL variants were generated: human (*Homo sapiens*) AXL (Genbank accession no. NP_068713.2), human-cynomolgus monkey chimeric AXL in which the human extracellular domain (ECD) was replaced with the ECD of cynomolgus monkey (*Macaca fascicularis*) AXL (translation of Genbank accession HB387229.1; aa 1-447), human-mouse chimeric AXL in which the human ECD was replaced with the ECD of mouse (*Mus musculus*) AXL (Genbank accession NP_033491.2; aa 1-441), human-mouse chimeric AXL in which the human Ig-like domain I (aa 1-134, also termed "Ig1 domain" herein) was replaced with the Ig-like domain I of mouse AXL, human-mouse chimeric AXL in which the human Ig-like domain II (aa 148-194, also termed "Ig2 domain" herein) was replaced by the Ig-like domain II of mouse AXL, human-mouse chimeric ALX in which the human FNIII-like domain I (aa 227-329, also termed "FN1 domain" herein) was replaced with the FNIII-like domain I of mouse AXL, human-mouse chimeric AXL in which the human FNIII-like domain II (aa 340-444, also termed "FN2 domain" herein) was replaced by the FNIII-like domain II of mouse AXL. In addition, the following codon-optimized constructs for various AXL ECD variants were generated: the extracellular domain (ECD) of human AXL (aa 1-447) with a C-terminal His tag (AXLECDHis), the FNIII-like domain II of human AXL (aa 327-447) with a N-terminal signal peptide and a C-terminal His tag (AXL-FN2ECDHis), and the Ig1- and Ig2-like domains of human AXL (aa 1-227) with a C-terminal His tag (AXL-Ig12ECDHis).

The constructs contained suitable restriction sites for cloning and an optimal Kozak (GCCGCCACC) sequence [141]. The constructs were cloned in the mammalian expression vector pcDNA3.3 (Invitrogen).

AXL Expression in EL4 Cells

EL4 cells were stable transfected with the pcDNA3.3 vector containing the full human AXL coding sequence and stable clones were selected after selection with the antibiotic agent, G418, (Geneticin).

Purification of His-Tagged AXL

AXLECDHis, AXL-FN2ECDHis, and AXL-Ig12ECDHis were expressed in HEK-293F cells. The His-tag enables purification with immobilized metal affinity chromatography. In this process, a chelator fixed onto the chromatographic resin is charged with $Co^{2+}$ cations. His-tagged protein containing supernatants were incubated with the resin in batch mode (i.e. solution). The His-tagged protein binds strongly to the resin beads, while other proteins present in the culture supernatant do not bind or bind weakly compared to the His-tagged proteins. After incubation the beads are retrieved from the supernatant and packed into a column. The column is washed in order to remove weakly bound proteins. The strongly bound His-tagged proteins are then eluted with a buffer containing imidazole, which competes with the binding of His to $Co^{2+}$. The eluent is removed from the protein by buffer exchange on a desalting column.

Immunization Antibodies IgG1-AXL-061, IgG1-AXL-107, IgG1-AXL-183, IgG1-AXL-613, and IgG1-AXL-726 were derived from the following immunizations: HCo12-BalbC (IgG1-AXL-107), HCo17-BalbC (IgG1-AXL-183, IgG1-AXL-726) and HCo20 (IgG1-AXL-061, IgG1-AXL-613) transgenic mice (Medarex, San Jose, Calif., USA) which were immunized alternatingly intraperitoneally (IP) with 20 µg of the AXLECDHis protein (IgG1-AXL-511, IgG1-AXL-613, IgG1-AXL-183), 20 µg AXL-FN2ECDHIS plus 20 µg AXL-Ig2ECDHis (IgG1-AXL-726), or 20 µg AXL-Ig12ECDHis (IgG1-AXL-107) and subcutaneously (SC; at the tail base) with the same protein, with an interval of 14 days. In total 8 immunizations were performed: 4 IP and 4 SC immunizations. For most immunizations, the first immunization was performed in complete Freunds' adjuvant (CFA; Difco Laboratories, Detroit, Mich., USA) and all subsequent immunizations in incomplete Freunds' adjuvant (IFA; Difco Laboratories, Detroit, Mich., USA). Antibody IgG1-AXL-183 was derived from immunizations that were all performed in Sigma adjuvant system (Sigma-Aldrich, St. Louis, Mo., USA).

Antibodies IgG1-AXL-137, IgG1-AXL-148, IgG1-AXL-154, IgG1-AXL-171, and IgG1-AXL-733 were derived from the following immunizations: HCo12-BalbC (IgG1-AXL-137, IgG1-AXL-148), HCo17-BalbC (IgG1-AXL-154, IgG1-AXL-733), and HCo20-BalbC (IgG1-AXL-171) transgenic mice (Medarex, San Jose, Calif., USA) were immunized with 20 µg of the AXLECDHis protein in CFA. Subsequently, mice were immunized alternating intraperitoneally (IP) with EL4 cells transfected with full length human AXL in PBS and subcutaneously (SC; at the tail base) with the AXLECDHis protein in IFA, with an interval of 14 days.

Mice with at least two sequential AXL specific antibody titers of 200 (serum dilutions of 1/200) or higher, detected in the antigen specific screening FMAT assay as described below, were boosted 3-4 days prior to fusion (10 µg of AXL-derived protein in PBS injected intravenously).

Homogeneous Antigen Specific Screening Assay

The presence of anti-AXL antibodies in sera of immunized mice or HuMab (human monoclonal antibody) hybridoma or transfectoma culture supernatant was determined by homogeneous antigen specific screening assays using Fluorometric Micro volume Assay Technology (FMAT; Applied Biosystems, Foster City, Calif., USA). For this, two different test designs with combinations of either 4 or 8 cell based assays were used.

The 4 cell based assay test design was used for the testing of sera from immunized mice and as primary screening test for hybridoma or transfectoma culture supernatant. In the 4 assay test design samples were analyzed for binding of human antibodies to A431 (DSMZ) and MDA-MB-231 cells (both expressing AXL at the cell surface) as well as binding to TH1021-AXL (HEK-293F cells transiently expressing full length human AXL; produced as described above) and HEK293 wild-type cells (negative control which does not express AXL), respectively.

Hybridoma or transfectoma culture supernatant samples were additionally subjected to an 8 cell based assay test design. In the 8 assay test design samples were analyzed for binding of human antibodies to TH1021-hAXL (HEK-293F cells transiently expressing the human AXL), TH1021-cAXL (HEK-293F cells transiently expressing human-cynomolgus AXL chimeras in which the human ECD had been replaced with the ECD of cynomolgus monkey AXL), TH1021-mAXL (HEK-293F cells transiently expressing human-mouse AXL chimeras in which the human ECD had been replaced with the ECD of mouse AXL), TH1021-mIg1 (HEK-293F cells transiently expressing the human AXL with the Ig-like domain I being replaced by the Ig-like domain I of mouse AXL), TH1021-mIg2 (HEK-293F cells transiently expressing human AXL with the Ig-like domain II being replaced by the Ig-like domain II of mouse AXL), TH1021-mFN1 (HEK-293F cells transiently expressing human AXL with the FNIII-like domain I being replaced by the FNIII-like domain I of mouse AXL), TH1021-mFN2 (HEK-293F cells transiently expressing human AXL with the FNIII-like domain II being replaced by the FNIII-like domain II of mouse AXL), and HEK293 wild-type cells (negative control which does not express AXL), respectively.

Samples were added to the cells to allow binding to AXL. Subsequently, binding of HuMab was detected using a fluorescent conjugate (Goat anti-Human IgG Fc gamma-DyLight649; Jackson ImmunoResearch). The AXL specific humanized mouse antibody A0704P (produced in HEK-293F cells) was used as a positive control and HuMab-mouse pooled serum and ChromPure Human IgG, whole molecule (Jackson ImmunoResearch), respectively, were used as negative controls. The samples were scanned using an Applied Biosystems 8200 Cellular Detection System (8200 CDS) and mean fluorescence was used as read-out. Samples were stated positive when counts were higher than 50 and counts x fluorescence was at least three times higher than the negative control.

HuMab Hybridoma Generation

The HuMab mouse with sufficient antigen-specific titer development (described above) was sacrificed and the spleen and lymph nodes flanking the abdominal aorta and vena cava were collected. Fusion of splenocytes and lymph node cells to a mouse myeloma cell line (SP2.0 cells) was done by electrofusion using a CytoPulse CEEF 50 Electrofusion System (Cellectis, Paris, France), essentially according to the manufacturer's instructions. Next, the primary wells were sub-cloned using the ClonePix system (Genetix, Hampshire, UK). To this end, specific primary well hybridomas were seeded in semisolid medium made from 40% CloneMedia (Genetix, Hampshire, UK) and 60% HyQ 2× complete media (Hyclone, Waltham, USA). The sub clones were retested according to the antigen-specific binding assay as described above and scanned using the IsoCyte sytem (Molecular Devices, LLC, Sunnyvale, Calif.). IgG levels were measured using an Octet (Fortebio, Menlo Park, USA) in order to select the best producing clone per primary well for further expansion. Further expansion and culturing of the resulting HuMab hybridomas were done based upon standard protocols (e.g. as described in Coligan J. E., Bierer, B. E., Margulies, D. H., Shevach, E. M. and Strober, W., eds. Current Protocols in Immunology, John Wiley & Sons, Inc., 2006). Clones derived by this process were designated PC1021.

Mass Spectrometry of Purified Antibodies

Small 0.8 ml aliquots of antibody containing hybridoma supernatant from 6-well or Hyperflask stage were purified using PhyTip columns containing Protein G resin (PhyNexus Inc., San Jose, USA) on a Sciclone ALH 3000 workstation (Caliper Lifesciences, Hopkinton, USA). The PhyTip columns were used according to manufacturer's instructions, but buffers were replaced by: Binding Buffer PBS (B. Braun, Medical B.V., Oss, Netherlands) and Elution Buffer 0.1M Glycine-HCl pH 2.7 (Fluka Riedel-de Haën, Buchs, Germany). After purification, samples were neutralized with 2M Tris-HCl pH 9.0 (Sigma-Aldrich, Zwijndrecht, Netherlands). Alternatively, in some cases larger volumes of culture supernatant were purified using Protein A affinity column chromatography.

After purification, the samples were placed in a 384-well plate (Waters, 100 µl square well plate, part#186002631). Samples were deglycosylated overnight at 37° C. with N-glycosidase F. DTT (15 mg/ml) was added (1 µl/well) and incubated for 1 h at 37° C. Samples (5 or 6 µl) were desalted on an Acquity UPLC™ (Waters, Milford, USA) with a BEH300 C18, 1.7 µm, 2.1×50 mm column at 60° C. MQ water and LC-MS grade acetonitrile (Biosolve, cat no 01204101, Valkenswaard, The Netherlands) with both 0.1% formic acid (Fluka, cat no 56302, Buchs, Germany), were used as Eluent A and B, respectively. Time-of-flight electrospray ionization mass spectra were recorded on-line on a micrOTOF™ mass spectrometer (Bruker, Bremen, Germany) operating in the positive ion mode. Prior to analysis, a 900-3000 m/z scale was calibrated with ES tuning mix (Agilent Technologies, Santa Clara, USA). Mass spectra were deconvoluted with DataAnalysis™ software v. 3.4 (Bruker) using the Maximal Entropy algorithm searching for molecular weights between 5 and 80 kDa.

After deconvolution the resulting heavy and light chain masses (under reducing conditions) for all samples were compared in order to find duplicate antibodies. In the comparison of the heavy chains the possible presence of C-terminal lysine variants was taken into account. This resulted in a list of unique antibodies, where unique is defined as a unique combination of heavy and light chains. In case duplicate antibodies were found, the results from other tests were used to decide which antibody was the best material to continue experiments with.

Sequence Analysis of the AXL Antibody Variable Domains and Cloning in Expression Vectors Total RNA was prepared from 0.2 to 5×10$^6$ hybridoma cells and 5'-RACE-Complementary DNA (cDNA) was prepared from 100 ng total RNA, using the SMART RACE cDNA Amplification kit (Clontech), according to the manufacturer's instructions. VH and VL coding regions were amplified by PCR and cloned directly, in frame, in the pG1f and pKappa expression vectors, by ligation independent cloning (Aslanidis, C. and P. J. de Jong, Nucleic Acids Res 1990; 18(20): 6069-74). For each antibody, 12 VL clones and 12 VH clones were sequenced. The resulting sequences are shown in the Table 1. CDR sequences were defined according to IMGT [22] and [23]. Clones with a correct Open Reading Frame (ORF) were selected for further study and expression. Vectors of all combinations of heavy chains and light chains that were found were transiently co-expressed in Freestyle™ 293-F cells using 293fectin.

For antibodies IgG1-AXL-154, IgG1-AXL-183 and IgG1-AXL-726, the following variants with point mutations in the variable domains were generated: IgG1-AXL-154-M103L, IgG1-AXL-183-N52Q and IgG1-AXL-726-M101L. Mutants were generated by site-directed mutagenesis using the Quickchange II mutagenesis kit (Stratagene).

AXL Control Antibodies

In some of the Examples a comparison antibody against AXL was used (IgG1-YW327.652) that have been previously described [142] and [143]. The VH and VL sequences for these AXL-specific antibodies were cloned into the pG1f and pKappa expression vectors.

b12 Antibody

In some of the examples the antibody b12, a gp120 specific antibody [144] was used as a negative control.

Expression

Antibodies were expressed as IgG1,κ. Plasmid DNA mixtures encoding both heavy and light chains of antibodies were transiently transfected to Freestyle HEK293F cells (Invitrogen, US) using 293fectin (Invitrogen, US) essentially as described by the manufacturer.

Purification of Antibodies

Culture supernatant was filtered over 0.2 µm dead-end filters, loaded on 5 mL MabSelect SuRe columns (GE Health Care) and eluted with 0.1 M sodium citrate-NaOH, pH 3. The eluate was immediately neutralized with 2M Tris-HCl, pH 9 and dialyzed overnight to 12.6 mM NaH2PO4, 140 mM NaCl, pH 7.4 (B.Braun). Alternatively, subsequent to purification, the eluate was loaded on a HiPrep Desalting column and the antibody was exchanged into 12.6 mM NaH2PO4, 140 mM NaCl, pH 7.4 (B.Braun) buffer. After dialysis or exchange of buffer, samples were sterile filtered over 0.2 µm dead-end filters. Purity was determined by SDS-PAGE and IgG concentration was measured using an Octet (Fortebio, Menlo Park, USA). Purified antibodies were stored at 4° C.

The antibody IgG1-AXL-511 was generated by the following method:

Expression Constructs for AXL

The following codon-optimized constructs for expression of various full-length AXL variants were generated: human (*Homo sapiens*) AXL (Genbank accession no. NP_068713.2), human-cynomolgus monkey chimeric AXL in which the human extracellular domain (ECD) was replaced with the ECD of cynomolgus monkey (*Macaca fascicularis*) AXL (translation of Genbank accession HB387229.1; aa 1-447), human-mouse chimeric AXL in which the human ECD was replaced with the ECD of mouse (*Mus musculus*) AXL (Genbank accession NP_033491.2; aa 1-441), human-mouse chimeric AXL in which the human Ig-like domain I (aa 1-147, also termed "Ig1 domain" herein) was replaced with the Ig-like domain I of mouse AXL, human-mouse chimeric AXL in which the human Ig-like domain II (aa 148-227, also termed "Ig2 domain" herein) was replaced by the Ig-like domain II of mouse AXL, human-mouse chimeric ALX in which the human FNIII-like domain I (aa 228-326, also termed "FN1 domain" herein) was replaced with the FNIII-like domain I of mouse AXL, human-mouse chimeric AXL in which the human FNIII-like domain II (aa 327-447, also termed "FN2 domain" herein) was replaced by the FNIII-like domain II of mouse AXL. In addition, the following codon-optimized constructs for various AXL ECD variants were generated: the extracellular domain (ECD) of human AXL (aa 1-447) with a C-terminal His tag (AXLECDHis), the FNIII-like domain II of human AXL (aa 327-447) with a N-terminal signal peptide and a C-terminal His tag (AXL-FN2ECDHis), and the Ig1- and Ig2-like domains of human AXL (aa 1-227) with a C-terminal His tag (AXL-Ig12ECDHis).

The constructs contained suitable restriction sites for cloning and an optimal Kozak (GCCGCCACC) sequence (Kozak et al. (1999) Gene 234: 187-208). The constructs were cloned in the mammalian expression vector pcDNA3.3 (Invitrogen).

AXL Expression in EL4 Cells

EL4 cells were stable transfected with the pcDNA3.3 vector containing the full length human AXL coding sequence and stable clones were selected after selection with the antibiotic agent, G418, (Geneticin).

Purification of His-Tagged AXL

AXLECDHis, AXL-FN2ECDHis, and AXL-Ig12ECDHis were expressed in HEK293F cells and purified with immobilized metal affinity chromatography.

Immunization

Material from 4 transgenic mice expressing human antibody gene sequences was used for selecting antibodies. Mice immunized with various immunization protocols and with various antibody responses and yielding various numbers of antibodies from the traditional hybridoma process were chosen. Mouse A (3.5% hits in the hybridoma process) was an HCo17-BALB/c transgenic mouse (Bristol-Myers Squibb, Redwood City, Calif., USA) was immunized alternatingly intraperitoneally (IP) with 20 μg AXL-FN2ECDHIS plus 20 μg AXL-Ig12ECDHis) and subcutaneously (SC) at the tail base) with the same protein, with an interval of 14 days. In total 8 immunizations were performed: 4 IP and 4 SC immunizations. For most immunizations, the first immunization was performed in complete Freunds' adjuvant (CFA; Difco Laboratories, Detroit, Mich., USA) and all subsequent immunizations in incomplete Freunds' adjuvant (IFA; Difco Laboratories, Detroit, Mich., USA). Mouse B (0% hits in the hybridoma process) was a HCo12 transgenic mouse (Medarex) immunized with 20 μg of the AXLECDHis protein using a similar immunization protocol as mouse A. Mouse C (38% hits in the hybridoma process) was a HCo12-BALB/c mouse immunized alternating intraperitoneally (IP) with EL4 cells transfected with full length human AXL in PBS and subcutaneously (SC; at the tail base) with the AXLECDHis protein in IFA, with an interval of 14 days. Mouse D (0% hits in the hybridoma process) was a HCo12 transgenic mouse (Medarex) immunized with 20 μg of the AXL-Ig12ECDHis protein in using a similar immunization protocol as mouse A.

Mice with at least two sequential AXL specific antibody titers of 200 (serum dilutions of 1/200) or higher, were boosted 3-4 days prior to fusion (10 μg of AXL-derived protein in PBS injected intravenously).

Isolation of RNA from Spleen Cells

Total RNA was isolated from spleen cells using the Mini RNA easy kit (Qiagen). First strand cDNA for 5'-RACE was synthesized using 150 ng of RNA using the SMART RACE cDNA Amplification kit (Clontech, Mountain View, Calif., USA), PrimeScript Reverse Transcriptase (Clontech) and the SMART HA oligo and oligodT as primers. VL encoding regions were amplified by PCR using Advantage 2 polymerase (Clontech), the primers RACEkLIC4shortFW2 (320 nM), RACEkLIC4LongFW2 (80 nM) and RACEkLI-CRV_PmIA3 (400 nM), performing 35 cycles of 30 seconds at 95° C., and 1 minute at 68° C. VH encoding regions were amplified by PCR using Pfu Ultra II Fusion HS DNA polymerase (Stratagene), the primers RACEG1LIC3shortFW (320 nM), RACEG1LIC3longFW (80 nM) and RACEG1LIC3RV2 (400 nM), performing 40 cycles of 20 seconds at 95° C., 20 seconds at 66° C. and 30 seconds at 72° C., ending with a finale extension step of 3 minutes at 72° C. VH or VL encoding PCR products were separated using agarose gel electrophoresis and DNA products of the expected size were cut from the gel and purified using the Qiagen MiniElute kit. VH and VL coding regions amplified by PCR were cloned, in frame, in the mammalian expression vectors pG1f (containing the human IgG1 constant region encoding DNA sequence) for the VH region and pKappa (containing the kappa light chain constant region encoding DNA sequence) for the VL region, by ligation independent cloning (Aslanidis, C. and P. J. de Jong, Nucleic Acids Res 1990; 18(20): 6069-74) in *E. coli* strain DH5αT1R (Life technologies), yielding single bacterial colonies each containing a single HC or LC expression vector.

Primer Sequences

| Primer name | Primer sequence |
|---|---|
| SMARTIIA | 5'-AAGCAGTGGTATCAACGCAGAGTACGCGGG |
| RACEkLIC4shortFW2 | 5'-ACGGACGGCAGGACCACT |
| RACEkLIC4LongFW2 | 5'-ACGGACGGCAGGACCACTAAGCAGGGTATCAACGCAGA |
| RACEkLICRV_PmIA3 | 5'-CAGCAGGCACACCACTGAGGCAGTTCCAGATTTC |
| RACEG1LIC3shortFW | 5'-ACGGACGGCAGGACCAGT |
| RACEG1LIC3longFW | 5'-ACGGACGGCAGGACCAGTAAGCAGTGGTATCAACGCAGAGT |
| RACEG1LIC3RV2 | 5 -GGAGGAGGGCGCCAGTGGGAAGACCGA |
| CMV P f (RRA2) | 5'-GCCAGATATACGCGTTGACA |
| TK pA r (RRA2) | 5'-GATCTGCTATGGCAGGGCCT |

LEE PCR

Linear expression elements (LEE's) were produced by amplifying the fragment containing the CMV promoter, HC or LC encoding regions and the poly A signal containing elements from the expression plasmids. For this the regions were amplified using Accuprime Taq DNA polymerase (Life Technologies) and the primers CMVPf(Bsal)2 and TkpA (Bsal)r, performing 35 cycles of 45 seconds at 94° C., 30 seconds at 55° C. and 2 (LC) or 3 (HC) minutes at 68° C., using material of *E. coli* (strain DH5α) colonies, containing the plasmids, as a DNA template.

Transient Expression in HEK-293 Cells

Antibodies were expressed as IgG1,κ. Plasmid DNA mixtures encoding both heavy and light chains of antibodies were transiently transfected in Freestyle 293-F (HEK293F) cells (Life technologies, USA) using 293fectin (Life technologies) essentially as described by Vink, T., et al. (2014) ('A simple, robust and highly efficient transient expression system for producing antibodies', Methods, 65 (1), 5-10).

For LEE expression of Abs 1 μl of the HC LEE PCR reaction mixture, 1 μl of the LC PCR reaction mixture and 1 μl of a 30 ng/μl enhancing mix containing a mix of 3 expression enhancing plasmids as described in Vink, T., et al. (2014), were mixed and transfected in HEK293F cells in a total volume of 100 μl using 293 fectin as transfection reagent, according to the instructions of the manufacturer (Life technologies), using 96 well plates as vessel, essentially as described supra.

AXLECDHis ELISA

ELISA plates (Greiner, Netherlands) were coated with 100 µl/well of 0.5 µg/ml AXLECDHis in Phosphate buffered saline (PBS) and incubated for 16 hours at room temperature (RT). The coating solution was removed and the wells were blocked by adding 150 µl PBSTC (PBS containing 0.1% tween-20 and 2% chicken serum) well and incubating for 1 hour at RT. The plates were washed three times with 300 µl PBST (PBS containing 0.1% tween-20)/well and 100 µl of test solution was added, followed by an incubation of 1 hour at RT. After washing three times with 300 µl of PBST/well, 100 µl antibody goat anti human IgG coupled with horse radish peroxidase (diluted 1/3000) was added and incubated for 1 hour at RT. After washing three times with 300 µl of PBST/well, 100 µl of ABTS (1 mg/ml) solution was added and incubated at RT until sufficient signal was observed and the reaction was stopped by adding 100 µl of 2% oxalic acid solution. 96 well plates were measured on an ELISA reader at 405 nm.

Diversity Screen

Samples were analyzed for binding of antibodies to TH1021-hAXL (HEK293F cells transiently expressing the human AXL), TH1021-cAXL (HEK293F cells transiently expressing human-cynomolgus AXL chimeras in which the human ECD had been replaced with the ECD of cynomolgus monkey AXL), TH1021-mAXL (HEK293F cells transiently expressing human-mouse AXL chimeras in which the human ECD had been replaced with the ECD of mouse AXL), TH1021-mIg1 (HEK293F cells transiently expressing the human AXL with the Ig-like domain I being replaced by the Ig-like domain I of mouse AXL), TH1021-mIg2 (HEK293F cells transiently expressing human AXL with the Ig-like domain II being replaced by the Ig-like domain II of mouse AXL), TH1021-mFN1 (HEK293F cells transiently expressing human AXL with the FNIII-like domain I being replaced by the FNIII-like domain I of mouse AXL), TH1021-mFN2 (HEK293F cells transiently expressing human AXL with the FNIII-like domain II being replaced by the FNIII-like domain II of mouse AXL), and HEK293F cells (negative control which does not express AXL), respectively.

Samples from the LEE expression were added to the cells to allow binding to the various AXL constructs. Subsequently, binding of antibodies was detected using a fluorescent conjugate (Goat anti-Human IgG Fc gamma-DyLight649; Jackson ImmunoResearch). The samples were scanned using an Applied Biosystems 8200 Cellular Detection System (8200 CDS) and mean fluorescence was used as read-out. Samples were stated positive when counts were higher than 50 and counts x fluorescence was at least three times higher than the negative control.

Provision of HC and LC Pools:

For each mouse, 352 HC expression vector containing bacterial colonies and 384 LC expression vector containing bacterial colonies were picked and amplified by LEE PCR. Part of the LEE reaction was sequenced (AGOWA). The percentage proper VH insert containing constructs differed largely between the 4 mice, mouse A (50%), mouse B (23%), mouse C (90%) and mouse D (14%) and resembled the variation of hits obtained in the hybridoma process, see supra. The HC diversity in the mice with only a limited amount of proper inserts were dominated by a large group of identical HCs, 65/83 in mouse B and 46/49 in mouse D. For mouse B and D the unique HCs (9 for mouse B, 4 for mouse D) were selected. For mouse A and C no selection was made.

Co-Transfection of HCs with a LC Pool

The single HC encoding LEE's were co-transfected with a pool of 96 LC encoding LEE's using the LEE transfection protocol.

HC Selection of AXL Binding Antibodies

For mouse B and D, supernatants from the LEE co-transfections of the single HC with the pooled LCs were analyzed for AXL binding of the produced antibody mixtures by the AXL ELISA. 7 of the 9 HCs from mouse B resulted in AXL binding and 4 out of 4 of the HC from mouse D resulted in AXL binding.

For mouse A and C supernatants from the LEE co-transfections of the single HC with the pooled LCs were analyzed for AXL binding of the produced antibody mixtures by the diversity screen. This screen enabled both the identification of AXL binding HCs and a rough epitope mapping, by identifying the loss of binding of antibodies to AXL variants. From mouse A approximately 40% of the HCs bound to human AXL, most of which lost binding either to the Ig1 or FNIII-2 domain, when these domains were replaced by the mouse equivalent. From mouse C approximately 70% of the HCs bound to human AXL, most of which lost binding either to the Ig1 or Ig2 domain, when these domains were replaced by the mouse equivalent. Based on binding as determined by AXL ELISA or the diversity screen, HC sequence information and loss of binding to specific AXL domains in the diversity screen a total of 12 unique HCs were selected for determination of the best LC.

Co-Transfection of HCs with Single LCs

Each single HC LEE of the 12 unique selected HCs was co-transfected with 96 single LC LEEs from the LC pool of the corresponding mice.

LC Selection of AXL Binding Antibodies

Supernatants of the LEE expression of the single HC/LC combinations were analyzed for AXL binding of the produced antibody by the AXL ELISA. For each HC at least 6 LCs were found and a single LC was selected as best, based on both the ELISA results and the LC sequence information. AXL binding antibodies were identified from all 4 mice, even the mice which were not successful in the hybridoma process.

Binding Affinity of Antibody 511

The affinity of one anti-AXL antibody (clone 511) was determined.

Affinity was determined using Bio-Layer Interferometry on a ForteBio OctetRED384. Anti-human Fc Capture (AHC) biosensors (ForteBio, Portsmouth, UK; cat no. 18-5064) were loaded for 150 s with hIgG (1 µg/mL) aiming at a loading response of 1 nm. After a baseline (150 s) the association (1000 s) and dissociation (2000 s) of AXLECDHis (as described in Example 1) was determined, using a concentration range of 10 µg/mL-0.16 µg/mL (218 nM-3 nM) with 2-fold dilution steps. For calculations, the theoretical molecular mass of AXLECDHis based on the amino acid sequence was used, i.e. 46 kDa. Experiments were carried out on an OctetRED384, while shaking at 1000 rpm and at 30° C. Each antibody was tested in three independent experiments.

Data was analyzed with ForteBio Data Analysis Software v7.0.3.1, using the 1:1 model and a global full fit with 1000 s association time and 1000 s dissociation time unless stated otherwise. A dissociation time of 1000 s (instead of the 2000 s dissociation time that was acquired) was used since this resulted in better fits. Data traces were corrected by subtraction of a reference curve (antibody without AXLEC-DHis), the Y-axis was aligned to the last 5 s of the baseline, and interstep correction as well as Savitzky-Golay filtering was applied.

The affinity ($K_D$) of clone 511 for AXL was $23*10^{-9}$ M ($k_{on}$ $1.7*10^5$ 1/Ms and a $k_{dis}$ of $3.9*10^{-3}$ 1/s).

Duostatin-3 Synthesis.

Preparation of Compound 3:

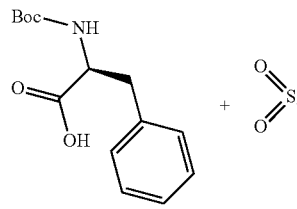 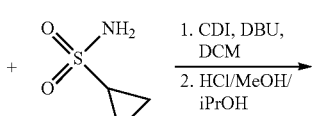

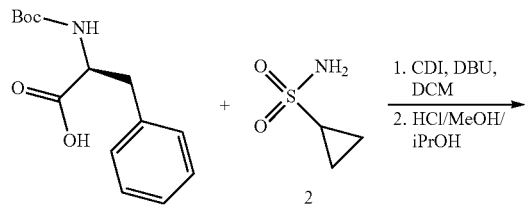

Preparation of Compound 5:

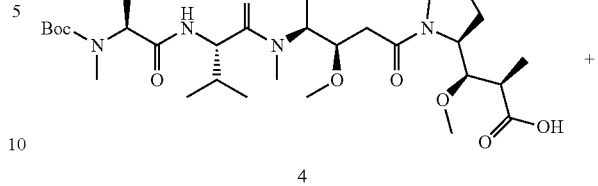

4

3

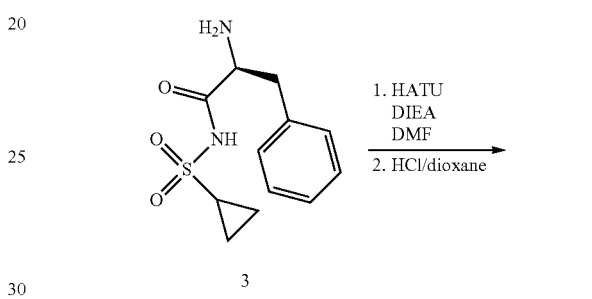

5

To a solution of Boc-L-phenylalanine 1 (5.36 g, 20.2 mmol) in 30 mL of methylene chloride (DCM), carbonyldiimidazole (CDI, 4.26 g, 26.3 mmol) was added and stirred for 1 hour. Then added a solution of 2 (3.67 g, 30.3 mmol) and 2,4-diaminobutyric acid (DBU, 4.5 mL, 30 mmol) in 15 mL of DCM. The mixture was heated at 40° C. for 16 hours. The mixture was diluted with 60 mL of DCM and 40 mL of water, then neutralized to pH 7 with conc. HCl. The DCM extract was collected, washed with 0.2M HCl (60 mL), then with brine (60 mL), dried over Na2SO4, and evaporated to give 7.47 g of Boc protected sulfonamide. This material was suspended in 40 mL of methanol, then 200 mL of 6N HCl/isopropanol was added and the mixture was stirred for 2 hours. The solvent was evaporated under vacuum, 100 mL of ether was then added. The precipitate was collected by filtration and dried to give compound 3 as HCl salt (5.93 g, 96%); MS m/z 269.1 (M+H).

To a solution of compound 4 (1.09 g, 1.6 mmol) in 10 mL of N,N-Dimethylformamide (DMF) was added 2-(IH-7-azabenzotriazol-I-yl)-I,I, 3,3-tetramethyl uranium hexafluorophosphate (HATU, 0.61 g, 1.6 mmol), diisopropylethylamine (DIEA, 0.56 mL), and compound 3 (0.49 g, 1.6 mmol) in that order. The mixture was stirred for 1 hour and diluted with 100 mL of water and 4 mL of acetic acid. The precipitate was collected by filtration, dried under vacuum and added to 10 mL of 4M HCl/dioxane. After 30 min, 200 mL of ether was added and insoluble precipitate was collected and purified by HPLC to give compound 5 as tetrahydrofuran salt (TFA, 1.3 g, 88%); MS m/z 835.5 (M+H). Compound 5 is referred to as duostatin-3 throughout the manuscript.

Preparation of Compound 7:

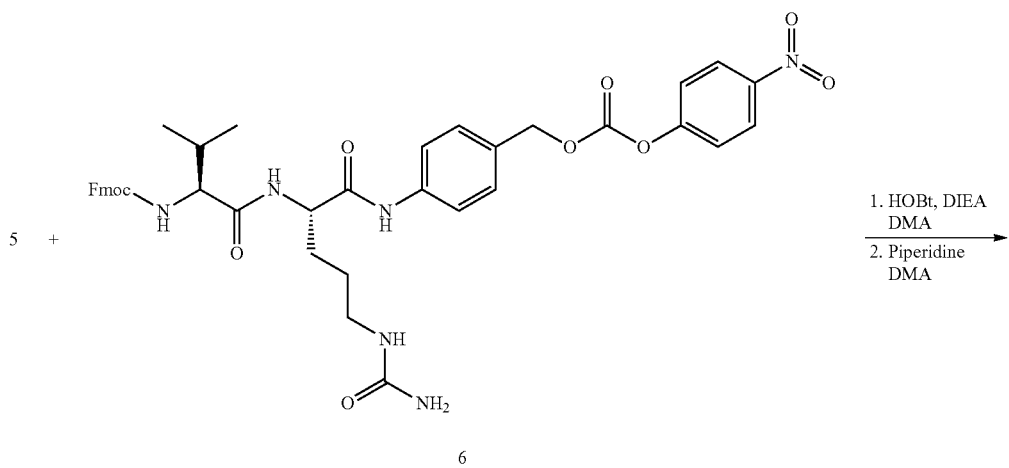

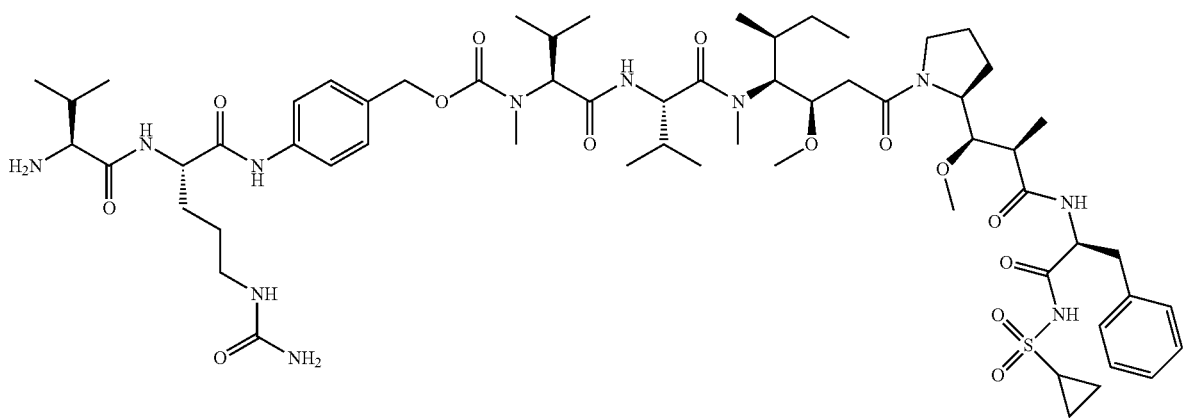

To a solution of compound 5 (500 mg, 0.527 mmol) in 5 mL of DMF was added compound 6 (483 mg, 0.631 mmol), N-Hydroxybenzotriazole (HOBt, 40 mg, 0.296 mmol), and DIEA (0.27 mL). The mixture was stirred for 16 hours after which 0.4 mL of piperidine was added. After 1 hour, the mixture was diluted with 100 mL of ether and the precipitate was collected and dried to give compound 7 as HCl salt (640 mg, 95%); MS m/z 1240.7 (M+H).

Preparation of Compound 9

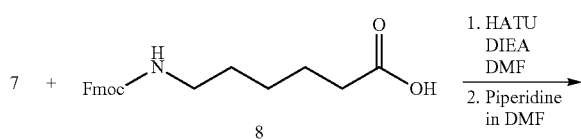

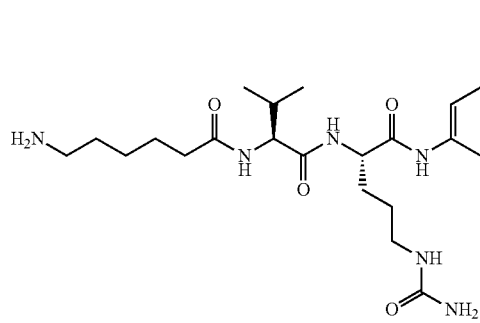
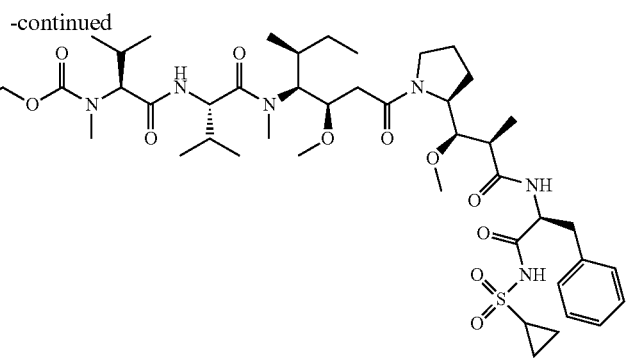

9

To a solution of compound 8 (219 mg, 0.62 mmol) in 5 mL of DMF was added HATU (236 mg, 0.62 mmol), DIEA (0.15 mL), and compound 7 (316 mg, 1.6 mmol), respectively. After 1 hour, 0.2 mL of piperidine was added and the mixture was stirred for 30 min, then purified by HPLC to give compound 9 as TFA salt (235 mg, 64%); MS m/z 1353.8 (M+H).

Preparation of Compound 11:

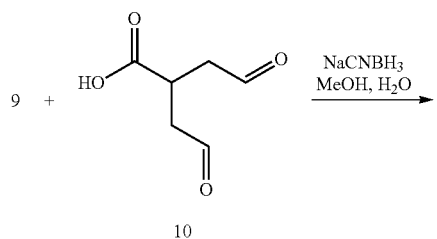

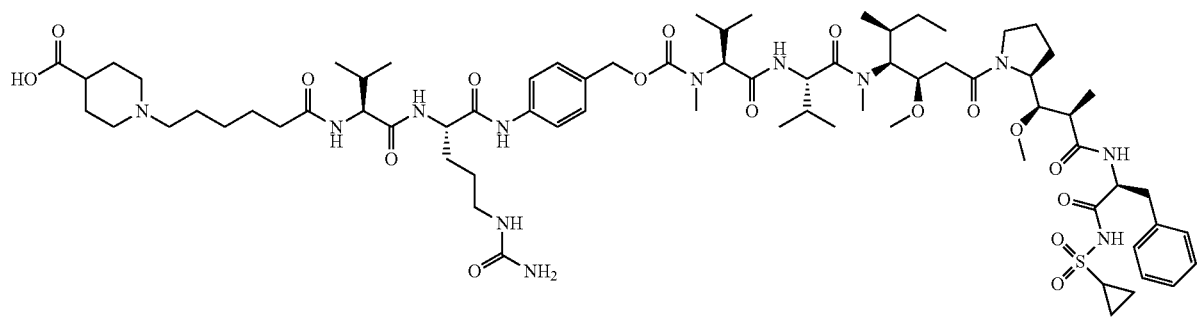

11

To a solution of compound 9 (235 mg, 0.16 mmol) in 2 mL of methanol and 1 mL of water was added a solution of dialdehyde 10 (1.6 mL of 0.3M in iPrOH) and NaCNBH3 (180 mg, 2.85 mmol). The mixture was stirred for 2 hours at RT, and then purified by HPLC giving rise to compound 11 as TFA salt (126 mg, 50%); MS m/z 1465.8 (M+H)

Generation of AXL-Specific Antibody-Drug Conjugates (ADC).

Purified AXL antibodies IgG1-AXL-148, IgG1-AXL-183 and IgG1-AXL-726 as well as the negative control antibody IgG1-b12 were conjugated with Duostatin-3 by Concortis Biosystems, Inc. (San Diego, Calif.) through covalent conjugation using the K-lock AV1-valine-citruline (vc) linker [58], [148], and [149].

The anti-AXL antibody drug conjugates were subsequently analyzed for concentration (by absorbance at 280 nm), the drug to antibody ratio (the 'DAR') by reverse phase chromatography (RP-HPLC) and hydrophobic interaction chromatography (HIC), the amount of unconjugated drug (by reverse phase chromatography), the percentage aggregation (by size-exclusion chromatography, SEC-HPLC) and the endotoxin levels (by LAL). The results were as follows (Table 2):

TABLE 2

|  | IgG1-AXL-148-vcDuostatin3 | IgG1-AXL-183-vcDuostatin3 | IgG1-AXL-726-vcDuostatin3 | IgG1-b12-vcDuostatin3 |
|---|---|---|---|---|
| Concentration (mg/mL) | 6.57 | 3.40 | 5.93 | 3.36 |
| DAR by HIC-HPLC | 1.71 | 1.79 | 1.77 | 2.05 |
| % unconjugated drug | 6.67 | 4.16 | 5.38 | 4.19 |
| % aggregate by SEC-HPLC | 3.71% | 3.35 | 3.42 | 1.75 |

Example 2—Binding Characteristics of AXL Antibodies

Binding affinity of AXL antibodies

The affinities of the panel of 9 anti-AXL antibodies as well as 3 variants of these antibodies with single amino acid mutations in the variable domains (IgG1-AXL-154-M103L, IgG1-AXL-183-N52Q, IgG1-AXL-726-M101L), were determined.

Affinities were determined using Bio-Layer Interferometry on a ForteBio OctetRED384. Anti-human Fc Capture (AHC) biosensors (ForteBio, Portsmouth, UK; cat no. 18-5064) were loaded for 150 s with hIgG (1 µg/mL) aiming at a loading response of 1 nm. After a baseline (150 s) the association (1000 s) and dissociation (2000 s) of AXLEC-DHis (as described in Example 1) was determined, using a concentration range of 10 µg/mL-0.16 µg/mL (218 nM-3 nM) with 2-fold dilution steps. For calculations, the theoretical molecular mass of AXLECDHis based on the amino acid sequence was used, i.e. 46 kDa. Experiments were carried out on an OctetRED384, while shaking at 1000 rpm and at 30° C. Each antibody was tested in three independent experiments.

Data was analyzed with ForteBio Data Analysis Software v7.0.3.1, using the 1:1 model and a global full fit with 1000 s association time and 1000 s dissociation time unless stated otherwise. A dissociation time of 1000 s (instead of the 2000 s dissociation time that was acquired) was used since this resulted in better fits. For antibody IgG1-AXL-154 and IgG1-AXL-154-M103L a dissociation time of 500 s was used. For IgG1-AXL-012 and IgG1-AXL-094 dissociation times of 200 s were used. Data traces were corrected by subtraction of a reference curve (antibody without AXLEC-DHis), the Y-axis was aligned to the last 5 s of the baseline, and interstep correction as well as Savitzky-Golay filtering was applied.

The affinities ($K_D$) of the anti-AXL antibodies ranged from $0.3*10^{-9}$M to $63*10^{-9}$M (Table 3). For mutant IgG1-AXL-183-N52Q the $K_D$ was lower than for wild-type IgG1-AXL-183, due to an approximately 2.5-fold higher dissociation rate. The observed kinetics of the other two mutants were similar to the kinetics of the wild-type IgGs.

TABLE 3

| | Binding affinity (OCTET) | | |
|---|---|---|---|
| Antibody | KD (M) | Kon (1/Ms) | Kdis (1/s) |
| IgG1-AXL-107 | $16*10^{-9}$ | $2.8*10^5$ | $4.1*10^{-3}$ |
| IgG1-AXL-148 | $20*10^{-9}$ | $2.3*10^5$ | $4.4*10^{-3}$ |
| IgG1-AXL-154 | $7.2*10^{-9}$ | $2.6*10^5$ | $1.9*10^{-3}$ |
| IgG1-AXL-154-M103L | $7.8*10^{-9}$ | $2.7*10^5$ | $2.0*10^{-3}$ |
| IgG1-AXL-171 | $17*10^{-9}$ | $1.1*10^5$ | $1.8*10^{-3}$ |
| IgG1-AXL-183 | $10.2*10^{-9}$ | $4.1*10^4$ | $4.2*10^{-4}$ |
| IgG1-AXL-183-N52Q | $24*10^{-9}$ | $4.2*10^4$ | $1.0*10^{-3}$ |
| IgG1-AXL-613 | $1.5*10^{-9}$ | $5.4*10^5$ | $8.0*10^{-4}$ |

TABLE 3-continued

| | Binding affinity (OCTET) | | |
|---|---|---|---|
| Antibody | KD (M) | Kon (1/Ms) | Kdis (1/s) |
| IgG1-AXL-726 | $0.6*10^{-9}$ | $2.4*10^5$ | $1.3*10^{-4}$ |
| IgG1-AXL-726-M101L | $0.3*10^{-9}$ | $2.1*10^5$ | $6.9*10^{-5}$ |
| IgG1-AXL-733 | $63*10^{-9}$ | $1.6*10^5$ | $9.7*10^{-3}$ |

Binding of AXL Antibodies to Human, Mouse and Cynomolgus AXL

HEK293T cells were transiently transfected with expression constructs for full length human AXL, human AXL with a cynomolgus monkey extracellular domain (ECD) or human AXL with a mouse ECD (see Example 1). Binding of HuMab-AXL antibodies to these cells was evaluated by flow cytometry. Transfected HEK293 cells were incubated with serial dilutions of AXL-antibodies (final concentration range 0.0024-10 µg/mL) for 30 minutes at 4° C. After washing three times in PBS/0.1% BSA/0.02% azide, cells were incubated with R-Phycoerythrin (PE)-conjugated goat-anti-human IgG F(ab')2 (Jackson ImmunoResearch Laboratories, Inc., West Grove, Pa.; cat. No. 109-116-098) diluted 1/100 in PBS/0.1% BSA/0.02% azide (final volume 100 µL). Next, cells were washed twice in PBS/0.1% BSA/0.02% azide, resuspended in 120 µL PBS/0.1% BSA/0.02% azide and analyzed on a FACS Cantoll (BD Biosciences).

Binding curves were analyzed using non-linear regression (sigmoidal dose-response with variable slope) using Graph-Pad Prism V5.04 software (GraphPad Software, San Diego, Calif., USA).

Figure 1B:
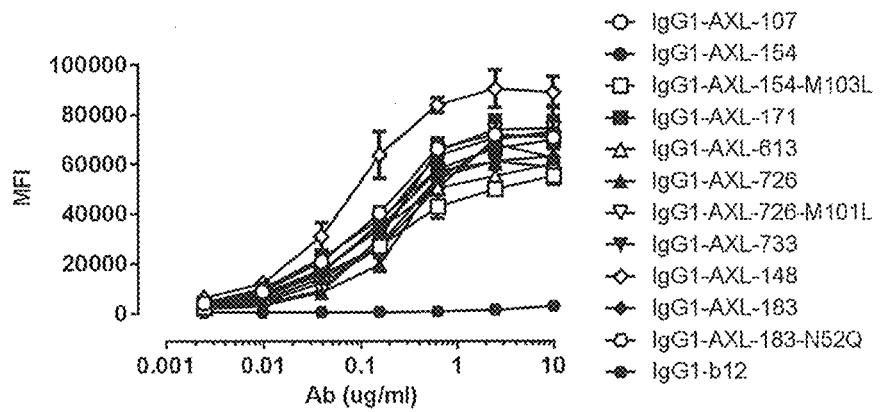
Figure 1C:
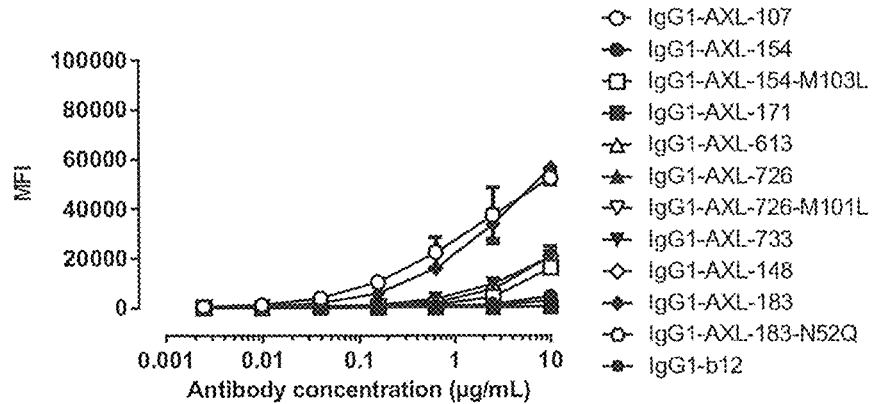

FIG. 1A shows that the HuMab-AXL antibodies showed dose-dependent binding to the HEK293 cells expressing human AXL-ECD. Furthermore, HuMab-AXL antibodies recognized AXL with a cynomolgus monkey ECD, with $EC_{50}$ values in the same range as for fully human AXL (FIG. 1B). In contrast, binding of HuMabs to AXL with a mouse ECD was low (IgG1-AXL-107, IgG1-AXL-154, IgG1-AXL-154-M103L, IgG1-AXL-733, IgG1-AXL-183, IgG1-AXL-183-N52Q) or not detectable (IgG1-AXL-171, IgG1-AXL-613, IgG1-AXL-726, IgG1-AXL-726-M101L, IgG1-AXL-148; FIG. 1C). As expected, the negative control antibody IgG1-b12 showed (FIG. 1) no binding to cells expressing any of the AXL variants. Table 4 shows the $EC_{50}$ values and standard deviations for binding of the anti-AXL antibodies to human AXL or human AXL with a cynomolgus AXL ECD (determined in at least 3 experiments). $EC_{50}$ values for binding to human AXL with a mouse AXL ECD could not be determined to very low or absent binding.

TABLE 4

| Antibody | Binding EC50 (µg/mL) | |
|---|---|---|
| | human AXL Average (s.d.) | cynomolgus AXL Average (s.d.) |
| IgG1-AXL-107 | 0.050 (0.004) | 0.149 (0.021) |
| IgG1-AXL-154 | 0.105 (0.003) | 0.160 (0.027) |
| IgG1-AXL-154-M103L | 0.110 (0.038) | 0.161 (0.042) |
| IgG1-AXL-171 | 0.073 (0.023) | 0.157 (0.057) |
| IgG1-AXL-613 | 0.040 (0.023) | 0.146 (0.023) |
| IgG1-AXL-726 | 0.288 (0.206) | 0.349 (0.160) |
| IgG1-AXL-726-M101L | 0.184 (0.117) | 0.250 (0.066) |
| IgG1-AXL-733 | 0.176 (0.094) | 0.254 (0.114) |
| IgG1-AXL-148 | 0.094 (0.059) | 0.152 (0.080) |
| IgG1-AXL-183 | 0.526 (0.177) | 0.309 (0.086) |
| IgG1-AXL-183-N52Q | 0.350 (0.206) | 0.324 (0.121) |

Competition Between AXL Antibodies and Gas6 for AXL Binding

It was tested whether the AXL ligand Gas6 interfered with binding of the AXL antibodies to AXL. Therefore, AXL-positive A431 cells were incubated for 15 minutes at 4° C. with 10 µg/mL recombinant human Gas6 (R&D Systems, Abingdon, UK; cat. No. 885-GS). Subsequently, serial dilutions of AXL antibodies were prepared (final concentration range 0.014-10 µg/mL), added to the cells and incubated for 30 minutes at 4° C. After washing three times in PBS/0.1% BSA/0.02% azide, cells were incubated in 100 µL with secondary antibody at 4° C. for 30 min in the dark. As a secondary antibody binding the Fc region, R-Phycoerythrin (PE)-conjugated goat-anti-human IgG F(ab')2 (Jackson ImmunoResearch Laboratories, Inc., West Grove, Pa.; cat. No. 109-116-098) diluted 1/100 in PBS/0.1% BSA/0.02% azide, was used. Next, cells were washed twice in PBS/0.1% BSA/0.02% azide, resuspended in 120 µL PBS/0.1% BSA/0.02% azide and analyzed on a FACS Cantoll (BD Biosciences).

Alternatively, A431 cells were pre-incubated with 10 µg/mL AXL antibodies (15 minutes, 4° C.) to assess if the AXL ligand Gas6 could still bind in presence of AXL antibodies. After antibody pre-incubation, serial dilutions of recombinant human Gas6 (R&D Systems, Abingdon, UK; cat. No. 885-GS) were added to the cells at final concentrations of 0.001-20 µg/mL and incubated for 30 minutes at 4° C. After washing three times in PBS/0.1% BSA/0.02% azide, cells were incubated with mouse anti-Gas6 IgG2a (R&D Systems; cat no. MAB885) at 4° C. for 30 min. After washing three times in PBS/0.1% BSA/0.02% azide, cells were incubated with FITC-labelled goat anti-mouse IgG (Dako, Heverlee, Belgium; cat no. F049702) at 4° C. for 30 min in the dark. Next, cells were washed twice in PBS/0.1% BSA/0.02% azide, resuspended in 120 µL PBS/0.1% BSA/0.02% azide and analyzed on a FACS Cantoll (BD Biosciences).

Binding curves were analyzed using non-linear regression (sigmoidal dose-response with variable slope) using Graph-Pad Prism V5.04 software (GraphPad Software, San Diego, Calif., USA).

In experiments (n=3) in which A431 cells were pre-incubated with Gas6, the maximal binding values of anti-AXL antibodies was comparable to antibody binding in absence of Gas6 (maximal binding after Gas6 pre-incubation was 90-108% of binding without Gas6 pre-incubation) (Table 4). The $EC_{50}$ values for AXL antibody binding with or without Gas6 pre-incubation were in the same range, or somewhat enhanced after Gas6 pre-incubation (Table 5).

The binding of control AXL antibody YW327.652 to A431 cells was greatly reduced in the presence of Gas6 compared to binding without Gas. Maximal binding of YW327.652 in the presence of Gas6 was 19% of binding without Gas6, and the EC50 value for binding to A431 cells was 21-fold higher when cells had been pre-incubated with Gas6.

In experiments in which A431 cells were pre-incubated with anti-AXL antibodies, Gas6 binding was evaluated (n=3). Binding of Gas6 to A431 cells was similar with or without pre-incubation with HuMab-AXL antibodies. Average EC50 concentrations of Gas6 binding when cells were pre-incubated with HuMabs (0.34-0.83 µg/mL) and maximal Gas6 binding were similar to Gas6 binding in the presence of negative control antibody b12 (EC50 concentration: 0.40 µg/mL; 95-115% of Gas6 binding in the presence of the b12 control antibody). The binding of Gas6 to A431 cells was greatly reduced in the presence of control AXL antibody YW327.652 compared to pre-incubation with b12 (the EC50 concentration was 14-fold higher). Maximal binding of Gas6 in the presence of control antibody YW327.652 was 17% of binding in the presence of negative control antibody b12.

TABLE 5

| | Antibody binding to A431 cells | | Maximal | Gas6 binding to A431 cells | |
|---|---|---|---|---|---|
| Antibody | EC50 w/o Gas6 EC50 (µg/mL) mean (s.d.) | EC50 in presence of Gas6 (µg/mL) mean (s.d.) | binding in presence of Gas6 binding in absence of Gas6) mean (s.d.) | EC50 in presence of AXL antibodies (µg/mL) mean (s.d.) | Maximal binding in presence of AXL antibodies (% of binding in prescence of control antibody) mean (s.d.) |
| IgG1-AXL-107 | 0.16 (0.17) | 0.94 (1.18) | 91 (5) | 0.78 (0.54) | 96 (8) |
| IgG1-AXL-148 | 0.11 (0.13) | 0.20 (0.30) | 93 (5) | 0.73 (0.52) | 106 (7) |
| IgG1-AXL-154 | 0.42 (0.55) | 0.76 (0.78) | 99 (13) | 0.44 (0.28) | 95 (10) |
| IgG1-AXL-171 | 0.18 (0.21) | 0.32 (0.40) | 95 (5) | 0.69 (0.42) | 108 (5) |
| IgG1-AXL-183 | 0.69 (0.72) | 1.19 (1.11) | 90 (19) | 0.34 (0.13) | 115 (8) |
| IgG1-AXL-511 | 0.12 (0.11) | 0.30 (0.31) | 93 (15) | 0.74 (0.44) | 113 (6) |
| IgG1-AXL-613 | 0.09 (0.09) | 0.10 (0.10) | 108 (22) | 0.57 (0.36) | 100 (11) |
| IgG1-AXL-726 | 0.32 (0.35) | 0.55 (0.69) | 97 (10) | 0.77 (0.58) | 98 (10) |
| IgG1-AXL-733 | 0.49 (0.51) | 0.62 (0.23) | 93 (5) | 0.83 (0.54) | 96 (5) |
| YW327.6S2 | 0.09 (0.09) | 1.90 (1.04)* | 41 (24) | 5.53 (7.09)* | 17 (10) |
| b12 | n.a.[a] | n.a. | n.a. | 0.40 (0.11) | 100 |

[a]n.a., not applicable
*EC50 values less accurate due to low binding.

Example 3—Epitope Mapping Studies Anti-AXL Antibody Panel

Determining the AXL Domain Specificity Using Human-Mouse AXL Chimeric Molecules

The AXL domain specificity of the AXL antibodies was determined using a panel of human-mouse chimeric AXL mutants. Five different chimeric AXL molecules were generated, in which either the human Ig-like domain I (Ig1), the Ig-like domain II (Ig2), the human FNIII-like domain I (FN1) or the human FNIII-like domain II domain (FN2) were replaced with their murine homologs.

The following codon-optimized constructs for expression of the AXL human-mouse chimeras were generated and expressed in HEK293F cells as described in Example 1:

*Homo sapiens* AXL (p33-HAHs-AXL):
(SEQ ID NO: 130)
MAWRCPRMGRVPLAWCLALCGWACMYPYDVPDYAAPRGTQAEESPFVGNP
GNITGARGLTGTLRCQLQVQGEPPEVHWLRDGQILELADSTQTQVPLGED
EQDDWIVVSQLRITSLQLSDTGQYQCLVFLGHQTFVSQPGYVGLEGLPYF
LEEPEDRTVAANTPFNLSCQAGPPEPVDLLWLQDAVPLATAPGHGPQRS
LHVPGLNKTSSFSCEAHNAKGVTTSRTATITVLPQQPRNLHLVSRQPTEL
EVAWTPGLSGIYPLTHCTLQAVLSNDGMGIQAGEPDPPEEPLTSQASVPP
HQLRLGSLHPHTPYHIRVACTSSQGPSSWTHWLPVETPEGVPLGPPENIS
ATRNGSQAFVHWQEPRAPLQGTLLGYRLAYQGQDTPEVLMDIGLRQEVTL
ELQGDGSVSNLTVCVAAYTAAGDGPWSLPVPLEAWRPGQAQPVHQLVKEP
STPAFSWPWWYVLLGAVVAAACVLILALFLVHRRKKETRYGEVFEPTVER
GELVVRYRVRKSYSRRTTEATLNSLGISEELKEKLRDVMVDRHKVALGKT
LGEGEFGAVMEGQLNQDDSILKVAVKTMKIAICTRSELEDFLSEAVCMKE
FDHPNVMRLIGVCFQGSERESFPAPVVILPFMKHGDLHSFLLYSRLGDQP
VYLPTQMLVKFMADIASGMEYLSTKRFIHRDLAARNCMLNENMSVCVADF
GLSKKIYNGDYYRQGRIAKMPVKWIAIESLADRVYTSKSDVWSFGVTMWE
IATRGQTPYPGVENSEIYDYLRQGNRLKQPADCLDGLYALMSRCWELNPQ
DRPSFTELREDLENTLKALPPAQEPDEILYVNMDEGGGYPEPPGAAGGAD
PPTQPDPKDSCSCLTAAEVHPAGRYVLCPSTTPSPAQPADRGSPAAPGQE
DGA

*Mus musculus* AXL (p33-HAMm-AXL):
(SEQ ID NO: 131)
MAWRCPRMGRVPLAWCLALCGWACMYPYDVPDYAAHKDTQTEAGSPFVGN
PGNITGARGLTGTLRCELQVQGEPPEVVWLRDGQILELADNTQTQVPLGE
DWQDEWKVVSQLRISALQLSDAGEYQCMVHLEGRTFVSQPGFVGLEGLPY
FLEEPEDKAVPANTPFNLSCQAQGPPEPVTLLWLQDAVPLAPVTGHSSQH
SLQTPGLNKTSSFSCEAHNAKGVTTSRTATITVLPQRPHHLHVVSRQPTE
LEVAWTPGLSGIYPLTHCNLQAVLSDDGVGIWLGKSDPPEDPLTLQVSVP
PHQLRLEKLLPHTPYHIRISCSSSQGPSPWTHWLPVETTEGVPLGPPENV
SAMRNGSQVLVRWQEPRVPLQGTLLGYRLAYRGQDTPEVLMDIGLTREVT
LELRGDRPVANLTVSVTAYTSAGDGPWSLPVPLEPWRPGQGQPLHHLVSE
PPPRAFSWPWWYVLLGAVVAAACVLILALFLVHRRKKETRYGEVFEPTVE
RGELVVRYRVRKSYSRRTTEATLNSLGISEELKEKLRDVMVDRHKVALGK
TLGEGEFGAVMEGQLNQDDSILKVAVKTMKIAICTRSELEDFLSEAVCMK
EFDHPNVMRLIGVCFQGSERESFPAPVVILPFMKHGDLHSFLLYSRLGDQ
PVYLPTQMLVKFMADIASGMEYLSTKRFIHRDLAARNCMLNENMSVCVAD
FGLSKKIYNGDYYRQGRIAKMPVKWIAIESLADRVYTSKSDVWSFGVTMW
EIATRGQTPYPGVENSEIYDYLRQGNRLKQPADCLDGLYALMSRCWELNP
QDRPSFTELREDLENTLKALPPAQEPDEILYVNMDEGGGYPEPPGAAGGA
DPPTQPDPKDSCSCLTAAEVHPAGRYVLCPSTTPSPAQPADRGSPAAPGQ
EDGA

*Homo sapiens* AXL - *Mus musculus* Ig1 domain (p33-AXL-mIg1):
(SEQ ID NO: 132)
MGRVPLAWWLALCCWGCAAHKDTQTEAGSPFVGNPGNITGARGLTGTLRC
ELQVQGEPPEVVWLRDGQILELADNTQTQVPLGEDWQDEWKVVSQLRISA
LQLSDAGEYQCMVHLEGRTFVSQPGFVGLEGLPYFLEEPEDRTVAANTPF
NLSCQAQGPPEPVDLLWLQDAVPLATAPGHGPQRSLHVPGLNKTSSFSCE
AHNAKGVTTSRTATITVLPQQPRNLHLVSRQPTELEVAWTPGLSGIYPLT
HCTLQAVLSDDGMGIQAGEPDPPEEPLTSQASVPPHQLRLGSLHPHTPYH
IRVACTSSQGPSSWTHWLPVETPEGVPLGPPENISATRNGSQAFVHWQEP
RAPLQGTLLGYRLAYQGQDTPEVLMDIGLRQEVTLELQGDGSVSNLTVCV
AAYTAAGDGPWSLPVPLEAWRPGQAQPVHQLVKEPSTPAFSWPWWYVLLG
AVVAAACVLILALFLVHRRKKETRYGEVFEPTVERGELVVRYRVRKSYSR
RTTEATLNSLGISEELKEKLRDVMVDRHKVALGKTLGEGEFGAVMEGQLN
QDDSILKVAVKTMKIAICTRSELEDFLSEAVCMKEFDHPNVMRLIGVCFQ
GSERESFPAPVVILPFMKHGDLHSFLLYSRLGDQPVYLPTQMLVKFMADI
ASGMEYLSTKRFIHRDLAARNCMLNENMSVCVADFGLSKKIYNGDYYRQG
RIAKMPVKWIAIESLADRVYTSKSDVWSFGVTMWEIATRGQTPYPGVENS
EIYDYLRQGNRLKQPADCLDGLYALMSRCWELNPQDRPSFTELREDLENT
LKALPPAQEPDEILYVNMDEGGGYPEPPGAAGGADPPTQPDPKDSCSCLT
AAEVHPAGRYVLCPSTTPSPAQPADRGSPAAPGQEDGA

*Homo sapiens* AXL - *Mus musculus* Ig2 domain (p33-AXL-mIg2):
(SEQ ID NO: 133)
MAWRCPRMGRVPLAWCLALCGWACMAPRGTQAEESPFVGNPGNITGARGL
TGTLRCQLQVQGEPPEVHWLRDGQILELADSTQTQVPLGEDEQDDWIVVS
QLRITSLQLSDTGQYQCLVFLGHQTFVSQPGYVGLEGLPYFLEEPEDKAV
PANTPFNLSCQAQGPPEPVTLLWLQDAVPLAPVTGHSSQHSLQTPGLNKT
SSFSCEAHNAKGVTTSRTATITVLPQQPRNLHLVSRQPTELEVAWTPGLS
GIYPLTHCTLQAVLSDDGMGIQAGEPDPPEEPLTSQASVPPHQLRLGSLH
PHTPYHIRVACTSSQGPSSWTHWLPVETPEGVPLGPPENISATRNGSQAF
VHWQEPRAPLQGTLLGYRLAYQGQDTPEVLMDIGLRQEVTLELQGDGSVS
NLTVCVAAYTAAGDGPWSLPVPLEAWRPGQAQPVHQLVKEPSTPAFSWPW
WYVLLGAVVAAACVLILALFLVHRRKKETRYGEVFEPTVERGELVVRYRV

```
RKSYSRRTTEATLNSLGISEELKEKLRDVMVDRHKVALGKTLGEGEFGAV

MEGQLNQDDSILKVAVKTMKIAICTRSELEDFLSEAVCMKEFDHPNVMRL

IGVCFQGSERESFPAPVVILPFMKHGDLHSFLLYSRLGDQPVYLPTQMLV

KFMADIASGMEYLSTKRFIHRDLAARNCMLNENMSVCVADFGLSKKIYNG

DYYRQGRIAKMPVKWIAIESLADRVYTSKSDVWSFGVTMWEIATRGQTPY

PGVENSEIYDYLRQGNRLKQPADCLDGLYALMSRCWELNPQDRPSFTELR

EDLENTLKALPPAQEPDEILYVNMDEGGGYPEPPGAAGGADPPTQPDPKD

SCSCLTAAEVHPAGRYVLCPSTTPSPAQPADRGSPAAPGQEDGA

Homo sapiens AXL - Mus musculus FN1
domain (p33-AXL-mFN1):
                                  (SEQ ID NO: 134)
MAWRCPRMGRVPLAWCLALCGWACMAPRGTQAEESPFVGNPGNITGARGL

TGTLRCQLQVQGEPPEVHWLRDGQILELADSTQTQVPLGEDEQDDWIVVS

QLRITSLQLSDTGQYQCLVFLGHQTFVSQPGYVGLEGLPYFLEEPEDRTV

AANTPFNLSCQAQGPPEPVDLLWLQDAVPLATAPGHGPQRSLHVPGLNKT

SSFSCEAHNAKGVTTSRTATITVLPQRPHHLHVVSRQPTELEVAWTPGLS

GIYPLTHCNLQAVLSDDGVGIWLGKSDPPEDPLTLQVSVPPHQLRLEKLL

PHTPYHIRISCSSSQGPSPWTHWLPVETTEGVPLGPPENISATRNGSQAF

VHWQEPRAPLQGTLLGYRLAYQGQDTPEVLMDIGLRQEVTLELQGDGSVS

NLTVCVAAYTAAGDGPWSLPVPLEAWRPGQAQPVHQLVKEPSTPAFSWPW

WYVLLGAVVAAACVLILALFLVHRRKKETRYGEVFEPTVERGELVVRYRV

RKSYSRRTTEATLNSLGISEELKEKLRDVMVDRHKVALGKTLGEGEFGAV

MEGQLNQDDSILKVAVKTMKIAICTRSELEDFLSEAVCMKEFDHPNVMRL

IGVCFQGSERESFPAPVVILPFMKHGDLHSFLLYSRLGDQPVYLPTQMLV

KFMADIASGMEYLSTKRFIHRDLAARNCMLNENMSVCVADFGLSKKIYNG

DYYRQGRIAKMPVKWIAIESLADRVYTSKSDVWSFGVTMWEIATRGQTPY

PGVENSEIYDYLRQGNRLKQPADCLDGLYALMSRCWELNPQDRPSFTELR

EDLENTLKALPPAQEPDEILYVNMDEGGGYPEPPGAAGGADPPTQPDPKD

SCSCLTAAEVHPAGRYVLCPSTTPSPAQPADRGSPAAPGQEDGA

Homo sapiens AXL - Mus musculus FN2
domain (p33-AXL-mFN2):
                                  (SEQ ID NO: 135)
MAWRCPRMGRVPLAWCLALCGWACMAPRGTQAEESPFVGNPGNITGARGL

TGTLRCQLQVQGEPPEVHWLRDGQILELADSTQTQVPLGEDEQDDWIVVS

QLRITSLQLSDTGQYQCLVFLGHQTFVSQPGYVGLEGLPYFLEEPEDRTV

AANTPFNLSCQAQGPPEPVDLLWLQDAVPLATAPGHGPQRSLHVPGLNKT

SSFSCEAHNAKGVTTSRTATITVLPQQPRNLHLVSRQPTELEVAWTPGLS

GIYPLTHCTLQAVLSDDGMGIQAGEPDPPEEPLTSQASVPPHQLRLGSLH

PHTPYHIRVACTSSQGPSSWTHWLPVETPEGVPLGPPENVSAMRNGSQVL

VRWQEPRVPLQGTLLGYRLAYRGQDTPEVLMDIGLTREVTLELRGDRPVA

NLTVSVTAYTSAGDGPWSLPVPLEPWRPGQGQPLHHLVSEPPPRAFSWPW

WYVLLGAVVAAACVLILALFLVHRRKKETRYGEVFEPTVERGELVVRYRV

RKSYSRRTTEATLNSLGISEELKEKLRDVMVDRHKVALGKTLGEGEFGAV

MEGQLNQDDSILKVAVKTMKIAICTRSELEDFLSEAVCMKEFDHPNVMRL

IGVCFQGSERESFPAPVVILPFMKHGDLHSFLLYSRLGDQPVYLPTQMLV

KFMADIASGMEYLSTKRFIHRDLAARNCMLNENMSVCVADFGLSKKIYNG

DYYRQGRIAKMPVKWIAIESLADRVYTSKSDVWSFGVTMWEIATRGQTPY

PGVENSEIYDYLRQGNRLKQPADCLDGLYALMSRCWELNPQDRPSFTELR

EDLENTLKALPPAQEPDEILYVNMDEGGGYPEPPGAAGGADPPTQPDPKD

SCSCLTAAEVHPAGRYVLCPSTTPSPAQPADRGSPAAPGQEDGA
```

Binding of 1 µg/mL anti-AXL antibody to the human-mouse AXL chimeras was determined by flow cytometry, as described in Example 2. IgG1-b12 was included as an isotype control IgG1.

Figure 2A:
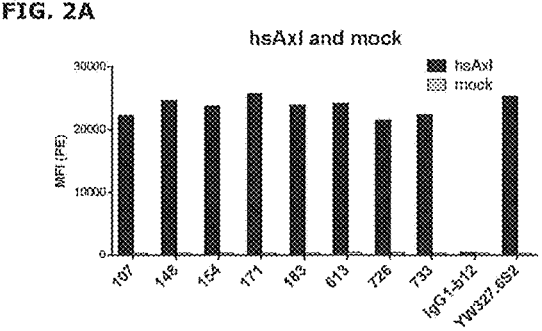
FIGS. 2A-2F: Binding of anti-AXL antibodies to mouse-human AXL chimeras was performed as described in Example 3. The following Homo sapiens AXL (hsAXL) and Mus musculus AXL (mmAXL) chimeric proteins were tested.
Figure 2B:
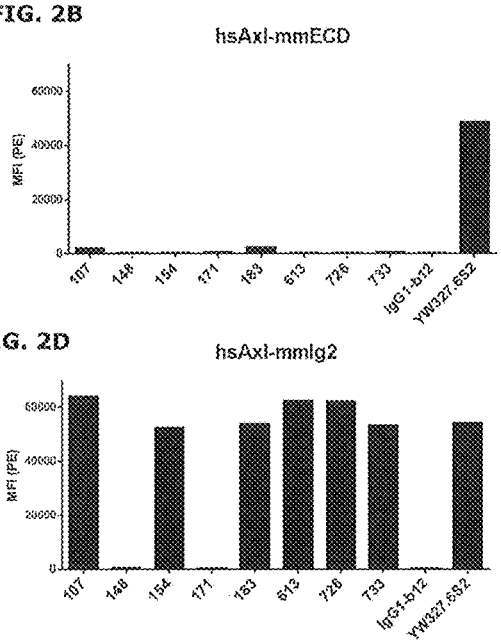

All anti-AXL antibodies showed binding to human AXL (FIG. 2A), whereas binding was abrogated or strongly reduced when the human AXL ECD was replaced with its murine homolog (FIG. 2B). The human-mouse cross-reactive monoclonal AXL antibody YW327.6S2 was included to confirm expression of hsAXL-mmECD.

Figure 2C:
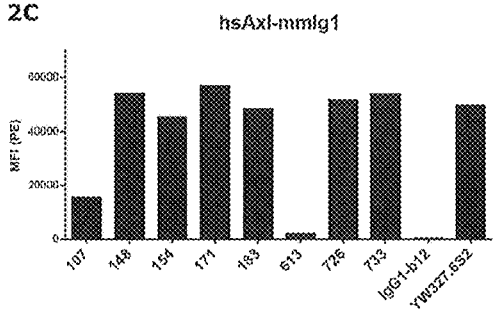
Figure 2D:
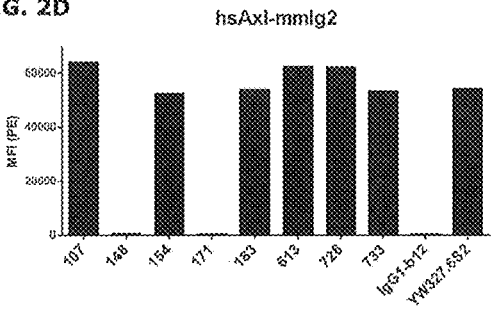
Figure 2E:
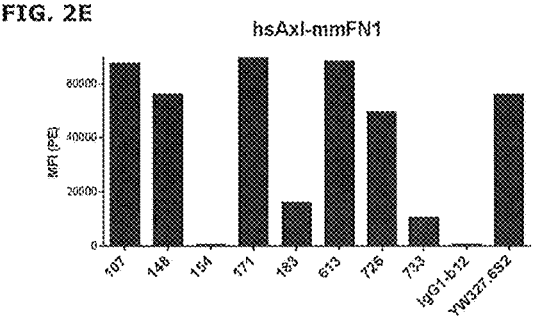
Figure 2F:
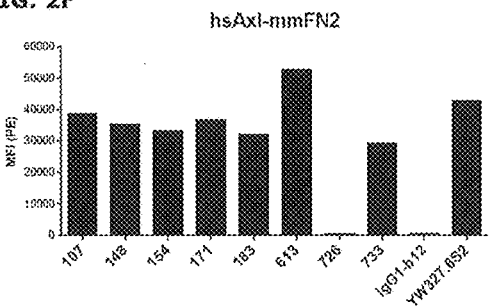
Figure 3:
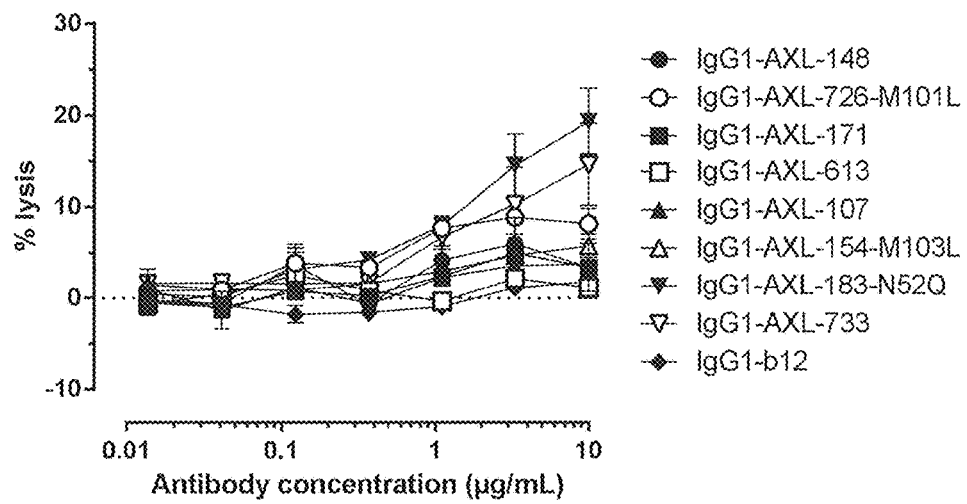
FIG. 3: Anti-AXL antibody-dependent cell-mediated cytotoxicity in A431 cells. Antibody-dependent cell-mediated cytotoxicity by anti-AXL antibodies in A431 cells was determined as described in Example 4.
Figure 4:
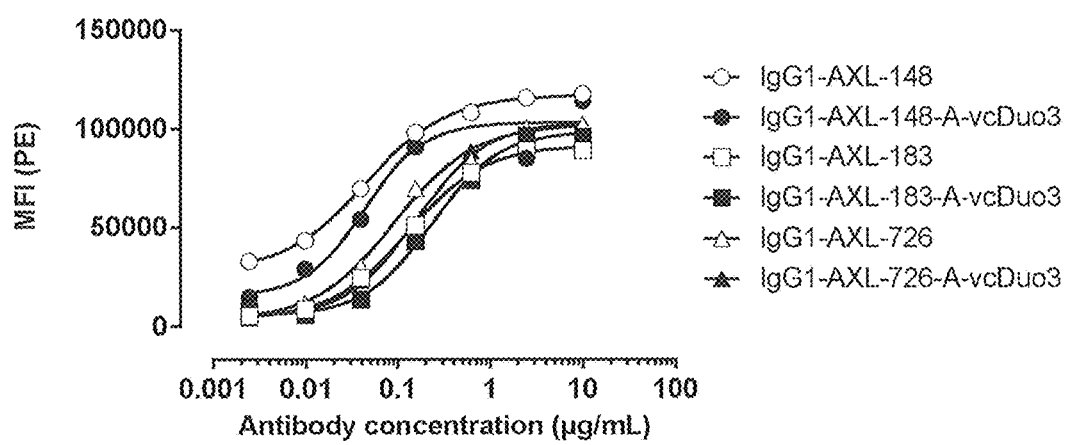
FIG. 4: Binding characteristics of AXL antibody-drug conjugates (AXL-ADCs). Binding of AXL-ADCs on HEK293T cells transiently transfected with human AXL was determined as described in Example 5. Data shown are mean fluorescence intensities (MFI) of one representative experiment.

Anti-AXL antibody 107 and 613 showed strongly reduced binding to hsAXL-mmIg1 (FIG. 2C), indicating recognition of an epitope in the AXL Ig1 domain. IgG1-AXL-148 and IgG1-AXL-171 showed strongly reduced binding to hsAXL-mmIg2 (FIG. 2D), indicating recognition of an epitope in the AXL Ig2 domain. IgG1-AXL-154, IgG1-AXL-183 and IgG1-AXL-733 showed reduced binding to hsAXL-mmFN1 (FIG. 2E), indicative of a binding epitope in the AXL FN1 domain. Finally, binding of IgG1-AXL-726 was lost in hsAXL-mmFN2 (FIG. 2F), indicating recognition of an epitope within the FN2 domain.

AXL domain specificity for all anti-AXL antibodies is summarized in Table 6.

TABLE 6

| Antibody | AXL domain specificity | AXL aa's involved in binding |
|---|---|---|
| IgG1-AXL-107 | Ig1 | L121-Q129 |
| IgG1-AXL-148 | Ig2 | D170-R190 |
| IgG1-AXL-154 | Fn1 | Q272-A287, G297-P301 |
| IgG1-AXL-154-M103L | n.d.[a] | n.d. |
| IgG1-AXL-171 | Ig2 | P170, T182-R190 |
| IgG1-AXL-183 | Fn1 | Not resolved |
| IgG1-AXL-183-N52Q | n.d. | n.d. |
| IgG1-AXL-613 | Ig1 | T112-Q124 |
| IgG1-AXL-726 | Fn2 | A359, R386, Q436-K439 |
| IgG1-AXL-726-M101L | n.d. | n.d. |
| IgG1-AXL-733 | Fn1 | Not resolved |
| 1gG1-AXL-061 | Ig1 | 197-Q124 |
| 1gG1-AXL-137 | Ig1 | Q57, E92-T105 |
| YW327.6S2 | Ig1 | G39-D59 |

[a]n.d., not determined

High Resolution Epitope Mapping to Identify Amino Acids in the AXL Extracellular Domain Involved in Binding of AXL Antibodies To identify amino acids in the AXL extracellular domain involved in binding of anti-AXL antibodies, a library of AXL sequence variants was generated by recombination of AXL sequences derived from species with variable levels of homology with the human AXL sequence in the extracellular domain. Briefly, an expression plasmid encoding human AXL (Hs) was mixed with cloning plasmids encoding *Mus*

*musculus* (Mm), *Monodelphis domestica* (Md; opossum) *Anolis carolinensis* (Ac; lizard) and *Tetraodon nigroviridis* (Tn; pufferfish) AXL homologs or vice versa. A combination of two primers specific to either the cloning or the expression vector was used to perform a PCR amplifying the AXL extracellular domain (ECD) with abbreviated elongation time, forcing melting and reannealing of nascent DNA replication strands during PCR cycling. Full length ECD was amplified using a nested PCR, again specific to recombination products containing termini originating from both vectors.

Resulting AXL ECD PCR products were cloned into an expression vector creating full length AXL, and resulting plasmids were sequenced, ranked by maximal difference to the template vectors and selected to create a minimal ensemble with maximal differentiation power. Plasmids encoding AXL homologs from Hs, Mm, Md, Ac and Tn, four human/mouse chimeric plasmids encoding Hs AXL with murine Ig1, Ig2, Fn1 or Fn2 domains, and the sixteen most differentiating plasmids from the recombination library were transfected into HEK293-F cells according to the specifications supplied by the manufacturer (Life technologies). FACS binding data using 1 μg/mL anti-AXL antibodies were deconvoluted by scoring per amino acid if mutation did (+1) or did not (−1) correlate with loss of binding, after which a baseline correction and normalization to a scale of −5 to +5 was applied, resulting in an impact score per amino acid over the full ECD.

The deconvoluted binding data is summarized in Table 6 as the amino acids involved in binding. Antibodies of which the binding site could not be mapped to high resolution due to a lack of recombination events in the proximity of the binding site, are indicated as not resolved.

Example 4—Fc-Mediated Effector Functions

Antibody-Dependent Cell-Mediated Cytotoxicity (ADCC)

The ability of anti-AXL antibodies to induce ADCC of A431 epidermoid carcinoma cells was determined as explained below. As effector cells, peripheral blood mononuclear cells from healthy volunteers (UMC Utrecht, The Netherlands) were used.

Labeling of Target Cells

A431 cells were collected ($5\times10^6$ cells) in culture medium (RPMI 1640 culture medium supplemented with 10% fetal calf serum (FSC)), to which 100 μCi $^{51}$Cr (Chromium-51; Amersham Biosciences Europe GmbH, Roosendaal, The Netherlands) had been added, and the mixture was incubated in a 37° C. water bath for 1 hour (hr) while shaking. After washing of the cells (twice in PBS, 1200 rpm, 5 min), the cells were resuspended in RPMI1640/10% FSC and counted by trypan blue exclusion. Cells were diluted to a density of $1\times10^5$ cells/m L.

Preparation of Effector Cells

Peripheral blood mononuclear cells (healthy volunteers, UMC Utrecht, Utrecht, The Netherlands) were isolated from 45 mL of freshly drawn heparin blood by Ficoll (Bio Whittaker; lymphocyte separation medium, cat 17-829E) according to the manufacturer's instructions. After resuspension of cells in RPMI1640/10% FSC, cells were counted by trypan blue exclusion and diluted to a density of $1\times10^7$ cells/mL.

ADCC Set Up 50 μl of $^{51}$Cr-labeled targets cells were pipetted into 96-well plates, and 50 μl of antibody were added, diluted in RPMI1640/10% FSC (3-fold dilutions at final concentrations range 0.01-10 μg/mL). Cells were incubated (room temperature (RT), 15 min), and 50 μl effector cells were added, resulting in an effector to target ratio of 100:1 (for determination of maximal lysis, 100 μl 5% Triton-X100 was added instead of effector cells; for determination of spontaneous lysis, 50 μL target cells and 100 μL RPMI1640/10% FSC were used). Cells were incubated overnight at 37° C. and 5% $CO_2$. After spinning down cells (1200 rpm, 10 min), 70 μL of supernatant was harvested into micronic tubes, and counted in a gamma counter. The percentage specific lysis was calculated as follows:

% specific lysis=(cpm sample−cpm target cells only)/(cpm maximal lysis−cpm target cells only)

wherein cpm is counts per minute.

IgG1-AXL-183-N52Q, and IgG1-AXL-733 induced 15 to 21% ADCC in A431 cells at a concentration of 10 μg/mL (FIG. 3). IgG1-AXL-148, IgG1-AXL-726-M101L, IgG1-AXL-171, IgG1-AXL-613, IgG1-AXL-107, and IgG1-AXL-154-M103L did not induce significant ADCC in A431 cell at concentrations up to 10 μg/mL (FIG. 3).

Example 5—Binding Characteristics of AXL Antibody-Drug Conjugates (AXL-ADCs)

HEK293T cells were transiently transfected with expression constructs for full-length human AXL (see Example 1). Binding of anti-AXL antibodies and AXL-ADCs to these cells was evaluated by flow cytometry. Transiently transfected HEK293 cells were incubated with serial dilutions of anti-AXL antibodies or AXL-ADCs (4-fold dilutions; final concentration range 0.003-10 μg/mL) for 30 minutes at 4° C. After washing three times in PBS/0.1% BSA/0.02% azide, cells were incubated in 100 μL with secondary antibody at 4° C. for 30 min in the dark. As a secondary antibody, R-Phycoerythrin (PE)-conjugated goat-anti-human IgG F(ab')2 (Jackson ImmunoResearch Laboratories, Inc., West Grove, Pa.; cat. No. 109-116-098) diluted 1/100 in PBS/0.1% BSA/0.02% azide, was used. Next, cells were washed twice in PBS/0.1% BSA/0.02% azide, resuspended in 120 μL PBS/0.1% BSA/0.02% azide and analyzed on a FACS Cantoll (BD Biosciences).

Binding curves were analyzed using non-linear regression (sigmoidal dose-response with variable slope) using GraphPad Prism V5.04 software (GraphPad Software, San Diego, Calif., USA).

FIG. 4 shows that binding of the anti-AXL antibodies to the HEK293 cells expressing human AXL-ECD was similar to the binding of the AXL-ADCs.

Example 6—In Vitro Cytotoxicity Induced by AXL-Specific Antibody Drug Conjugates LCLC-103H cells (human large cell lung cancer) cells were cultured in RPMI 1640 with L-Glutamine (Cambrex; cat.no. BE12-115F) supplemented with 10% (vol/vol) heat inactivated Cosmic Calf Serum (Perbio; cat.no. SH30087.03), 2 mM L-glutamine (Cambrex; cat.no. US17-905C), 50 IU/mL penicillin, and 50 μg/mL streptomycin (Cambrex; cat.no. DE17-603E). MDA-MB-231 cells (human breast cancer) were cultured in DMEM (Cambrex; cat.no. BE12-709F) supplemented with 10% (vol/vol) heat inactivated Cosmic Calf Serum (Perbio; cat.no. SH30087.03), 1 mM Sodium Pyruvate (Cambrex; cat.no. 13E13-115E), 2 mM L-glutamine (Cambrex; cat.no. US17-905C), 100 μM MEM NEAA (Invitrogen; cat.no. 11140), 50 IU/mL penicillin, and 50 μg/mL streptomycin (Cambrex; cat.no. DE17-603E). The cell lines were maintained at 37° C. in a 5% (vol/vol) CO2 humidified incubator. LCLC-103H and MDA-MB-231 cells were cultured to near confluency, after which cells were trypsinized, resuspended in culture medium and passed through a cell strainer (BD Falcon, cat.no. 352340) to obtain a single cell suspension. $1 \times 10^3$ cells were seeded in each well of a 96-well culture plate, and cells were incubated for 30 min at room temperature and subsequently for 5 hrs at 37° C., 5% CO2 to allow adherence to the plate.

Serial dilutions (4-fold; final concentrations ranging from 0.00015 to 10 µg/mL) of AXL antibody drug conjugates (AXL-ADCs; see Example 1) were prepared in culture medium and added to the plates. Incubation of cells with 1 µM staurosporin (#56942-200, Sigma) was used as reference for 100% tumor cell kill. Untreated cells were used as reference for 0% tumor cell kill. Plates were incubated for 5 days at 37° C., 5% CO2. Next, CellTiter-Glo Reagent (Promega; cat.no. G7571) was added to the wells (20 µL per well) and plates were incubated for 1.5 hours at 37° C., 5% CO2. Subsequently, 180 µL per well was transferred to white 96-well Optiplate™ plates (PerkinElmer, Waltham, Mass.; cat.no. 6005299), which were incubated for 30 min at room temperature. Finally, luminescence was measured on an EnVision multiplate reader (Envision, Perkin Elmer).

Figure 5A:
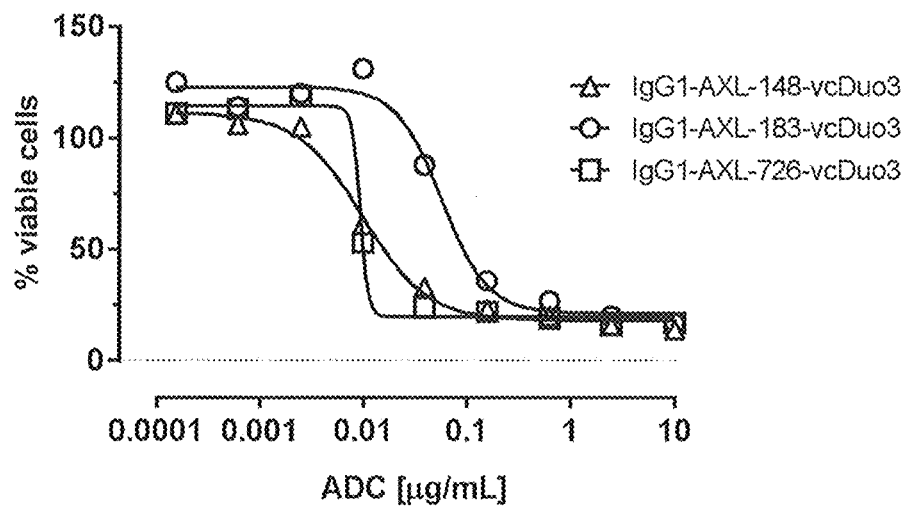
FIGS. 5A and 5B: In vitro cytotoxicity induced by AXL antibody-drug conjugates. Induction of cytotoxicity by AXL antibody-drug conjugates was determined as explained in Example 6.
Figure 5B:
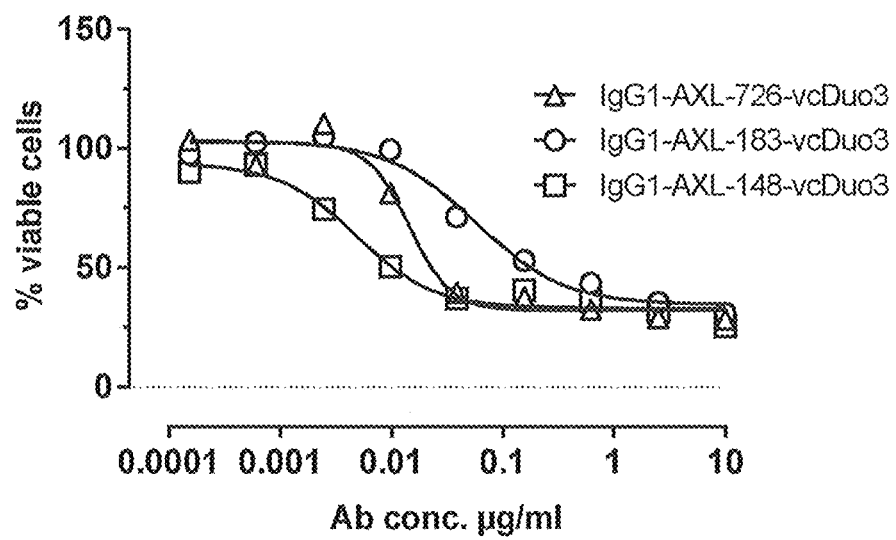

AXL-ADCs IgG1-AXL-148-vcDuo3, IgG1-AXL-183-vcDuo3, and IgG1-AXL-726-vcDuo3 induced cytotoxicity in LCLC-103H cells, with 1050 values between 0.01 and 0.06 µg/mL, as shown in FIG. 5A. Similarly, FIG. 5B shows that these AXL-ADCs induced cytoxicity of MDA-MB-231 cells with IC50 values between 0.005 and 0.015 µg/mL.

Example 7—Antibody VH and VL Variants that Allow Binding to AXL

Protein sequences of the VH and VL regions of the anti-AXL antibody panel (described in Example 1) were aligned and compared for AXL binding to identify critical or permissive changes of amino acid residues in the VH or VL regions. Therefore, antibodies with identical VH or VL regions were grouped and compared for binding to human AXL and differences in VL or VH sequences, respectively. Binding to human AXL transiently expressed by HEK-293F cells was assessed in the homogeneous antigen specific screening assay as described in Example 1. Numbering of amino acid positions for the alignments done in the present example was done based on the sequences put forth in FIG. 6, i.e. the first amino acid in the shown sequence was numbered as position '1', the second as position '2', etc.

First, antibodies with identical VL sequences were grouped.

Figures 6A, 6B, 6C, 6D, 6E:
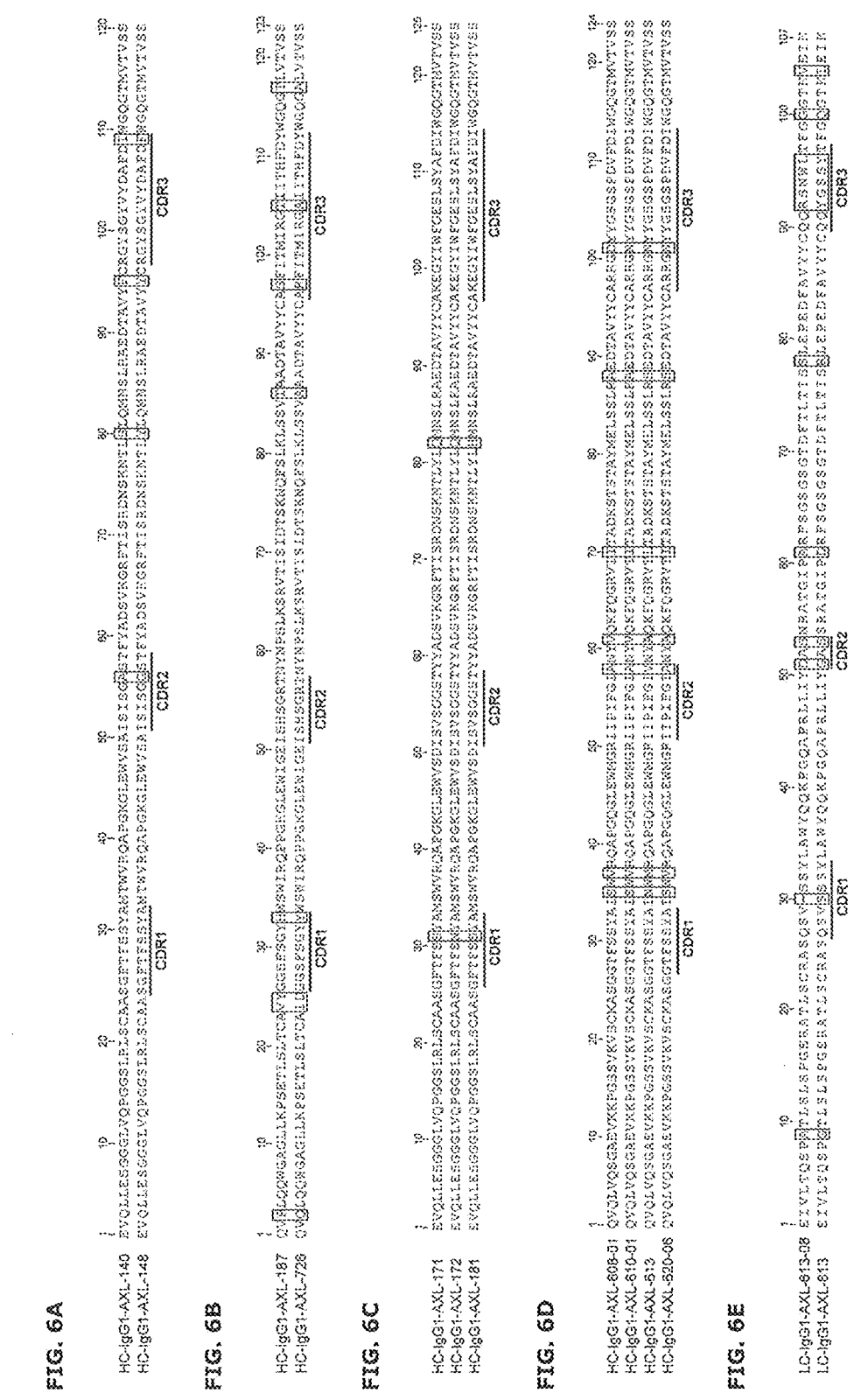

IgG1-AXL-148 and IgG1-AXL-140 were found to have an identical VL sequence, and showed 1 amino acid difference in the HC CDR3 region (F for I at amino acid position 109; FIG. 6A). Both antibodies bound to human AXL (Table 7), indicating that the amino acid at position 109 is not essential for antibody binding, assuming that a mutation identified in the CDR2 region (G for A at the amino acid position 56) does not compensate for loss of binding (FIG. 6A).

IgG1-AXL-726 and IgG1-AXL-187 were found to have an identical VL sequence and both antibodies bound to human AXL (Table 7). Two amino acid residue changes in the HC CDR3 region (R for S at position 97 and A for T at position 105; FIG. 6B) were allowed without losing binding, assuming that mutations identified in the CDR1 (Y for H at position 32) and/or in the framework regions (P3Q, V241, Y25D, T86A and T117A) do not compensate for loss of binding (FIG. 6B).

IgG1-AXL-171, IgG1-AXL-172 and IgG1-AXL-181 were found to have an identical VL sequence and all antibodies bound to human AXL (Table 7). The CDR3 regions of these three antibodies were identical, but an amino acid residue change in the HC CDR1 (S for N at position 31) or the framework region (H for Q at position 82) was allowed without losing binding (FIG. 6C).

IgG1-AXL-613, IgG1-AXL-608-01, IgG1-AXL-610-01 and IgG1-AXL-620-06 were found to have an identical VL sequence, and showed one amino acid difference in the HC CDR3 region (N for D at amino acid position 101; FIG. 6D). All antibodies bound to human AXL (Table 7), indicating that the amino acid at position 101 is not essential, assuming that mutations identified in the HC CDR2 (V for A at position 58) and/or in the framework regions (N35S, M37V, A61V, L70I, S88A) do not compensate for loss of binding (FIG. 6D).

Next, antibodies with identical VH sequences were grouped.

IgG1-AXL-613 and IgG1-AXL-613-08 were found to have an identical VH sequence, and showed five amino acid differences in the CDR3 region of the LC (RSNWL for YGSSY at positions 92 to 96; FIG. 6E). Both antibodies bound to human AXL (Table 7), indicating that the variation of amino acid at positions 92 to 96 are allowed and do not affect antibody binding, assuming that mutations identified in the CDR1 (deletion of the S at position 30), CDR2 (G51D), and/or in the framework regions (G9A, S54N, R78S, Q100G, L104V) do not compensate for loss of binding (FIG. 6E).

TABLE 7

| Antibody | EC50 (µg/mL) | Maximal binding (Arbitrary units) |
|---|---|---|
| IgG1-AXL-140 | 0.0026 | 2889 |
| IgG1-AXL-148 | 0.0036 | 3499 |
| IgG1-AXL-171 | 0.003 | 2575 |
| IgG1-AXL-172 | 0.0055 | 5378 |
| IgG1-AXL-181 | 0.008 | 3598 |
| IgG1-AXL-187 | 0.0065 | 2563 |
| IgG1-AXL-608-01 | 0.0035 | 3318 |
| IgG1-AXL-610-01 | 0.0023 | 2947 |
| IgG1-AXL-613 | 0.0072 | 5211 |
| IgG1-AXL-613-08 | 0.0242 | 2209 |
| IgG1-AXL-620-06 | 0.0034 | 4352 |
| IgG1-AXL-726 | 0.0471 | 3154 |

Example 8—In Vitro Cytotoxicity Induced by MMAE-Conjugated AXL Antibodies

Conjugation of MMAE to Anti-AXL Antibodies

Anti-AXL antibodies were purified by Protein A chromatography according to standard procedures and conjugated to vcMMAE. The drug-linker vcMMAE was alkylated to the cysteines of the reduced antibodies according to procedures described in the literature (see [150], [151], and [152]). The reaction was quenched by the addition of an excess of N-acetylcysteine. Any residual unconjugated drug was removed by purification and the final anti-AXL antibody drug conjugates were formulated in PBS. The anti-AXL antibody drug conjugates were subsequently analyzed for concentration (by absorbance at 280 nm), the drug to antibody ratio (DAR) by reverse phase chromatography (RP-HPLC) and hydrophobic interaction chromatography (HIC), the amount of unconjugated drug (by reverse phase chromatography), the percentage aggregation (by size-exclusion chromatography, SEC-HPLC) and the endotoxin levels (by LAL). The results are shown below in Table 8.

TABLE 8

Overview of different characteristics of the antibody-drug conjugates.

| Assay | ADC | | | | | | | | | |
|---|---|---|---|---|---|---|---|---|---|---|
| | IgG1-AXL-107 | IgG1-AXL-148 | IgG1-AXL-154-M103L | IgG1-AXL-171 | IgG1-AXL-183-N52Q | IgG1-AXL-511 | IgG1-AXL-613 | IgG1-AXL-726-M101L | IgG1-AXL-733 | IgG1-b12 |
| Concentration (mg/mL) | 7.18 | 9.63 | 6.57 | 3.69 | 6.71 | 5.77 | 6.17 | 7.37 | 7.71 | 1.58 |
| DAR by HIC | 3.97 | 3.96 | 3.71 | 3.65 | 3.92 | 3.87 | 4.23 | 4.12 | 4.08 | 4.00 |
| % unconjugated antibody | 4.68 | 5.58 | 6.13 | 7.11 | 8.68 | 8.35 | 5.13 | 4.99 | 3.74 | 1.89 |
| % aggregate by SEC-HPLC | 6.3 | 2.28 | 2.9 | 3.3 | 5.2 | 5.1 | 6.4 | 4.0 | 3.5 | 2.5 |
| Endotoxin (EU/mg) | 2.3 | 1.2 | 2.6 | 3.1 | 5.9 | 4.5 | 2.0 | 3.6 | 7.6 | 11.5 |

Cell Culture

LCLC 103H cells (human large cell lung cancer) and A431 cells (DMSZ, Braunschweig, Germany) were cultured in RPMI 1640 with L-Glutamine (Cambrex; cat.no. BE12-115F) supplemented with 10% (vol/vol) heat inactivated Cosmic Calf Serum (Perbio; cat.no. SH30087.03), 2 mM L-glutamine (Cambrex; cat.no. US17-905C), 50 IU/mL penicillin, and 50 µg/mL streptomycin (Cambrex; cat.no. DE17-603E). MDA-MB231 cells were cultured in DMEM with high glucose and HEPES (Lonza #BE12-709F), Donor Bovine Serum with Iron (Life Technologies #10371-029), 2 mM L-glutamine (Lonza #BE17-605E), 1 mM Sodium Pyruvate (Lonza #BE13-115E), and MEM Non-Essential Amino Acids Solution (Life Technologies #11140). The cell lines were maintained at 37° C. in a 5% (vol/vol) $CO_2$ humidified incubator. LCLC-103H, A431 and MDA-MB231 cells were cultured to near confluency, after which cells were trypsinized, resuspended in culture medium and passed through a cell strainer (BD Falcon, cat.no. 352340) to obtain a single cell suspension. $1 \times 10^3$ cells were seeded in each well of a 96-well culture plate, and cells were incubated for 30 min at room temperature and subsequently for 5 hrs at 37° C., 5% $CO_2$ to allow adherence to the plate.

Cytotoxicity Assay

Serial dilutions (final concentrations ranging from 0.00015 to 10 µg/mL) of MMAE-conjugated AXL-antibodies were prepared in culture medium and added to the plates. Incubation of cells with 1 µM staurosporin (#56942-200, Sigma) was used as reference for 100% tumor cell kill. Untreated cells were used as reference for 100% cell growth. Plates were incubated for 5 days at 37° C., 5% $CO_2$. Next, CellTiter-Glo Reagent (Promega; cat.no. G7571) was added to the wells (20 µL per well) and plates were incubated for 1.5 hours at 37° C., 5% $CO_2$. Subsequently, 180 µL per well was transferred to white 96-well Optiplate™ plates (PerkinElmer, Waltham, Mass.; cat.no. 6005299), which were incubated for 30 min at room temperature. Finally, luminescence was measured on an EnVision multiplate reader (Envision, Perkin Elmer).

Figure 7:
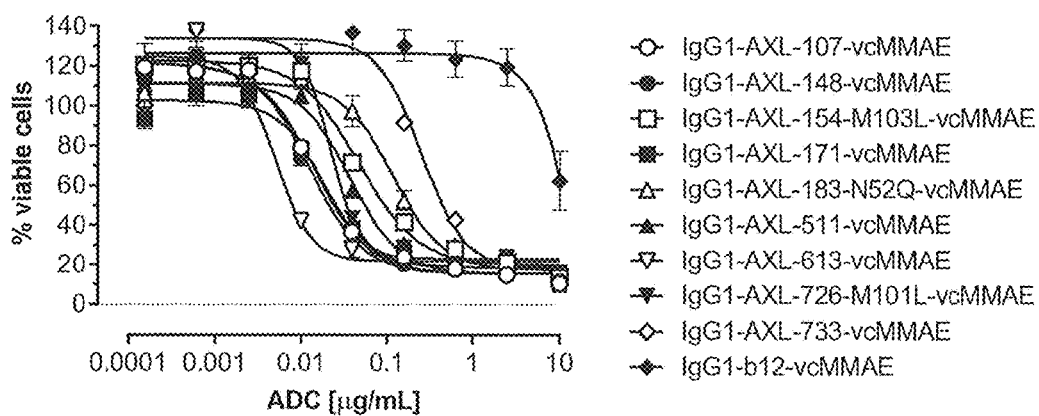
FIG. 7: Induction of cytotoxicity by ADCs in LCLC-103H cells was determined as described in Example 8.

MMAE-conjugated AXL-antibodies induced 50% cell kill in LCLC-103H cells at concentrations between 0.004 and 0.219 µg/mL as shown in Table 9a and FIG. 7.

Figure 15A:
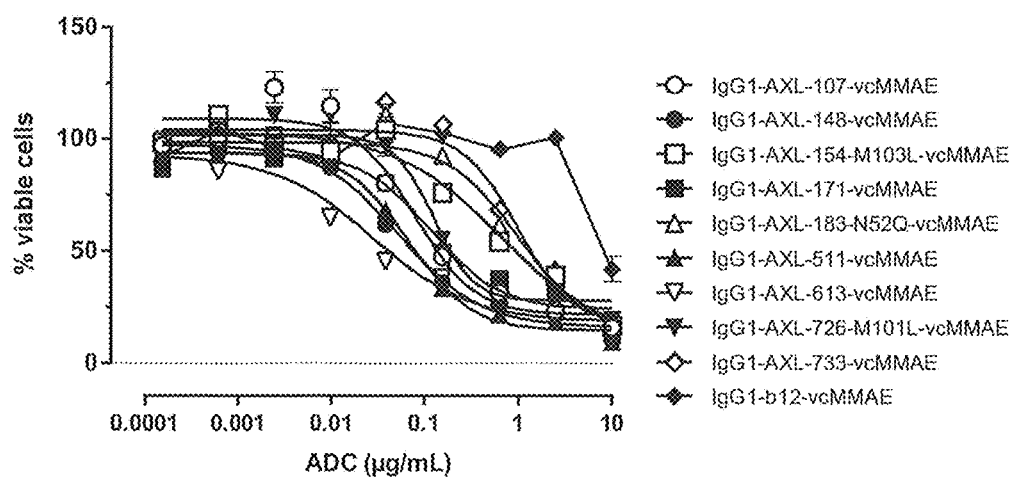
FIGS. 15A and 15B: Induction of cytotoxicity by AXL-ADCs in A431 cells (FIG. 15A) and MDA-MB231 cells (FIG. 15B) was determined as described in Example 8.
Figure 15B:
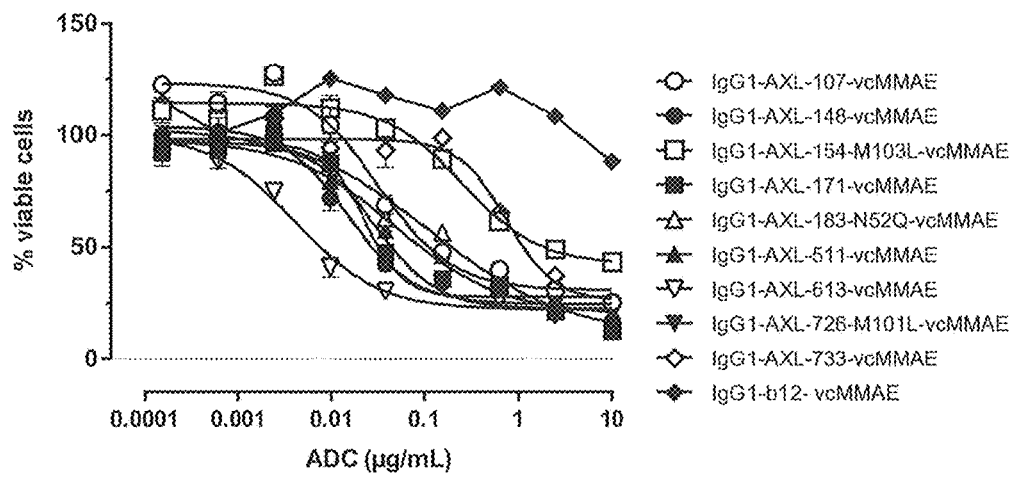

Similarly, AXL-ADCs efficiently induced cytotoxicity in A431 cells (Table 9b) and FIG. 15A) and MDA-MB231 cells (Table 9b and FIG. 15B).

TABLE 9a

Cytotoxicity of MMAE-conjugated-AXL-antibodies in LCLC-103H cells (EC50 values)

| ADC | EC50 (µg/mL) |
|---|---|
| IgG1-AXL-613-vcMMAE | 0.004 |
| IgG1-AXL-148-vcMMAE | 0.012 |
| IgG1-AXL-171-vcMMAE | 0.018 |
| IgG1-AXL-726-M101L-vcMMAE | 0.018 |
| IgG1-AXL-107-vcMMAE | 0.022 |
| IgG1-AXL-511-vcMMAE | 0.032 |
| IgG1-AXL-154-M103L-vcMMAE | 0.044 |
| IgG1-AXL-183-N52Q-vcMMAE | 0.113 |
| IgG1-AXL-733-vcMMAE | 0.219 |

TABLE 9b

Cytotoxicity of MMAE-conjugated AXL antibodies in A431 and MDA-MB-231 cells (EC50 values).

| | EC50 (µg/mL) | | | |
|---|---|---|---|---|
| | A431 (n = 3) | | MDA-MB231 (n = 2) | |
| ADC | Mean | s.d. | Mean | s.d. |
| IgG1-AXL-107-vcMMAE | 0.154 | 0.066 | 0.037 | 0.005 |
| IgG1-AXL-148-vcMMAE | 0.070 | 0.013 | 0.012 | 0.004 |
| IgG1-AXL-154-M103L-vcMMAE | 0.719 | 0.091 | 0.396 | 0.195 |
| IgG1-AXL-171-vcMMAE | 0.206 | 0.074 | 0.035 | 0.006 |
| IgG1-AXL-183-N52Q-vcMMAE | 1.157 | 0.160 | 0.139 | 0.028 |
| IgG1-AXL-511-vcMMAE | 0.093 | 0.020 | 0.052 | 0.003 |
| IgG1-AXL-613-vcMMAE | 0.109 | 0.078 | 0.005 | 0.001 |
| IgG1-AXL-726-M101L-vcMMAE | 0.270 | 0.157 | 0.022 | 0.002 |
| IgG1-AXL-733-vcMMAE | 1.253 | 0.228 | 0.881 | 0.182 |

Example 9—Therapeutic Treatment of LCLC-103H Tumor Xenografts in SCID Mice with MMAE-Conjugated Anti-AXL Antibodies The in vivo efficacy of MMAE-conjugated anti-AXL antibodies was determined in established subcutaneous (SC) LCLC-103H xenograft tumors in SCID mice. $5 \times 10^6$ LCLC-103H (large cell lung carcinoma) tumor cells (obtained from Leibniz-Institut DSMZ-Deutsche Sammlung von Mikroorganismen and Zellkulturen GmbH (DSMZ)) in 200 µL PBS were injected subcutaneously in the right flank of female SCID mice. Starting 14-21 days after tumor cell inoculation, when the average tumor size was >100-200 $mm^3$ and distinct tumor growth was observed, a single injection with 1 mg/kg (20 μg/mouse) IgG1-AXL-vcMMAE antibodies (as described in Supplementary Example 1) or control (unconjugated IgG1-b12) was given intraperitoneally (100 μL/mouse). Tumor volume was determined at least two times per week. Tumor volumes (mm$^3$) were calculated from caliper (PLEXX) measurements as: 0.52×(length)× (width)$^2$.

Figure 8:
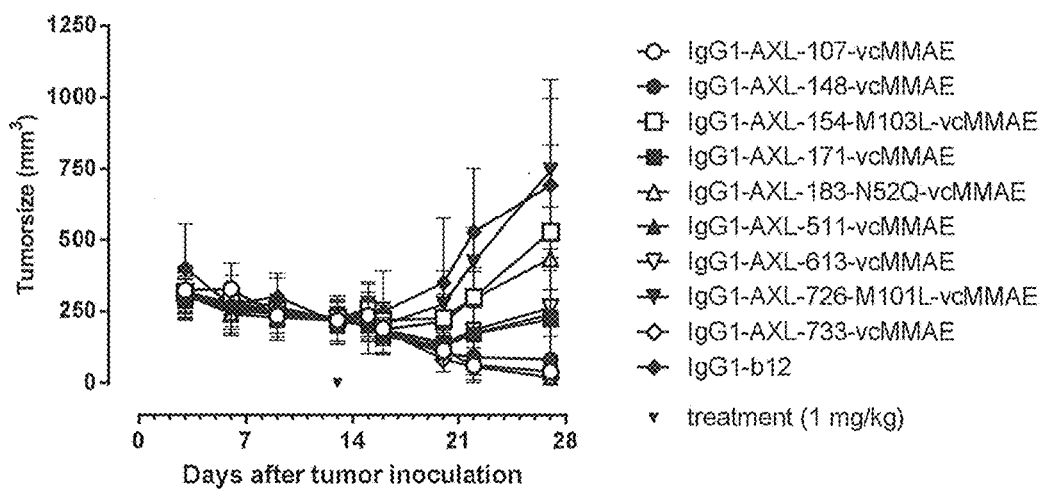
FIG. 8: Anti-tumor activity by MMAE-conjugated AXL antibodies in a therapeutic LCLC-103H xenograft model as described in Example 9.

The panel of anti-AXL-vcMMAE antibodies showed a broad range of anti-tumor activity in established SC LCLC-103H tumors (FIG. 8). Clones IgG1-AXL-733-vcMMAE, IgG1-AXL-107-vcMMAE and IgG1-AXL-148-vcMMAE induced tumor regression, clones AXL-171-vcMMAE, IgG1-AXL-511-vcMMAE and IgG1-AXL-613-vcMMAE induced tumor growth inhibition, and clones IgG1-AXL-154-M103L-vcMMAE, IgG1-AXL-183-N52Q-vcMMAE, and IgG1-AXL-726-M101L-vcMMAE showed no or only minor tumor growth inhibition.

Statistical analysis on the last day that all groups were intact (day 30) using One Way ANOVA (Dunnett's multiple comparisons test versus control IgG1-b12) indicated a highly significant difference ($p<0.0001$) in tumor volume between IgG1-b12 versus IgG1-AXL-733-vcMMAE, IgG1-AXL-107-vcMMAE and IgG1-AXL-148-vcMMAE. Treatment with these clones led in some mice within these groups to complete tumor reduction. Treatment with clones IgG1-AXL-171-vcMMAE, IgG1-AXL-511-vcMMAE and IgG1-AXL-613-vcMMAE also showed significant tumor growth inhibition compared to IgG1-b12, but the differences were less pronounced ($p<0.05$ to $p<0.001$). The tumor growth of mice treated with clones IgG1-AXL-154-M103L-vcMMAE, IgG1-AXL-183-N52Q-vcMMAE, and IgG1-AXL-726-M101L-vcMMAE was not significant affected compared to the IgG1-b12 control.

Anti-tumor activity of anti-AXL-vcMMAE antibodies was observed in various other in vivo tumor models. In two cell line-derived xenograft models (A431; epidermoid adenocarcinoma, and MDA-MB-231; breast cancer) anti-AXL-vcMMAE antibodies induced tumor growth inhibition, and tumor regression was induced by anti-AXL-vcMMAE antibodies in two patient-derived xenograft models from patients with pancreas cancer and cervical cancer.

Example 10—Anti-Tumor Efficacy of AXL-ADCs in a Pancreas Cancer Patient-Derived Xenograft (PDX) Model with Heterogeneous Target Expression The anti-tumor activity of IgG1-AXL-107-vcMMAE, IgG1-AXL-148-vcMMAE, and IgG1-AXL-733-vcMMAE was determined in the PAXF1657 pancreas cancer PDX model (experiments performed by Oncotest, Freiburg, Germany). Human pancreas tumor tissue was subcutaneously implanted in the left flank of 5-7 weeks old female NMRI nu/nu mice. Randomization of animals was performed as follows: animals bearing a tumor with a volume between 50-250 mm$^3$, preferably 80-200 mm$^3$, were distributed in 7 experimental groups (8 animals per group), considering a comparable median and mean of group tumor volume. At day of randomization (day 0), the 3 ADCs were dosed intravenously (i.v.) at either 4 mg/kg or 2 mg/kg, and the control group received a single dose of IgG1-b12 (4 mg/kg). Tumor volumes (mm$^3$) were monitored twice weekly and were calculated from caliper (PLEXX) measurements as: 0.52×(length)×(width)$^2$.

Staining of PAXF1657 tumors was performed with standard immunohistochemistry techniques. Briefly, frozen tissues were fixated with acetone for 10 minutes and endogenous peroxidase was exhausted using hydrogen peroxidase. Subsequently, tissue sections were blocked with normal mouse serum and staining was performed by incubation with 5 μg/mL of a pool of 5 IgG1-AXL antibodies (IgG1-AXL-061, IgG1-AXL-137, IgG1-AXL-148, IgG1-AXL-183, IgG1-AXL-726). After incubation with the secondary, horseradish peroxidase (HRP) conjugated antibody, HRP was visualized with amino-ethyl carbazole (AEC; resulting in a red color). Each slide was counterstained with hematoxylin (blue) to identify nuclei and coverslipped in glycergel. Immunostained tissue slices were digitized on manual Zeiss microscope (AxioSkop) at 10× and 40× magnifications.

Figure 9:
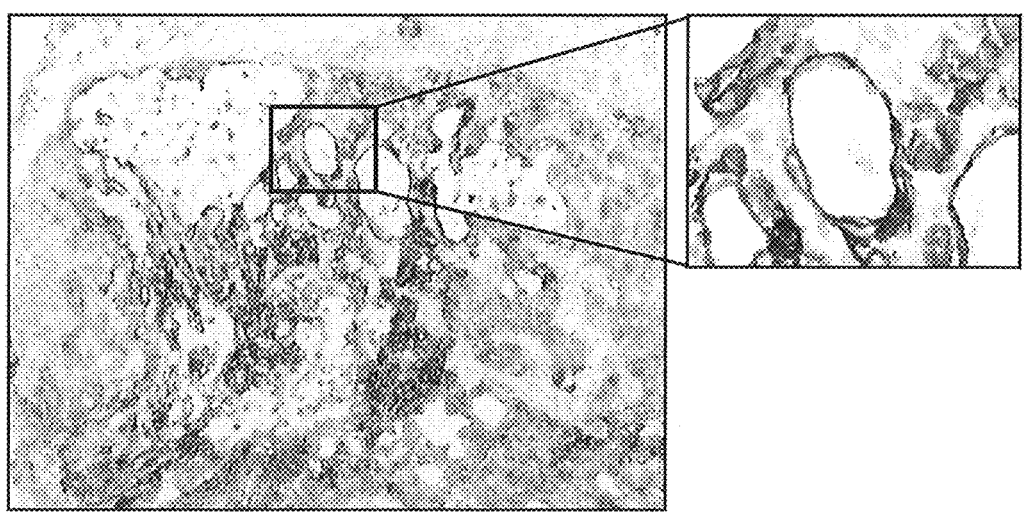
FIG. 9: Immunohistochemical staining of frozen PAXF1657 tumor sections (pancreas cancer PDX model) using a pool of AXL monoclonal antibodies as described in Example 10.

FIG. 9 shows heterogeneous AXL expression in PAXF1657 tumors. Whereas strong AXL staining is observed in some tumor cells, other cells do not show AXL staining. In black and white photo the AXL staining appears as dark grey. Hematoxylin staining (nuclei) appears as light grey.

Figure 10A:
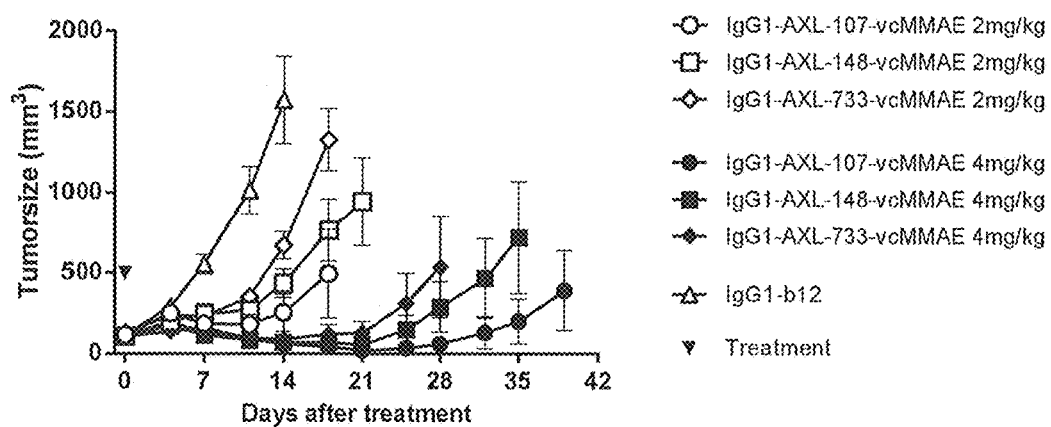
FIGS. 10A-10C.

FIG. 10A shows that treatment of mice with 2 mg/kg IgG1-AXL-107-vcMMAE, IgG1-AXL-148-vcMMAE and IgG1-AXL-733-vcMMAE significantly reduced the growth of PAXF1657 tumors compared to the control group. At a dose of 4 mg/kg IgG1-AXL-107-vcMMAE, IgG1-AXL-148-vcMMAE and IgG1-AXL-733-vcMMAE induced tumor regression of PAXF1657 tumors. On day 14 after treatment, the average tumor size in mice that had been treated with 2 mg/kg or 4 mg/kg IgG1-AXL-107-MMAE, IgG1-AXL-148-MMAE or IgG1-AXL-733-MMAE was significantly smaller than in mice that had been treated with an isotype control IgG (IgG1-b12) ($p<0.001$; Tukey's multiple comparison test).

Figure 10B:
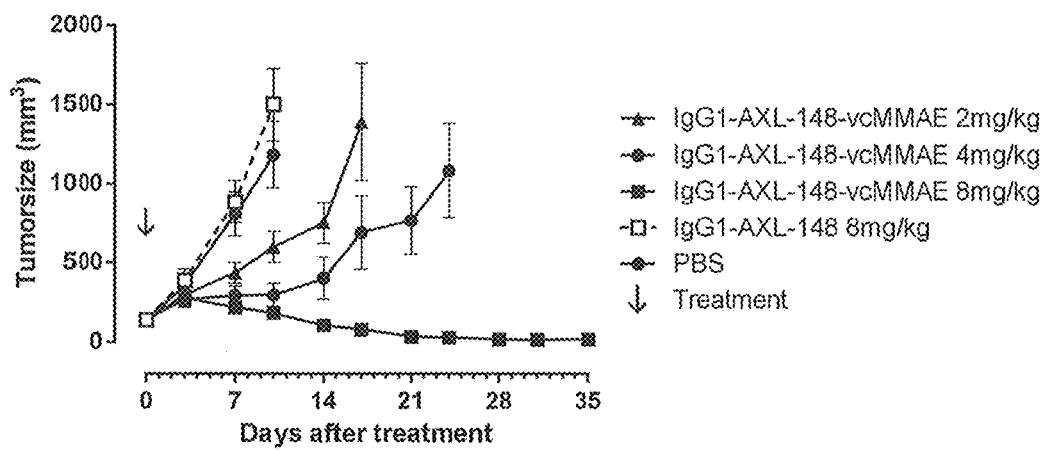

Treatment of mice with unconjugated IgG1-AXL-148 did not result in anti-tumor activity in the PAXF1657 model (FIG. 10B). Conjugated IgG1-AXL-148-vcMMAE, however, induced dose-dependent antitumor activity in this model (FIG. 10B), illustrating that the therapeutic capacity of AXL-ADCs is dependent on the cytotoxic activity of MMAE.

Figure 10C:
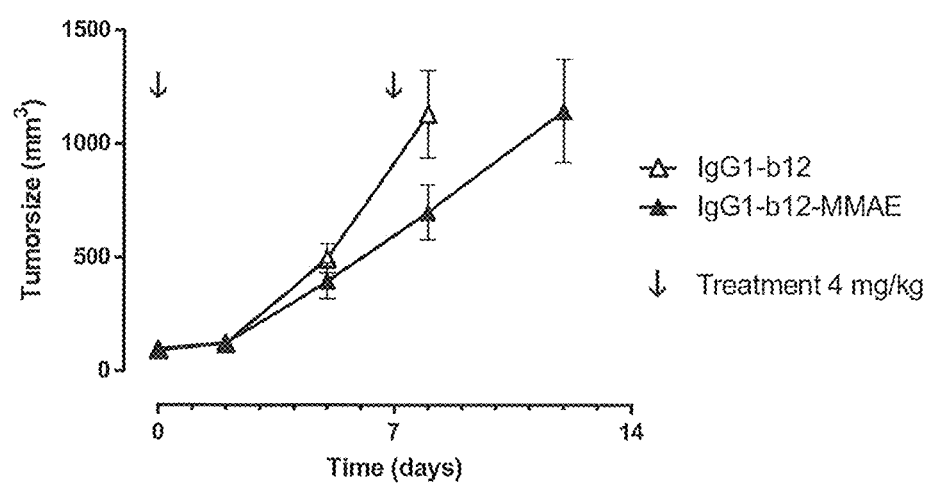

Moreover, treatment of mice with the untargeted ADC IgG1-b12-vcMMAE did not show anti-tumor activity in the PAXF1657 model (FIG. 10C), illustrating that the therapeutic capacity of AXL-ADCs also depends on specific target binding.

Example 11—AXL Antibodies Binding to the Ig1 Domain

The AXL domain specificity of AXL antibodies IgG1-AXL-061, IgG1-AXL-107, IgG1-AXL-137, and IgG1-AXL-613 was determined using a panel of human-mouse chimeric AXL mutants. The human-mouse cross-reactive monoclonal AXL antibody YW327.6S2 was included to confirm expression of hsAXL-mmECD. IgG1-b12 was included as isotype control antibody. Five different chimeric AXL molecules were generated and expressed in HEK293F as described in Example 3. In brief, the human Ig-like domain I (Ig1), the Ig-like domain II (Ig2), the human FNIII-like domain I (FN1) or the human FNIII-like domain II domain (FN2) were replaced with their murine homologs. Binding of 1 μg/mL anti-AXL antibody to the human-mouse AXL chimeras was determined by flow cytometry, as described in Example 2.

Figure 11A:
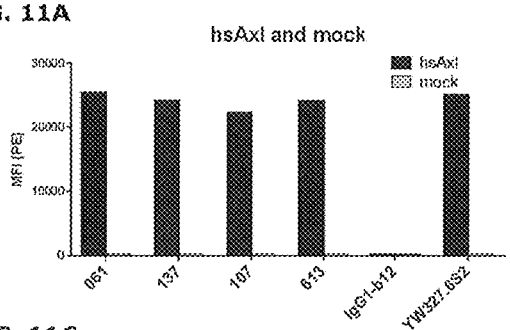
FIGS. 11A-11F: Binding of anti-AXL antibodies to mouse-human AXL chimeras was performed as described in Example 11. The following Homo sapiens AXL (hsAXL) and Mus musculus AXL (mmAXL) chimeric proteins were tested.
Figure 11B:
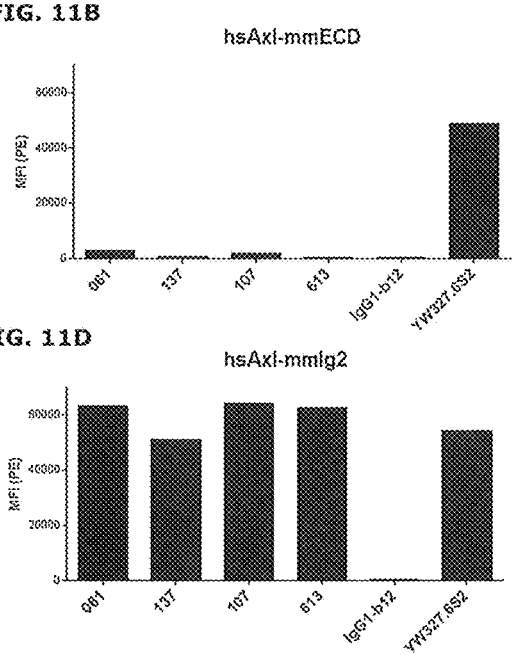

All anti-AXL antibodies showed binding to human AXL (FIG. 11A), whereas binding was abrogated when the human AXL ECD was replaced with its murine homolog (FIG.

11B). As expected, the human-mouse cross-reactive monoclonal AXL antibody YW327.6S2 showed binding to hsAXL-mmECD, confirming proper expression of hsAXL-mmECD.

Figure 11C:
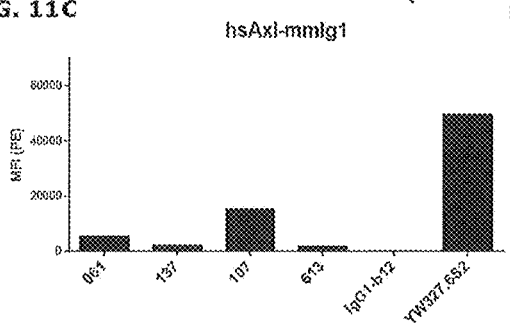
Figure 11D:
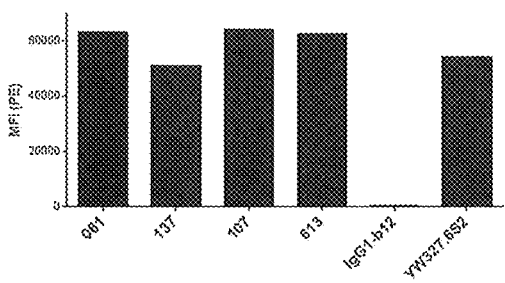
Figure 11E:
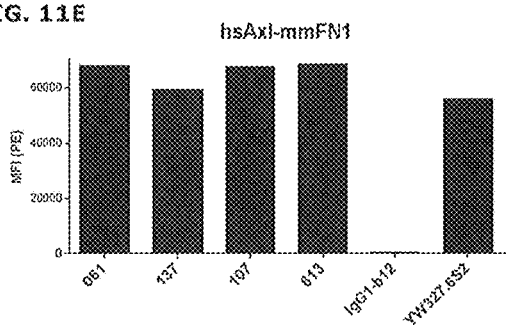
Figure 11F:
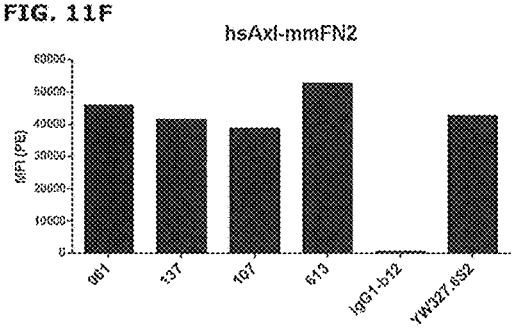

AXL antibodies IgG1-AXL-061, IgG1-AXL-107, IgG1-AXL-137, and IgG1-AXL-613 showed strongly reduced binding to hsAXL-mmIg1 (FIG. 11C), illustrating recognition of an epitope in the AXL Ig1 domain. In line with this, binding of IgG1-AXL-061, IgG1-AXL-107, IgG1-AXL-137, and IgG1-AXL-613 to hsAXL-mmIg2 (FIG. 11D), hsAXL-mmFN1 (FIG. 11E) or hsAXL-mmFN2 (FIG. 11F) was not affected. The human-mouse cross-reactive monoclonal AXL antibody YW327.6S2 showed binding to all chimeric AXL variants, confirming proper expression of these proteins.

Example 12—AXL Antibodies IgG1-AXL-107 and IgG1-AXL-613 Bind to the Ig1 Domain but do not Compete with Gas6 Binding It was tested whether the binding of the AXL antibodies IgG1-AXL-061, IgG1-AXL-107, IgG1-AXL-137, or IgG1-AXL-613 interfered with binding of AXL ligand Gas6 to AXL. Therefore, binding of Gas6 to A431 cells that had been pre-incubated with 10 µg/mL AXL antibodies was tested as described in Example 2. Pre-incubation with AXL antibody YW327.6S2, that was described to compete with Gas6 for AXL binding, IgG1-b12 (isotype control) or medium (negative control) were included as controls.

Binding curves were analyzed using non-linear regression (sigmoidal dose-response with variable slope) using GraphPad Prism V5.04 software (GraphPad Software, San Diego, Calif., USA).

Figure 12:
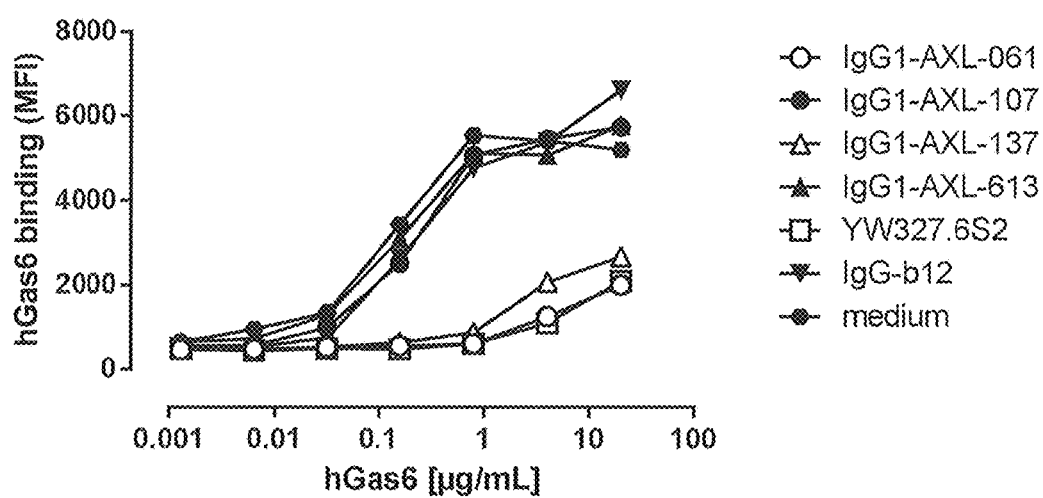
FIG. 12: Binding of human Gas6 (hGas6) on A431 cells that had been pre-incubated with antibodies binding to the Ig1 domain of AXL. Data shown are mean fluorescence intensities (MFI) of one representative experiment.

FIG. 12 and Table 11 shows that binding of Gas6 to A431 cells that had been pre-incubated with IgG1-AXL-107 and IgG1-AXL-613 antibodies was similar to the IgG1-b12 and medium controls. This illustrates that binding of IgG1-AXL-107 and IgG1-AXL-613 to AXL does not interfere with Gas6 binding, as shown in Example 2. The binding of Gas6 to A431 cells was largely reduced in the presence of IgG1-AXL-061, IgG1-AXL-137 and control AXL antibody YW327.6S2 compared to the IgG1-b12 and medium controls.

In experiments in which A431 cells were pre-incubated with Gas6, the maximal binding values of IgG1-AXL-107 and IgG1-AXL-613 were comparable to antibody binding in absence of Gas6 (maximal binding after Gas6 pre-incubation was 91-108% of binding without Gas6 pre-incubation) (Table 11). The $EC_{50}$ values for IgG1-AXL-107 and IgG1-AXL-613 binding with or without Gas6 pre-incubation were in the same range, or somewhat higher after Gas6 pre-incubation (Table 11), illustrating that IgG1-AXL-107 and IgG1-AXL-613 do not compete with Gas6 binding.

Similar to control antibody YW327.6S2, the binding of IgG1-AXL-061 and IgG1-AXL-137 to A431 cells was greatly reduced in the presence of Gas6 compared to binding without Gas6 (maximal binding after Gas6 pre-incubation was 40-43% of binding without Gas6 pre-incubation; Table 11). The $EC_{50}$ values for IgG1-AXL-061 and IgG1-AXL-137 could not properly be determined after Gas6 pre-incubation (Table 11). This shows that IgG1-AXL-061 and IgG1-AXL-137 compete with Gas6 for binding to AXL.

These data demonstrate that antibodies binding to the AXL Ig1 domain have differential effect on Gas6 binding.

TABLE 11

| | Antibody binding to A431 cells | | | Gas6 binding to A431 cells | |
|---|---|---|---|---|---|
| Antibody | EC50 w/o Gas6 EC50 (µg/mL) mean (s.d.) | EC50 in presence of Gas6 (µg/mL) mean (s.d.) | Maximal binding in presence of Gas6 (% of binding in absence of Gas6) mean (s.d.) | EC50 in presence of AXL antibodies (µg/mL) mean (s.d.) | Maximal binding in presence of AXL antibodies (% of binding in presence of control antibody) mean (s.d.) |
| IgG1-AXL-061 | 0.15 (n.a.) | n.a. | 43 (28) | n.a. | 22 (8) |
| IgG1-AXL-107 | 0.16 (0.17) | 0.94 (1.18) | 91 (5) | 0.78 (0.54) | 96 (8) |
| IgG1-AXL-137 | 0.11 (0.10) | n.a. | 40 (18) | n.a | 36 (4) |
| IgG1-AXL-613 | 0.09 (0.09) | 0.10 (0.10) | 108 (22) | 0.57 (0.36) | 100 (11) |
| YW327.6S2 | 0.09 (0.09) | 1.90 (1.04)* | 41 (24) | 5.53 (7.09)* | 17 (10) |
| b12 | n.a.[a] | n.a. | n.a. | 0.40 (0.11) | 100 |

[a] n.a., not applicable
*EC50 values less accurate due to low binding.

Example 13—In Vivo Anti-Tumor Efficacy of AXL-ADCs in Xenograft Models with and without Autocrine (Endogenous) Gas6 Production Gas6 Production of A431 and LCLC-103H Tumor Cells It was tested whether A431 cells and LCLC-103H cells produce Gas6. Therefore, cells were grown in complete culture medium for 3 days. Gas6 levels in supernatant were determined using the Quantikine Human Gas6 ELISA (R&D Systems, Minneapolis, Minn.) according to manufacturer's instructions. This assay uses the quantitative sandwich ELISA technique. A monoclonal Ab specific for human Gas6 has been pre-coated onto a microplate. Standards and samples are pipetted into the wells and any human Gas6 present is bound by the immobilized Ab. After washing away any unbound substances, an enzyme-linked polyclonal Ab specific for human Gas6 is added to the wells. Following a wash to remove any unbound Ab-enzyme reagent, a substrate is added to the wells and color develops in proportion to the amount of human Gas6 bound in the initial step. The color development is stopped and the intensity of the color is measured.

Cell culture medium conditioned by A431 cells was found to contain 2576 ng/mL Gas6, while the concentration of Gas6 in medium conditioned by LCLC-103H cells was more than 20-fold less (Table 12).

TABLE 12

Gas6 production in tumor cell conditioned medium.

| Cell line | Gas6 in supernatant (ng/mL) |
| --- | --- |
| LCLC-103H | 126 |
| A431 | 2576 |

Anti-Tumor Activity of AXL-ADCs In Vivo

The in vivo anti-tumor activity of IgG1-AXL-061-vcMMAE (Ig1 binder), IgG1-AXL-107-vcMMAE (Ig1-binder), IgG1-AXL-137-vcMMAE (Ig1-binder), IgG1-AXL-148-vcMMAE (Ig2-binder), IgG1-AXL-183-vcMMAE (FN1-binder), and IgG1-AXL-726-vcMMAE (FN2-binder) was determined in the A431 (epidermoid carcinoma) tumor model, that produces high levels of Gas6, and the LCLC-103H (large cell lung carcinoma) tumor model, that produces low levels of Gas6.

Tumor induction was performed by subcutaneous injection of $5 \times 10^6$ A431 or LCLC-103H tumor cells (both obtained from Leibniz-Institut—Deutsche Sammlung von Mikroorganismen and Zellkulturen GmbH (DSMZ)) in 200 μL PBS in the right flank of female SCID mice. Treatment was started 14-21 days after tumor cell inoculation, when the average tumor size was >100-200 mm$^3$ and distinct tumor growth was observed. Mice received a single injection or a total of 4 biweekly intraperitoneal injections with IgG1-AXL-vcMMAE ADCs or control antibody (unconjugated IgG1-b12), as indicated. Tumor volume was determined at least two times per week. Tumor volumes (mm$^3$) were calculated from caliper (PLEXX) measurements as: $0.52 \times$ (length)$\times$(width)$^2$.

Figure 13A:
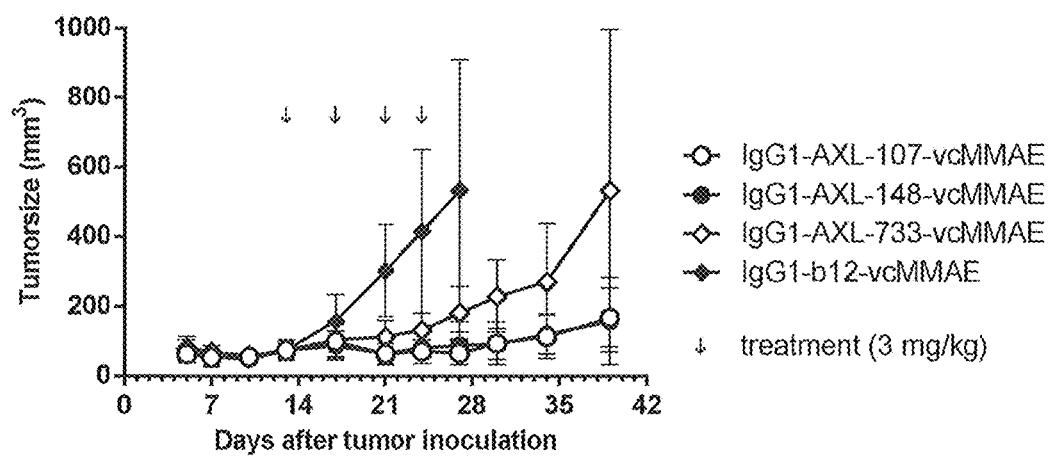
FIGS. 13A and 13B: Anti-tumor activity of MMAE-conjugated AXL antibodies in a therapeutic A431 xenograft model, that produces high levels of endogeneous Gas6, as described in Example 13.

FIG. 13A shows that treatment of mice with 3 mg/kg IgG1-AXL-107-vcMMAE, IgG1-AXL-148-vcMMAE and IgG1-AXL-733-vcMMAE induced growth inhibition of A431 tumors.

Figure 13B:
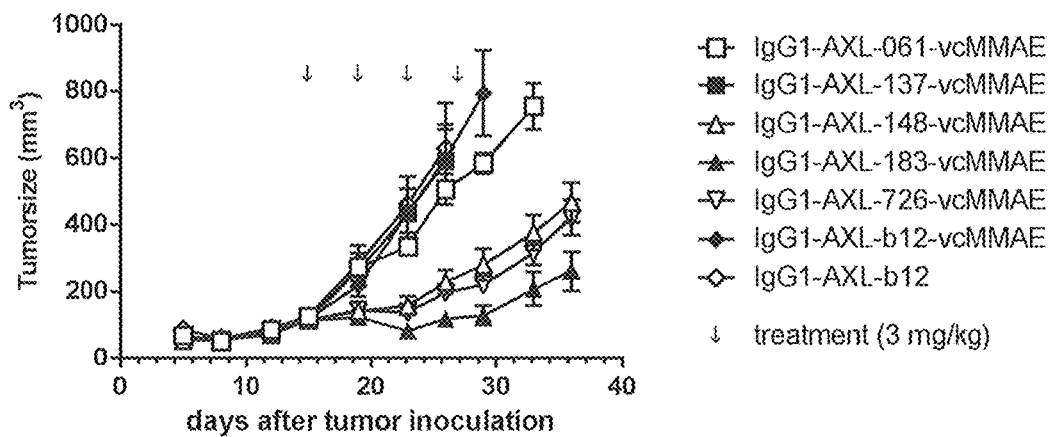

FIG. 13B shows that treatment of mice with 3 mg/kg IgG1-AXL-148-vcMMAE, IgG1-AXL-183-vcMMAE (FN1 binder) and IgG1-AXL-726-vcMMAE (FN2 binder) induced growth inhibition of A431 tumors. In contrast, clones IgG1-AXL-061-vcMMAE and IgG1-AXL-137-vcMMAE did not show anti-tumor activity in the A431 xenograft model.

Figure 14A:
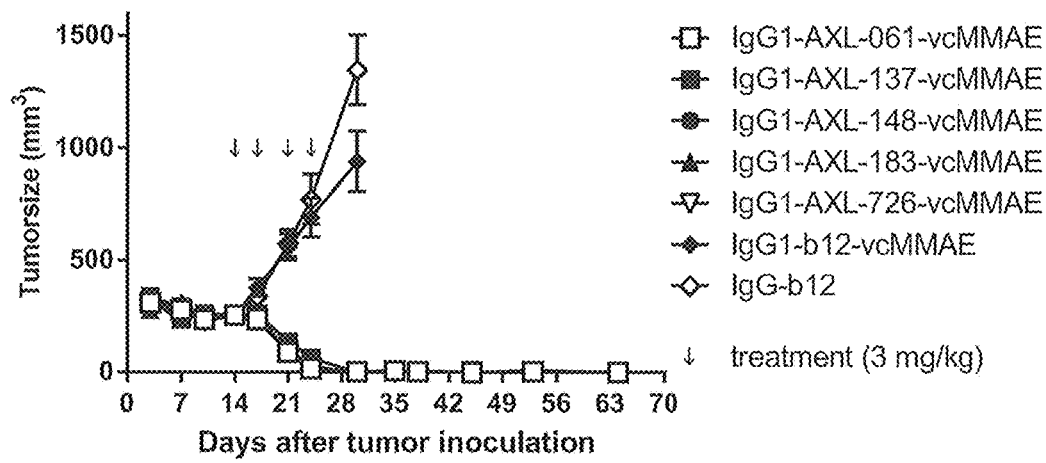
FIGS. 14A and 14B: Anti-tumor activity of MMAE-conjugated AXL antibodies in a therapeutic LCLC-103H xenograft model, that expresses low levels of endogenous Gas6, as described in Example 13.
Figure 14B:
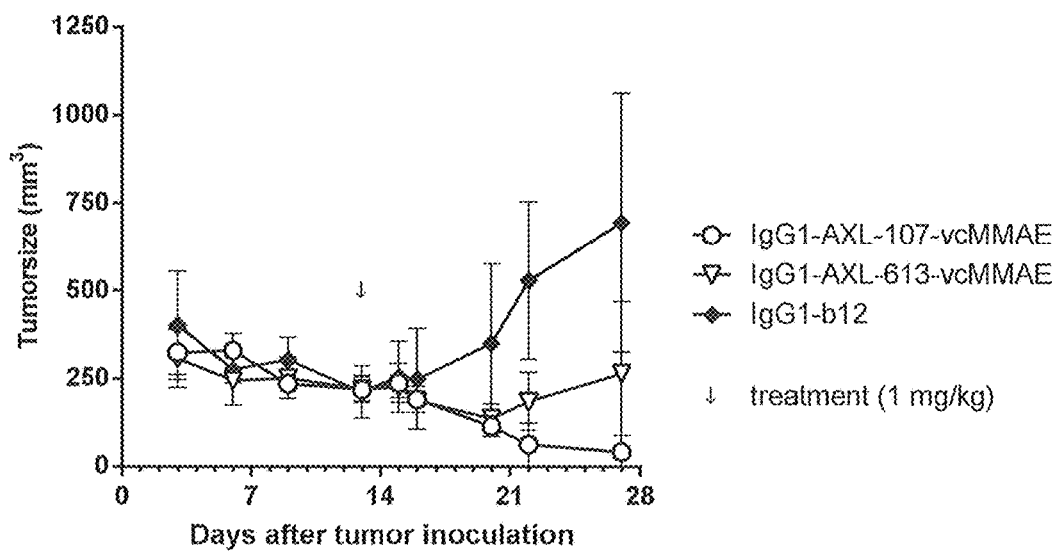

FIG. 14A shows that treatment of mice with 3 mg/kg IgG1-AXL-061-vcMMAE, IgG1-AXL-137-vcMMAE, IgG1-AXL-148-vcMMAE, IgG1-AXL-183-vcMMAE and IgG1-AXL-726-vcMMAE induced tumor regression in the LCLC-103H xenograft model. Similarly, treatment of mice with 1 mg/kg IgG1-AXL-107-vcMMAE or 1 mg/kg IgG1-AXL-613-vcMMAE induced regression of LCLC-103H tumors (FIG. 14B).

In summary, all AXL-ADCs showed anti-tumor activity in the LCLC-103H xenograft model that produces low levels of Gas6. In the A431 xenograft model, that produces high levels of Gas6, anti-tumor activity was only observed for those AXL-ADCs that did not compete with the AXL ligand Gas6.

Example 14—AXL Expression in Different Tumor Indications

Expression of AXL was evaluated in freshly cut paraffin embedded and formalin fixated (FFPE) tumor tissue micro arrays (TMA) comprising tissue cores from patients with thyroid, esophageal, ovarian, pancreatic, lung, breast, cervical or endometrial cancer, or malignant melanoma. TMAs were obtained from US BioMax.

FFPE tumor array slides were deparaffinized and subjected to antigen retrieval (pH 6) and endogenous peroxidase was exhausted by incubation with 0.1% H2O2 in citrate/phosphate buffer. To detect AXL expression, the TMAs were incubated with rabbit-anti-AXL (Santa Cruz, cat nr: sc-20741) at a concentration of 1 μg/mL for 60 min (room temperature (RT)). To identify (tumor) cells of epithelial origin, TMAs were incubated with rabbit-anti-cytokeratin (Abcam, cat. Nr. ab9377) at a dilution of 1:50 for 60 min (RT). After a washing step, the TMAs were incubated with peroxidase conjugated, anti-rabbit IgG dextran polymer (ImmunoLogic, cat no: DPVR55HRP) to detect binding of rabbit Anti-AXL and rabbit anti-cytokeratin antibodies. Finally, binding of anti-rabbit IgG dextran polymer was visualized with di-amino-benzadine (DAB; brown color; DAKO, cat no: K346811). In the TMA with malignant melanoma tissue cores, binding of anti-rabbit IgG dextran polymer was visualized with amino-ethyl carbazole (AEC; red color; Vector, SK4200). Nuclei in TMAs were visualized with hematoxylin (blue color).

AXL and cytokeratin immunostained TMAs were digitized with an Aperio slide scanner at 20x magnification and immunostaining was quantified with tissue image analysis software (Definiens Tissue Studio software, version 3.6.1), using a cell-based algorithm. The algorithm was designed to identify and quantify the percentage of AXL- or cytokeratin-positive cells in the biopsies (range 0-100%) and to quantify AXL staining intensity in AXL-positive tumor cells (optical density (OD); range 0-3) in each tumor core. Tumor cells were scored AXL positive, when AXL OD was at least 0.1. The percentage of AXL positive tumor cells per tumor core (range 0-100%) was calculated by dividing the total number of AXL positive cells by the total number of cytokeratin-positive cells in sequential tumor cores. The average AXL staining intensity (OD) in each tumor core was calculated by dividing the sum of AXL OD of all AXL positive tumor cells by the number of AXL positive tumor cells.

Tumor array from patients with malignant melanoma were scored manually. AXL staining intensity was scored as either weak (1+), moderate (2+) or strong (3+) and the percentage AXL positive melanoma cells was scored in 10% intervals (range 0-100%).

Figure 16:
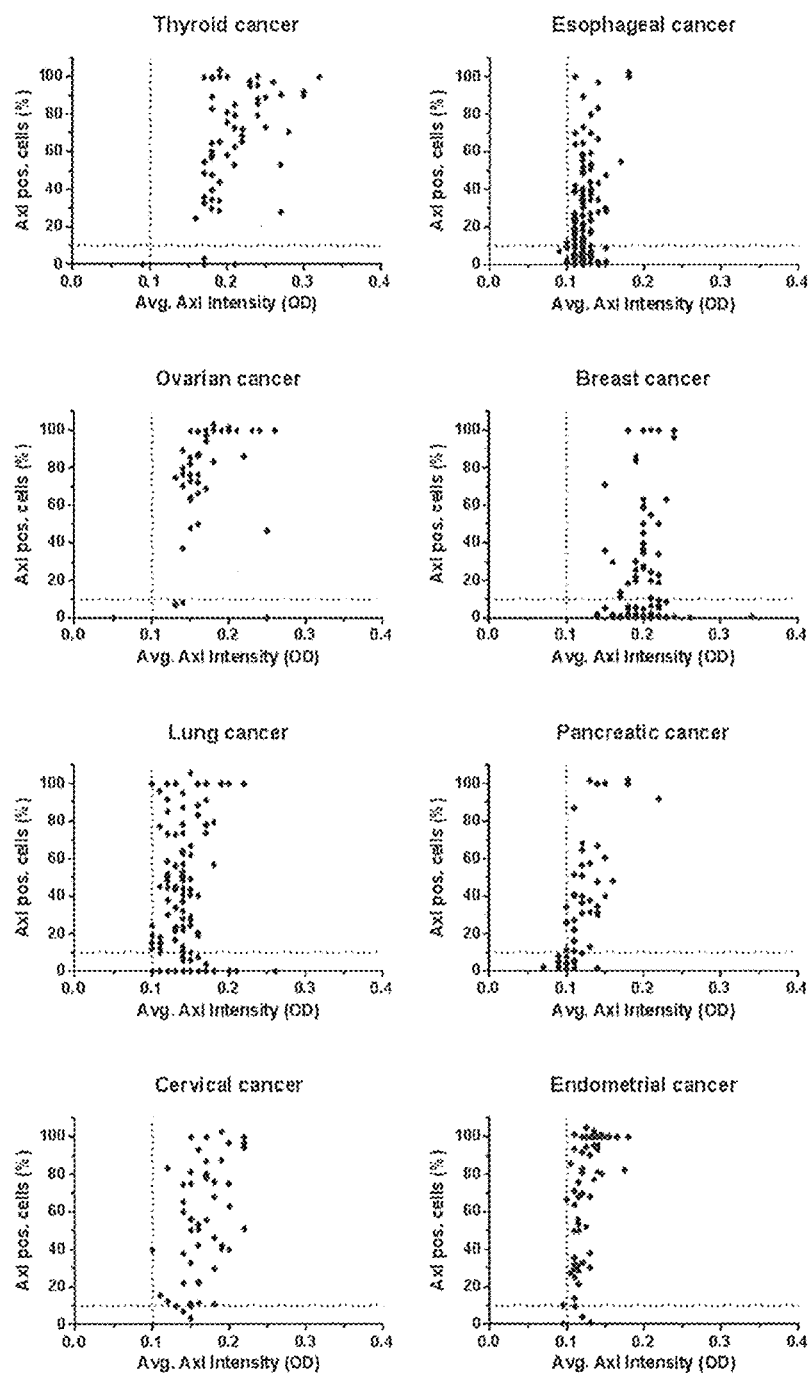
FIG. 16. AXL staining in thyroid, esophageal, ovarian, breast, lung, pancreatic, cervical and endometrial cancer. The average AXL staining intensity (OD) of AXL-positive cells is plotted on the X-axis, and the percentage of AXL-positive tumor cells is plotted on the Y-axis. Each dot represents a tumor core, derived from an individual patent.
Figure 17:
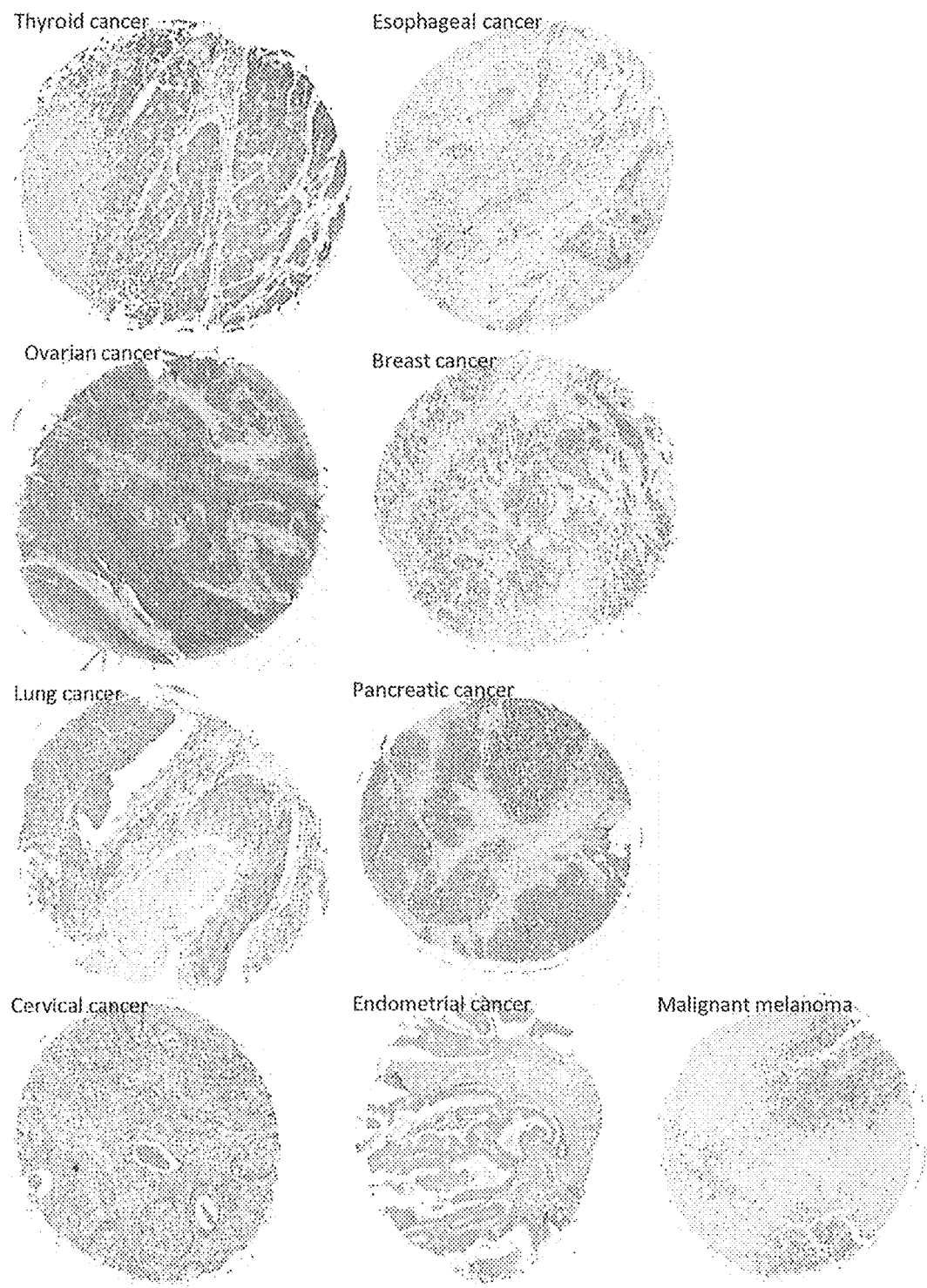
FIG. 17. Representative examples of AXL-immunostained tumor cores for different tumor indication.

FIG. 16 provides a graphical representation of AXL expression in tumor cores of thyroid, esophageal, ovarian, breast, lung, pancreatic, cervical and endometrial cancer. Table 13 shows the percentage of tumor cores that showed AXL expression in more than 10% of tumor cells, for each indication. FIG. 17 shows a representative example of a tissue core immunostained for AXL, for each indication. The figures illustrate heterogeneous expression of AXL in the tumor issue.

TABLE 13

| Tumor indication | Subtype | % tumor cores (patients) with >10% AXL-positive tumor cells |
|---|---|---|
| Esophageal cancer | Adenocarcinoma (n = 19) | 73 |
|  | Squamous cell carcinoma (n = 60) | 55 |
| Ovarian cancer | All subtypes (n = 52) | 90 |
| Pancreatic cancer | All subtypes (n = 58) | 60 |
| Lung cancer (NSCLC) | Squamous cell carcinoma SSC (n = 52) | 63 |
|  | Adenocarcinoma (n = 48) | 67 |
| Lung cancer (SCLC) | SCLC (n = 5) | 60 |
| Thyroid cancer | All subtypes (n = 48) | 92 |
| Uterine cancer | All subtypes (n = 60) | 88 |
| Breast cancer | TNBC (n = 54) | 24 |
| Cervical cancer | All subtypes (n = 54) | 93 |
| Melanoma | Malignant melanoma (n = 67) | 6 |

Abbreviations used: NSCLC, non small cell lung cancer; SLCL, small cell lung cancer; TNBC, triple negative breast cancer Example 15—AXL Antibodies Specifically Bind AXL but not Other TAM Receptor Family Members Expression of Human AXL, MER, and TYRO3 in HEK-293F Cells The following codon-optimized constructs for expression of various full-length proteins were generated: human (*Homo sapiens*) AXL (Genbank accession no. NP_068713.2), human MER (Genbank accession no. EAW52096.1, and human TYRO3 (Genbank accession no. Q06418.1). The constructs contained suitable restriction sites for cloning and an optimal Kozak (GCCGCCACC) sequence [Kozak et al. (1999) Gene 234: 187-208]. The constructs were cloned in the mammalian expression vector pcDNA3.3 (Invitrogen)

Freestyle™ 293-F (a HEK-293 subclone adapted to suspension growth and chemically defined Freestyle medium, (HEK-293F)) cells were obtained from Invitrogen and transfected with the expression plasmids using 293fectin (Invitrogen), according to the manufacturer's instructions and grown for 24-48 hours.

Binding Study of AXL Antibodies to Human AXL, Human MER, or Human TYRO3

HEK-293F cells transiently transfected with expression constructs for full length human AXL, MER, or TYRO3 were evaluated for binding of HuMab-AXL antibodies by flow cytometry. Transfected HEK-293F cells were incubated with serial dilutions of AXL-antibodies (4-fold dilutions; final concentration range 0.002-10 µg/mL) for 30 minutes at 4° C. After washing three times in PBS/0.1% BSA/0.02% azide, cells were incubated with R-Phycoerythrin (PE)-conjugated goat-anti-human IgG F(ab')2 (Jackson ImmunoResearch Laboratories, Inc., West Grove, Pa.; cat. No. 109-116-098) diluted 1/100 in PBS/0.1% BSA/0.02% azide (final volume 100 µL). Next, cells were washed twice in PBS/0.1% BSA/0.02% azide, resuspended in 120 µL PBS/0.1% BSA/0.02% azide and analyzed on a FACS Cantoll (BD Biosciences). Staining with mouse anti-human Mer (R&D Systems, cat. Mab8912) and mouse anti-human Tyro3 (Dtk) (R&D Systems, cat. MAB859) were included as controls for expression, IgG1-b12 was included as a non-binding isotype control antibody. Binding curves were analyzed using non-linear regression (sigmoidal dose-response with variable slope) using GraphPad Prism V5.04 software (GraphPad Software, San Diego, Calif., USA).

Figure 18A:
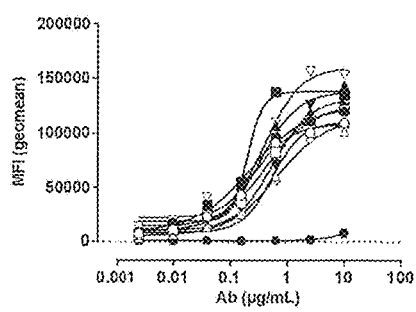
FIGS. 18A-18G. AXL antibodies specifically bind AXL but not to other TAM receptor family members. Binding of HuMab-AXL antibodies to HEK293 cells transfected with human AXL (FIG. 18A), human MER (FIG. 18B), human TYRO3 (FIG. 18C), or untransfected HEK293 cells (FIG. 18D). To confirm proper expression of transfected cells, untransfected HEK293F cells and cells transfected with AXL (FIG. 18E), MER (FIG. 18F), or TYRO3 (FIG. 18G) were stained with MER- and TYRO3-specific antibodies. Data shown are mean fluorescence intensities (MFI) of one representative experiment, as described in Example 15.
Figure 18B:
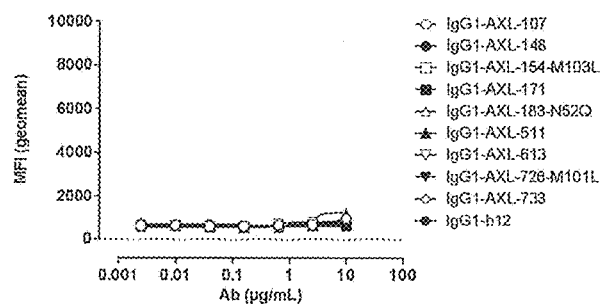
Figure 18C:
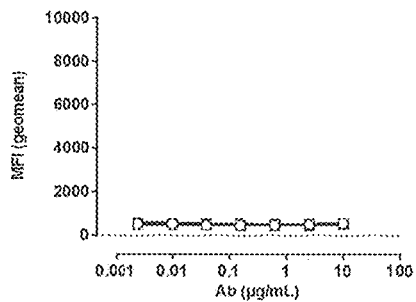
Figure 18D:
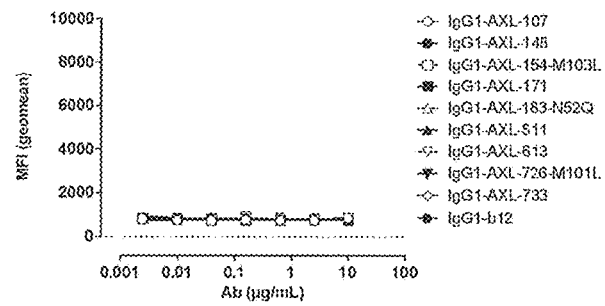
Figure 18E:
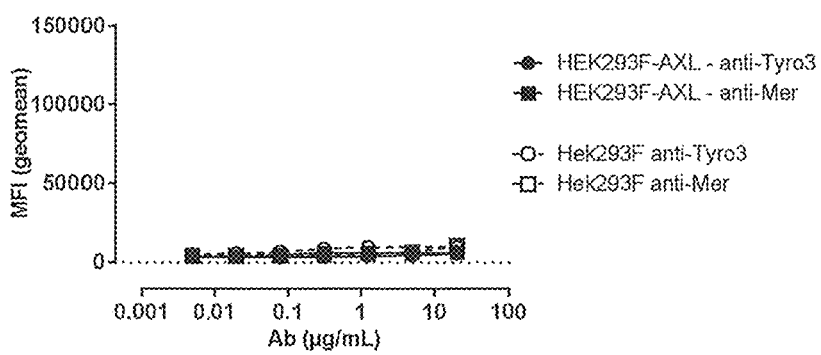
Figure 18F:
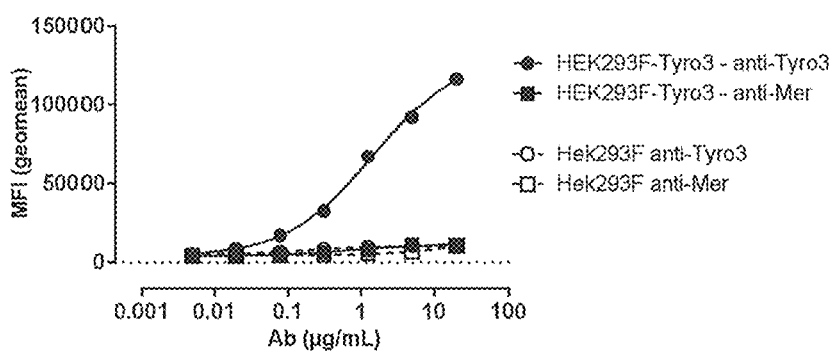
Figure 18G:
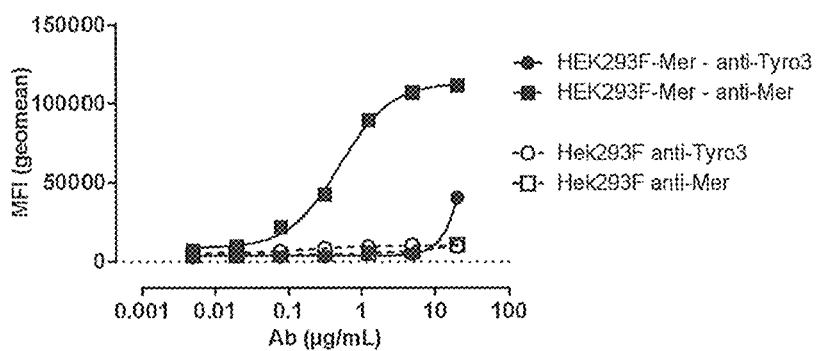
Figure 19A:
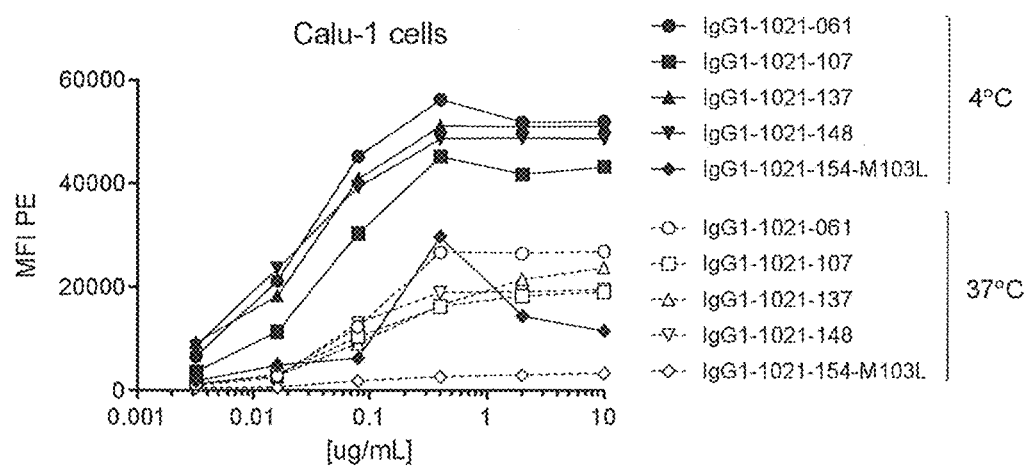
FIGS. 19A-19D. Detection of AXL antibodies on the plasma membrane of tumor cell lines that had been incubated with AXL-antibodies for 1 hour at 4° C., followed by an overnight incubation 4° C. or 37° C. In both MDA-MB-231 (FIGS. 19A and 19B) and Calu-1 cells (FIGS. 19C and 19D), more antibody was detected on the plasma membrane of cells that had been incubated at 4° C. than on cells that had been incubated at 37° C., illustrating internalization of membrane-bound antibody at 37° C.
Figure 19B:
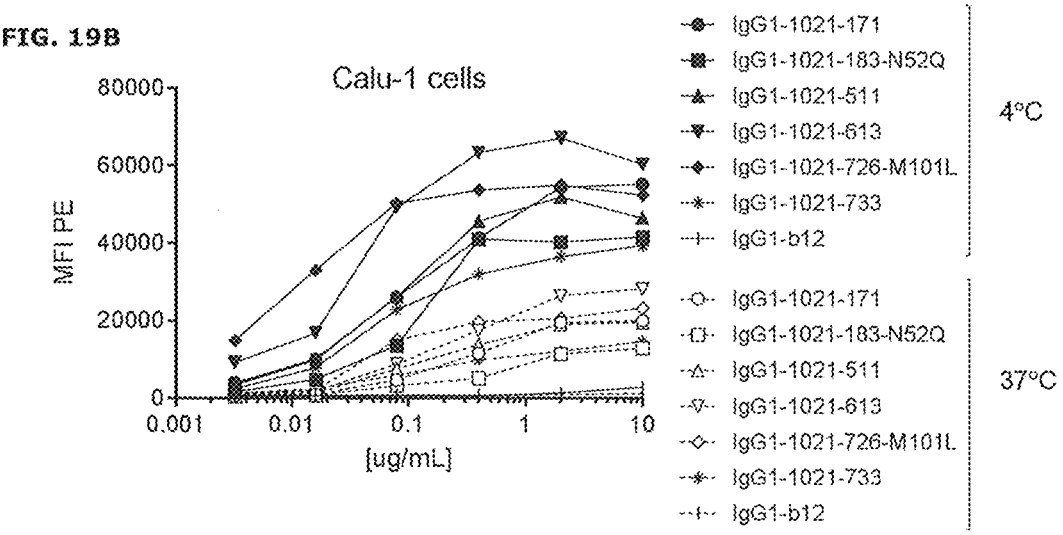
Figure 19C:
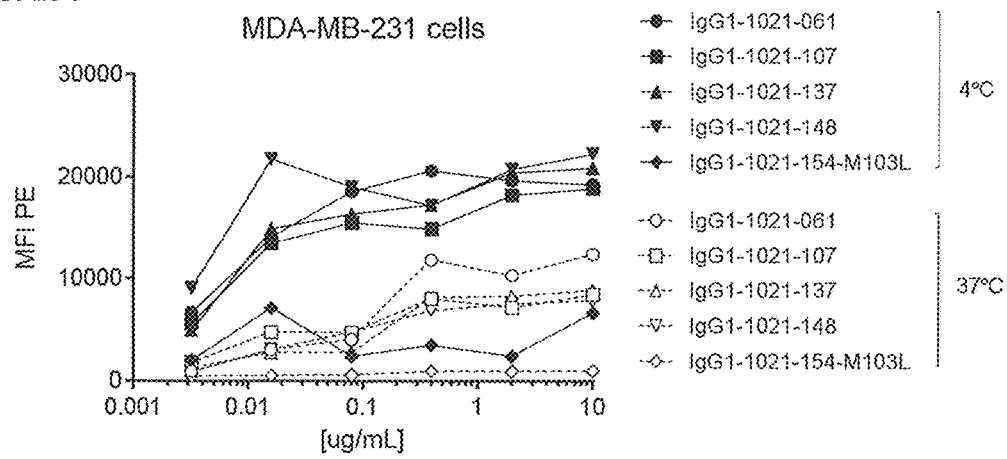
Figure 19D:
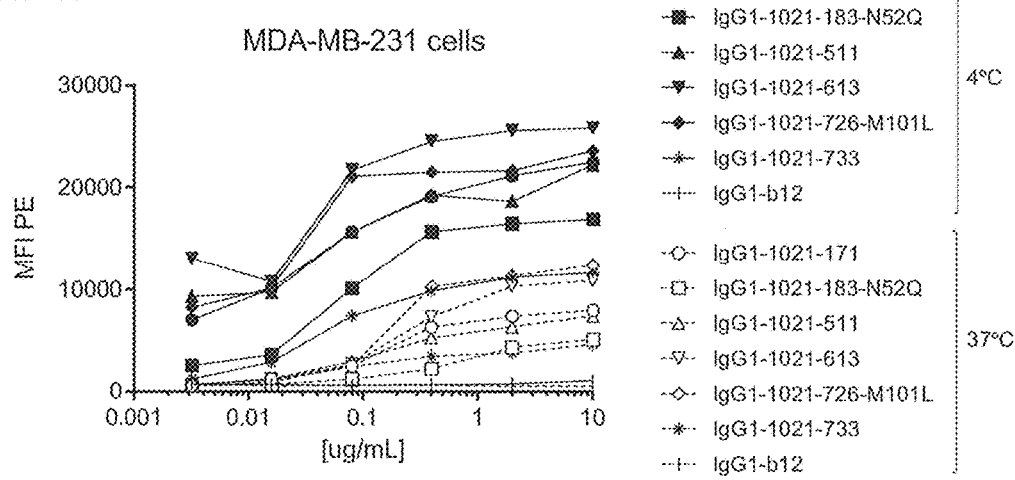

FIG. 18A shows that Humab-AXL antibodies showed dose-dependent binding to the HEK293 cells expressing human AXL. In contrast, no binding of HuMab-AXL antibodies to cells expressing MER (FIG. 18B) or TYRO3 (FIG. 18C) or to untransfected HEK293 cells (FIG. 18D) was observed. Staining with MER- and Tyro3-specific antibodies confirmed that transfected cells showed proper expression of MER (FIG. 18F) or TYRO3 (FIG. 18G), respectively.

Example 16—Internalization of Cell Surface Bound AXL Antibodies

Internalization of Cell Surface Bound HuMab-AXL Evaluated by Flow Cytometry.

Internalization of cell surface bound HuMab-AXL antibodies to MDA-MB-231 and Calu-1 cells (human lung carcinoma cell line; ATCC, catalognumber HTB-54) was evaluated by flow cytometry. 50,000 cells were seeded in 96-well tissue culture plates and allowed to attach for 6 hrs at 37° C. Plates were incubated at 4° C. for 30 minutes before incubation with serial dilutions of AXL-antibodies (final concentration range 0.0032-10 µg/mL) at 4° C. for 1 hour. Subsequently, the medium was replaced by tissue culture medium without antibody and cells were incubated overnight (16-18 hours) at 37° C. or 4° C. Subsequently, the cells were detached with 40 µL warm trypsin solution, washed with ice-cold PBS/0.1% BSA/0.02% azide, and incubated for 30 minutes at 4° C. with R-Phycoerythrin (PE)-conjugated goat-anti-human IgG F(ab')2 (Jackson ImmunoResearch Laboratories, Inc., West Grove, Pa.; cat. No. 109-116-098) diluted 1/100 in PBS/0.1% BSA/0.02% azide (final volume 100 µL), to detect AXL-antibodies on the cell surface. Finally, cells were washed twice in PBS/0.1% BSA/0.02% azide, resuspended in 120 µL PBS/0.1% BSA/0.02% azide and analyzed on a FACS Cantoll (BD Biosciences).

Binding curves were analyzed using non-linear regression (sigmoidal dose-response with variable slope) using GraphPad Prism V5.04 software (GraphPad Software, San Diego, Calif., USA).

FIG. 19 shows that, for all AXL HuMab antibodies and at all concentrations tested, more antibody was detected on the plasma membrane of cells that had been incubated at 4° C. after antibody binding, compared to cells that had been incubated at 37° C. This illustrates that, at 37° C., AXL antibodies are internalized upon binding to the plasma membrane.

Fab-TAMRA/QSY7 Internalization and Intracellular Degradation Assay

Internalization of AXL antibodies was assessed in the Fab-TAMRA/QSY7 internalization assay. This assay uses a fluorophore (TAMRA) and quencher (QSY7) pair. In close proximity, for example, upon conjugation to the same protein, TAMRA fluorescence is quenched by QSY7. In this example, goat-anti-human IgG Fab-fragments (Jackson Immunoresearch) were conjugated with TAMRA/QSY7 (Fab-TAMRA/QSY7) as described (Ogawa et al. Mol Pharm 2009; 6(2):386-395), and AXL HuMab (1.5 µg/mL) were preincubated with Fab-TAMRA/QSY7 (12 µg/mL; 30 min, 4° C.). The complex was subsequently added to LCLC-103H cells and incubated for 24 h incubation in the dark, under shaking conditions (200 rpm, 37° C.). Internalization of the HuMab-Fab-TAMRA/QSY7 complex and intracellular degradation in the endosomes and lysosomes causes dissociation of TAMRA/QSY7, resulting in dequenching of TAMRA. TAMRA fluorescence of LCLC-103H cells that had been incubated with AXL antibodies complexed with Fab-TAMRA/QSY7 was measured on a FACS Canto-II (BD Biosciences).

Figure 20:
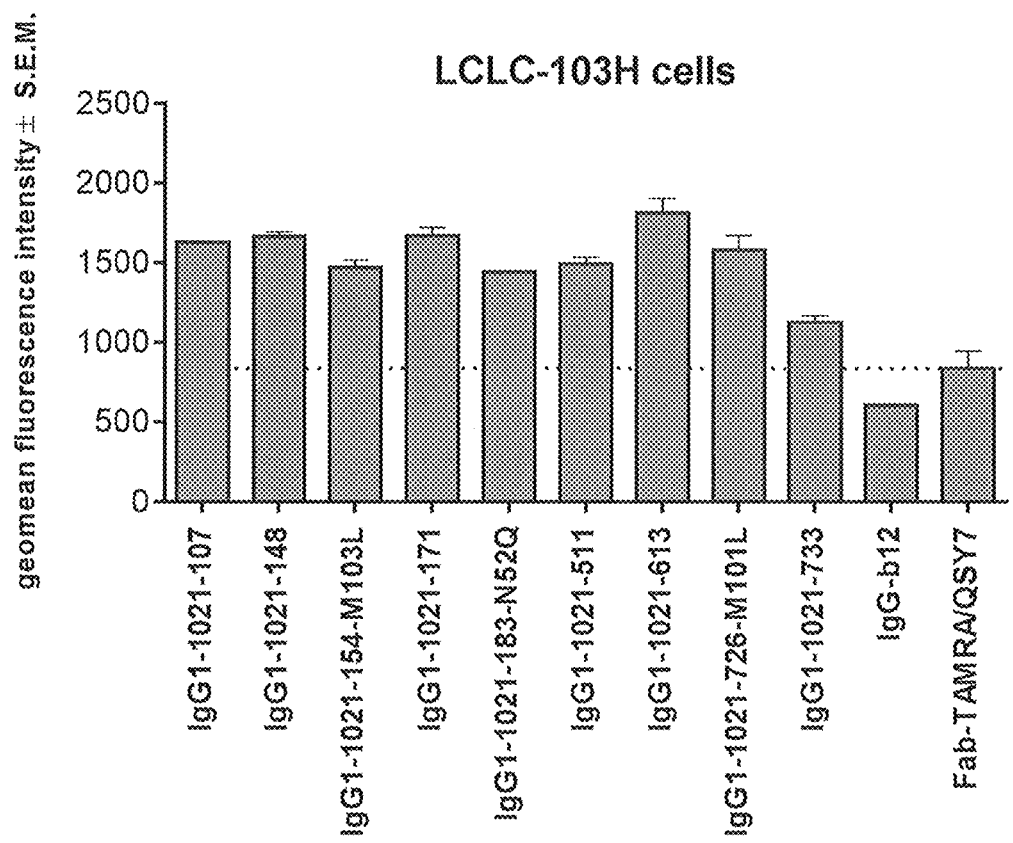
FIG. 20. Geomean fluorescence intensity of LCLC-103H cells after incubation with AXL antibodies that had been complexed to Fab-TAMRA/QSY7. IgG1-b12 and Fab-TAMRA/QSY7 alone were included as negative controls.

As shown in FIG. 20, the fluorescence intensity of LCLC-103H cells was enhanced upon incubation with AXL-antibody-Fab-TAM RA/QSY7 complex, compared to IgG1-b12-Fab-TAMRA/QSY7 or Fab-TAMRA/QSY7 alone. This illustrates that AXL antibodies are internalized upon binding to LCLC-103H cells.

Example 17—Anti-Tumor Efficacy of AXL-ADCs in an Esophageal Cancer Patient-Derived Xenograft (PDX) Model The anti-tumor activity of IgG1-AXL-107-vcMMAE was evaluated in the subcutaneous esophageal PDX model ES0195 in BALB/c nude mice (experiments performed by Crown Bioscience. Taicang Jiangsu Province, China). Tumor fragments from donor mice bearing patient-derived esophageal xenografts (ES0195) were used for inoculation into BALB/c nude mice. Each mouse was inoculated subcutaneously at the right flank with one tumor fragment (2-3 mm in diameter) and tumors were allowed to grow until the tumor volume was about 150 mm$^3$. Randomization of animals was performed as follows: animals bearing a tumor with a volume of about 150 mm$^3$ were distributed in 5 experimental groups (8 animals per group), considering a comparable median and mean of group tumor volume. The treatment groups were: IgG1-b12, IgG1-b12-vcMMAE, IgG1-AXL-107, IgG1-AXL-107-vcMMAE, and paclitaxel. The antibodies and ADCs were dosed intravenously (i.v.) at 4 mg/kg at day of randomization (day 0) and day 7. Paclitaxel was dosed intra-peritoneally (i.p.) at 20 mg/kg at day 0, 7, and 14. Tumor volumes (mm$^3$) were monitored twice weekly and were calculated from caliper (PLEXX) measurements as: 0.52×(length)×(width)2.

Figure 21A:
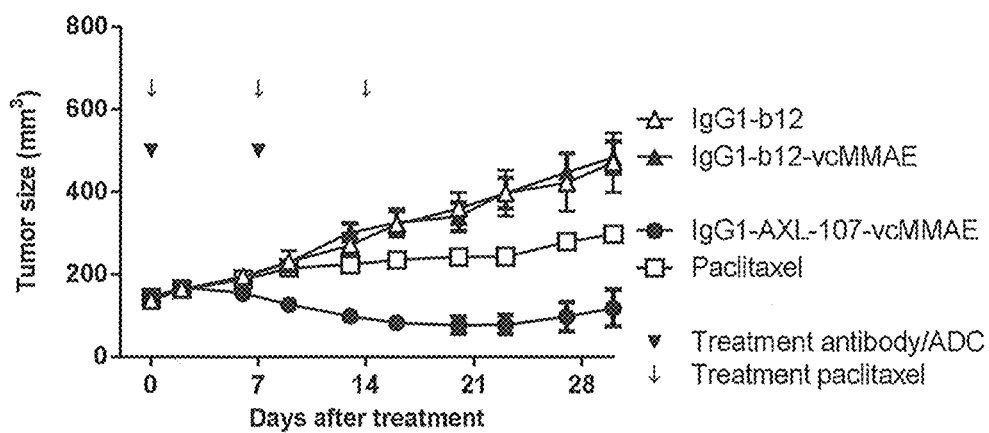
FIGS. 21A and 21B.
Figure 21B:
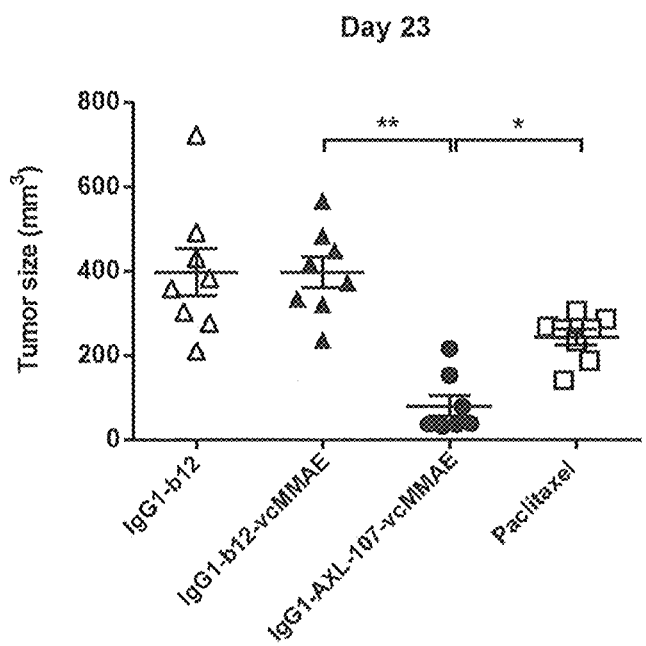

FIG. 21 shows that treatment of mice with IgG1-AXL-107-vcMMAE induced tumor regression of ES0195 tumors compared to the IgG1-b12 and IgG1-b12-MMAE control groups (p<0.001 at day 23, one-way ANOVA test). Treatment of mice with the untargeted ADC IgG1-b12-vcMMAE did not show anti-tumor activity in this model, illustrating that the therapeutic capacity of AXL-ADCs depends on specific target binding. Mice that were treated with paclitaxel showed tumor growth inhibition, but this was less effective compared to treatment with IgG1-AXL-107-vcMMAE (p<0.05 at day 23, one-way ANOVA test).

Example 18—Anti-Tumor Efficacy of AXL-ADCs in a Cervical Cancer Patient-Derived Xenograft (PDX) Model The anti-tumor activity of IgG1-AXL-183-vcMMAE and IgG1-AXL-726-vcMMAE was evaluated in the patient derived cervix carcinoma xenograft CEXF 773 model in NMRI nu/nu mice (Harlan, Netherlands). Experiments were performed by Oncotest (Freiburg, Germany).

Tumor fragments were obtained from xenografts in serial passage in nude mice. After removal from donor mice, tumors were cut into fragments (4-5 mm diameter) and placed in PBS (with 10% penicillin/streptomycin) until subcutaneous implantation. Mice under isofluorane anesthesia received unilateral, subcutaneous tumor implants in the flank. Tumors were allowed to grow until the tumor volume was 50-250 mm$^3$.

Randomization of animals was performed as follows: animals bearing a tumor with a volume of 50-250 mm$^3$ were distributed in 4 experimental groups (8 animals per group), considering a comparable median and mean of group tumor volume. The treatment groups were: IgG1-b12, IgG1-b12-vcMMAE, IgG1-AXL-183-vcMMAE and IgG1-AXL-726-vcMMAE. The antibodies and ADCs were dosed intravenously (i.v.) at 4 mg/kg on the day of randomization (day 0) and on day 7. Tumor volumes (mm$^3$) were monitored twice weekly and were calculated from caliper (PLEXX) measurements as: 0.52×(length)×(width)$^2$.

Figure 22A:
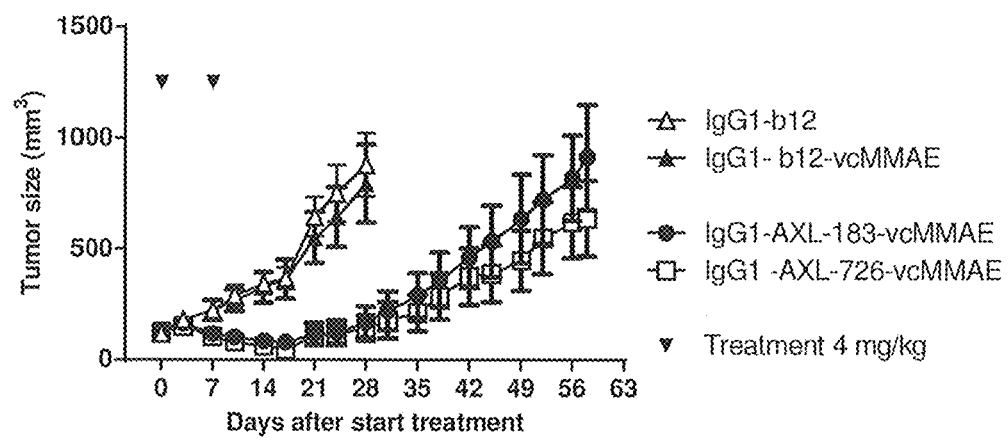
(FIG. 22A) Average tumor size after therapeutic treatment with IgG1-AXL-183-vcMMAE or IgG1-AXL-726-vcMMAE in the cervical cancer PDX model CEXF 773. IgG1-b12 and IgG1-b12-MMAE were included as isotype control antibody and isotype control ADC, respectively.
Figure 22B:
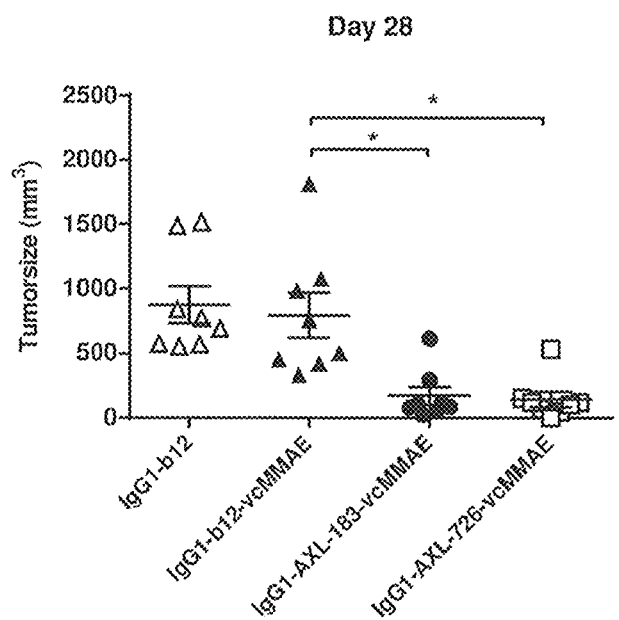
(FIG. 22B) Tumor size in individual mice on day 28 after initiation of treatment in the cervical cancer PDX model CEXF 773. * $p<0.001$.

FIG. 22 shows that treatment of mice with IgG1-AXL-183-vcMMAE or IgG1-AXL-726-vcMMAE induced tumor regression of CEXF 773 tumors compared to the IgG1-b12 and IgG1-b12-MMAE control groups. Treatment of mice with the untargeted ADC IgG1-b12-vcMMAE did not show anti-tumor activity in this model, illustrating that the therapeutic capacity of AXL-ADCs depends on specific target binding. Statistical analysis of tumor size at day 28 (Kruskal-Wallis and Mantel-Cox using a tumor size cut-off 500 mm$^3$), showed that the average tumor size in mice treated with IgG1-AXL-183-vcMMAE or IgG1-AXL-726-vcMMAE was significantly smaller than in mice that had been treated with IgG1-b12 and IgG1-b12-vcMMAE (p<0.001). IgG1-AXL-183-vcMMAE and IgG1-AXL-726-vcMMAE were equally effective.

Example 19—Anti-Tumor Efficacy of AXL-ADCs in an Orthotopic Breast Cancer Xenograft Model The anti-tumor activity of IgG1-AXL-183-vcMMAE and IgG1-AXL-726-vcMMAE was evaluated in in an orthotopic MDA-MB-231 D3H2LN xenograft model.

MDA-MB-231-luc D3H2LN Bioware cells (mammary gland adenocarcinoma; Perkin Elmer, Waltham, Mass.) were implanted in the mammary fat pad of 6-11 week old, female SCID (C.B-17/IcrPrkdc-scid/CRL) mice (Charles-River) under isofluorane anesthesia. Tumors were allowed to grow and mice were randomized when tumors reached a volume of ~325 mm$^3$. Therefore, mice were distributed in 4 experimental groups (6-7 animals per group), considering a comparable median and mean of group tumor volume. The treatment groups were: IgG1-b12, IgG1-b12-vcMMAE, IgG1-AXL-183-vcMMAE and IgG1-AXL-726-vcMMAE. The animals received a total of 4 biweekly doses of 3 mg/kg antibody or ADC starting at the day of randomization. Tumor volumes (mm$^3$) were monitored twice weekly and were calculated from caliper (PLEXX) measurements as: 0.52×(length)×(width)$^2$.

Figure 23A:
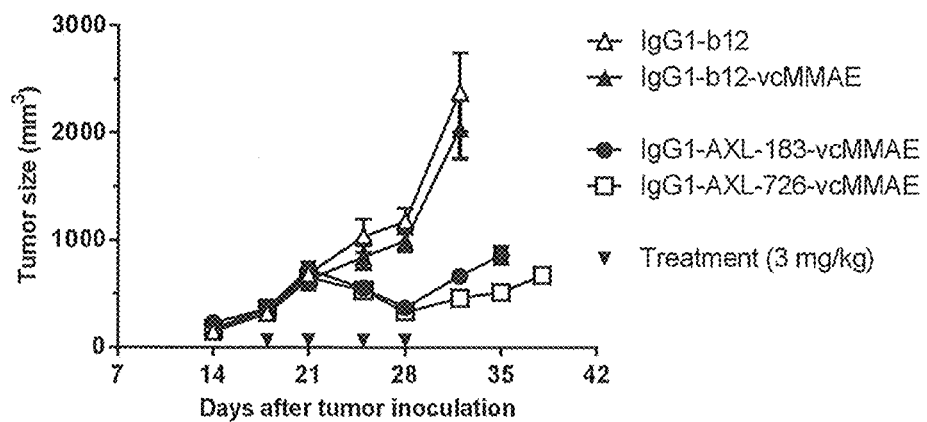
FIGS. 23A and 23B. Therapeutic activity of AXL-ADCs in an orthotopic breast cancer xenograft model.
Figure 23B:
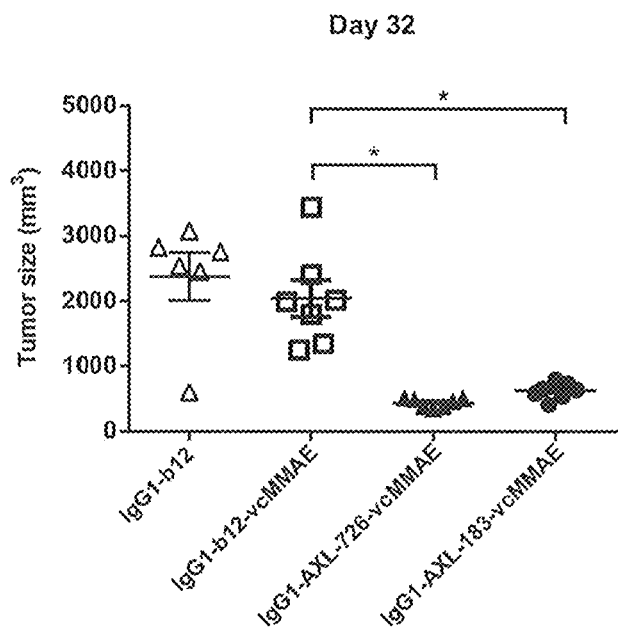

FIG. 23 shows that treatment of mice with IgG1-AXL-183-vcMMAE or IgG1-AXL-726-vcMMAE induced tumor regression of MDA-MB-231 tumors compared to the IgG1-b12 and IgG1-b12-MMAE control groups. Treatment of mice with the untargeted ADC IgG1-b12-vcMMAE did not show anti-tumor activity in this model, showing that the therapeutic capacity of AXL-ADCs depends on specific target binding. Statistical analysis of tumor size at day 32 (One Way Anova test), showed that the average tumor size in mice that had been treated with IgG1-AXL-183-vcMMAE or IgG1-AXL-726-vcMMAE was significantly smaller than in mice that had been treated with IgG1-b12 and IgG1-b12-vcMMAE (P<0.001). No differences were observed between the IgG1-AXL-183-vcMMAE and IgG1-AXL-726-vcMMAE treatment groups, illustrating that these induced equally effective anti-tumor activity.

Example 20—In Vitro Cytotoxicity Induced by AXL-Specific Antibody Drug Conjugates is Dependent on Target Expression The in vitro cytotoxicity of IgG1-AXL-107-vcMMAE was tested in human tumor cell lines with different levels of AXL expression.

Cell Culture

LS174T cells (human colorectal adenocarcinoma cell line; ATCC, cat no CL-188) were cultured in Minimum Essential Medium (MEM) with Glutamax, Hepes and Phenol Red (Life Technologies, cat no 42360-024). Components are 10% Donor Bovine Serium with Iron (DBSI) (Life Technologies, cat no 10371-029) and 1% Sodium Pyruvate (100 mM; Lonza, cat no 13E13-115E) and 1% Penicillin/Streptomycin (Lonza, cat no DE17-603E).

NCI-H226 cells (human lung squamous cell carcinoma; ATCC, cat no CRL-5826), NCI-H661 cells (human large cell lung cancer; ATCC, cat no HTB-183), and NCI-H1299 cells (human non-small cell lung cancer; ATCC, cat no CRL-5803) were cultured in RPMI 1640 Medium (ATCC Modification; Life Technologies, cat no A10491-01). Components are 10% Donor Bovine Serium with Iron (DBSI; Life Technologies, cat no 10371-029) and 1% Penicillin/Streptomycin (Lonza, cat no DE17-603E).

SKOV-3 cells (human ovarian adenocarcinoma; ATCC, cat no HTB-77) were cultured in McCoy's 5A Medium with L-glutamine and HEPES (Lonza, cat no BE12-168F). Components are 10% Donor Bovine Serium with Iron (DBSI; Life Technologies, cat no 10371-029) and 1% Penicillin/Streptomycin (Lonza, cat no DE17-603E).

Calu-1 cells (human lung epidermoid carcinoma; ATCC, cat no HTB-54) were cultured in McCoy's 5A Medium with Catopeptone, without HEPES (Life Technologies, cat no 26600-023). Components are 10% Donor Bovine Serium with Iron (DBSI; Life Technologies, cat no 10371-029) and 1% L-glutamine (200 nM) in 0.85% NaCl solution (Lonza, cat no BE17-605F) and 1% Penicillin/Streptomycin (Lonza, cat no DE17-603E). Calu-1 cells are resistant to EGFR targeted therapy.

LCLC-103H cells (human large cell lung cancer), A431 cells (human epidermoid adenocarcinoma) and MDA-MB-231 cells (human breast cancer) were cultured as described in Example 8.

Quantification of AXL Expression on the Plasma Membrane of Human Tumor Cell Lines AXL expression on the plasma membrane of human tumor cell lines was assessed by indirect immunofluorescence using QIFIKIT (DAKO, Cat nr K0078) with mouse monoclonal antibody Z49M (Santa Cruz biotechnology, Cat nr sc-73719). Adherent cells were trypsinized and passed through a cell strainer to obtain single cell suspensions. Cells were pelleted by centrifugation for 5 minutes at 1,200 rpm, washed with PBS and resuspended at a concentration of $1 \times 10^6$ cells/mL. The next steps were performed on ice. 100 µL of the single cell suspensions (100,000 cells per well) were seeded in polystyrene 96-well round-bottom plates (Greiner Bio-One, Cat nr 650101). Cells were pelleted by centrifugation for 3 minutes at 300×g and resuspended in 50 µL antibody sample or mouse IgG1 isotype control sample (BD/Pharmingen, Cat nr 555746) at a concentration of 10 µg/mL. After an incubation of 30 minutes at 4° C., cells were pelleted and resuspended in 150 µL FACS buffer. Set-up and calibration beads were added to the plate according to the manufacturer's instructions. Cells and beads in parallel were washed two more times with 150 µL FACS buffer and resuspended in 50 µL FITC-conjugated goat-anti-mouse IgG (1/50; DAKO, Cat nr K0078). Secondary antibody was incubated for 30 minutes at 4° C. in the dark. Cells and beads were washed twice with 150 µL FACS buffer and resuspended in 100 µL FACS buffer. Immunofluorescence was measured on a FACS Canto II (BD Biosciences) by recording 10,000 events within the gate of viable cells. The mean fluorescence intensity of the calibration beads was used to calculate the calibration curve using GraphPad Prism software (GraphPad Software, San Diego, Calif., USA). For each cell line, the antibody binding capacity (ABC), an estimate for the number of AXL molecules expressed on the plasma membrane, was calculated using the mean fluorescence intensity of the AXL antibody-stained cells, based on the equation of the calibration curve (interpolation of unknowns from the standard curve, using GraphPad Software).

Cytotoxicity Assay

For LCLC-103H, A431, MDA-MB-231, NCI-H226, NCI-H661, NCI-H1299, LS174T and SKOV-3 cells, the in vitro cytotoxicity assay was performed as described in Example 8. For Calu-1, the cytotoxicity assay was performed as described in Example 8, with the adaptation that the cell cultures were incubated for 11 instead of 5 days. Dose-response curves were generated using Graphpad Prism software, using non-linear regression analysis. The percentage of viable cells at an IgG1-AXL-107-vcMMAE concentration of 1 µg/mL was interpolated from the dose-response curves.

Figure 24:
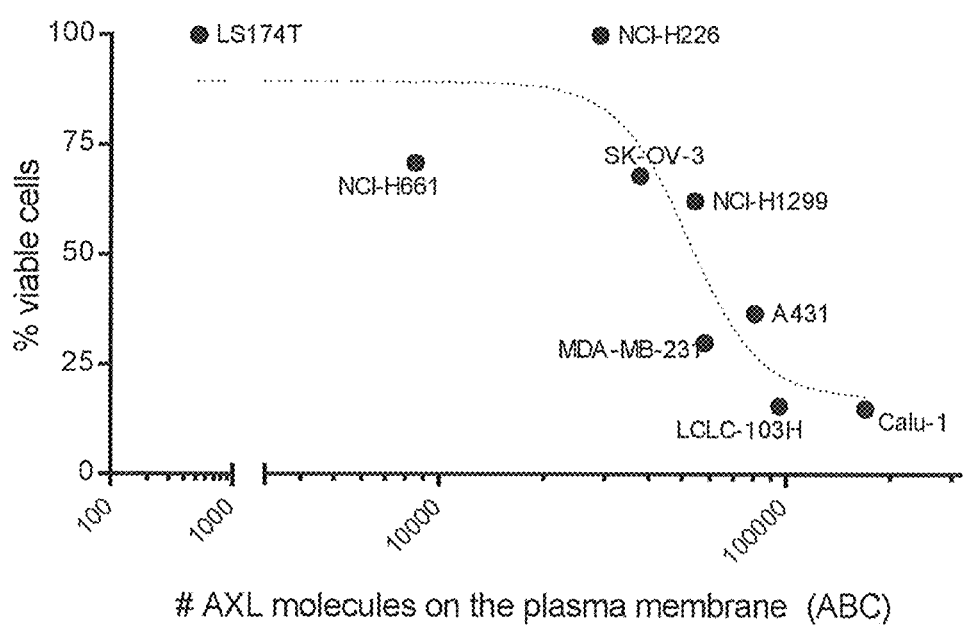
FIG. 24. Cytotoxicity of IgG1-AXL-107-vcMMAE in human tumor cell lines with different levels of AXL expression on the plasma membrane. AXL expression in the plasma membrane of human tumor cell lines was assessed using Qifikit analysis, and the cytotoxicity of IgG1-AXL-107-vcMMAE was expressed as the percentage of viable tumor cells that remained in the cell cultures after exposure to 1 μg/mL IgG1-AXL-107-vcMMAE.

As shown in FIG. 24, IgG1-AXL-107-vcMMAE induced the most potent cytotoxicity in cell lines with high AXL expression, whereas cytotoxicity was low or absent in cell lines with low AXL expression. The figure also illustrates that IgG1-AXL-107-vcMMAE is effective in induction of cytotoxicity in cells resistant to EGFR targeted therapy, such as Calu-1.

REFERENCES

[1] Paccez et al, Int. J. Cancer: 134, 1024-1033 (2013)
[2] Leconet et al, Oncogene, 1-10 (2013)
[3] Linger et al, Expert Opin. Ther. Targets, 14(10):1073-1090 (2010)
[4] Li et al, Oncogene, 28, 3442-3455 (2009)
[5] Ye et al, Oncogene, 1-11 (2010)
[6] Alley et al, Current Opinion in Chem. Bio., 4, 529-537 (2010)
[7] Iida et al, Anticancer Research, 34:1821-1828 (2014)
[8] WO 2012/175691; INSERM
[9] WO 2012/175692; INSERM
[10] WO 2013/064685; PF Medicament
[11] WO 2013/090776; INSERM
[12] WO 2009/063965; Chugain Pharmaceuticals
[13] WO 2010/131733
[14] Hfizi et al., 2006, FEBS Journal, 273; 5231-5244
[15] WO 2007/059782; Genmab A/S
[16] Ward et al., Nature 341, 544-546 (1989)
[17] Holt et al; Trends Biotechnol. 2003 November; 21(11): 484-90
[18] Revets et al; Expert Opin Biol Ther. 2005 January; 5(1):111-24
[19] Bird et al., Science 242, 423-426 (1988)
[20] Huston et al., PNAS USA 85, 5879-5883 (1988)
[21] Fundamental Immunology Ch. 7 (Paul, W., ed., 2nd ed. Raven Press, N.Y. (1989)
[22] Lefranc M P. et al., Nucleic Acids Research, 27, 209-212, 1999
[23] Brochet X. Nucl. Acids Res. 36, W503-508 (2008)

[24] Korshunov et al, Clinical Science, 2012
[25] Sambrook et al, Molecular Cloning: A laboratory Manual, New York: Cold Spring Harbor Laboratory Press, 1989, Ch. 15
[26] Kabat, E. A. et al., Sequences of proteins of immunological interest. 5th Edition—US Department of Health and Human Services, NIH publication No. 91-3242, pp 662, 680, 689 (1991)
[27] WO 2004/010957; Seattle Genetics, Inc.
[28] U.S. Pat. No. 7,659,241; Seattle Genetics, Inc.
[29] Wu et al., Generation and Characterization of a Dual Variable Domain Immunoglobulin (DVD-Ig™) Molecule, In: Antibody Engineering, Springer Berlin Heidelberg (2010)
[30] WO 2011/131746; Genmab A/S
[31] WO/2002/020039; Trion Pharma/Fresenius Biotech
[32] WO9850431; Genetech
[33] WO2011117329; Roche
[34] EP1870459; Amgen
[35] WO2009089004; Amgen
[36] US201000155133; Chugai
[37] WO2010129304; Oncomed
[38] WO2007110205; EMD Serono
[39] WO 2010/015792; Regeneron
[40] WO11143545; Pfizer/Rinat
[41] WO2012058768; Zymeworks/Merck
[42] WO2011028952; Xencor
[43] WO 2009/080254; Roche
[44] WO2008003116; F-Star
[45] U.S. Pat. No. 7,262,028; Crucell/Merus
[46] U.S. Pat. No. 7,612,181; Abbott
[47] WO20100226923; Unilever, Sanofi Aventis
[48] US007951918; Biogen Idec
[49] CN 102250246; Changzhou Adam Biotech Inc
[50] WO2012025525; Roche
[51] WO2012025530; Roche
[52] WO2008157379; Macrogenics
[53] WO2010/080538; Macrogenics
[54] Goodman et al., Goodman and Gilman's The Pharmacological Basis Of Therapeutics, 8th Ed., Macmillan Publishing Co., 1990
[55] Vitetta, Immunol. Today 14, 252 (1993)
[56] U.S. Pat. No. 5,194,594
[57] US 2005/0238649
[58] WO 2013/173391; Concortis Biosystems, Corp.
[59] Junghans et al., in Cancer Chemotherapy and Biotherapy 655-686 (2d edition, Chafner and Longo, eds., Lippincott Raven (1996))
[60] U.S. Pat. No. 4,681,581
[61] U.S. Pat. No. 4,735,210
[62] U.S. Pat. No. 5,101,827
[63] U.S. Pat. No. 5,102,990
[64] U.S. Pat. No. 5,648,471
[65] U.S. Pat. No. 5,697,902
[66] U.S. Pat. No. 4,766,106
[67] U.S. Pat. No. 4,179,337
[68] U.S. Pat. No. 4,495,285
[69] U.S. Pat. No. 4,609,546
[70] Hunter et al., Nature 144, 945 (1962), David et al., Biochemistry 13, 1014 (1974)
[71] Pain et al., J. Immunol. Meth. 40, 219 (1981)
[72] Nygren, J. Histochem. and Cytochem. 30, 407 (1982)
[73] Antibody Engineering Handbook, edited by Osamu Kanemitsu, published by Chijin Shokan (1994)
[74] WO 2002/083180; Syngenta BV
[75] WO 2004/043493; Syngenta BV
[76] WO 2007/018431; Syngenta BV
[77] WO 2007/089149; Syngenta BV
[78] WO 2009/017394; Syngenta BV
[79] WO 2010/62171; Syngenta BV
[80] U.S. Pat. No. 6,989,452; Medarex
[81] Remington: The Science and Practice of Pharmacy, 19th Edition, Gennaro, Ed., Mack Publishing Co., Easton, Pa., 1995
[82] Sustained and Controlled Release Drug Delivery Systems, J. R. Robinson, ed., Marcel Dekker, Inc., New York, 1978
[83] Sykes and Johnston, Nat Biotech 17, 355-59 (1997)
[84] U.S. Pat. No. 6,077,835
[85] WO 00/70087
[86] Schakowski et al., Mol Ther 3, 793-800 (2001)
[87] WO 00/46147
[88] Benvenisty and Reshef, PNAS USA 83, 9551-55 (1986)
[89] Wigler et al., Cell 14, 725 (1978)
[90] Coraro and Pearson, Somatic Cell Genetics 7, 603 (1981)
[91] U.S. Pat. No. 5,589,466
[92] U.S. Pat. No. 5,973,972
[93] Van Heeke & Schuster, J Biol Chem 264, 5503-5509 (1989)
[94] F. Ausubel et al., ed. Current Protocols in Molecular Biology, Greene Publishing and Wiley InterScience New York (1987)
[95] Grant et al., Methods in Enzymol 153, 516-544 (1987)
[96] Lonberg, N. et al., Nature 368, 856 859 (1994)
[97] Lonberg, N. Handbook of Experimental Pharmacology 113, 49 101 (1994)
[98] Lonberg, N. and Huszar, D., Intern. Rev. Immunol. Vol. 13 65 93 (1995)
[99] Harding, F. and Lonberg, N. Ann. N.Y. Acad. Sci 764 536 546 (1995)
[100] Taylor, L. et al., Nucleic Acids Research 20, 6287 6295 (1992)
[101] Chen, J. et al., International Immunology 5, 647 656 (1993)
[102] Tuaillon et al., J. Immunol. 152, 2912 2920 (1994)
[103] Taylor, L. et al., International Immunology 6, 579 591 (1994)
[104] Fishwild, D. et al., Nature Biotechnology 14, 845 851 (1996)
[105] U.S. Pat. No. 5,545,806
[106] U.S. Pat. No. 5,569,825
[107] U.S. Pat. No. 5,625,126
[108] U.S. Pat. No. 5,633,425
[109] U.S. Pat. No. 5,789,650
[110] U.S. Pat. No. 5,877,397
[111] U.S. Pat. No. 5,661,016
[112] U.S. Pat. No. 5,814,318
[113] U.S. Pat. No. 5,874,299
[114] U.S. Pat. No. 5,770,429
[115] U.S. Pat. No. 5,545,807
[116] WO 98/024884
[117] WO 94/025585
[118] WO 93/001227
[119] WO 92/022645
[120] WO 92/003918
[121] WO 01/009187.
[122] Shieh, Neoplasia 2005
[123] Koorstra, Cancer Biol Ther 2009
[124] Hector, Cancer Biol Ther 2010
[125] Sun, Ann Oncol 2003
[126] Srivastava (ed.), Radiolabeled Monoclonal Antibodies For Imaging And Therapy (Plenum Press 1988), Chase

[127] "Medical Applications of Radioisotopes," in Remington's Pharmaceutical Sciences, 18th Edition, Gennaro et al., (eds.), pp. 624-652 (Mack Publishing Co., 1990)
[128] Brown, "Clinical Use of Monoclonal Antibodies," in Biotechnology And Pharmacy 227-49, Pezzuto et al., (eds.) (Chapman & Hall 1993)
[129] U.S. Pat. No. 5,057,313
[130] U.S. Pat. No. 6,331,175
[131] U.S. Pat. No. 5,635,483
[132] U.S. Pat. No. 5,780,588
[133] Woyke et al (2001) Antimicrob. Agents and Chemother. 45(12): 3580-3584
[134] U.S. Pat. No. 5,663,149
[135] Pettit et al., (1998) Antimicrob. Agents and Chemother. 42:2961-2965
[136] Senter et al., Proceedings of the American Association for Cancer Research. Volume 45, abstract number 623, presented Mar. 28, 2004
[137] US 2005/0238649
[138] U.S. Pat. No. 7,498,298; Seattle Genetics, Inc.
[139] U.S. Ser. No. 11/833,954; Seattle Genetics, Inc.
[140] WO 2005/081711; Seattle Genetics, Inc.
[141] Kozak et al. (1999) Gene 234: 187-208
[142] EP 2 220 131; U3 Pharma
[143] WO 2011/159980; Genentech
[144] Barbas, CF. J Mol Biol. 1993 Apr. 5; 230(3):812-23
[145] U.S. Pat. No. 7,829,531; Seattle Genetics, Inc.
[146] U.S. Pat. No. 7,851,437; Seattle Genetics, Inc.
[147] U.S. Ser. No. 11/833,028; Seattle Genetics, Inc.
[148] WO 2013/173392; Concortis Biosystems, Corp.
[149] WO 2013/173393; Concortis Biosystems, Corp.
[150] Sun et al. (2005) Bioconjugate Chem. 16: 1282-1290
[151] McDonagh et al., (2006) Protein Eng. Design Sel. 19: 299-307
[152] Alley et al., (2008) Bioconjugate Chem. 19: 759-765

The invention claimed is:

1. An immunoconjugate comprising (a) an antibody which binds to AXL (SEQ ID NO: 130) and comprises a heavy chain variable (VH) region and a light chain variable (VL) region, wherein the VH region comprises the CDR1, CDR2, and CDR3 sequences set forth in SEQ ID NOs: 36, 37, and 38, respectively, and the VL region comprises the CDR1, CDR2, and CDR3 sequences set forth in SEQ ID NO: 39, the amino acid sequence GAS, and SEQ ID NO: 40, respectively, (b) a mc-vc-PAB linker, and (c) a cytotoxic agent, which is MMAE.

2. The immunoconjugate of claim 1, wherein the VH and VL regions comprise the amino acid sequences of SEQ ID NOs: 1 and 2, respectively.

3. The immunoconjugate of claim 1, wherein MMAE is linked to the antibody via the mc-vc-PAB linker, wherein the cytotoxic agent and the linker have the chemical structure;

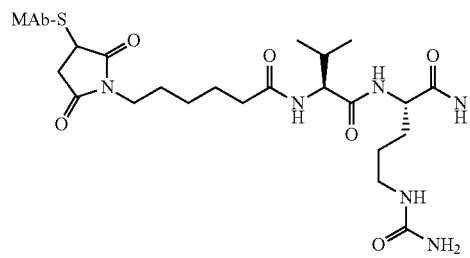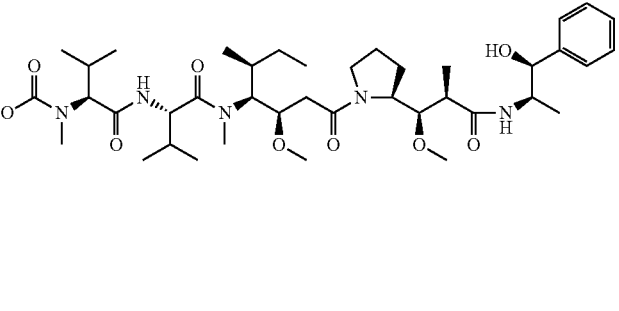

wherein MAb is the antibody.

4. The immunoconjugate according to claim 1, wherein the MMAE is conjugated to the antibody via a cysteine thiol or a lysine.

5. The immunoconjugate of claim 1, wherein cytotoxic agent loading (p) is 1 to 8.

6. The immunoconjugate of claim 1, wherein cytotoxic agent loading (p) is 10 to 30.

7. The immunoconjugate of claim 1, wherein said antibody comprises a heavy chain of an isotype selected from the group consisting of IgG1, IgG2, IgG3, and IgG4.

8. The immunoconjugate of claim 1, wherein the antibody is a full-length monoclonal antibody.

9. The immunoconjugate of claim 1, wherein the antibody is a full-length monoclonal IgG1,κ antibody.

10. The immunoconjugate of claim 1, wherein the antibody is a monovalent antibody.

11. The immunoconjugate of claim 1, wherein the antibody is an antigen-binding fragment of an immunoglobulin molecule.

12. The immunoconjugate of claim 1, wherein the antibody is a single-chain antibody.

13. The immunoconjugate of claim 1, wherein the antibody is a human antibody.

14. A pharmaceutical composition comprising the immunoconjugate of claim 1, and a pharmaceutical acceptable carrier.

15. A kit comprising the immunoconjugate of claim 1.

16. The immunoconjugate of claim 6, wherein cytotoxic agent loading (p) is 1 to 20.

17. The immunoconjugate of claim 6, wherein cytotoxic agent loading (p) is 2 to 6.

18. The immunoconjugate of claim 6, wherein cytotoxic agent loading (p) is 2 to 4.

19. An immunoconjugate comprising (a) an antibody which binds to AXL (SEQ ID NO: 130) and comprises a heavy chain variable (VH) region and a light chain variable (VL) region, wherein the VH region comprises the amino acid sequence of SEQ ID NO: 1 and the VL region comprises the amino acid sequence of SEQ ID NO: 2, (b) a mc-vc-PAB linker, and (c) a cytotoxic agent, which is MMAE.

20. The immunoconjugate of claim 19, wherein the combination of the MMAE and the mc-vc-PAB linker has the chemical structure;

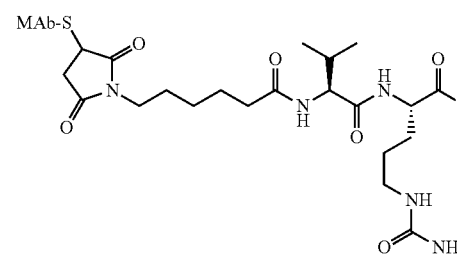

wherein MAb is the antibody.

21. The immunoconjugate according to claim 19, wherein the MMAE is conjugated to the antibody via a cysteine thiol or a lysine.

22. The immunoconjugate of claim 19, wherein cytotoxic agent loading (p) is 1 to 8.

23. The immunoconjugate of claim 19, wherein cytotoxic agent loading (p) is 10 to 30.

24. The immunoconjugate of claim 19, wherein said antibody comprises a heavy chain of an isotype selected from the group consisting of IgG1, IgG2, IgG3, and IgG4.

25. The immunoconjugate of claim 19, wherein the antibody is a full-length monoclonal antibody.

26. The immunoconjugate of claim 19, wherein the antibody is a full-length monoclonal IgG1,κ antibody.

27. The immunoconjugate of claim 19, wherein the antibody is a monovalent antibody.

28. The immunoconjugate of claim 19, wherein the antibody is a single-chain antibody.

29. The immunoconjugate of claim 19, wherein the antibody is an antigen-binding fragment of an immunoglobulin molecule.

30. The immunoconjugate of claim 19, wherein the antibody is a human antibody.

31. A pharmaceutical composition comprising the antibody of claim 19, and a pharmaceutical acceptable carrier.

32. A kit comprising the immunoconjugate of claim 19.

33. The immunoconjugate of claim 19, wherein cytotoxic agent loading (p) is 1 to 20.

34. The immunoconjugate of claim 19, wherein cytotoxic agent loading (p) is 2 to 6.

35. The immunoconjugate of claim 19, wherein cytotoxic agent loading (p) is 2 to 4.

* * * * *

UNITED STATES PATENT AND TRADEMARK OFFICE
CERTIFICATE OF CORRECTION

Page 1 of 1

PATENT NO. : 10,500,276 B2
APPLICATION NO. : 16/270317
DATED : December 10, 2019
INVENTOR(S) : Esther Breij et al.

It is certified that error appears in the above-identified patent and that said Letters Patent is hereby corrected as shown below:

On the Title Page

At Column 1, in item (30), Line 1 of the "Foreign Application Priority Data" section, delete "2014 00380" and insert --PA 2014 00380--.

At Column 1, in item (30), Line 2 of the "Foreign Application Priority Data" section, delete "2014 00489" and insert --PA 2014 00489--.

At Column 1, in item (30), Line 3 of the "Foreign Application Priority Data" section, delete "2014 00746" and insert --PA 2014 00746--.

At Column 1, in item (30), Line 4 of the "Foreign Application Priority Data" section, delete "2015 00283" and insert --PA 2015 00283--.

Signed and Sealed this
Twenty-eighth Day of July, 2020

Andrei Iancu
*Director of the United States Patent and Trademark Office*

SEQUENCE LISTING

```
<160> NUMBER OF SEQ ID NOS: 147

<210> SEQ ID NO 1
<211> LENGTH: 116
<212> TYPE: PRT
<213> ORGANISM: homo sapiens

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Thr Ser Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Trp Ile Ala Phe Asp Ile Trp Gly Gln Gly Thr Met Val
            100                 105                 110

Thr Val Ser Ser
        115

<210> SEQ ID NO 2
<211> LENGTH: 108
<212> TYPE: PRT
<213> ORGANISM: homo sapiens

<400> SEQUENCE: 2

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80
```

```
Pro Glu Asp Phe Ala Val Tyr Tyr Cys Gln Gln Tyr Gly Ser Ser Pro
                85                  90                  95

Tyr Thr Phe Gly Gln Gly Thr Lys Leu Glu Ile Lys
            100                 105

<210> SEQ ID NO 3
<211> LENGTH: 120
<212> TYPE: PRT
<213> ORGANISM: homo sapiens

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Lys Gly Leu Glu Trp Val
        35                  40                  45

Ser Ala Ile Ser Ile Ser Gly Ala Ser Thr Phe Tyr Ala Asp Ser Val
    50                  55                  60

Lys Gly Arg Phe Thr Ile Ser Arg Asp Asn Ser Lys Asn Thr Leu Ser
65                  70                  75                  80

Leu Gln Met Asn Ser Leu Arg Ala Glu Asp Thr Ala Val Tyr Phe Cys
                85                  90                  95

Arg Gly Tyr Ser Gly Tyr Val Tyr Asp Ala Phe Asp Ile Trp Gly Gln
            100                 105                 110

Gly Thr Met Val Thr Val Ser Ser
        115                 120

<210> SEQ ID NO 4
<211> LENGTH: 107
<212> TYPE: PRT
<213> ORGANISM: homo sapiens

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 5
<211> LENGTH: 120
<212> TYPE: PRT
<213> ORGANISM: homo sapiens

<400> SEQUENCE: 5

Glu Val Gln Leu Leu Glu Ser Gly Gly Gly Leu Val Gln Pro Gly Gly
1               5                   10                  15
```

Ser Leu Arg Leu Ser Cys Ala Ala Ser Gly Phe Thr Phe Ser Ser Tyr
            20                  25                  30

Ala Met Thr Trp Val Arg Gln Ala Pro Gly Lys Gly Leu Glu Trp Val
        35                  40                  45

Ser Ala Ile Ser Ile Ser Gly Gly Ser Thr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Arg Gly Tyr Ser Gly Tyr Val Tyr Asp Ala Phe Asp Phe Trp Gly Gln
                100                 105                 110

Gly Thr Met Val Thr Val Ser Ser
            115                 120

<210> SEQ ID NO 6
<211> LENGTH: 107
<212> TYPE: PRT
<213> ORGANISM: homo sapiens

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
                100                 105

<210> SEQ ID NO 7
<211> LENGTH: 121
<212> TYPE: PRT
<213> ORGANISM: homo sapiens

<400> SEQUENCE: 7

Glu Val Gln Leu Leu Asp Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Ile Gly Gly Gly Asn Ala Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Ala Asp Thr Ala Val Tyr Tyr Cys
                85                  90                  95

Ala Lys Pro Gly Phe Ile Met Val Arg Gly Pro Leu Asp Tyr Trp Gly
                100                 105                 110

Gln Gly Ala Leu Val Thr Val Ser Ser
        115                 120

<210> SEQ ID NO 8
<211> LENGTH: 121
<212> TYPE: PRT
<213> ORGANISM: homo sapiens

<400> SEQUENCE: 8

Glu Val Gln Leu Leu Asp Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Ile Gly Gly Gly Asn Ala Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Ala Asp Thr Ala Val Tyr Tyr Cys
                85                  90                  95

Ala Lys Pro Gly Phe Ile Leu Val Arg Gly Pro Leu Asp Tyr Trp Gly
            100                 105                 110

Gln Gly Ala Leu Val Thr Val Ser Ser
        115                 120

<210> SEQ ID NO 9
<211> LENGTH: 108
<212> TYPE: PRT
<213> ORGANISM: homo sapiens

<400> SEQUENCE: 9

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asn Ser
            20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Tyr Thr Phe Gly Gln Gly Thr Lys Leu Glu Ile Lys
            100                 105

<210> SEQ ID NO 10
<211> LENGTH: 125
<212> TYPE: PRT
<213> ORGANISM: homo sapiens

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val

```
                35                  40                  45
Ser Asp Ile Ser Val Ser Gly Gly Ser Thr Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Glu Gly Tyr Ile Trp Phe Gly Glu Ser Leu Ser Tyr Ala Phe
                100                 105                 110
Asp Ile Trp Gly Gln Gly Thr Met Val Thr Val Ser Ser
                115                 120                 125

<210> SEQ ID NO 11
<211> LENGTH: 107
<212> TYPE: PRT
<213> ORGANISM: homo sapiens

<400> SEQUENCE: 11

Glu Ile Val Leu Thr Gln Ser Pro Gly Thr Leu Ser Leu Ser Pro Gly
 1               5                  10                  15
Glu Arg Ala Thr Leu Ser Cys Arg Ala Ser Gln Ser Val Ser Ser Ser
                 20                  25                  30
Tyr Leu Ala Trp Tyr Gln Gln Lys Pro Gly Gln Ala Pro Arg Leu Leu
             35                  40                  45
Ile Tyr Gly Ala Ser Ser Arg Ala Thr Gly Ile Pro Asp Arg Phe Ser
 50                  55                  60
Gly Ser Gly Ser Gly Thr Asp Phe Thr Leu Thr Ile Ser Arg Leu Glu
 65                  70                  75                  80
Pro Glu Asp Phe Ala Val Tyr Tyr Cys Gln Gln Tyr Gly Arg Ser Phe
                 85                  90                  95
Thr Phe Gly Pro Gly Thr Lys Val Asp Ile Lys
                100                 105

<210> SEQ ID NO 12
<211> LENGTH: 125
<212> TYPE: PRT
<213> ORGANISM: homo sapiens

<400> SEQUENCE: 12

Glu Val Gln Leu Leu Glu Ser Gly Gly Gly Leu Val Gln Pro Gly Gly
 1               5                  10                  15
Ser Leu Arg Leu Ser Cys Ala Ala Ser Gly Phe Thr Phe Ser Asn Tyr
                 20                  25                  30
Ala Met Ser Trp Val Arg Gln Ala Pro Gly Lys Gly Leu Glu Trp Val
             35                  40                  45
Ser Asp Ile Ser Val Ser Gly Gly Ser Thr Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Glu Gly Tyr Ile Trp Phe Gly Glu Ser Leu Ser Tyr Ala Phe
                100                 105                 110
Asp Ile Trp Gly Gln Gly Thr Met Val Thr Val Ser Ser
                115                 120                 125
```

<210> SEQ ID NO 13
<211> LENGTH: 107
<212> TYPE: PRT
<213> ORGANISM: homo sapiens

<400> SEQUENCE: 13

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Arg Ser Phe
                85                  90                  95

Thr Phe Gly Pro Gly Thr Lys Val Asp Ile Lys
            100                 105
```

<210> SEQ ID NO 14
<211> LENGTH: 125
<212> TYPE: PRT
<213> ORGANISM: homo sapiens

<400> SEQUENCE: 14

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asp Ile Ser Val Ser Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu His Met Asn Ser Leu Arg Ala Glu Asp Thr Ala Val Tyr Tyr Cys
                85                  90                  95

Ala Lys Glu Gly Tyr Ile Trp Phe Gly Glu Ser Leu Ser Tyr Ala Phe
            100                 105                 110

Asp Ile Trp Gly Gln Gly Thr Met Val Thr Val Ser Ser
        115                 120                 125
```

<210> SEQ ID NO 15
<211> LENGTH: 107
<212> TYPE: PRT
<213> ORGANISM: homo sapiens

<400> SEQUENCE: 15

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60
```

```
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Arg Ser Phe
                 85                  90                  95

Thr Phe Gly Pro Gly Thr Lys Val Asp Ile Lys
            100                 105

<210> SEQ ID NO 16
<211> LENGTH: 117
<212> TYPE: PRT
<213> ORGANISM: homo sapiens

<400> SEQUENCE: 16

Gln Val Gln Leu Gln Gln Trp Gly Ala Gly Leu Leu Lys Pro Ser Glu
  1               5                  10                  15

Thr Leu Ser Leu Thr Cys Ala Val Tyr Gly Gly Ser Phe Ser Gly Tyr
                 20                  25                  30

Tyr Trp Ser Trp Ile Arg Gln Pro Pro Gly Lys Gly Leu Glu Trp Ile
             35                  40                  45

Gly Glu Ile Asn Gln Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ser Val Tyr Tyr Cys Ala
                 85                  90                  95

Ser Gly Asn Trp Asp His Phe Phe Asp Tyr Trp Gly Gln Gly Thr Leu
            100                 105                 110

Val Thr Val Ser Ser
            115

<210> SEQ ID NO 17
<211> LENGTH: 117
<212> TYPE: PRT
<213> ORGANISM: homo sapiens

<400> SEQUENCE: 17

Gln Val Gln Leu Gln Gln Trp Gly Ala Gly Leu Leu Lys Pro Ser Glu
  1               5                  10                  15

Thr Leu Ser Leu Thr Cys Ala Val Tyr Gly Gly Ser Phe Ser Gly Tyr
                 20                  25                  30

Tyr Trp Ser Trp Ile Arg Gln Pro Pro Gly Lys Gly Leu Glu Trp Ile
             35                  40                  45

Gly Glu Ile Gln Gln Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ser Val Tyr Tyr Cys Ala
                 85                  90                  95

Ser Gly Asn Trp Asp His Phe Phe Asp Tyr Trp Gly Gln Gly Thr Leu
            100                 105                 110

Val Thr Val Ser Ser
            115

<210> SEQ ID NO 18
<211> LENGTH: 107
<212> TYPE: PRT
<213> ORGANISM: homo sapiens
```

<400> SEQUENCE: 18

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln His Lys Pro Gly Lys Ala Pro Lys Leu Leu Ile
        35                  40                  45

Tyr Ala Thr Ser Ser Leu Gln Ser Gly Val Thr Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Lys Ser Phe Pro Trp
                85                  90                  95

Thr Phe Gly Gln Gly Thr Lys Val Glu Ile Lys
            100                 105

<210> SEQ ID NO 19
<211> LENGTH: 123
<212> TYPE: PRT
<213> ORGANISM: homo sapiens

<400> SEQUENCE: 19

Gln Val Pro Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

His Trp Ser Trp Ile Arg Gln Pro Pro Gly Lys Gly Leu Glu Trp Ile
        35                  40                  45

Gly Glu Ile Ser His Ser Gly Arg Thr Asn Tyr Asn Pro Ser Leu Lys
50                  55                  60

Ser Arg Val Thr Ile Ser Ile Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Ser Phe Ile Thr Met Ile Arg Gly Thr Ile Ile Thr His Phe Asp Tyr
            100                 105                 110

Trp Gly Gln Gly Thr Leu Val Thr Val Ser Ser
        115                 120

<210> SEQ ID NO 20
<211> LENGTH: 107
<212> TYPE: PRT
<213> ORGANISM: homo sapiens

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr His Ser Tyr Pro Tyr
                85                  90                  95

Thr Phe Gly Gln Gly Thr Lys Leu Glu Ile Lys
            100                 105

<210> SEQ ID NO 21
<211> LENGTH: 124
<212> TYPE: PRT
<213> ORGANISM: homo sapiens

<400> SEQUENCE: 21

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Phe Gly Ile Ala Asn Tyr Val Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ala Glu Asp Thr Ala Val Tyr Tyr Cys
                85                  90                  95

Ala Arg Arg Gly Asp Tyr Tyr Gly Ser Gly Ser Pro Asp Val Phe Asp
            100                 105                 110

Ile Trp Gly Gln Gly Thr Met Val Thr Val Ser Ser
        115                 120

<210> SEQ ID NO 22
<211> LENGTH: 107
<212> TYPE: PRT
<213> ORGANISM: homo sapiens

<400> SEQUENCE: 22

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Tyr
                85                  90                  95

Thr Phe Gly Gln Gly Thr Lys Leu Glu Ile Lys
            100                 105

<210> SEQ ID NO 23
<211> LENGTH: 124
<212> TYPE: PRT
<213> ORGANISM: homo sapiens

<400> SEQUENCE: 23

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr

```
            20                  25                  30
Ala Ile Ser Trp Val Arg Gln Ala Pro Gly Gln Gly Leu Glu Trp Met
        35                  40                  45
Gly Arg Ile Ile Pro Ile Phe Gly Ile Ala Asn Tyr Val Gln Lys Phe
    50                  55                  60
Gln Gly Arg Val Thr Ile Thr Ala Asp Lys Ser Thr Ser Thr Ala Tyr
65                  70                  75                  80
Met Glu Leu Ser Ser Leu Arg Ala Glu Asp Thr Ala Val Tyr Tyr Cys
                85                  90                  95
Ala Arg Arg Gly Asn Tyr Tyr Gly Ser Gly Ser Pro Asp Val Phe Asp
            100                 105                 110
Ile Trp Gly Gln Gly Thr Met Val Thr Val Ser Ser
        115                 120

<210> SEQ ID NO 24
<211> LENGTH: 107
<212> TYPE: PRT
<213> ORGANISM: homo sapiens

<400> SEQUENCE: 24

Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Ser
            20                  25                  30
Tyr Leu Ala Trp Tyr Gln Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Gly Ser Ser Tyr
                85                  90                  95
Thr Phe Gly Gln Gly Thr Lys Leu Glu Ile Lys
            100                 105

<210> SEQ ID NO 25
<211> LENGTH: 124
<212> TYPE: PRT
<213> ORGANISM: homo sapiens

<400> SEQUENCE: 25

Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Asn Trp Met Arg Gln Ala Pro Gly Gln Gly Leu Glu Trp Met
        35                  40                  45
Gly Arg Ile Ile Pro Ile Phe Gly Ile Val Asn Tyr Ala Gln Lys Phe
    50                  55                  60
Gln Gly Arg Val Thr Leu Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Arg Gly Asn Tyr Tyr Gly Ser Gly Ser Pro Asp Val Phe Asp
            100                 105                 110
Ile Trp Gly Gln Gly Thr Met Val Thr Val Ser Ser
```

<210> SEQ ID NO 26
<211> LENGTH: 107
<212> TYPE: PRT
<213> ORGANISM: homo sapiens

<400> SEQUENCE: 26

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Tyr
                85                  90                  95

Thr Phe Gly Gln Gly Thr Lys Leu Glu Ile Lys
            100                 105

<210> SEQ ID NO 27
<211> LENGTH: 124
<212> TYPE: PRT
<213> ORGANISM: homo sapiens

<400> SEQUENCE: 27

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Asn Trp Met Arg Gln Ala Pro Gly Gln Gly Leu Glu Trp Met
        35                  40                  45

Gly Arg Ile Ile Pro Ile Phe Gly Ile Val Asn Tyr Ala Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Asn Tyr Tyr Gly Ser Gly Ser Pro Asp Val Phe Asp
            100                 105                 110

Ile Trp Gly Gln Gly Thr Met Val Thr Val Ser Ser
        115                 120

<210> SEQ ID NO 28
<211> LENGTH: 106
<212> TYPE: PRT
<213> ORGANISM: homo sapiens

<400> SEQUENCE: 28

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

```
Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Leu Thr
                85                  90                  95

Phe Gly Gly Gly Thr Lys Val Glu Ile Lys
            100                 105

<210> SEQ ID NO 29
<211> LENGTH: 124
<212> TYPE: PRT
<213> ORGANISM: homo sapiens

<400> SEQUENCE: 29

Gln Val Gln Leu Val Gln Ser Gly Ala Glu Val Lys Lys Pro Gly Ser
1               5                   10                  15

Ser Val Lys Val Ser Cys Lys Ala Ser Gly Thr Phe Ser Ser Tyr
                20                  25                  30

Ala Ile Ser Trp Val Arg Gln Ala Pro Gly Gln Gly Leu Glu Trp Met
            35                  40                  45

Gly Arg Ile Ile Pro Ile Phe Gly Ile Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Asn Tyr Tyr Gly Ser Gly Ser Pro Asp Val Phe Asp
            100                 105                 110

Ile Trp Gly Gln Gly Thr Met Val Thr Val Ser Ser
        115                 120

<210> SEQ ID NO 30
<211> LENGTH: 107
<212> TYPE: PRT
<213> ORGANISM: homo sapiens

<400> SEQUENCE: 30

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Tyr
                85                  90                  95

Thr Phe Gly Gln Gly Thr Lys Leu Glu Ile Lys
            100                 105

<210> SEQ ID NO 31
<211> LENGTH: 123
<212> TYPE: PRT
<213> ORGANISM: homo sapiens
```

<400> SEQUENCE: 31

Gln Val Gln Leu Gln Gln Trp Gly Ala Gly Leu Leu Lys Pro Ser Glu
1               5                   10                  15

Thr Leu Ser Leu Thr Cys Ala Ile Asp Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Ser His Ser Gly Arg Thr Asn Tyr Asn Pro Ser Leu Lys
    50                  55                  60

Ser Arg Val Thr Ile Ser Ile Asp Thr Ser Lys Asn Gln Phe Ser Leu
65                  70                  75                  80

Lys Leu Ser Ser Val Ala Ala Ala Asp Thr Ala Val Tyr Tyr Cys Ala
                85                  90                  95

Arg Phe Ile Thr Met Ile Arg Gly Ala Ile Ile Thr His Phe Asp Tyr
            100                 105                 110

Trp Gly Gln Gly Ala Leu Val Thr Val Ser Ser
        115                 120

<210> SEQ ID NO 32
<211> LENGTH: 123
<212> TYPE: PRT
<213> ORGANISM: homo sapiens

<400> SEQUENCE: 32

Gln Val Gln Leu Gln Gln Trp Gly Ala Gly Leu Leu Lys Pro Ser Glu
1               5                   10                  15

Thr Leu Ser Leu Thr Cys Ala Ile Asp Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Ser His Ser Gly Arg Thr Asn Tyr Asn Pro Ser Leu Lys
    50                  55                  60

Ser Arg Val Thr Ile Ser Ile Asp Thr Ser Lys Asn Gln Phe Ser Leu
65                  70                  75                  80

Lys Leu Ser Ser Val Ala Ala Ala Asp Thr Ala Val Tyr Tyr Cys Ala
                85                  90                  95

Arg Phe Ile Thr Leu Ile Arg Gly Ala Ile Ile Thr His Phe Asp Tyr
            100                 105                 110

Trp Gly Gln Gly Ala Leu Val Thr Val Ser Ser
        115                 120

<210> SEQ ID NO 33
<211> LENGTH: 107
<212> TYPE: PRT
<213> ORGANISM: homo sapiens

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr His Ser Tyr Pro Tyr
                 85                  90                  95

Thr Phe Gly Gln Gly Thr Lys Leu Glu Ile Lys
            100                 105
```

<210> SEQ ID NO 34
<211> LENGTH: 120
<212> TYPE: PRT
<213> ORGANISM: homo sapiens

<400> SEQUENCE: 34

```
Gln Val Gln Leu Val Glu Ser Gly Gly Val Val Gln Pro Gly Arg
 1               5                  10                  15

Ser Leu Arg Leu Ser Cys Ala Ala Ser Gly Phe Ser Phe Ser Thr Tyr
                 20                  25                  30

Ala Met His Trp Val Arg Gln Ala Pro Gly Lys Gly Leu Glu Trp Val
                 35                  40                  45

Ala Val Ile Ser Tyr Asp Gly Asp Asn Lys Tyr Ser Ala Asp Ser Val
                 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Arg Lys Leu Gly Ile Asp Ala Phe Asp Ile Trp Gly Gln
                100                 105                 110

Gly Thr Met Val Thr Val Ser Ser
                115                 120
```

<210> SEQ ID NO 35
<211> LENGTH: 107
<212> TYPE: PRT
<213> ORGANISM: homo sapiens

<400> SEQUENCE: 35

```
Ala Ile Gln Leu Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Ala
                 20                  25                  30

Leu Ala Trp Tyr Gln Gln Lys Pro Gly Lys Ala Pro Lys Leu Leu Ile
                 35                  40                  45

Tyr Asp Ala Ser Ser Leu Glu Ser Gly Val Pro Ser Arg Phe Ser Gly
                 50                  55                  60

Ser Gly Ser Gly Thr Asp Phe Thr Leu Thr Ile Ser Gly Leu Gln Pro
 65                  70                  75                  80

Glu Asp Phe Ala Thr Tyr Tyr Cys Gln Gln Phe Asn Ser Tyr Pro Phe
                 85                  90                  95

Thr Phe Gly Pro Gly Thr Lys Val Asp Ile Lys
                100                 105
```

<210> SEQ ID NO 36
<211> LENGTH: 8
<212> TYPE: PRT
<213> ORGANISM: homo sapiens

<400> SEQUENCE: 36

```
Gly Phe Thr Phe Ser Ser Tyr Ala
```

```
1               5

<210> SEQ ID NO 37
<211> LENGTH: 8
<212> TYPE: PRT
<213> ORGANISM: homo sapiens

<400> SEQUENCE: 37

Thr Ser Gly Ser Gly Ala Ser Thr
1               5

<210> SEQ ID NO 38
<211> LENGTH: 9
<212> TYPE: PRT
<213> ORGANISM: homo sapiens

<400> SEQUENCE: 38

Ala Lys Ile Trp Ile Ala Phe Asp Ile
1               5

<210> SEQ ID NO 39
<211> LENGTH: 7
<212> TYPE: PRT
<213> ORGANISM: homo sapiens

<400> SEQUENCE: 39

Gln Ser Val Ser Ser Ser Tyr
1               5

<210> SEQ ID NO 40
<211> LENGTH: 9
<212> TYPE: PRT
<213> ORGANISM: homo sapiens

<400> SEQUENCE: 40

Gln Gln Tyr Gly Ser Ser Pro Tyr Thr
1               5

<210> SEQ ID NO 41
<211> LENGTH: 8
<212> TYPE: PRT
<213> ORGANISM: homo sapiens

<400> SEQUENCE: 41

Gly Phe Thr Phe Ser Ser Tyr Ala
1               5

<210> SEQ ID NO 42
<211> LENGTH: 8
<212> TYPE: PRT
<213> ORGANISM: homo sapiens

<400> SEQUENCE: 42

Ile Ser Ile Ser Gly Ala Ser Thr
1               5

<210> SEQ ID NO 43
<211> LENGTH: 13
<212> TYPE: PRT
<213> ORGANISM: homo sapiens

<400> SEQUENCE: 43

Arg Gly Tyr Ser Gly Tyr Val Tyr Asp Ala Phe Asp Ile
1               5                   10
```

```
<210> SEQ ID NO 44
<211> LENGTH: 6
<212> TYPE: PRT
<213> ORGANISM: homo sapiens

<400> SEQUENCE: 44

Gln Gly Ile Ser Asn Trp
1               5

<210> SEQ ID NO 45
<211> LENGTH: 9
<212> TYPE: PRT
<213> ORGANISM: homo sapiens

<400> SEQUENCE: 45

Gln Gln Tyr Asn Ser Tyr Pro Leu Thr
1               5

<210> SEQ ID NO 46
<211> LENGTH: 8
<212> TYPE: PRT
<213> ORGANISM: homo sapiens

<400> SEQUENCE: 46

Gly Phe Thr Phe Ser Ser Tyr Ala
1               5

<210> SEQ ID NO 47
<211> LENGTH: 8
<212> TYPE: PRT
<213> ORGANISM: homo sapiens

<400> SEQUENCE: 47

Ile Ser Ile Ser Gly Gly Ser Thr
1               5

<210> SEQ ID NO 48
<211> LENGTH: 13
<212> TYPE: PRT
<213> ORGANISM: homo sapiens

<400> SEQUENCE: 48

Arg Gly Tyr Ser Gly Tyr Val Tyr Asp Ala Phe Asp Phe
1               5                   10

<210> SEQ ID NO 49
<211> LENGTH: 6
<212> TYPE: PRT
<213> ORGANISM: homo sapiens

<400> SEQUENCE: 49

Gln Gly Ile Ser Asn Trp
1               5

<210> SEQ ID NO 50
<211> LENGTH: 9
<212> TYPE: PRT
<213> ORGANISM: homo sapiens

<400> SEQUENCE: 50

Gln Gln Tyr Asn Ser Tyr Pro Leu Thr
1               5

<210> SEQ ID NO 51
```

```
<211> LENGTH: 8
<212> TYPE: PRT
<213> ORGANISM: homo sapiens

<400> SEQUENCE: 51

Gly Phe Thr Phe Ser Ser Tyr Ala
1               5

<210> SEQ ID NO 52
<211> LENGTH: 8
<212> TYPE: PRT
<213> ORGANISM: homo sapiens

<400> SEQUENCE: 52

Ile Ser Ile Gly Gly Gly Asn Ala
1               5

<210> SEQ ID NO 53
<211> LENGTH: 14
<212> TYPE: PRT
<213> ORGANISM: homo sapiens

<400> SEQUENCE: 53

Ala Lys Pro Gly Phe Ile Met Val Arg Gly Pro Leu Asp Tyr
1               5                   10

<210> SEQ ID NO 54
<211> LENGTH: 14
<212> TYPE: PRT
<213> ORGANISM: homo sapiens

<400> SEQUENCE: 54

Ala Lys Pro Gly Phe Ile Leu Val Arg Gly Pro Leu Asp Tyr
1               5                   10

<210> SEQ ID NO 55
<211> LENGTH: 7
<212> TYPE: PRT
<213> ORGANISM: homo sapiens

<400> SEQUENCE: 55

Gln Ser Val Ser Asn Ser Tyr
1               5

<210> SEQ ID NO 56
<211> LENGTH: 9
<212> TYPE: PRT
<213> ORGANISM: homo sapiens

<400> SEQUENCE: 56

Gln Gln Tyr Gly Ser Ser Pro Tyr Thr
1               5

<210> SEQ ID NO 57
<211> LENGTH: 8
<212> TYPE: PRT
<213> ORGANISM: homo sapiens

<400> SEQUENCE: 57

Gly Phe Thr Phe Ser Ser Tyr Ala
1               5

<210> SEQ ID NO 58
<211> LENGTH: 8
<212> TYPE: PRT
```

<213> ORGANISM: homo sapiens

<400> SEQUENCE: 58

Ile Ser Val Ser Gly Gly Ser Thr
1               5

<210> SEQ ID NO 59
<211> LENGTH: 18
<212> TYPE: PRT
<213> ORGANISM: homo sapiens

<400> SEQUENCE: 59

Ala Lys Glu Gly Tyr Ile Trp Phe Gly Glu Ser Leu Ser Tyr Ala Phe
1               5                   10                  15

Asp Ile

<210> SEQ ID NO 60
<211> LENGTH: 7
<212> TYPE: PRT
<213> ORGANISM: homo sapiens

<400> SEQUENCE: 60

Gln Ser Val Ser Ser Ser Tyr
1               5

<210> SEQ ID NO 61
<211> LENGTH: 8
<212> TYPE: PRT
<213> ORGANISM: homo sapiens

<400> SEQUENCE: 61

Gln Gln Tyr Gly Arg Ser Phe Thr
1               5

<210> SEQ ID NO 62
<211> LENGTH: 8
<212> TYPE: PRT
<213> ORGANISM: homo sapiens

<400> SEQUENCE: 62

Gly Phe Thr Phe Ser Asn Tyr Ala
1               5

<210> SEQ ID NO 63
<211> LENGTH: 8
<212> TYPE: PRT
<213> ORGANISM: homo sapiens

<400> SEQUENCE: 63

Ile Ser Val Ser Gly Gly Ser Thr
1               5

<210> SEQ ID NO 64
<211> LENGTH: 18
<212> TYPE: PRT
<213> ORGANISM: homo sapiens

<400> SEQUENCE: 64

Ala Lys Glu Gly Tyr Ile Trp Phe Gly Glu Ser Leu Ser Tyr Ala Phe
1               5                   10                  15

Asp Ile

<210> SEQ ID NO 65

```
<211> LENGTH: 7
<212> TYPE: PRT
<213> ORGANISM: homo sapiens

<400> SEQUENCE: 65

Gln Ser Val Ser Ser Tyr
1               5

<210> SEQ ID NO 66
<211> LENGTH: 8
<212> TYPE: PRT
<213> ORGANISM: homo sapiens

<400> SEQUENCE: 66

Gln Gln Tyr Gly Arg Ser Phe Thr
1               5

<210> SEQ ID NO 67
<211> LENGTH: 8
<212> TYPE: PRT
<213> ORGANISM: homo sapiens

<400> SEQUENCE: 67

Gly Phe Thr Phe Ser Ser Tyr Ala
1               5

<210> SEQ ID NO 68
<211> LENGTH: 8
<212> TYPE: PRT
<213> ORGANISM: homo sapiens

<400> SEQUENCE: 68

Ile Ser Val Ser Gly Gly Ser Thr
1               5

<210> SEQ ID NO 69
<211> LENGTH: 18
<212> TYPE: PRT
<213> ORGANISM: homo sapiens

<400> SEQUENCE: 69

Ala Lys Glu Gly Tyr Ile Trp Phe Gly Glu Ser Leu Ser Tyr Ala Phe
1               5                   10                  15

Asp Ile

<210> SEQ ID NO 70
<211> LENGTH: 7
<212> TYPE: PRT
<213> ORGANISM: homo sapiens

<400> SEQUENCE: 70

Gln Ser Val Ser Ser Tyr
1               5

<210> SEQ ID NO 71
<211> LENGTH: 8
<212> TYPE: PRT
<213> ORGANISM: homo sapiens

<400> SEQUENCE: 71

Gln Gln Tyr Gly Arg Ser Phe Thr
1               5

<210> SEQ ID NO 72
```

<211> LENGTH: 8
<212> TYPE: PRT
<213> ORGANISM: homo sapiens

<400> SEQUENCE: 72

Gly Gly Ser Phe Ser Gly Tyr Tyr
1               5

<210> SEQ ID NO 73
<211> LENGTH: 5
<212> TYPE: PRT
<213> ORGANISM: homo sapiens

<400> SEQUENCE: 73

Ile Asn Gln Ser Gly
1               5

<210> SEQ ID NO 74
<211> LENGTH: 7
<212> TYPE: PRT
<213> ORGANISM: homo sapiens

<400> SEQUENCE: 74

Ile Gln Gln Ser Gly Ser Thr
1               5

<210> SEQ ID NO 75
<211> LENGTH: 11
<212> TYPE: PRT
<213> ORGANISM: homo sapiens

<400> SEQUENCE: 75

Ala Ser Gly Asn Trp Asp His Phe Phe Asp Tyr
1               5                   10

<210> SEQ ID NO 76
<211> LENGTH: 6
<212> TYPE: PRT
<213> ORGANISM: homo sapiens

<400> SEQUENCE: 76

Gln Gly Ile Ser Ser Trp
1               5

<210> SEQ ID NO 77
<211> LENGTH: 9
<212> TYPE: PRT
<213> ORGANISM: homo sapiens

<400> SEQUENCE: 77

Gln Gln Ala Lys Ser Phe Pro Trp Thr
1               5

<210> SEQ ID NO 78
<211> LENGTH: 8
<212> TYPE: PRT
<213> ORGANISM: homo sapiens

<400> SEQUENCE: 78

Gly Gly Ser Phe Ser Gly Tyr His
1               5

<210> SEQ ID NO 79
<211> LENGTH: 7
<212> TYPE: PRT

<213> ORGANISM: homo sapiens

<400> SEQUENCE: 79

Ile Ser His Ser Gly Arg Thr
1               5

<210> SEQ ID NO 80
<211> LENGTH: 17
<212> TYPE: PRT
<213> ORGANISM: homo sapiens

<400> SEQUENCE: 80

Ala Ser Phe Ile Thr Met Ile Arg Gly Thr Ile Ile Thr His Phe Asp
1               5                   10                  15
Tyr

<210> SEQ ID NO 81
<211> LENGTH: 6
<212> TYPE: PRT
<213> ORGANISM: homo sapiens

<400> SEQUENCE: 81

Gln Gly Ile Ser Ser Trp
1               5

<210> SEQ ID NO 82
<211> LENGTH: 9
<212> TYPE: PRT
<213> ORGANISM: homo sapiens

<400> SEQUENCE: 82

Gln Gln Tyr His Ser Tyr Pro Tyr Thr
1               5

<210> SEQ ID NO 83
<211> LENGTH: 8
<212> TYPE: PRT
<213> ORGANISM: homo sapiens

<400> SEQUENCE: 83

Gly Gly Thr Phe Ser Ser Tyr Ala
1               5

<210> SEQ ID NO 84
<211> LENGTH: 8
<212> TYPE: PRT
<213> ORGANISM: homo sapiens

<400> SEQUENCE: 84

Ile Ile Pro Ile Phe Gly Ile Ala
1               5

<210> SEQ ID NO 85
<211> LENGTH: 17
<212> TYPE: PRT
<213> ORGANISM: homo sapiens

<400> SEQUENCE: 85

Ala Arg Arg Gly Asp Tyr Tyr Gly Ser Gly Ser Pro Asp Val Phe Asp
1               5                   10                  15
Ile

<210> SEQ ID NO 86

```
<211> LENGTH: 7
<212> TYPE: PRT
<213> ORGANISM: homo sapiens

<400> SEQUENCE: 86

Gln Ser Val Ser Ser Tyr
1               5

<210> SEQ ID NO 87
<211> LENGTH: 8
<212> TYPE: PRT
<213> ORGANISM: homo sapiens

<400> SEQUENCE: 87

Gln Gln Tyr Gly Ser Ser Tyr Thr
1               5

<210> SEQ ID NO 88
<211> LENGTH: 8
<212> TYPE: PRT
<213> ORGANISM: homo sapiens

<400> SEQUENCE: 88

Gly Gly Thr Phe Ser Ser Tyr Ala
1               5

<210> SEQ ID NO 89
<211> LENGTH: 8
<212> TYPE: PRT
<213> ORGANISM: homo sapiens

<400> SEQUENCE: 89

Ile Ile Pro Ile Phe Gly Ile Ala
1               5

<210> SEQ ID NO 90
<211> LENGTH: 17
<212> TYPE: PRT
<213> ORGANISM: homo sapiens

<400> SEQUENCE: 90

Ala Arg Arg Gly Asn Tyr Tyr Gly Ser Gly Ser Pro Asp Val Phe Asp
1               5                   10                  15

Ile

<210> SEQ ID NO 91
<211> LENGTH: 7
<212> TYPE: PRT
<213> ORGANISM: homo sapiens

<400> SEQUENCE: 91

Gln Ser Val Ser Ser Tyr
1               5

<210> SEQ ID NO 92
<211> LENGTH: 8
<212> TYPE: PRT
<213> ORGANISM: homo sapiens

<400> SEQUENCE: 92

Gln Gln Tyr Gly Ser Ser Tyr Thr
1               5

<210> SEQ ID NO 93
```

```
<211> LENGTH: 8
<212> TYPE: PRT
<213> ORGANISM: homo sapiens

<400> SEQUENCE: 93

Gly Gly Thr Phe Ser Ser Tyr Ala
1               5

<210> SEQ ID NO 94
<211> LENGTH: 8
<212> TYPE: PRT
<213> ORGANISM: homo sapiens

<400> SEQUENCE: 94

Ile Ile Pro Ile Phe Gly Ile Val
1               5

<210> SEQ ID NO 95
<211> LENGTH: 17
<212> TYPE: PRT
<213> ORGANISM: homo sapiens

<400> SEQUENCE: 95

Ala Arg Arg Gly Asn Tyr Tyr Gly Ser Gly Ser Pro Asp Val Phe Asp
1               5                   10                  15

Ile

<210> SEQ ID NO 96
<211> LENGTH: 7
<212> TYPE: PRT
<213> ORGANISM: homo sapiens

<400> SEQUENCE: 96

Gln Ser Val Ser Ser Ser Tyr
1               5

<210> SEQ ID NO 97
<211> LENGTH: 8
<212> TYPE: PRT
<213> ORGANISM: homo sapiens

<400> SEQUENCE: 97

Gln Gln Tyr Gly Ser Ser Tyr Thr
1               5

<210> SEQ ID NO 98
<211> LENGTH: 8
<212> TYPE: PRT
<213> ORGANISM: homo sapiens

<400> SEQUENCE: 98

Gly Gly Thr Phe Ser Ser Tyr Ala
1               5

<210> SEQ ID NO 99
<211> LENGTH: 8
<212> TYPE: PRT
<213> ORGANISM: homo sapiens

<400> SEQUENCE: 99

Ile Ile Pro Ile Phe Gly Ile Val
1               5

<210> SEQ ID NO 100
```

```
<211> LENGTH: 17
<212> TYPE: PRT
<213> ORGANISM: homo sapiens

<400> SEQUENCE: 100

Ala Arg Arg Gly Asn Tyr Tyr Gly Ser Gly Ser Pro Asp Val Phe Asp
1               5                   10                  15

Ile

<210> SEQ ID NO 101
<211> LENGTH: 6
<212> TYPE: PRT
<213> ORGANISM: homo sapiens

<400> SEQUENCE: 101

Gln Ser Val Ser Ser Tyr
1               5

<210> SEQ ID NO 102
<211> LENGTH: 8
<212> TYPE: PRT
<213> ORGANISM: homo sapiens

<400> SEQUENCE: 102

Gln Gln Arg Ser Asn Trp Leu Thr
1               5

<210> SEQ ID NO 103
<211> LENGTH: 8
<212> TYPE: PRT
<213> ORGANISM: homo sapiens

<400> SEQUENCE: 103

Gly Gly Thr Phe Ser Ser Tyr Ala
1               5

<210> SEQ ID NO 104
<211> LENGTH: 8
<212> TYPE: PRT
<213> ORGANISM: homo sapiens

<400> SEQUENCE: 104

Ile Ile Pro Ile Phe Gly Ile Ala
1               5

<210> SEQ ID NO 105
<211> LENGTH: 18
<212> TYPE: PRT
<213> ORGANISM: homo sapiens

<400> SEQUENCE: 105

Ala Arg Arg Gly Asn Tyr Tyr Gly Ser Gly Ser Pro Asp Val Phe Asp
1               5                   10                  15

Ile Ser

<210> SEQ ID NO 106
<211> LENGTH: 7
<212> TYPE: PRT
<213> ORGANISM: homo sapiens

<400> SEQUENCE: 106

Gln Ser Val Ser Ser Ser Tyr
1               5
```

<210> SEQ ID NO 107
<211> LENGTH: 8
<212> TYPE: PRT
<213> ORGANISM: homo sapiens

<400> SEQUENCE: 107

Gln Gln Tyr Gly Ser Ser Tyr Thr
1               5

<210> SEQ ID NO 108
<211> LENGTH: 8
<212> TYPE: PRT
<213> ORGANISM: homo sapiens

<400> SEQUENCE: 108

Gly Gly Ser Phe Ser Gly Tyr Tyr
1               5

<210> SEQ ID NO 109
<211> LENGTH: 7
<212> TYPE: PRT
<213> ORGANISM: homo sapiens

<400> SEQUENCE: 109

Ile Ser His Ser Gly Arg Thr
1               5

<210> SEQ ID NO 110
<211> LENGTH: 17
<212> TYPE: PRT
<213> ORGANISM: homo sapiens

<400> SEQUENCE: 110

Ala Arg Phe Ile Thr Met Ile Arg Gly Ala Ile Ile Thr His Phe Asp
1               5                   10                  15

Tyr

<210> SEQ ID NO 111
<211> LENGTH: 17
<212> TYPE: PRT
<213> ORGANISM: homo sapiens

<400> SEQUENCE: 111

Ala Arg Phe Ile Thr Leu Ile Arg Gly Ala Ile Ile Thr His Phe Asp
1               5                   10                  15

Tyr

<210> SEQ ID NO 112
<211> LENGTH: 6
<212> TYPE: PRT
<213> ORGANISM: homo sapiens

<400> SEQUENCE: 112

Gln Gly Ile Ser Ser Trp
1               5

<210> SEQ ID NO 113
<211> LENGTH: 9
<212> TYPE: PRT
<213> ORGANISM: homo sapiens

<400> SEQUENCE: 113

Gln Gln Tyr His Ser Tyr Pro Tyr Thr

```
1               5

<210> SEQ ID NO 114
<211> LENGTH: 8
<212> TYPE: PRT
<213> ORGANISM: homo sapiens

<400> SEQUENCE: 114

Gly Phe Ser Phe Ser Thr Tyr Ala
1               5

<210> SEQ ID NO 115
<211> LENGTH: 8
<212> TYPE: PRT
<213> ORGANISM: homo sapiens

<400> SEQUENCE: 115

Ile Ser Tyr Asp Gly Asp Asn Lys
1               5

<210> SEQ ID NO 116
<211> LENGTH: 13
<212> TYPE: PRT
<213> ORGANISM: homo sapiens

<400> SEQUENCE: 116

Ala Arg Gly Arg Lys Leu Gly Ile Asp Ala Phe Asp Ile
1               5                   10

<210> SEQ ID NO 117
<211> LENGTH: 6
<212> TYPE: PRT
<213> ORGANISM: homo sapiens

<400> SEQUENCE: 117

Gln Gly Ile Ser Ser Ala
1               5

<210> SEQ ID NO 118
<211> LENGTH: 9
<212> TYPE: PRT
<213> ORGANISM: homo sapiens

<400> SEQUENCE: 118

Gln Gln Phe Asn Ser Tyr Pro Phe Thr
1               5

<210> SEQ ID NO 119
<211> LENGTH: 8
<212> TYPE: PRT
<213> ORGANISM: homo sapiens
<220> FEATURE:
<221> NAME/KEY: MISC_FEATURE
<222> LOCATION: (6)..(6)
<223> OTHER INFORMATION: Wherein X is A or G

<400> SEQUENCE: 119

Ile Ser Ile Ser Gly Xaa Ser Thr
1               5

<210> SEQ ID NO 120
<211> LENGTH: 13
<212> TYPE: PRT
<213> ORGANISM: homo sapiens
<220> FEATURE:
<221> NAME/KEY: Misc
```

<222> LOCATION: (13)..(13)
<223> OTHER INFORMATION: Wherein X is I of F

<400> SEQUENCE: 120

Arg Gly Tyr Ser Gly Tyr Val Tyr Asp Ala Phe Asp Xaa
1               5                   10

<210> SEQ ID NO 121
<211> LENGTH: 8
<212> TYPE: PRT
<213> ORGANISM: homo sapiens
<220> FEATURE:
<221> NAME/KEY: MISC_FEATURE
<222> LOCATION: (8)..(8)
<223> OTHER INFORMATION: Wherein X is I or F

<400> SEQUENCE: 121

Gly Gly Ser Phe Ser Gly Tyr Xaa
1               5

<210> SEQ ID NO 122
<211> LENGTH: 17
<212> TYPE: PRT
<213> ORGANISM: homo sapiens
<220> FEATURE:
<221> NAME/KEY: MISC_FEATURE
<222> LOCATION: (2)..(2)
<223> OTHER INFORMATION: Wherein X is S or R
<220> FEATURE:
<221> NAME/KEY: MISC_FEATURE
<222> LOCATION: (10)..(10)
<223> OTHER INFORMATION: Wherein X is T or A

<400> SEQUENCE: 122

Ala Xaa Phe Ile Thr Met Ile Arg Gly Xaa Ile Ile Thr His Phe Asp
1               5                   10                  15
Tyr

<210> SEQ ID NO 123
<211> LENGTH: 8
<212> TYPE: PRT
<213> ORGANISM: homo sapiens
<220> FEATURE:
<221> NAME/KEY: MISC_FEATURE
<222> LOCATION: (6)..(6)
<223> OTHER INFORMATION: Wherein X is S or N

<400> SEQUENCE: 123

Gly Phe Thr Phe Ser Xaa Tyr Ala
1               5

<210> SEQ ID NO 124
<211> LENGTH: 8
<212> TYPE: PRT
<213> ORGANISM: homo sapiens

<400> SEQUENCE: 124

Ile Ser Val Ser Gly Gly Ser Thr
1               5

<210> SEQ ID NO 125
<211> LENGTH: 18
<212> TYPE: PRT
<213> ORGANISM: homo sapiens

<400> SEQUENCE: 125

Ala Lys Glu Gly Tyr Ile Trp Phe Gly Glu Ser Leu Ser Tyr Ala Phe

```
1               5                  10                 15
Asp Ile

<210> SEQ ID NO 126
<211> LENGTH: 8
<212> TYPE: PRT
<213> ORGANISM: homo sapiens
<220> FEATURE:
<221> NAME/KEY: MISC_FEATURE
<222> LOCATION: (8)..(8)
<223> OTHER INFORMATION: Wherein X is A or V

<400> SEQUENCE: 126

Ile Ile Pro Ile Phe Gly Ile Xaa
1               5

<210> SEQ ID NO 127
<211> LENGTH: 17
<212> TYPE: PRT
<213> ORGANISM: homo sapiens
<220> FEATURE:
<221> NAME/KEY: MISC_FEATURE
<222> LOCATION: (5)..(5)
<223> OTHER INFORMATION: Wherein X is D or N

<400> SEQUENCE: 127

Ala Arg Arg Gly Xaa Tyr Tyr Gly Ser Gly Ser Pro Asp Val Phe Asp
1               5                  10                 15

Ile

<210> SEQ ID NO 128
<211> LENGTH: 7
<212> TYPE: PRT
<213> ORGANISM: homo sapiens
<220> FEATURE:
<221> NAME/KEY: MISC_FEATURE
<222> LOCATION: (4)..(4)
<223> OTHER INFORMATION: Wherein X is S or deleted

<400> SEQUENCE: 128

Gln Ser Val Xaa Ser Ser Tyr
1               5

<210> SEQ ID NO 129
<211> LENGTH: 8
<212> TYPE: PRT
<213> ORGANISM: homo sapiens
<220> FEATURE:
<221> NAME/KEY: MISC_FEATURE
<222> LOCATION: (3)..(3)
<223> OTHER INFORMATION: Wherein X is R or Y
<220> FEATURE:
<221> NAME/KEY: MISC_FEATURE
<222> LOCATION: (4)..(4)
<223> OTHER INFORMATION: Wherein X is S or G
<220> FEATURE:
<221> NAME/KEY: MISC_FEATURE
<222> LOCATION: (4)..(4)
<223> OTHER INFORMATION: Wherein X is S or G
<220> FEATURE:
<221> NAME/KEY: MISC_FEATURE
<222> LOCATION: (5)..(5)
<223> OTHER INFORMATION: Wherein X is N or S
<220> FEATURE:
<221> NAME/KEY: MISC_FEATURE
<222> LOCATION: (6)..(6)
<223> OTHER INFORMATION: Wherein X is W or S
<220> FEATURE:
<221> NAME/KEY: MISC_FEATURE
<222> LOCATION: (6)..(6)
```

```
<223> OTHER INFORMATION: Wherein X is W or S
<220> FEATURE:
<221> NAME/KEY: MISC_FEATURE
<222> LOCATION: (7)..(7)
<223> OTHER INFORMATION: Wherein X is L or Y

<400> SEQUENCE: 129

Gln Gln Xaa Xaa Xaa Xaa Xaa Thr
1               5

<210> SEQ ID NO 130
<211> LENGTH: 894
<212> TYPE: PRT
<213> ORGANISM: homo sapiens

<400> SEQUENCE: 130

Met Ala Trp Arg Cys Pro Arg Met Gly Arg Val Pro Leu Ala Trp Cys
1               5                   10                  15

Leu Ala Leu Cys Gly Trp Ala Cys Met Ala Pro Arg Gly Thr Gln Ala
                20                  25                  30

Glu Glu Ser Pro Phe Val Gly Asn Pro Gly Asn Ile Thr Gly Ala Arg
        35                  40                  45

Gly Leu Thr Gly Thr Leu Arg Cys Gln Leu Gln Val Gln Gly Glu Pro
    50                  55                  60

Pro Glu Val His Trp Leu Arg Asp Gly Gln Ile Leu Glu Leu Ala Asp
65                  70                  75                  80

Ser Thr Gln Thr Gln Val Pro Leu Gly Glu Asp Glu Gln Asp Asp Trp
                85                  90                  95

Ile Val Val Ser Gln Leu Arg Ile Thr Ser Leu Gln Leu Ser Asp Thr
            100                 105                 110

Gly Gln Tyr Gln Cys Leu Val Phe Leu Gly His Gln Thr Phe Val Ser
        115                 120                 125

Gln Pro Gly Tyr Val Gly Leu Glu Gly Leu Pro Tyr Phe Leu Glu Glu
    130                 135                 140

Pro Glu Asp Arg Thr Val Ala Ala Asn Thr Pro Phe Asn Leu Ser Cys
145                 150                 155                 160

Gln Ala Gln Gly Pro Pro Glu Pro Val Asp Leu Leu Trp Leu Gln Asp
                165                 170                 175

Ala Val Pro Leu Ala Thr Ala Pro Gly His Gly Pro Gln Arg Ser Leu
            180                 185                 190

His Val Pro Gly Leu Asn Lys Thr Ser Ser Phe Ser Cys Glu Ala His
        195                 200                 205

Asn Ala Lys Gly Val Thr Thr Ser Arg Thr Ala Thr Ile Thr Val Leu
    210                 215                 220

Pro Gln Gln Pro Arg Asn Leu His Leu Val Ser Arg Gln Pro Thr Glu
225                 230                 235                 240

Leu Glu Val Ala Trp Thr Pro Gly Leu Ser Gly Ile Tyr Pro Leu Thr
                245                 250                 255

His Cys Thr Leu Gln Ala Val Leu Ser Asp Asp Gly Met Gly Ile Gln
            260                 265                 270

Ala Gly Glu Pro Asp Pro Pro Glu Glu Pro Leu Thr Ser Gln Ala Ser
        275                 280                 285

Val Pro Pro His Gln Leu Arg Leu Gly Ser Leu His Pro His Thr Pro
    290                 295                 300

Tyr His Ile Arg Val Ala Cys Thr Ser Ser Gln Gly Pro Ser Ser Trp
305                 310                 315                 320
```

-continued

```
Thr His Trp Leu Pro Val Glu Thr Pro Glu Gly Val Pro Leu Gly Pro
                325                 330                 335

Pro Glu Asn Ile Ser Ala Thr Arg Asn Gly Ser Gln Ala Phe Val His
            340                 345                 350

Trp Gln Glu Pro Arg Ala Pro Leu Gln Gly Thr Leu Leu Gly Tyr Arg
        355                 360                 365

Leu Ala Tyr Gln Gly Gln Asp Thr Pro Glu Val Leu Met Asp Ile Gly
    370                 375                 380

Leu Arg Gln Glu Val Thr Leu Glu Leu Gln Gly Asp Gly Ser Val Ser
385                 390                 395                 400

Asn Leu Thr Val Cys Val Ala Ala Tyr Thr Ala Ala Gly Asp Gly Pro
                405                 410                 415

Trp Ser Leu Pro Val Pro Leu Glu Ala Trp Arg Pro Gly Gln Ala Gln
            420                 425                 430

Pro Val His Gln Leu Val Lys Glu Pro Ser Thr Pro Ala Phe Ser Trp
        435                 440                 445

Pro Trp Trp Tyr Val Leu Leu Gly Ala Val Val Ala Ala Ala Cys Val
    450                 455                 460

Leu Ile Leu Ala Leu Phe Leu Val His Arg Arg Lys Lys Glu Thr Arg
465                 470                 475                 480

Tyr Gly Glu Val Phe Glu Pro Thr Val Glu Arg Gly Glu Leu Val Val
                485                 490                 495

Arg Tyr Arg Val Arg Lys Ser Tyr Ser Arg Arg Thr Thr Glu Ala Thr
            500                 505                 510

Leu Asn Ser Leu Gly Ile Ser Glu Glu Leu Lys Glu Lys Leu Arg Asp
        515                 520                 525

Val Met Val Asp Arg His Lys Val Ala Leu Gly Lys Thr Leu Gly Glu
    530                 535                 540

Gly Glu Phe Gly Ala Val Met Glu Gly Gln Leu Asn Gln Asp Asp Ser
545                 550                 555                 560

Ile Leu Lys Val Ala Val Lys Thr Met Lys Ile Ala Ile Cys Thr Arg
                565                 570                 575

Ser Glu Leu Glu Asp Phe Leu Ser Glu Ala Val Cys Met Lys Glu Phe
            580                 585                 590

Asp His Pro Asn Val Met Arg Leu Ile Gly Val Cys Phe Gln Gly Ser
        595                 600                 605

Glu Arg Glu Ser Phe Pro Ala Pro Val Val Ile Leu Pro Phe Met Lys
    610                 615                 620

His Gly Asp Leu His Ser Phe Leu Leu Tyr Ser Arg Leu Gly Asp Gln
625                 630                 635                 640

Pro Val Tyr Leu Pro Thr Gln Met Leu Val Lys Phe Met Ala Asp Ile
                645                 650                 655

Ala Ser Gly Met Glu Tyr Leu Ser Thr Lys Arg Phe Ile His Arg Asp
            660                 665                 670

Leu Ala Ala Arg Asn Cys Met Leu Asn Glu Asn Met Ser Val Cys Val
        675                 680                 685

Ala Asp Phe Gly Leu Ser Lys Lys Ile Tyr Asn Gly Asp Tyr Tyr Arg
    690                 695                 700

Gln Gly Arg Ile Ala Lys Met Pro Val Lys Trp Ile Ala Ile Glu Ser
705                 710                 715                 720

Leu Ala Asp Arg Val Tyr Thr Ser Lys Ser Asp Val Trp Ser Phe Gly
                725                 730                 735

Val Thr Met Trp Glu Ile Ala Thr Arg Gly Gln Thr Pro Tyr Pro Gly
```

```
                    740                 745                 750
Val Glu Asn Ser Glu Ile Tyr Asp Tyr Leu Arg Gln Gly Asn Arg Leu
                755                 760                 765

Lys Gln Pro Ala Asp Cys Leu Asp Gly Leu Tyr Ala Leu Met Ser Arg
    770                 775                 780

Cys Trp Glu Leu Asn Pro Gln Asp Arg Pro Ser Phe Thr Glu Leu Arg
785                 790                 795                 800

Glu Asp Leu Glu Asn Thr Leu Lys Ala Leu Pro Pro Ala Gln Glu Pro
                805                 810                 815

Asp Glu Ile Leu Tyr Val Asn Met Asp Glu Gly Gly Gly Tyr Pro Glu
                820                 825                 830

Pro Pro Gly Ala Ala Gly Gly Ala Asp Pro Pro Thr Gln Pro Asp Pro
                835                 840                 845

Lys Asp Ser Cys Ser Cys Leu Thr Ala Ala Glu Val His Pro Ala Gly
                850                 855                 860

Arg Tyr Val Leu Cys Pro Ser Thr Thr Pro Ser Pro Ala Gln Pro Ala
865                 870                 875                 880

Asp Arg Gly Ser Pro Ala Ala Pro Gly Gln Glu Asp Gly Ala
                885                 890

<210> SEQ ID NO 131
<211> LENGTH: 904
<212> TYPE: PRT
<213> ORGANISM: Mus Musculus

<400> SEQUENCE: 131

Met Ala Trp Arg Cys Pro Arg Met Gly Arg Val Pro Leu Ala Trp Cys
1               5                   10                  15

Leu Ala Leu Cys Gly Trp Ala Cys Met Tyr Pro Tyr Asp Val Pro Asp
                20                  25                  30

Tyr Ala Ala His Lys Asp Thr Gln Thr Glu Ala Gly Ser Pro Phe Val
                35                  40                  45

Gly Asn Pro Gly Asn Ile Thr Gly Ala Arg Gly Leu Thr Gly Thr Leu
    50                  55                  60

Arg Cys Glu Leu Gln Val Gln Gly Glu Pro Pro Glu Val Val Trp Leu
65                  70                  75                  80

Arg Asp Gly Gln Ile Leu Glu Leu Ala Asp Asn Thr Gln Thr Gln Val
                85                  90                  95

Pro Leu Gly Glu Asp Trp Gln Asp Glu Trp Lys Val Val Ser Gln Leu
                100                 105                 110

Arg Ile Ser Ala Leu Gln Leu Ser Asp Ala Gly Glu Tyr Gln Cys Met
    115                 120                 125

Val His Leu Glu Gly Arg Thr Phe Val Ser Gln Pro Gly Phe Val Gly
    130                 135                 140

Leu Glu Gly Leu Pro Tyr Phe Leu Glu Glu Pro Glu Asp Lys Ala Val
145                 150                 155                 160

Pro Ala Asn Thr Pro Phe Asn Leu Ser Cys Gln Ala Gln Gly Pro Pro
                165                 170                 175

Glu Pro Val Thr Leu Leu Trp Leu Gln Asp Ala Val Pro Leu Ala Pro
                180                 185                 190

Val Thr Gly His Ser Ser Gln His Ser Leu Gln Thr Pro Gly Leu Asn
    195                 200                 205

Lys Thr Ser Ser Phe Ser Cys Glu Ala His Asn Ala Lys Gly Val Thr
    210                 215                 220
```

-continued

```
Thr Ser Arg Thr Ala Thr Ile Thr Val Leu Pro Gln Arg Pro His His
225                 230                 235                 240

Leu His Val Val Ser Arg Gln Pro Thr Glu Leu Glu Val Ala Trp Thr
            245                 250                 255

Pro Gly Leu Ser Gly Ile Tyr Pro Leu Thr His Cys Asn Leu Gln Ala
            260                 265                 270

Val Leu Ser Asp Asp Gly Val Gly Ile Trp Leu Gly Lys Ser Asp Pro
            275                 280                 285

Pro Glu Asp Pro Leu Thr Leu Gln Val Ser Val Pro His Gln Leu
    290                 295                 300

Arg Leu Glu Lys Leu Leu Pro His Thr Pro Tyr His Ile Arg Ile Ser
305                 310                 315                 320

Cys Ser Ser Ser Gln Gly Pro Ser Pro Trp Thr His Trp Leu Pro Val
            325                 330                 335

Glu Thr Thr Glu Gly Val Pro Leu Gly Pro Pro Glu Asn Val Ser Ala
            340                 345                 350

Met Arg Asn Gly Ser Gln Val Leu Val Arg Trp Gln Glu Pro Arg Val
            355                 360                 365

Pro Leu Gln Gly Thr Leu Leu Gly Tyr Arg Leu Ala Tyr Arg Gly Gln
    370                 375                 380

Asp Thr Pro Glu Val Leu Met Asp Ile Gly Leu Thr Arg Glu Val Thr
385                 390                 395                 400

Leu Glu Leu Arg Gly Asp Arg Pro Val Ala Asn Leu Thr Val Ser Val
            405                 410                 415

Thr Ala Tyr Thr Ser Ala Gly Asp Gly Pro Trp Ser Leu Pro Val Pro
            420                 425                 430

Leu Glu Pro Trp Arg Pro Gly Gln Gly Gln Pro Leu His His Leu Val
            435                 440                 445

Ser Glu Pro Pro Arg Ala Phe Ser Trp Pro Trp Trp Tyr Val Leu
    450                 455                 460

Leu Gly Ala Val Val Ala Ala Ala Cys Val Leu Ile Leu Ala Leu Phe
465                 470                 475                 480

Leu Val His Arg Arg Lys Lys Glu Thr Arg Tyr Gly Glu Val Phe Glu
            485                 490                 495

Pro Thr Val Glu Arg Gly Glu Leu Val Val Arg Tyr Arg Val Arg Lys
            500                 505                 510

Ser Tyr Ser Arg Arg Thr Thr Glu Ala Thr Leu Asn Ser Leu Gly Ile
            515                 520                 525

Ser Glu Glu Leu Lys Glu Lys Leu Arg Asp Val Met Val Asp Arg His
    530                 535                 540

Lys Val Ala Leu Gly Lys Thr Leu Gly Glu Gly Glu Phe Gly Ala Val
545                 550                 555                 560

Met Glu Gly Gln Leu Asn Gln Asp Asp Ser Ile Leu Lys Val Ala Val
            565                 570                 575

Lys Thr Met Lys Ile Ala Ile Cys Thr Arg Ser Glu Leu Glu Asp Phe
            580                 585                 590

Leu Ser Glu Ala Val Cys Met Lys Glu Phe Asp His Pro Asn Val Met
            595                 600                 605

Arg Leu Ile Gly Val Cys Phe Gln Gly Ser Glu Arg Glu Ser Phe Pro
    610                 615                 620

Ala Pro Val Val Ile Leu Pro Phe Met Lys His Gly Asp Leu His Ser
625                 630                 635                 640

Phe Leu Leu Tyr Ser Arg Leu Gly Asp Gln Pro Val Tyr Leu Pro Thr
```

```
                    645                 650                 655
Gln Met Leu Val Lys Phe Met Ala Asp Ile Ala Ser Gly Met Glu Tyr
                660                 665                 670

Leu Ser Thr Lys Arg Phe Ile His Arg Asp Leu Ala Ala Arg Asn Cys
            675                 680                 685

Met Leu Asn Glu Asn Met Ser Val Cys Val Ala Asp Phe Gly Leu Ser
        690                 695                 700

Lys Lys Ile Tyr Asn Gly Asp Tyr Tyr Arg Gln Gly Arg Ile Ala Lys
705                 710                 715                 720

Met Pro Val Lys Trp Ile Ala Ile Glu Ser Leu Ala Asp Arg Val Tyr
                725                 730                 735

Thr Ser Lys Ser Asp Val Trp Ser Phe Gly Val Thr Met Trp Glu Ile
            740                 745                 750

Ala Thr Arg Gly Gln Thr Pro Tyr Pro Gly Val Glu Asn Ser Glu Ile
        755                 760                 765

Tyr Asp Tyr Leu Arg Gln Gly Asn Arg Leu Lys Gln Pro Ala Asp Cys
    770                 775                 780

Leu Asp Gly Leu Tyr Ala Leu Met Ser Arg Cys Trp Glu Leu Asn Pro
785                 790                 795                 800

Gln Asp Arg Pro Ser Phe Thr Glu Leu Arg Glu Asp Leu Glu Asn Thr
                805                 810                 815

Leu Lys Ala Leu Pro Pro Ala Gln Glu Pro Asp Glu Ile Leu Tyr Val
            820                 825                 830

Asn Met Asp Glu Gly Gly Gly Tyr Pro Glu Pro Gly Ala Ala Gly Gly
        835                 840                 845

Gly Ala Asp Pro Pro Thr Gln Pro Asp Pro Lys Asp Ser Cys Ser Cys
    850                 855                 860

Leu Thr Ala Ala Glu Val His Pro Ala Gly Arg Tyr Val Leu Cys Pro
865                 870                 875                 880

Ser Thr Thr Pro Ser Pro Ala Gln Pro Ala Asp Arg Gly Ser Pro Ala
                885                 890                 895

Ala Pro Gly Gln Glu Asp Gly Ala
            900

<210> SEQ ID NO 132
<211> LENGTH: 894
<212> TYPE: PRT
<213> ORGANISM: homo sapiens

<400> SEQUENCE: 132

Met Ala Trp Arg Cys Pro Arg Met Gly Arg Val Pro Leu Ala Trp Cys
1               5                   10                  15

Leu Ala Leu Cys Gly Trp Ala Cys Met Ala Pro Arg Gly Thr Gln Ala
            20                  25                  30

Glu Glu Ser Pro Phe Val Gly Asn Pro Gly Asn Ile Thr Gly Ala Arg
        35                  40                  45

Gly Leu Thr Gly Thr Leu Arg Cys Gln Leu Gln Val Gln Gly Glu Pro
    50                  55                  60

Pro Glu Val His Trp Leu Arg Asp Gly Gln Ile Leu Glu Leu Ala Asp
65                  70                  75                  80

Ser Thr Gln Thr Gln Val Pro Leu Gly Glu Asp Glu Gln Asp Asp Trp
                85                  90                  95

Ile Val Val Ser Gln Leu Arg Ile Thr Ser Leu Gln Leu Ser Asp Thr
            100                 105                 110
```

```
Gly Gln Tyr Gln Cys Leu Val Phe Leu Gly His Gln Thr Phe Val Ser
            115                 120                 125

Gln Pro Gly Tyr Val Gly Leu Glu Gly Leu Pro Tyr Phe Leu Glu Glu
        130                 135                 140

Pro Glu Asp Lys Ala Val Pro Ala Asn Thr Pro Phe Asn Leu Ser Cys
145                 150                 155                 160

Gln Ala Gln Gly Pro Pro Glu Pro Val Thr Leu Leu Trp Leu Gln Asp
                165                 170                 175

Ala Val Pro Leu Ala Pro Val Thr Gly His Ser Ser Gln His Ser Leu
            180                 185                 190

Gln Thr Pro Gly Leu Asn Lys Thr Ser Ser Phe Ser Cys Glu Ala His
        195                 200                 205

Asn Ala Lys Gly Val Thr Thr Ser Arg Thr Ala Thr Ile Thr Val Leu
210                 215                 220

Pro Gln Gln Pro Arg Asn Leu His Leu Val Ser Arg Gln Pro Thr Glu
225                 230                 235                 240

Leu Glu Val Ala Trp Thr Pro Gly Leu Ser Gly Ile Tyr Pro Leu Thr
                245                 250                 255

His Cys Thr Leu Gln Ala Val Leu Ser Asp Asp Gly Met Gly Ile Gln
            260                 265                 270

Ala Gly Glu Pro Asp Pro Pro Glu Glu Pro Leu Thr Ser Gln Ala Ser
        275                 280                 285

Val Pro Pro His Gln Leu Arg Leu Gly Ser Leu His Pro His Thr Pro
290                 295                 300

Tyr His Ile Arg Val Ala Cys Thr Ser Ser Gln Gly Pro Ser Ser Trp
305                 310                 315                 320

Thr His Trp Leu Pro Val Glu Thr Pro Glu Gly Val Pro Leu Gly Pro
                325                 330                 335

Pro Glu Asn Ile Ser Ala Thr Arg Asn Gly Ser Gln Ala Phe Val His
            340                 345                 350

Trp Gln Glu Pro Arg Ala Pro Leu Gln Gly Thr Leu Leu Gly Tyr Arg
        355                 360                 365

Leu Ala Tyr Gln Gly Gln Asp Thr Pro Glu Val Leu Met Asp Ile Gly
370                 375                 380

Leu Arg Gln Glu Val Thr Leu Glu Leu Gln Gly Asp Gly Ser Val Ser
385                 390                 395                 400

Asn Leu Thr Val Cys Val Ala Ala Tyr Thr Ala Ala Gly Asp Gly Pro
                405                 410                 415

Trp Ser Leu Pro Val Pro Leu Glu Ala Trp Arg Pro Gly Gln Ala Gln
            420                 425                 430

Pro Val His Gln Leu Val Lys Glu Pro Ser Thr Pro Ala Phe Ser Trp
        435                 440                 445

Pro Trp Trp Tyr Val Leu Leu Gly Ala Val Val Ala Ala Ala Cys Val
450                 455                 460

Leu Ile Leu Ala Leu Phe Leu Val His Arg Arg Lys Lys Glu Thr Arg
465                 470                 475                 480

Tyr Gly Glu Val Phe Glu Pro Thr Val Glu Arg Gly Glu Leu Val Val
                485                 490                 495

Arg Tyr Arg Val Arg Lys Ser Tyr Ser Arg Arg Thr Thr Glu Ala Thr
            500                 505                 510

Leu Asn Ser Leu Gly Ile Ser Glu Glu Leu Lys Glu Lys Leu Arg Asp
        515                 520                 525

Val Met Val Asp Arg His Lys Val Ala Leu Gly Lys Thr Leu Gly Glu
```

```
                530             535             540
Gly Glu Phe Gly Ala Val Met Glu Gly Gln Leu Asn Gln Asp Asp Ser
545                 550                 555                 560

Ile Leu Lys Val Ala Val Lys Thr Met Lys Ile Ala Ile Cys Thr Arg
                565                 570                 575

Ser Glu Leu Glu Asp Phe Leu Ser Glu Ala Val Cys Met Lys Glu Phe
            580                 585                 590

Asp His Pro Asn Val Met Arg Leu Ile Gly Val Cys Phe Gln Gly Ser
        595                 600                 605

Glu Arg Glu Ser Phe Pro Ala Pro Val Val Ile Leu Pro Phe Met Lys
    610                 615                 620

His Gly Asp Leu His Ser Phe Leu Leu Tyr Ser Arg Leu Gly Asp Gln
625                 630                 635                 640

Pro Val Tyr Leu Pro Thr Gln Met Leu Val Lys Phe Met Ala Asp Ile
                645                 650                 655

Ala Ser Gly Met Glu Tyr Leu Ser Thr Lys Arg Phe Ile His Arg Asp
            660                 665                 670

Leu Ala Ala Arg Asn Cys Met Leu Asn Glu Asn Met Ser Val Cys Val
        675                 680                 685

Ala Asp Phe Gly Leu Ser Lys Lys Ile Tyr Asn Gly Asp Tyr Tyr Arg
    690                 695                 700

Gln Gly Arg Ile Ala Lys Met Pro Val Lys Trp Ile Ala Ile Glu Ser
705                 710                 715                 720

Leu Ala Asp Arg Val Tyr Thr Ser Lys Ser Asp Val Trp Ser Phe Gly
                725                 730                 735

Val Thr Met Trp Glu Ile Ala Thr Arg Gly Gln Thr Pro Tyr Pro Gly
            740                 745                 750

Val Glu Asn Ser Glu Ile Tyr Asp Tyr Leu Arg Gln Gly Asn Arg Leu
        755                 760                 765

Lys Gln Pro Ala Asp Cys Leu Asp Gly Leu Tyr Ala Leu Met Ser Arg
    770                 775                 780

Cys Trp Glu Leu Asn Pro Gln Asp Arg Pro Ser Phe Thr Glu Leu Arg
785                 790                 795                 800

Glu Asp Leu Glu Asn Thr Leu Lys Ala Leu Pro Pro Ala Gln Glu Pro
                805                 810                 815

Asp Glu Ile Leu Tyr Val Asn Met Asp Glu Gly Gly Gly Tyr Pro Glu
            820                 825                 830

Pro Pro Gly Ala Ala Gly Gly Ala Asp Pro Pro Thr Gln Pro Asp Pro
        835                 840                 845

Lys Asp Ser Cys Ser Cys Leu Thr Ala Ala Glu Val His Pro Ala Gly
    850                 855                 860

Arg Tyr Val Leu Cys Pro Ser Thr Thr Pro Ser Pro Ala Gln Pro Ala
865                 870                 875                 880

Asp Arg Gly Ser Pro Ala Ala Pro Gly Gln Glu Asp Gly Ala
                885                 890

<210> SEQ ID NO 133
<211> LENGTH: 894
<212> TYPE: PRT
<213> ORGANISM: homo sapiens

<400> SEQUENCE: 133

Met Ala Trp Arg Cys Pro Arg Met Gly Arg Val Pro Leu Ala Trp Cys
1               5                   10                  15
```

```
Leu Ala Leu Cys Gly Trp Ala Cys Met Ala Pro Arg Gly Thr Gln Ala
            20                  25                  30

Glu Glu Ser Pro Phe Val Gly Asn Pro Gly Asn Ile Thr Gly Ala Arg
        35                  40                  45

Gly Leu Thr Gly Thr Leu Arg Cys Gln Leu Gln Val Gln Gly Glu Pro
    50                  55                  60

Pro Glu Val His Trp Leu Arg Asp Gly Gln Ile Leu Glu Leu Ala Asp
65                  70                  75                  80

Ser Thr Gln Thr Gln Val Pro Leu Gly Glu Asp Gln Asp Asp Trp
                85                  90                  95

Ile Val Val Ser Gln Leu Arg Ile Thr Ser Leu Gln Leu Ser Asp Thr
                100                 105                 110

Gly Gln Tyr Gln Cys Leu Val Phe Leu Gly His Gln Thr Phe Val Ser
            115                 120                 125

Gln Pro Gly Tyr Val Gly Leu Glu Gly Leu Pro Tyr Phe Leu Glu Glu
        130                 135                 140

Pro Glu Asp Lys Ala Val Pro Ala Asn Thr Pro Phe Asn Leu Ser Cys
145                 150                 155                 160

Gln Ala Gln Gly Pro Pro Glu Pro Val Thr Leu Leu Trp Leu Gln Asp
                165                 170                 175

Ala Val Pro Leu Ala Pro Val Thr Gly His Ser Ser Gln His Ser Leu
            180                 185                 190

Gln Thr Pro Gly Leu Asn Lys Thr Ser Ser Phe Ser Cys Glu Ala His
        195                 200                 205

Asn Ala Lys Gly Val Thr Thr Ser Arg Thr Ala Thr Ile Thr Val Leu
210                 215                 220

Pro Gln Gln Pro Arg Asn Leu His Leu Val Ser Arg Gln Pro Thr Glu
225                 230                 235                 240

Leu Glu Val Ala Trp Thr Pro Gly Leu Ser Gly Ile Tyr Pro Leu Thr
                245                 250                 255

His Cys Thr Leu Gln Ala Val Leu Ser Asp Asp Gly Met Gly Ile Gln
            260                 265                 270

Ala Gly Glu Pro Asp Pro Pro Glu Glu Pro Leu Thr Ser Gln Ala Ser
        275                 280                 285

Val Pro Pro His Gln Leu Arg Leu Gly Ser Leu His Pro His Thr Pro
290                 295                 300

Tyr His Ile Arg Val Ala Cys Thr Ser Ser Gln Gly Pro Ser Ser Trp
305                 310                 315                 320

Thr His Trp Leu Pro Val Glu Thr Pro Glu Gly Val Pro Leu Gly Pro
                325                 330                 335

Pro Glu Asn Ile Ser Ala Thr Arg Asn Gly Ser Gln Ala Phe Val His
            340                 345                 350

Trp Gln Glu Pro Arg Ala Pro Leu Gln Gly Thr Leu Leu Gly Tyr Arg
        355                 360                 365

Leu Ala Tyr Gln Gly Gln Asp Thr Pro Glu Val Leu Met Asp Ile Gly
    370                 375                 380

Leu Arg Gln Glu Val Thr Leu Glu Leu Gln Gly Asp Gly Ser Val Ser
385                 390                 395                 400

Asn Leu Thr Val Cys Val Ala Ala Tyr Thr Ala Ala Gly Asp Gly Pro
                405                 410                 415

Trp Ser Leu Pro Val Pro Leu Glu Ala Trp Arg Pro Gly Gln Ala Gln
            420                 425                 430

Pro Val His Gln Leu Val Lys Glu Pro Ser Thr Pro Ala Phe Ser Trp
```

```
            435                 440                 445
Pro Trp Trp Tyr Val Leu Leu Gly Ala Val Ala Ala Cys Val
450                 455                 460

Leu Ile Leu Ala Leu Phe Leu Val His Arg Arg Lys Lys Glu Thr Arg
465                 470                 475                 480

Tyr Gly Glu Val Phe Glu Pro Thr Val Glu Arg Gly Glu Leu Val Val
                    485                 490                 495

Arg Tyr Arg Val Arg Lys Ser Tyr Ser Arg Arg Thr Thr Glu Ala Thr
                500                 505                 510

Leu Asn Ser Leu Gly Ile Ser Glu Glu Leu Lys Glu Lys Leu Arg Asp
                515                 520                 525

Val Met Val Asp Arg His Lys Val Ala Leu Gly Lys Thr Leu Gly Glu
                530                 535                 540

Gly Glu Phe Gly Ala Val Met Glu Gly Gln Leu Asn Gln Asp Asp Ser
545                 550                 555                 560

Ile Leu Lys Val Ala Val Lys Thr Met Lys Ile Ala Ile Cys Thr Arg
                    565                 570                 575

Ser Glu Leu Glu Asp Phe Leu Ser Glu Ala Val Cys Met Lys Glu Phe
                580                 585                 590

Asp His Pro Asn Val Met Arg Leu Ile Gly Val Cys Phe Gln Gly Ser
                595                 600                 605

Glu Arg Glu Ser Phe Pro Ala Pro Val Val Ile Leu Pro Phe Met Lys
610                 615                 620

His Gly Asp Leu His Ser Phe Leu Leu Tyr Ser Arg Leu Gly Asp Gln
625                 630                 635                 640

Pro Val Tyr Leu Pro Thr Gln Met Leu Val Lys Phe Met Ala Asp Ile
                    645                 650                 655

Ala Ser Gly Met Glu Tyr Leu Ser Thr Lys Arg Phe Ile His Arg Asp
                660                 665                 670

Leu Ala Ala Arg Asn Cys Met Leu Asn Glu Asn Met Ser Val Cys Val
                675                 680                 685

Ala Asp Phe Gly Leu Ser Lys Lys Ile Tyr Asn Gly Asp Tyr Tyr Arg
                690                 695                 700

Gln Gly Arg Ile Ala Lys Met Pro Val Lys Trp Ile Ala Ile Glu Ser
705                 710                 715                 720

Leu Ala Asp Arg Val Tyr Thr Ser Lys Ser Asp Val Trp Ser Phe Gly
                    725                 730                 735

Val Thr Met Trp Glu Ile Ala Thr Arg Gly Gln Thr Pro Tyr Pro Gly
                740                 745                 750

Val Glu Asn Ser Glu Ile Tyr Asp Tyr Leu Arg Gln Gly Asn Arg Leu
                755                 760                 765

Lys Gln Pro Ala Asp Cys Leu Asp Gly Leu Tyr Ala Leu Met Ser Arg
                770                 775                 780

Cys Trp Glu Leu Asn Pro Gln Asp Arg Pro Ser Phe Thr Glu Leu Arg
785                 790                 795                 800

Glu Asp Leu Glu Asn Thr Leu Lys Ala Leu Pro Pro Ala Gln Glu Pro
                    805                 810                 815

Asp Glu Ile Leu Tyr Val Asn Met Asp Glu Gly Gly Gly Tyr Pro Glu
                820                 825                 830

Pro Pro Gly Ala Ala Gly Gly Ala Asp Pro Pro Thr Gln Pro Asp Pro
                835                 840                 845

Lys Asp Ser Cys Ser Cys Leu Thr Ala Ala Glu Val His Pro Ala Gly
850                 855                 860
```

```
Arg Tyr Val Leu Cys Pro Ser Thr Thr Pro Ser Pro Ala Gln Pro Ala
865                 870                 875                 880

Asp Arg Gly Ser Pro Ala Ala Pro Gly Gln Glu Asp Gly Ala
                885                 890

<210> SEQ ID NO 134
<211> LENGTH: 894
<212> TYPE: PRT
<213> ORGANISM: homo sapiens

<400> SEQUENCE: 134

Met Ala Trp Arg Cys Pro Arg Met Gly Arg Val Pro Leu Ala Trp Cys
1               5                   10                  15

Leu Ala Leu Cys Gly Trp Ala Cys Met Ala Pro Arg Gly Thr Gln Ala
                20                  25                  30

Glu Glu Ser Pro Phe Val Gly Asn Pro Gly Asn Ile Thr Gly Ala Arg
            35                  40                  45

Gly Leu Thr Gly Thr Leu Arg Cys Gln Leu Gln Val Gln Gly Glu Pro
        50                  55                  60

Pro Glu Val His Trp Leu Arg Asp Gly Gln Ile Leu Glu Leu Ala Asp
65                  70                  75                  80

Ser Thr Gln Thr Gln Val Pro Leu Gly Glu Asp Gln Asp Asp Trp
                85                  90                  95

Ile Val Val Ser Gln Leu Arg Ile Thr Ser Leu Gln Leu Ser Asp Thr
                100                 105                 110

Gly Gln Tyr Gln Cys Leu Val Phe Leu Gly His Gln Thr Phe Val Ser
            115                 120                 125

Gln Pro Gly Tyr Val Gly Leu Glu Gly Leu Pro Tyr Phe Leu Glu Glu
        130                 135                 140

Pro Glu Asp Arg Thr Val Ala Ala Asn Thr Pro Phe Asn Leu Ser Cys
145                 150                 155                 160

Gln Ala Gln Gly Pro Pro Glu Pro Val Asp Leu Leu Trp Leu Gln Asp
                165                 170                 175

Ala Val Pro Leu Ala Thr Ala Pro Gly His Gly Pro Gln Arg Ser Leu
                180                 185                 190

His Val Pro Gly Leu Asn Lys Thr Ser Ser Phe Ser Cys Glu Ala His
            195                 200                 205

Asn Ala Lys Gly Val Thr Thr Ser Arg Thr Ala Thr Ile Thr Val Leu
        210                 215                 220

Pro Gln Arg Pro His His Leu His Val Val Ser Arg Gln Pro Thr Glu
225                 230                 235                 240

Leu Glu Val Ala Trp Thr Pro Gly Leu Ser Gly Ile Tyr Pro Leu Thr
                245                 250                 255

His Cys Asn Leu Gln Ala Val Leu Ser Asp Asp Gly Val Gly Ile Trp
            260                 265                 270

Leu Gly Lys Ser Asp Pro Pro Glu Asp Pro Leu Thr Leu Gln Val Ser
        275                 280                 285

Val Pro Pro His Gln Leu Arg Leu Glu Lys Leu Leu Pro His Thr Pro
    290                 295                 300

Tyr His Ile Arg Ile Ser Cys Ser Ser Ser Gln Gly Pro Ser Pro Trp
305                 310                 315                 320

Thr His Trp Leu Pro Val Glu Thr Thr Glu Gly Val Pro Leu Gly Pro
                325                 330                 335

Pro Glu Asn Ile Ser Ala Thr Arg Asn Gly Ser Gln Ala Phe Val His
```

-continued

```
                340                 345                 350
Trp Gln Glu Pro Arg Ala Pro Leu Gln Gly Thr Leu Leu Gly Tyr Arg
            355                 360                 365

Leu Ala Tyr Gln Gly Gln Asp Thr Pro Glu Val Leu Met Asp Ile Gly
        370                 375                 380

Leu Arg Gln Glu Val Thr Leu Glu Leu Gln Gly Asp Gly Ser Val Ser
385                 390                 395                 400

Asn Leu Thr Val Cys Val Ala Ala Tyr Thr Ala Ala Gly Asp Gly Pro
                405                 410                 415

Trp Ser Leu Pro Val Pro Leu Glu Ala Trp Arg Pro Gly Gln Ala Gln
            420                 425                 430

Pro Val His Gln Leu Val Lys Glu Pro Ser Thr Pro Ala Phe Ser Trp
        435                 440                 445

Pro Trp Trp Tyr Val Leu Leu Gly Ala Val Val Ala Ala Cys Val
            450                 455                 460

Leu Ile Leu Ala Leu Phe Leu Val His Arg Arg Lys Lys Glu Thr Arg
465                 470                 475                 480

Tyr Gly Glu Val Phe Glu Pro Thr Val Glu Arg Gly Glu Leu Val Val
                485                 490                 495

Arg Tyr Arg Val Arg Lys Ser Tyr Ser Arg Arg Thr Thr Glu Ala Thr
            500                 505                 510

Leu Asn Ser Leu Gly Ile Ser Glu Glu Leu Lys Glu Lys Leu Arg Asp
        515                 520                 525

Val Met Val Asp Arg His Lys Val Ala Leu Gly Lys Thr Leu Gly Glu
    530                 535                 540

Gly Glu Phe Gly Ala Val Met Glu Gly Gln Leu Asn Gln Asp Asp Ser
545                 550                 555                 560

Ile Leu Lys Val Ala Val Lys Thr Met Lys Ile Ala Ile Cys Thr Arg
                565                 570                 575

Ser Glu Leu Glu Asp Phe Leu Ser Glu Ala Val Cys Met Lys Glu Phe
            580                 585                 590

Asp His Pro Asn Val Met Arg Leu Ile Gly Val Cys Phe Gln Gly Ser
        595                 600                 605

Glu Arg Glu Ser Phe Pro Ala Pro Val Val Ile Leu Pro Phe Met Lys
    610                 615                 620

His Gly Asp Leu His Ser Phe Leu Leu Tyr Ser Arg Leu Gly Asp Gln
625                 630                 635                 640

Pro Val Tyr Leu Pro Thr Gln Met Leu Val Lys Phe Met Ala Asp Ile
                645                 650                 655

Ala Ser Gly Met Glu Tyr Leu Ser Thr Lys Arg Phe Ile His Arg Asp
            660                 665                 670

Leu Ala Ala Arg Asn Cys Met Leu Asn Glu Asn Met Ser Val Cys Val
        675                 680                 685

Ala Asp Phe Gly Leu Ser Lys Lys Ile Tyr Asn Gly Asp Tyr Tyr Arg
    690                 695                 700

Gln Gly Arg Ile Ala Lys Met Pro Val Lys Trp Ile Ala Ile Glu Ser
705                 710                 715                 720

Leu Ala Asp Arg Val Tyr Thr Ser Lys Ser Asp Val Trp Ser Phe Gly
                725                 730                 735

Val Thr Met Trp Glu Ile Ala Thr Arg Gly Gln Thr Pro Tyr Pro Gly
            740                 745                 750

Val Glu Asn Ser Glu Ile Tyr Asp Tyr Leu Arg Gln Gly Asn Arg Leu
        755                 760                 765
```

```
Lys Gln Pro Ala Asp Cys Leu Asp Gly Leu Tyr Ala Leu Met Ser Arg
    770             775                 780
Cys Trp Glu Leu Asn Pro Gln Asp Arg Pro Ser Phe Thr Glu Leu Arg
785             790                 795                 800
Glu Asp Leu Glu Asn Thr Leu Lys Ala Leu Pro Pro Ala Gln Glu Pro
                805                 810                 815
Asp Glu Ile Leu Tyr Val Asn Met Asp Glu Gly Gly Gly Tyr Pro Glu
                820                 825                 830
Pro Pro Gly Ala Ala Gly Gly Ala Asp Pro Pro Thr Gln Pro Asp Pro
            835                 840             845
Lys Asp Ser Cys Ser Cys Leu Thr Ala Ala Glu Val His Pro Ala Gly
            850                 855                 860
Arg Tyr Val Leu Cys Pro Ser Thr Thr Pro Ser Pro Ala Gln Pro Ala
865             870                 875                 880
Asp Arg Gly Ser Pro Ala Ala Pro Gly Gln Glu Asp Gly Ala
                885                 890
```

<210> SEQ ID NO 135
<211> LENGTH: 894
<212> TYPE: PRT
<213> ORGANISM: homo sapiens

<400> SEQUENCE: 135

```
Met Ala Trp Arg Cys Pro Arg Met Gly Arg Val Pro Leu Ala Trp Cys
1               5                   10                  15
Leu Ala Leu Cys Gly Trp Ala Cys Met Ala Pro Arg Gly Thr Gln Ala
            20                  25                  30
Glu Glu Ser Pro Phe Val Gly Asn Pro Gly Asn Ile Thr Gly Ala Arg
        35                  40                  45
Gly Leu Thr Gly Thr Leu Arg Cys Gln Leu Gln Val Gln Gly Glu Pro
    50                  55                  60
Pro Glu Val His Trp Leu Arg Asp Gly Gln Ile Leu Glu Leu Ala Asp
65              70                  75                  80
Ser Thr Gln Thr Gln Val Pro Leu Gly Glu Asp Glu Gln Asp Asp Trp
                85                  90                  95
Ile Val Val Ser Gln Leu Arg Ile Thr Ser Leu Gln Leu Ser Asp Thr
                100                 105                 110
Gly Gln Tyr Gln Cys Leu Val Phe Leu Gly His Gln Thr Phe Val Ser
            115                 120                 125
Gln Pro Gly Tyr Val Gly Leu Glu Gly Leu Pro Tyr Phe Leu Glu Glu
        130                 135                 140
Pro Glu Asp Arg Thr Val Ala Ala Asn Thr Pro Phe Asn Leu Ser Cys
145                 150                 155                 160
Gln Ala Gln Gly Pro Pro Glu Pro Val Asp Leu Leu Trp Leu Gln Asp
                165                 170                 175
Ala Val Pro Leu Ala Thr Ala Pro Gly His Gly Pro Gln Arg Ser Leu
                180                 185                 190
His Val Pro Gly Leu Asn Lys Thr Ser Ser Phe Ser Cys Glu Ala His
            195                 200                 205
Asn Ala Lys Gly Val Thr Thr Ser Arg Thr Ala Thr Ile Thr Val Leu
        210                 215                 220
Pro Gln Gln Pro Arg Asn Leu His Leu Val Ser Arg Gln Pro Thr Glu
225                 230                 235                 240
Leu Glu Val Ala Trp Thr Pro Gly Leu Ser Gly Ile Tyr Pro Leu Thr
```

```
            245                 250                 255
His Cys Thr Leu Gln Ala Val Leu Ser Asp Asp Gly Met Gly Ile Gln
            260                 265                 270

Ala Gly Glu Pro Asp Pro Pro Glu Glu Pro Leu Thr Ser Gln Ala Ser
            275                 280                 285

Val Pro Pro His Gln Leu Arg Leu Gly Ser Leu His Pro His Thr Pro
            290                 295                 300

Tyr His Ile Arg Val Ala Cys Thr Ser Ser Gln Gly Pro Ser Ser Trp
305                 310                 315                 320

Thr His Trp Leu Pro Val Glu Thr Pro Glu Gly Val Pro Leu Gly Pro
                    325                 330                 335

Pro Glu Asn Val Ser Ala Met Arg Asn Gly Ser Gln Val Leu Val Arg
                    340                 345                 350

Trp Gln Glu Pro Arg Val Pro Leu Gln Gly Thr Leu Leu Gly Tyr Arg
                    355                 360                 365

Leu Ala Tyr Arg Gly Gln Asp Thr Pro Glu Val Leu Met Asp Ile Gly
            370                 375                 380

Leu Thr Arg Glu Val Thr Leu Glu Leu Arg Gly Asp Arg Pro Val Ala
385                 390                 395                 400

Asn Leu Thr Val Ser Val Thr Ala Tyr Thr Ser Ala Gly Asp Gly Pro
                    405                 410                 415

Trp Ser Leu Pro Val Pro Leu Glu Pro Trp Arg Pro Gly Gln Gly Gln
                    420                 425                 430

Pro Leu His His Leu Val Ser Glu Pro Pro Arg Ala Phe Ser Trp
                    435                 440                 445

Pro Trp Trp Tyr Val Leu Leu Gly Ala Val Val Ala Ala Cys Val
            450                 455                 460

Leu Ile Leu Ala Leu Phe Leu Val His Arg Arg Lys Lys Glu Thr Arg
465                 470                 475                 480

Tyr Gly Glu Val Phe Glu Pro Thr Val Glu Arg Gly Glu Leu Val Val
                    485                 490                 495

Arg Tyr Arg Val Arg Lys Ser Tyr Ser Arg Arg Thr Thr Glu Ala Thr
                    500                 505                 510

Leu Asn Ser Leu Gly Ile Ser Glu Glu Leu Lys Glu Lys Leu Arg Asp
            515                 520                 525

Val Met Val Asp Arg His Lys Val Ala Leu Gly Lys Thr Leu Gly Glu
            530                 535                 540

Gly Glu Phe Gly Ala Val Met Glu Gly Gln Leu Asn Gln Asp Asp Ser
545                 550                 555                 560

Ile Leu Lys Val Ala Val Lys Thr Met Lys Ile Ala Ile Cys Thr Arg
                    565                 570                 575

Ser Glu Leu Glu Asp Phe Leu Ser Glu Ala Val Cys Met Lys Glu Phe
            580                 585                 590

Asp His Pro Asn Val Met Arg Leu Ile Gly Val Cys Phe Gln Gly Ser
            595                 600                 605

Glu Arg Glu Ser Phe Pro Ala Pro Val Val Ile Leu Pro Phe Met Lys
            610                 615                 620

His Gly Asp Leu His Ser Phe Leu Leu Tyr Ser Arg Leu Gly Asp Gln
625                 630                 635                 640

Pro Val Tyr Leu Pro Thr Gln Met Leu Val Lys Phe Met Ala Asp Ile
                    645                 650                 655

Ala Ser Gly Met Glu Tyr Leu Ser Thr Lys Arg Phe Ile His Arg Asp
                    660                 665                 670
```

```
Leu Ala Ala Arg Asn Cys Met Leu Asn Glu Asn Met Ser Val Cys Val
            675                 680                 685

Ala Asp Phe Gly Leu Ser Lys Lys Ile Tyr Asn Gly Asp Tyr Tyr Arg
690                 695                 700

Gln Gly Arg Ile Ala Lys Met Pro Val Lys Trp Ile Ala Ile Glu Ser
705                 710                 715                 720

Leu Ala Asp Arg Val Tyr Thr Ser Lys Ser Asp Val Trp Ser Phe Gly
                725                 730                 735

Val Thr Met Trp Glu Ile Ala Thr Arg Gly Gln Thr Pro Tyr Pro Gly
                740                 745                 750

Val Glu Asn Ser Glu Ile Tyr Asp Tyr Leu Arg Gln Gly Asn Arg Leu
                755                 760                 765

Lys Gln Pro Ala Asp Cys Leu Asp Gly Leu Tyr Ala Leu Met Ser Arg
770                 775                 780

Cys Trp Glu Leu Asn Pro Gln Asp Arg Pro Ser Phe Thr Glu Leu Arg
785                 790                 795                 800

Glu Asp Leu Glu Asn Thr Leu Lys Ala Leu Pro Pro Ala Gln Glu Pro
                805                 810                 815

Asp Glu Ile Leu Tyr Val Asn Met Asp Glu Gly Gly Gly Tyr Pro Glu
                820                 825                 830

Pro Pro Gly Ala Ala Gly Gly Ala Asp Pro Pro Thr Gln Pro Asp Pro
                835                 840                 845

Lys Asp Ser Cys Ser Cys Leu Thr Ala Ala Glu Val His Pro Ala Gly
850                 855                 860

Arg Tyr Val Leu Cys Pro Ser Thr Thr Pro Ser Pro Ala Gln Pro Ala
865                 870                 875                 880

Asp Arg Gly Ser Pro Ala Ala Pro Gly Gln Glu Asp Gly Ala
                885                 890

<210> SEQ ID NO 136
<211> LENGTH: 124
<212> TYPE: PRT
<213> ORGANISM: homo sapiens

<400> SEQUENCE: 136

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Asn Trp Val Arg Gln Ala Pro Gly Lys Gly Leu Glu Trp Val
            35                  40                  45

Ser Gly Ile Ser Gly Ser Gly Gly His Thr Tyr His Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Tyr Asp Ile Leu Thr Gly Tyr Tyr Asn Leu Leu Asp
            100                 105                 110

Tyr Trp Gly Gln Gly Thr Leu Val Thr Val Ser Ser
        115                 120

<210> SEQ ID NO 137
<211> LENGTH: 8
<212> TYPE: PRT
```

<213> ORGANISM: homo sapiens

<400> SEQUENCE: 137

Gly Phe Thr Phe Ser Ser Tyr Ala
1               5

<210> SEQ ID NO 138
<211> LENGTH: 8
<212> TYPE: PRT
<213> ORGANISM: homo sapiens

<400> SEQUENCE: 138

Ile Ser Gly Ser Gly Gly His Thr
1               5

<210> SEQ ID NO 139
<211> LENGTH: 17
<212> TYPE: PRT
<213> ORGANISM: homo sapiens

<400> SEQUENCE: 139

Ala Lys Asp Arg Tyr Asp Ile Leu Thr Gly Tyr Tyr Asn Leu Leu Asp
1               5                   10                  15

Tyr

<210> SEQ ID NO 140
<211> LENGTH: 107
<212> TYPE: PRT
<213> ORGANISM: homo sapiens

<400> SEQUENCE: 140

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Glu Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Ala Lys Val Glu Ile Lys
            100                 105

<210> SEQ ID NO 141
<211> LENGTH: 6
<212> TYPE: PRT
<213> ORGANISM: homo sapiens

<400> SEQUENCE: 141

Gln Gly Ile Ser Ser Trp
1               5

<210> SEQ ID NO 142
<211> LENGTH: 9
<212> TYPE: PRT
<213> ORGANISM: homo sapiens

<400> SEQUENCE: 142

Gln Gln Tyr Asn Ser Tyr Pro Leu Thr
1               5

<210> SEQ ID NO 143
<211> LENGTH: 123
<212> TYPE: PRT
<213> ORGANISM: homo sapiens

<400> SEQUENCE: 143

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Gly Tyr
            20                  25                  30

Gly Ile Ser Trp Val Arg Gln Ala Pro Gly Gln Gly Leu Glu Trp Ile
        35                  40                  45

Gly Trp Ile Ser Ala Tyr Asn Gly Asn Thr Asn Tyr Val Gln Asn Leu
    50                  55                  60

Gln Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp His Ile Ser Met Leu Arg Gly Ile Ile Arg Asn Tyr
            100                 105                 110

Trp Gly Gln Gly Thr Leu Val Thr Val Ser Ser
        115                 120

<210> SEQ ID NO 144
<211> LENGTH: 108
<212> TYPE: PRT
<213> ORGANISM: homo sapiens

<400> SEQUENCE: 144

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Ser Trp Pro Arg
                85                  90                  95

Leu Thr Phe Gly Gly Gly Thr Lys Val Glu Ile Lys
            100                 105

<210> SEQ ID NO 145
<211> LENGTH: 124
<212> TYPE: PRT
<213> ORGANISM: homo sapiens

<400> SEQUENCE: 145

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Arg Tyr
            20                  25                  30

Ala Ile Ser Trp Val Arg Gln Ala Pro Gly Gln Gly Leu Glu Trp Met

```
              35                  40                  45
Gly Arg Ile Ile Pro Ile Val Gly Ile Ala Asn Tyr Ala Gln Lys Phe
         50                  55                  60
Gln Gly Arg Val Thr Leu Thr Ala Asp Lys Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Glu Ala Gly Tyr Ser Ser Trp Tyr Ala Glu Tyr Phe Gln
            100                 105                 110
His Trp Gly Gln Gly Thr Leu Val Thr Val Ser Ser
            115                 120

<210> SEQ ID NO 146
<211> LENGTH: 108
<212> TYPE: PRT
<213> ORGANISM: homo sapiens

<400> SEQUENCE: 146

Glu Ile Val Leu Thr Gln Ser Pro Gly Thr Leu Ser Leu Ser Pro Gly
 1               5                  10                  15
Glu Arg Ala Thr Leu Ser Cys Arg Ala Ser Gln Ser Val Ser Ser Asn
             20                  25                  30
Tyr Leu Ala Trp Tyr Gln Gln Lys Pro Gly Gln Ala Pro Arg Leu Leu
         35                  40                  45
Ile Tyr Gly Ala Ser Ser Arg Ala Thr Gly Phe Pro Asp Arg Phe Ser
     50                  55                  60
Gly Ser Gly Ser Gly Thr Asp Phe Thr Leu Thr Ile Ser Arg Leu Glu
 65                  70                  75                  80
Pro Glu Asp Phe Ala Val Tyr Tyr Cys Gln Gln Tyr Gly Ser Ser Pro
                 85                  90                  95
Tyr Thr Phe Gly Gln Gly Thr Lys Leu Glu Ile Lys
            100                 105

<210> SEQ ID NO 147
<211> LENGTH: 893
<212> TYPE: PRT
<213> ORGANISM: Macaca fascicularis

<400> SEQUENCE: 147

Ala Trp Arg Cys Pro Arg Met Gly Arg Val Pro Leu Ala Trp Cys Leu
 1               5                  10                  15
Ala Leu Cys Gly Trp Val Cys Met Ala Pro Arg Gly Thr Gln Ala Glu
             20                  25                  30
Glu Ser Pro Phe Val Gly Asn Pro Gly Asn Ile Thr Gly Ala Arg Gly
         35                  40                  45
Leu Thr Gly Thr Leu Arg Cys Gln Leu Gln Val Gln Gly Glu Pro Pro
     50                  55                  60
Glu Val His Trp Leu Arg Asp Gly Gln Ile Leu Glu Leu Ala Asp Ser
 65                  70                  75                  80
Thr Gln Thr Gln Val Pro Leu Gly Glu Asp Glu Gln Asp Asp Trp Ile
                 85                  90                  95
Val Val Ser Gln Leu Arg Ile Ala Ser Leu Gln Leu Ser Asp Ala Gly
            100                 105                 110
Gln Tyr Gln Cys Leu Val Phe Leu Gly His Gln Asn Phe Val Ser Gln
            115                 120                 125
Pro Gly Tyr Val Gly Leu Glu Gly Leu Pro Tyr Phe Leu Glu Glu Pro
```

```
            130                 135                 140
Glu Asp Arg Thr Val Ala Ala Asn Thr Pro Phe Asn Leu Ser Cys Gln
145                 150                 155                 160

Ala Gln Gly Pro Pro Glu Pro Val Asp Leu Leu Trp Leu Gln Asp Ala
                165                 170                 175

Val Pro Leu Ala Thr Ala Pro Gly His Gly Pro Gln Arg Asn Leu His
                180                 185                 190

Val Pro Gly Leu Asn Lys Thr Ser Ser Phe Ser Cys Glu Ala His Asn
                195                 200                 205

Ala Lys Gly Val Thr Thr Ser Arg Thr Ala Thr Ile Thr Val Leu Pro
            210                 215                 220

Gln Gln Pro Arg Asn Leu His Leu Val Ser Arg Gln Pro Thr Glu Leu
225                 230                 235                 240

Glu Val Ala Trp Thr Pro Gly Leu Ser Gly Ile Tyr Pro Leu Thr His
                245                 250                 255

Cys Thr Leu Gln Ala Val Leu Ser Asp Asp Gly Met Gly Ile Gln Ala
                260                 265                 270

Gly Glu Pro Asp Pro Pro Glu Pro Leu Thr Leu Gln Ala Ser Val
                275                 280                 285

Pro Pro His Gln Leu Arg Leu Gly Ser Leu His Pro His Thr Pro Tyr
                290                 295                 300

His Ile Arg Val Ala Cys Thr Ser Ser Gln Gly Pro Ser Ser Trp Thr
305                 310                 315                 320

His Trp Leu Pro Val Glu Thr Pro Glu Gly Val Pro Leu Gly Pro Pro
                325                 330                 335

Glu Asn Ile Ser Ala Thr Arg Asn Gly Ser Gln Ala Phe Val His Trp
                340                 345                 350

Gln Glu Pro Arg Ala Pro Leu Gln Gly Thr Leu Leu Gly Tyr Arg Leu
                355                 360                 365

Ala Tyr Gln Gly Gln Asp Thr Pro Glu Val Leu Met Asp Ile Gly Leu
            370                 375                 380

Arg Gln Glu Val Thr Leu Glu Leu Gln Gly Asp Gly Ser Val Ser Asn
385                 390                 395                 400

Leu Thr Val Cys Val Ala Ala Tyr Thr Ala Ala Gly Asp Gly Pro Trp
                405                 410                 415

Ser Leu Pro Val Pro Leu Glu Ala Trp Arg Pro Gly Gln Ala Gln Pro
                420                 425                 430

Val His Gln Leu Val Lys Glu Thr Ser Ala Pro Ala Phe Ser Trp Pro
                435                 440                 445

Trp Trp Tyr Ile Leu Leu Gly Ala Val Val Ala Ala Ala Cys Val Leu
                450                 455                 460

Ile Leu Ala Leu Phe Leu Val His Arg Arg Lys Lys Glu Thr Arg Tyr
465                 470                 475                 480

Gly Glu Val Phe Glu Pro Thr Val Glu Arg Gly Glu Leu Val Val Arg
                485                 490                 495

Tyr Arg Val Arg Lys Ser Tyr Ser Arg Arg Thr Thr Glu Ala Thr Leu
                500                 505                 510
```

```
Asn Ser Leu Gly Ile Ser Glu Glu Leu Lys Glu Lys Leu Arg Asp Val
        515                 520                 525

Met Val Asp Arg His Lys Val Ala Leu Gly Lys Thr Leu Gly Glu Gly
    530                 535                 540

Glu Phe Gly Ala Val Met Glu Gly Gln Leu Asn Gln Asp Asp Ser Ile
545                 550                 555                 560

Leu Lys Val Ala Val Lys Thr Met Lys Ile Ala Ile Cys Thr Arg Ser
                565                 570                 575

Glu Leu Glu Asp Phe Leu Ser Glu Ala Val Cys Met Lys Glu Phe Asp
                580                 585                 590

His Pro Asn Val Met Arg Leu Ile Gly Val Cys Phe Gln Gly Ser Glu
            595                 600                 605

Arg Glu Ser Phe Pro Ala Pro Val Val Ile Leu Pro Phe Met Lys His
        610                 615                 620

Gly Asp Leu His Ser Phe Leu Leu Tyr Ser Arg Leu Gly Asp Gln Pro
625                 630                 635                 640

Val Tyr Leu Pro Thr Gln Met Leu Val Lys Phe Met Ala Asp Ile Ala
                645                 650                 655

Ser Gly Met Glu Tyr Leu Ser Thr Lys Arg Phe Ile His Arg Asp Leu
                660                 665                 670

Ala Ala Arg Asn Cys Met Leu Asn Glu Asn Met Ser Val Cys Val Ala
            675                 680                 685

Asp Phe Gly Leu Ser Lys Lys Ile Tyr Asn Gly Asp Tyr Tyr Arg Gln
        690                 695                 700

Gly Arg Ile Ala Lys Met Pro Val Lys Trp Ile Ala Ile Glu Ser Leu
705                 710                 715                 720

Ala Asp Arg Val Tyr Thr Ser Lys Ser Asp Val Trp Ser Phe Gly Val
                725                 730                 735

Thr Met Trp Glu Ile Ala Thr Arg Gly Gln Thr Pro Tyr Pro Gly Val
            740                 745                 750

Glu Asn Ser Glu Ile Tyr Asp Tyr Leu Arg Gln Gly Asn Arg Leu Lys
        755                 760                 765

Gln Pro Ala Asp Cys Leu Asp Gly Leu Tyr Ala Leu Met Ser Arg Cys
770                 775                 780

Trp Glu Leu Asn Pro Gln Asp Arg Pro Ser Phe Thr Glu Leu Arg Glu
785                 790                 795                 800

Asp Leu Glu Asn Thr Leu Lys Ala Leu Pro Pro Ala Gln Glu Pro Asp
                805                 810                 815

Glu Ile Leu Tyr Val Asn Met Asp Glu Gly Gly Gly Tyr Pro Glu Pro
                820                 825                 830

Pro Gly Ala Ala Gly Gly Ala Asp Pro Pro Thr Gln Leu Asp Pro Lys
            835                 840                 845

Asp Ser Cys Ser Cys Leu Thr Ser Ala Glu Val His Pro Ala Gly Arg
850                 855                 860

Tyr Val Leu Cys Pro Ser Thr Ala Pro Ser Pro Ala Gln Pro Ala Asp
865                 870                 875                 880

Arg Gly Ser Pro Ala Ala Pro Gly Gln Glu Asp Gly Ala
                885                 890
```